(12) United States Patent
Cha et al.

(10) Patent No.: US 10,580,996 B2
(45) Date of Patent: Mar. 3, 2020

(54) POLYCYCLIC COMPOUND AND ORGANIC LIGHT-EMITTING ELEMENT COMPRISING SAME

(71) Applicant: LG CHEM, LTD., Seoul (KR)

(72) Inventors: Yongbum Cha, Daejeon (KR); Wanpyo Hong, Daejeon (KR); Sung Kil Hong, Daejeon (KR)

(73) Assignee: LG CHEM, LTD., Seoul (KR)

( * ) Notice: Subject to any disclaimer, the term of this patent is extended or adjusted under 35 U.S.C. 154(b) by 238 days.

(21) Appl. No.: 15/577,495

(22) PCT Filed: Jun. 17, 2016

(86) PCT No.: PCT/KR2016/006012
§ 371 (c)(1),
(2) Date: Nov. 28, 2017

(87) PCT Pub. No.: WO2016/195459
PCT Pub. Date: Dec. 8, 2016

(65) Prior Publication Data
US 2018/0138421 A1    May 17, 2018

(30) Foreign Application Priority Data
Jun. 5, 2015 (KR) .................. 10-2015-0080191

(51) Int. Cl.
*H01L 51/50* (2006.01)
*H01L 51/00* (2006.01)
(Continued)

(52) U.S. Cl.
CPC ........ *H01L 51/0072* (2013.01); *C07D 209/80* (2013.01); *C07D 209/82* (2013.01); *C07D 209/88* (2013.01); *C07D 401/04* (2013.01); *C07D 401/10* (2013.01); *C07D 403/04* (2013.01); *C07D 403/10* (2013.01); *C07D 405/14* (2013.01); *C07D 413/10* (2013.01); *C07D 417/10* (2013.01); *C07D 471/04* (2013.01); *C07D 487/04* (2013.01);
(Continued)

(58) Field of Classification Search
None
See application file for complete search history.

(56) References Cited

U.S. PATENT DOCUMENTS

| | | |
|---|---|---|
| 2010/0032658 A1 | 2/2010 | Lee et al. |
| 2014/0239281 A1 | 8/2014 | Ise et al. |
| 2014/0367654 A1 | 12/2014 | Kim et al. |

FOREIGN PATENT DOCUMENTS

| | | |
|---|---|---|
| CN | 104513192 A | 4/2015 |
| JP | 48-11486 A | 2/1973 |

(Continued)

OTHER PUBLICATIONS

Waldmann, et al.: "Über ms-Benzacridan-Abkömmlinge", XP002786787, Journal Für Praktische Chemieliebigs Ann. Chem., vol. 156, No. 168, Aug. 8, 1940, p. 157. (with Machine Translation).
(Continued)

*Primary Examiner* — Gregory D Clark
(74) *Attorney, Agent, or Firm* — Dentons US LLP

(57) ABSTRACT

The present specification provides a multicyclic compound and an organic light emitting device including the same.

18 Claims, 1 Drawing Sheet

(51) Int. Cl.
  *C07D 403/04* (2006.01)
  *C09K 11/06* (2006.01)
  *C07D 209/82* (2006.01)
  *C07D 209/80* (2006.01)
  *C07D 209/88* (2006.01)
  *C07D 401/04* (2006.01)
  *C07D 401/10* (2006.01)
  *C07D 403/10* (2006.01)
  *C07D 405/14* (2006.01)
  *C07D 413/10* (2006.01)
  *C07D 417/10* (2006.01)
  *C07D 471/04* (2006.01)
  *C07D 487/04* (2006.01)
  *C07F 9/572* (2006.01)

(52) U.S. Cl.
  CPC ............ *C07F 9/5728* (2013.01); *C09K 11/06* (2013.01); *H01L 51/006* (2013.01); *H01L 51/0052* (2013.01); *H01L 51/0061* (2013.01); *H01L 51/0067* (2013.01); *H01L 51/0071* (2013.01); *H01L 51/0073* (2013.01); *H01L 51/0085* (2013.01); *C09K 2211/1018* (2013.01); *C09K 2211/1029* (2013.01); *C09K 2211/185* (2013.01); *H01L 51/5012* (2013.01); *H01L 51/5016* (2013.01); *H01L 51/5056* (2013.01); *H01L 51/5072* (2013.01); *H01L 51/5088* (2013.01); *H01L 51/5092* (2013.01); *H01L 51/5096* (2013.01)

(56) References Cited

FOREIGN PATENT DOCUMENTS

| | | | |
|---|---|---|---|
| JP | 2010059147 A | | 3/2010 |
| KR | 10-2012-0020816 A | | 3/2012 |
| KR | 10-2012-0081539 | * | 7/2012 ............ C09K 11/06 |
| KR | 10-2012-0081539 A | | 7/2012 |
| KR | 10-2012-0095765 A | | 8/2012 |
| KR | 10-2013-0007441 A | | 1/2013 |
| KR | 10-2015-0065383 A | | 6/2015 |

OTHER PUBLICATIONS

Shah: "Alkali-catalysed Cyclization of 3-(8'-Anthrapyrimidinylamino)benzanthrone", XP009509471, Indian Journal of Chemistry, Section B, Council of Scientific and Industrial Research (C SIR), vol. 14, Jan. 1, 1976, pp. 623-625.

* cited by examiner

【FIG. 1】
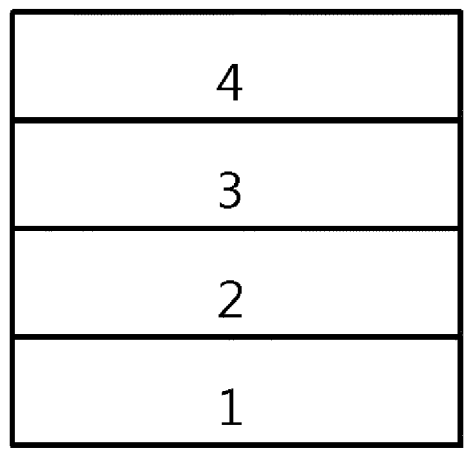
【FIG. 2】
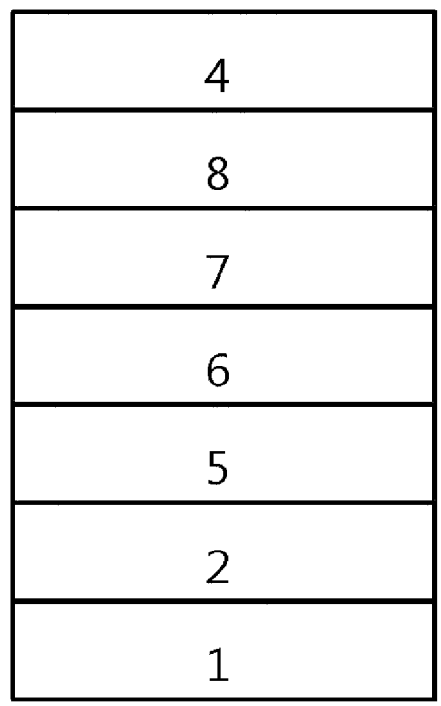

POLYCYCLIC COMPOUND AND ORGANIC LIGHT-EMITTING ELEMENT COMPRISING SAME

This application is a National Stage Entry of International Application No. PCT/KR2016/006012, filed Jun. 7, 2016, and claims the benefit of and priority to Korean Application No. 10-2015-0080191, filed Jun. 5, 2015, all of which are hereby incorporated by reference in their entirety for all purposes as if fully set forth herein.

TECHNICAL FIELD

The present specification claims priority to and the benefits of Korean Patent Application No. 10-2015-0080191, filed with the Korean Intellectual Property Office on Jun. 5, 2015, the entire contents of which are incorporated herein by reference.

The present specification relates to a multicyclic compound and an organic light emitting device including the same.

BACKGROUND ART

An organic light emission phenomenon generally refers to a phenomenon converting electrical energy to light energy using an organic material. An organic light emitting device using an organic light emission phenomenon normally has a structure including an anode, a cathode, and an organic material layer therebetween. Herein, the organic material layer is often formed in a multilayer structure formed with different materials in order to increase efficiency and stability of the organic light emitting device, and for example, may be formed with a hole injection layer, a hole transfer layer, a light emitting layer, an electron transfer layer, an electron injection layer and the like. When a voltage is applied between the two electrodes in such an organic light emitting device structure, holes and electrons are injected to the organic material layer from the anode and the cathode, respectively, and when the injected holes and electrons meet, excitons are formed, and light emits when these excitons fall back to the ground state.

Development of new materials for such an organic light emitting device has been continuously required.

DISCLOSURE

Technical Problem

The present specification describes a multicyclic compound and an organic light emitting device including the same.

Technical Solution

One embodiment of the present specification provides a compound represented by the following Chemical Formula 1:

[Chemical Formula 1]

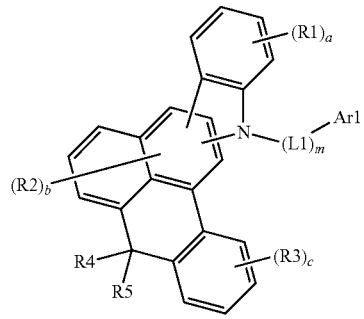

In Chemical Formula 1,

L1 is a direct bond; a substituted or unsubstituted arylene group; or a substituted or unsubstituted heteroarylene group, m is an integer of 0 to 5, when m is 2 or greater, L1s are the same as or different from each other, Ar1 is hydrogen; deuterium; a halogen group; a nitrile group; a nitro group; a hydroxyl group; a carbonyl group; an ester group; an imide group; an amino group; a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylheteroarylamine group; a substituted or unsubstituted arylphosphine group; a substituted or unsubstituted phosphine oxide group; a substituted or unsubstituted aryl group; or a substituted or unsubstituted heterocyclic group, a, b and c are each an integer of 0 to 4, R1 to R3 are the same as or different from each other, and each independently hydrogen; deuterium; a halogen group; a nitrile group; a nitro group; a hydroxyl group; a carbonyl group; an ester group; an imide group; an amino group; a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylheteroarylamine group; a substituted or unsubstituted arylphosphine group; a substituted or unsubstituted phosphine oxide group; a substituted or unsubstituted aryl group;

or a substituted or unsubstituted heterocyclic group, or may bond to adjacent groups to form a substituted or unsubstituted ring, when a is 2 or greater, R1s are the same as or different from each other, when b is 2 or greater, R2s are the same as or different from each other, when c is 2 or greater, R3s are the same as or different from each other, and R4 and R5 are the same as or different from each other, and each independently hydrogen; deuterium; a halogen group; a nitrile group; a nitro group; a hydroxyl group; a carbonyl group; an ester group; an imide group; an amino group; a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylheteroarylamine group; a substituted or unsubstituted arylphosphine group; or a substituted or unsubstituted phosphine oxide group.

According to one embodiment of the present specification, Chemical Formula 1 is represented by the following Chemical Formula 2-1 or Chemical Formula 2-2.

[Chemical Formula 2-1]

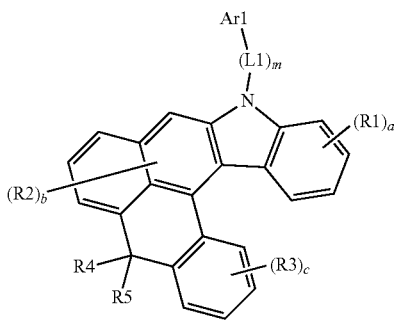

[Chemical Formula 2-2]

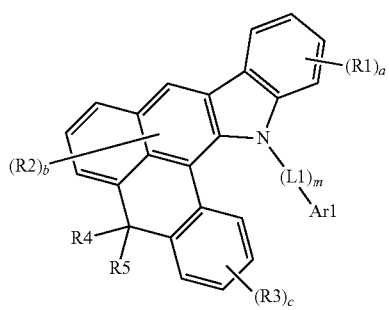

In Chemical Formula 2-1 and Chemical Formula 2-2, L1, m, Ar1, a, b, c and R1 to R5 have the same definitions as in Chemical Formula 1.

Another embodiment of the present specification provides an organic light emitting device comprising a first electrode; a second electrode provided opposite to the first electrode; and one or more organic material layers provided between the first electrode and the second electrode, wherein one or more layers of the organic material layers comprise the compound of Chemical Formula 1.

Advantageous Effects

Compounds described in the present specification can be used as a material of an organic material layer of an organic light emitting device. The compound according to at least one embodiment is capable of enhancing efficiency, obtaining a low driving voltage and/or enhancing a lifespan property in an organic light emitting device. Particularly, the compounds described in the present specification can be used as a material of hole injection, hole transfer, hole injection and hole transfer, electron blocking, light emission, hole blocking, electron transfer or electron injection.

DESCRIPTION OF DRAWINGS

FIG. 1 illustrates an organic light emitting device formed with a substrate (1), an anode (2), a light emitting layer (3) and a cathode (4).

FIG. 2 illustrates an organic light emitting device formed with a substrate (1), an anode (2), a hole injection layer (5), a hole transfer layer (6), a light emitting layer (7), an electron transfer layer (8) and a cathode (4).

1: Substrate
2: Anode
3: Light Emitting Layer
4: Cathode
5: Hole Injection Layer
6: Hole Transfer Layer
7: Light Emitting Layer
8: Electron Transfer Layer

BEST MODE FOR DISCLOSURE

Hereinafter, the present specification will be described in more detail.

One embodiment of the present specification provides a compound represented by Chemical Formula 1.

Examples of the substituents are described below, however, the substituents are not limited thereto.

The term "substituted or unsubstituted" in the present specification means being substituted with one or more substituents selected from the group consisting of deuterium; a halogen group; a nitrile group; a nitro group; a hydroxyl group; a germanium group; a carbonyl group; an ester group; an imide group; an amino group; a phosphine oxide group; an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylphosphine group; and a heterocyclic group, or being unsubstituted, or being substituted with a substituent linking two or more substituents among the substituents illustrated above, or being unsubstituted. For example, "a substituent linking two or more substituents" may include a biphenyl group. In other words, a biphenyl group may be an aryl group, or interpreted as a substituent linking two phenyl groups.

In the present specification, an "adjacent" group may mean a substituent substituting an atom directly linked to an atom substituted by the corresponding substituent, a substituent sterically most closely positioned to the corresponding substituent, or another substituent substituting an atom substituted by the corresponding substituent. For example, two substituents substituting ortho positions in a benzene ring, and two substituents substituting the same carbon in an aliphatic ring may be interpreted as groups "adjacent" to each other.

In the present specification,

means a site bonding to other substituents or bonding sites.

In the present specification, examples of the halogen group may include fluorine, chlorine, bromine or iodine.

In the present specification, the number of carbon atoms of the carbonyl group is not particularly limited, but is preferably from 1 to 40. Specifically, compounds having structures as below may be included, but the carbonyl group is not limited thereto.

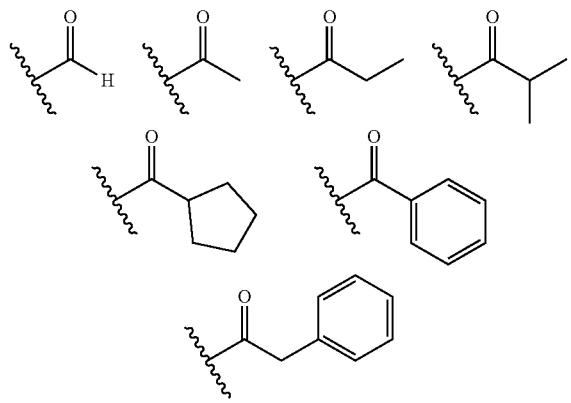

In the present specification, in the ester group, the oxygen of the ester group may be substituted with a linear, branched or cyclic alkyl group having 1 to 25 carbon atoms or an aryl group having 6 to 25 carbon atoms. Specifically, compounds having the following structural formulae may be included, but the ester group is not limited thereto.

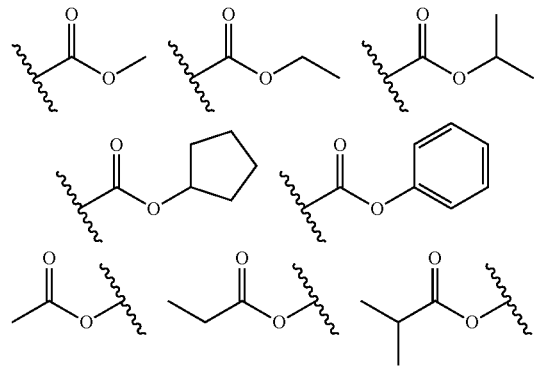

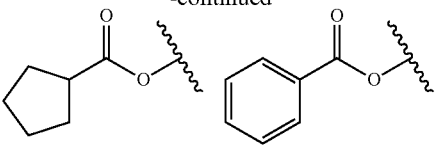

In the present specification, the number of carbon atoms of the imide group is not particularly limited, but is preferably from 1 to 25. Specifically, compounds having structures as below may be included, but the imide group is not limited thereto.

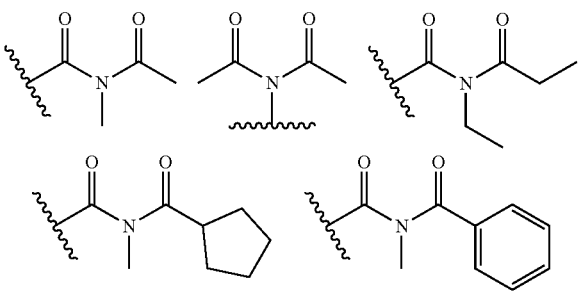

In the present specification, the silyl group may be represented by the chemical formula of $-SiRR'R''$, and R, R' and R'' may each be hydrogen; a substituted or unsubstituted alkyl group; or a substituted or unsubstituted aryl group. Specific examples of the silyl group may include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but are not limited thereto.

In the present specification, the boron group may be represented by the chemical formula of $-BRR'R''$, and R, R' and R'' may each be hydrogen; a substituted or unsubstituted alkyl group; or a substituted or unsubstituted aryl group. Specific examples of the boron group may include a trimethylboron group, a triethylboron group, a t-butyldimethylboron group, a triphenylboron group, a phenylboron group and the like, but are not limited thereto.

In the present specification, the alkyl group may be linear or branched, and although not particularly limited thereto, the number of carbon atoms is preferably from 1 to 40. According to one embodiment, the number of carbon atoms of the alkyl group is from 1 to 20. According to another embodiment, the number of carbon atoms of the alkyl group is from 1 to 10. According to another embodiment, the number of carbon atoms of the alkyl group is from 1 to 6. Specific examples of the alkyl group may include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethylpropyl, isohexyl, 4-methylhexyl, 5-methylhexyl and the like, but are not limited thereto.

In the present specification, the cycloalkyl group is not particularly limited, but preferably has 3 to 60 carbon atoms, and according to one embodiment, the number of carbon atoms of the cycloalkyl group is from 3 to 30. According to another embodiment, the number of the carbon atoms of the cycloalkyl group is from 3 to 20. According to another embodiment, the number of carbon atoms of the cycloalkyl group is from 3 to 6. Specific examples thereof may include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl and the like, but are not limited thereto.

In the present specification, the alkoxy group may be linear, branched or cyclic. The number of carbon atoms of the alkoxy group is not particularly limited, but is preferably from 1 to 20. Specific examples thereof may include methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy and the like, but are not limited thereto.

The alkyl group, the alkoxy group and other substituents including an alkyl group part described in the present specification include both a linear or a branched form.

In the present specification, the alkenyl group may be linear or branched, and although not particularly limited thereto, the number of carbon atoms is preferably from 2 to 40. According to one embodiment, the number of carbon atoms of the alkenyl group is from 2 to 20. According to another embodiment, the number of carbon atoms of the alkenyl group is from 2 to 10. According to another embodiment, the number of carbon atoms of the alkenyl group is from 2 to 6. Specific examples thereof may include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group and the like, but are not limited thereto.

In the present specification, examples of the arylamine group include a substituted or unsubstituted monoarylamine group, a substituted or unsubstituted diarylamine group, or a substituted or unsubstituted triarylamine group. The aryl group in the arylamine group may be a monocyclic aryl group or a multicyclic aryl group. The arylamine group including two or more aryl groups may include monocyclic aryl groups, multicyclic aryl groups, or both monocyclic aryl groups and multicyclic aryl groups.

Specific examples of the arylamine group may include phenylamine, naphthylamine, biphenylamine, anthracenylamine, 3-methyl-phenylamine, 4-methyl-naphthylamine, 2-methyl-biphenylamine, 9-methyl-anthracenylamine, a diphenylamine group, a phenylbiphenylamine group, a phenylnaphthylamine group, a dibiphenylamine group, an N-phenylfluoreneamine group, an N-biphenylfluoreneamine group, an N,N-diphenylfluoreneamine group, a ditolylamine group, a phenyltolylamine group, carbazole, a triphenylamine group and the like, but are not limited thereto.

In the present specification, examples of the heteroarylamine group include a substituted or unsubstituted monoheteroarylamine group, a substituted or unsubstituted diheteroarylamine group, or a substituted or unsubstituted triheteroarylamine group.

The heteroaryl group in the heteroarylamine group may be a monocyclic heterocyclic group or a multicyclic heterocyclic group. In the present specification, descriptions on the heterocyclic group described below may be applied except that the heteroaryl group is an aromatic group.

The heteroarylamine group including two or more heterocyclic groups may include monocyclic heterocyclic groups, multicyclic heterocyclic groups, or both monocyclic heterocyclic groups and multicyclic heterocyclic groups.

In the present specification, the arylheteroarylamine group means an amine group substituted with an aryl group and a heterocyclic group.

In the present specification, the number of carbon atoms of the amine group is not particularly limited, but is preferably from 1 to 30. In the amine group, the N atom may be substituted with an aryl group, an alkyl group, an arylalkyl group, a heterocyclic group and the like. Specific examples of the amine group may include a methylamine group, a dimethylamine group, an ethylamine group, a diethylamine group, a phenylamine group, a naphthylamine group, a biphenylamine group, an anthracenylamine group, a 9-methyl-anthracenylamine group, a diphenylamine group, a phenylnaphthylamine group, a ditolylamine group, a phenyltolylamine group, a triphenylamine group and the like, but are not limited thereto.

In the present specification, examples of the arylphosphine group include a substituted or unsubstituted monoarylphosphine group, a substituted or unsubstituted diarylphosphine group, or a substituted or unsubstituted triarylphosphine group. The aryl group in the arylphosphine group may be a monocyclic aryl group or a multicyclic aryl group. The arylphosphine group including two or more aryl groups may include monocyclic aryl groups, multicyclic aryl groups, or both monocyclic aryl groups and multicyclic aryl group.

In the present specification, the aryl group is not particularly limited, but preferably has 6 to 60 carbon atoms, and may be a monocyclic aryl group or a multicyclic aryl group. According to one embodiment, the number of carbon atoms of the aryl group is from 6 to 30. According to one embodiment, the number of carbon atoms of the aryl group is from 6 to 20. When the aryl group is a monocyclic aryl group, examples thereof may include a phenyl group, a biphenyl group, a terphenyl group and the like, but are not limited thereto. Examples of the multicyclic aryl group may include a naphthyl group, an anthracenyl group, a phenanthryl group, a pyrenyl group, a perylenyl group, a chrysenyl group, a fluorenyl group and the like, but are not limited thereto.

In the present specification, the fluorenyl group may be substituted, and two substituents bond to each other to form a spiro structure.

When the fluorenyl group is substituted,

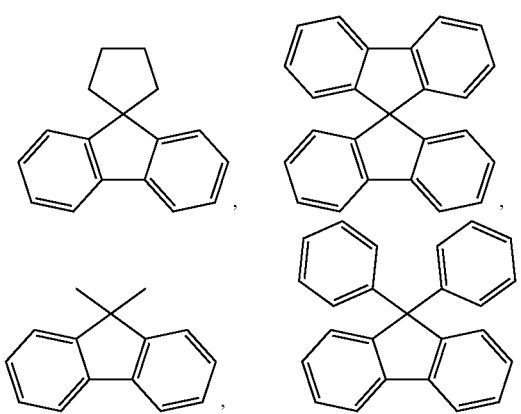

and the like may be included. However, the structure is not limited thereto.

In the present specification, the heterocyclic group is a heterocyclic group including one or more of N, O, P, S, Si and Se as a heteroatom, and although not particularly limited thereto, the number of carbon atoms is preferably from 2 to 60. Examples of the heterocyclic group may include a pyridyl group, a pyrrole group, a pyrimidyl group, a pyridazinyl group, a furanyl group, a thiophenyl group, an imidazole group, a pyrazole group, an oxazole group, an isoxazole group, a triazole group, an isothiazole group, a triazole group, an oxadiazole group, a thiadiazole group, dithiazole group, a tetrazole group, a pyranyl group, a thiopyranyl group, a pyrazinyl group, an oxazinyl group, a triazinyl group, a dioxynyl group, a triazinyl group, a tetrazinyl group, a quinolinyl group, an isoquinolinyl group, a quinolyl group, a quinazolinyl group, a quinoxalinyl group, a naphthyridinyl group, an acridyl group, a xanthenyl group, a phenanthridinyl group, a diazanaphthalenyl group, a triazaindenyl group, an indole group, an indolinyl group, an indolizinyl group, a phthalazinyl group, a pyridopyrimidinyl group, a pyridopyrazinyl group, a pyrazinopyrazinyl group, a benzothiazole group, a benzoxazole group, a benzimidazole group, a benzothiophene group, a benzofuranyl group, a dibenzothiophenyl group, a dibenzofuranyl group, a carbazole group, a benzocarbazole group, a dibenzocarbazole group, an indolocarbazole group, an indenocarbazole group, a phenazinyl group, an imidazopyridine group, a phenoxazinyl group, a phenanthridine group, a phenanthroline group, a phenothiazine group, an imidazopyridine group, an imidazophenanthridine group, a benzimidazoquinazoline group, a benzimidazophenanthridine group or the like, but are not limited thereto.

In the present specification, the germanium group may be represented by the chemical formula of —GeR$_a$R$_b$R$_c$, and R$_a$, R$_b$ and R$_c$ may each be hydrogen; a substituted or unsubstituted alkyl group; or a substituted or unsubstituted aryl group. Specific examples of the germanium group may include a trimethylgermanium group, a triethylgermanium group, a t-butyldimethylgermanium group or the like, but are not limited thereto.

In the present specification, descriptions on the aryl group provided above may be applied to the aryl group in the aryloxy group, the arylthio group, the arylthioxy group, the arylsulfoxy group, the arylphosphine group, the aralkyl group, the aralkylamine group, the aralkenyl group, the alkylaryl group, the arylamine group and the arylheteroarylamine group.

In the present specification, descriptions on the alkyl group provided above may be applied to the alkoxy group in the alkoxycarbonyl group, and descriptions on the carbonyl group provided above may be applied to the carbonyl group in the alkoxycarbonyl group.

In the present specification, descriptions on the alkyl group provided above may be applied to the alkyl group in the alkylthioxy group, the alkylsulfoxy group, the aralkyl group, the aralkylamine group, the alkylaryl group and the alkylamine group.

In the present specification, descriptions on the heterocyclic group provided above may be applied to the heteroaryl group in the heteroaryl group, the heteroarylamine group and the arylheteroarylamine group.

In the present specification, descriptions on the alkenyl group provided above may be applied to the alkenyl group in the aralkenyl group.

In the present specification, descriptions on the aryl group provided above may be applied to the arylene except for being a divalent.

In the present specification, descriptions on the heterocyclic group provided above may be applied to the heteroarylene except for being a divalent.

In the present specification, the meaning of bonding to adjacent groups to form a ring means bonding to adjacent groups to form a substituted or unsubstituted aliphatic hydrocarbon ring; a substituted or unsubstituted aromatic hydrocarbon ring; a substituted or unsubstituted aliphatic heteroring; a substituted or unsubstituted aromatic heteroring; or a fused ring thereof.

In the present specification, the aliphatic hydrocarbon ring, the aromatic hydrocarbon ring, the aliphatic heteroring and the aromatic heteroring may be monocyclic or multicyclic.

In the present specification, the aliphatic hydrocarbon ring means a ring formed only with carbon and hydrogen atoms as a ring that is not aromatic.

In the present specification, examples of the aliphatic hydrocarbon ring may include cyclopropane, cyclobutane, cyclobutene, cyclopentane, cyclopentene, cyclohexane, cyclohexene, 1,4-cyclohexadiene, cycloheptane, cycloheptene, cyclooctane, cyclooctene and the like, but are not limited thereto.

In the present specification, the aromatic hydrocarbon ring means an aromatic ring formed only with carbon and hydrogen atoms.

In the present specification, examples of the aromatic hydrocarbon ring may include benzene, naphthalene, anthracene, phenanthrene, perylene, fluoranthene, triphenylene, phenalene, pyrene, tetracene, chrysene, pentacene, fluorene, indene, acenaphthylene, benzofluorene, spirofluorene and the like, but are not limited thereto.

In the present specification, the aliphatic heteroring means an aliphatic ring including one or more of heteroatoms.

In the present specification, examples of the aliphatic heteroring may include oxirane, tetrahydrofuran, 1,4-dioxane, pyrrolidine, piperidine, morpholine, oxepane, azocane, thiocane and the like, but are not limited thereto.

In the present specification, the aromatic heteroring means an aromatic ring including one or more of heteroatoms.

In the present specification, examples of the aromatic heteroring may include pyridine, pyrrole, pyrimidine, pyridazine, furan, thiophene, imidazole, pyrazole, oxazole, isoxazole, triazole, isothiazole, triazole, oxadiazole, thiadiazole, dithiazole, tetrazole, pyran, thiopyran, diazine, oxazine, triazine, dioxin, triazine, tetrazine, isoquinoline, quinoline, quinol, quinazoline, quinoxaline, naphthyridine, acridine, phenanthridine, diazanaphthalene, triazaindene, indole, indolizine, benzothiazole, benzoxazole, benzimidazole, benzothiophene, benzofuran, dibenzothiophene, dibenzofuran, carbazole, benzocarbazole, dibenzocarbazole, phenazine, imidazopyridine, phenoxazine, phenanthridine, indolocarbazole, indenocarbazole and the like, but are not limited thereto.

According to one embodiment of the present disclosure, the compound represented by Chemical Formula 1 may be represented by any one of the following Chemical Formulae 3 to 5.

[Chemical Formula 3]

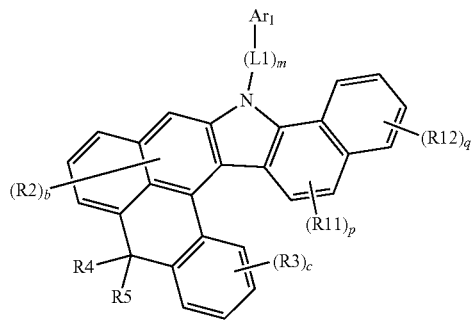

[Chemical Formula 4]

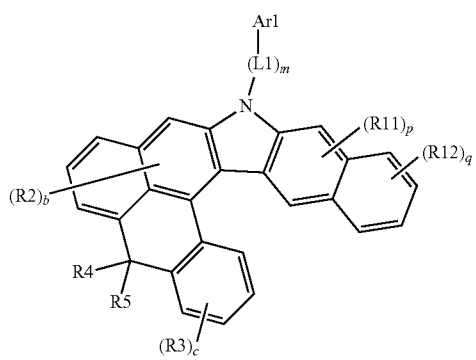

[Chemical Formula 5]

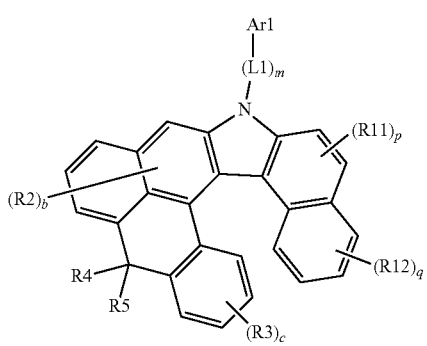

In Chemical Formulae 3 to 5,

R2 to R5, L1, Ar1, b, c and m each independently have the same definition as in Chemical Formula 1, p is an integer of 0 to 2, q is an integer of 0 to 4, R11 and R12 each independently have the same definition as R1 in Chemical Formula 1, when p is 2, R11s are the same as or different from each other, and when q is 2 or greater, R12s are the same as or different from each other.

According to one embodiment of the present disclosure, the compound represented by Chemical Formula 1 may be represented by any one of the following Chemical Formulae 6 to 8.

[Chemical Formula 6]

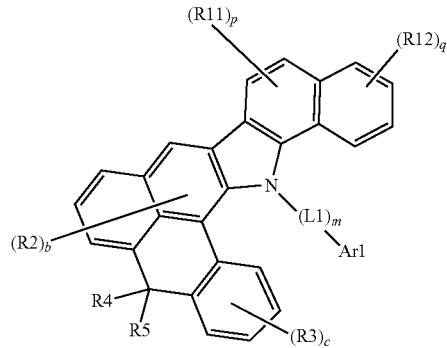

[Chemical Formula 7]

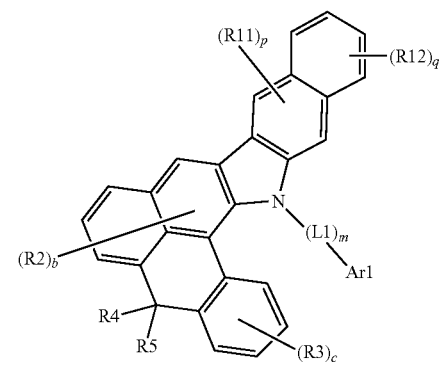

[Chemical Formula 8]

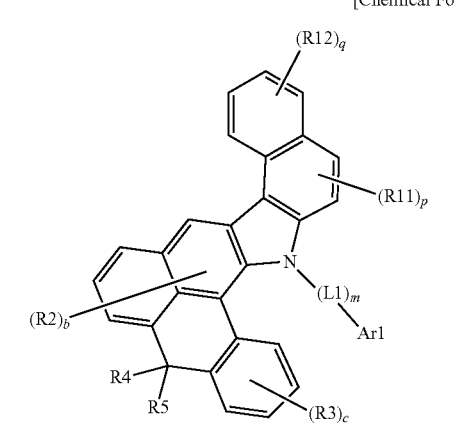

In Chemical Formulae 6 to 8,

R2 to R5, L1, Ar1, b, c and m each independently have the same definition as in Chemical Formula 1, p is an integer of 0 to 2, q is an integer of 0 to 4, R11 and R12 each independently have the same definition as R1 in Chemical Formula 1, when p is 2, R11s are the same as or different from each other, and when q is 2 or greater, R12s are the same as or different from each other.

In one embodiment of the present disclosure, L1 is a direct bond; a substituted or unsubstituted arylene group; or a substituted or unsubstituted heteroarylene group.

In one embodiment of the present disclosure, L1 is a direct bond; a substituted or unsubstituted arylene group having 6 to 30 carbon atoms; or a substituted or unsubstituted heteroarylene group having 1 to 30 carbon atoms.

In another embodiment, L1 may be a direct bond; or unsubstituted or substituted with one or more substituents selected from the group consisting of a substituted or unsubstituted phenylene group; a substituted or unsubstituted biphenylene group; a substituted or unsubstituted terphenylene group; a substituted or unsubstituted quaterphenylene group; a substituted or unsubstituted naphthylene group; a substituted or unsubstituted pyrenylene group; a substituted or unsubstituted phenanthrenylene group; a substituted or unsubstituted perylenylene group; a substituted or unsubstituted tetracenylene group; a substituted or unsubstituted triphenylene group; a substituted or unsubstituted fluoranthenylene group; a substituted or unsubstituted fluorenylene group; a substituted or unsubstituted pyrrolylene group; a substituted or unsubstituted furanylene group; a substituted or unsubstituted thiophenylene group; a substituted or unsubstituted pyridinylene group; a substituted or unsubstituted pyrazolylene group; a substituted or unsubstituted imidazolylene group; a substituted or unsubstituted oxazolylene group; a substituted or unsubstituted isoxazolylene group; a substituted or unsubstituted thiazolylene group; a substituted or unsubstituted isothiazolylene group; a substituted or unsubstituted pyridazinylene group; a substituted or unsubstituted pyrimidinylene group; a substituted or unsubstituted indolylene group; a substituted or unsubstituted isoindolylene group; a substituted or unsubstituted indolizinylene group; a substituted or unsubstituted quinolinylene group; a substituted or unsubstituted quinazolinylene group; a substituted or unsubstituted isoquinolinylene group; a substituted or unsubstituted quinoxalinylene group; a substituted or unsubstituted naphthyridinylene group; a substituted or unsubstituted acridinylene group; a substituted or unsubstituted xanthenylene group; a substituted or unsubstituted dibenzofuranylene group; a substituted or unsubstituted phenanthrolylene group; a substituted or unsubstituted dibenzothiophenylene group; and a substituted or unsubstituted carbazolylene group, or may be unsubstituted or substituted with a substituent linking two or more substituents among the substituents illustrated above.

According to one embodiment of the present specification, L1 is a direct bond; a substituted or unsubstituted phenylene group; a substituted or unsubstituted biphenylylene group; a substituted or unsubstituted terphenylene group; a substituted or unsubstituted quaterphenylene group; a substituted or unsubstituted naphthylene group; a substituted or unsubstituted anthracenylene group; a substituted or unsubstituted triphenylenylene group; a substituted or unsubstituted phenanthrolinylene group; a substituted or unsubstituted phenanthrenylene group; a substituted or unsubstituted pyridylene group; a substituted or unsubstituted pyrimidinylene group; a substituted or unsubstituted triazinylene group; a substituted or unsubstituted quinolinylene group; a substituted or unsubstituted quinazolinylene group; a substituted or unsubstituted carbazolylene group; a substituted or unsubstituted dibenzofuranylene group; or a substituted or unsubstituted dibenzothiophenylene group.

According to one embodiment of the present disclosure, L1 may be a direct bond, a phenylene group, a biphenylylene group, a terphenylene group, a quaterphenylene group, a naphthylene group, an anthracenyl group, a 9,9-dimethylfluorenylene group, a phenanthrenylene group, a pyridinylene group, a pyrimidinylene group, a triazinylene group, a quinolinylene group, a quinazolinylene group, a carbazolylene group, a dibenzofuranylene group or a dibenzothiophenylene group, and these may be further substituted.

In addition, L1 in the present specification may be a direct bond or any one substituent selected from among the following group, but is not limited thereto.

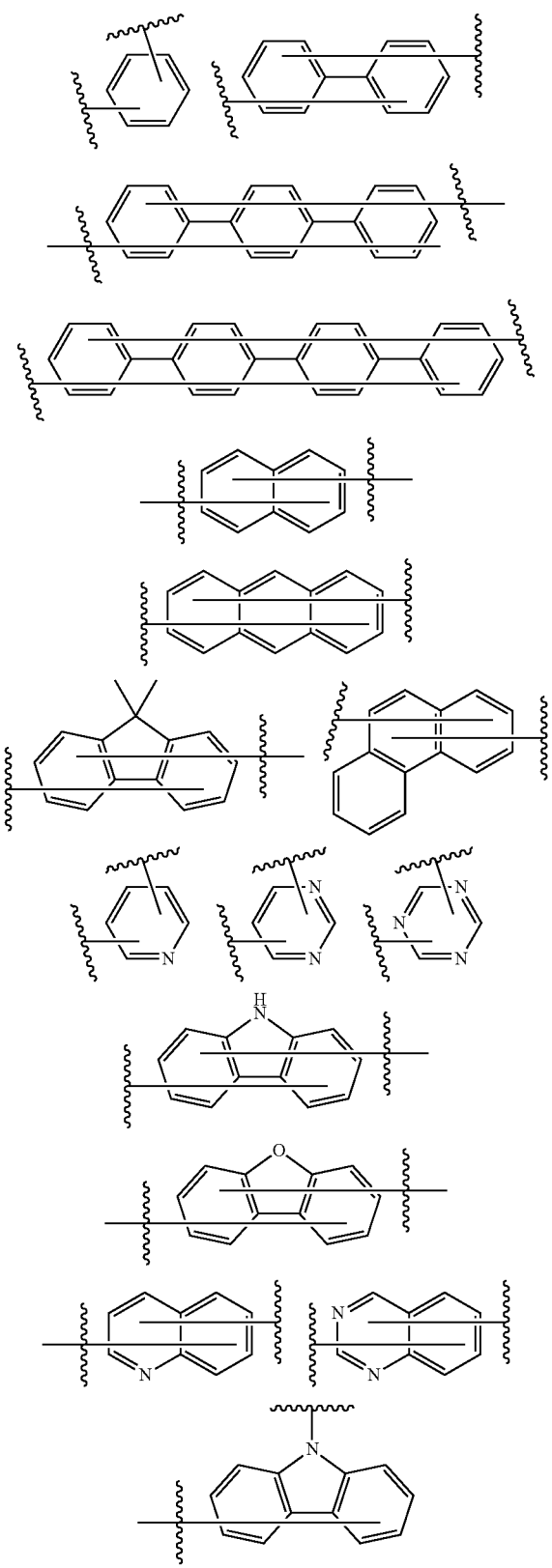

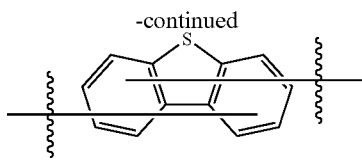

The structures may be unsubstituted or substituted with one or more substituents selected from the group consisting of deuterium; a halogen group; a nitrile group; a nitro group; a hydroxyl group; a carbonyl group; an ester group; an imide group; an amine group; a phosphine oxide group; an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylheteroarylamine group; an arylphosphine group; and a heterocyclic group.

According to one embodiment of the present disclosure, L1 is a direct bond; a substituted or unsubstituted phenylene group; a substituted or unsubstituted biphenylylene group; or a substituted or unsubstituted naphthylene group.

According to one embodiment of the present specification, L1 in Chemical Formula 1 may be selected from among the following structures.

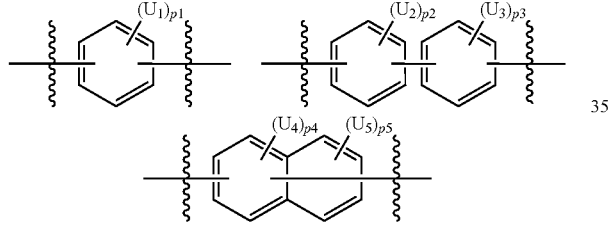

In the structural formulae, $U_1$ to $U_5$ are the same as or different from each other, and each independently hydrogen; deuterium; a halogen group; a substituted or unsubstituted alkyl group; a substituted or unsubstituted cycloalkyl group; a substituted or unsubstituted alkenyl group; a substituted or unsubstituted aryl group; a substituted or unsubstituted heterocyclic group; a substituted or unsubstituted alkylamine group; a substituted or unsubstituted heteroarylamine group; or a substituted or unsubstituted arylamine group, or adjacent two or more substituents bond to each other to form a substituted or unsubstituted ring, p1, p2 and p3 are an integer of 0 to 4, and p4 and p5 are an integer of 0 to 3, when p1 is 2 or greater, $U_1$s are the same as or different from each other, when p2 is 2 or greater, $U_2$s are the same as or different from each other, when p3 is 2 or greater, $U_3$s are the same as or different from each other, when p4 is 2 or greater, $U_4$s are the same as or different from each other, and when p5 is 2 or greater, $U_5$s are the same as or different from each other.

According to one embodiment of the present specification, L1 in Chemical Formula 1 may be selected from among the following structures.

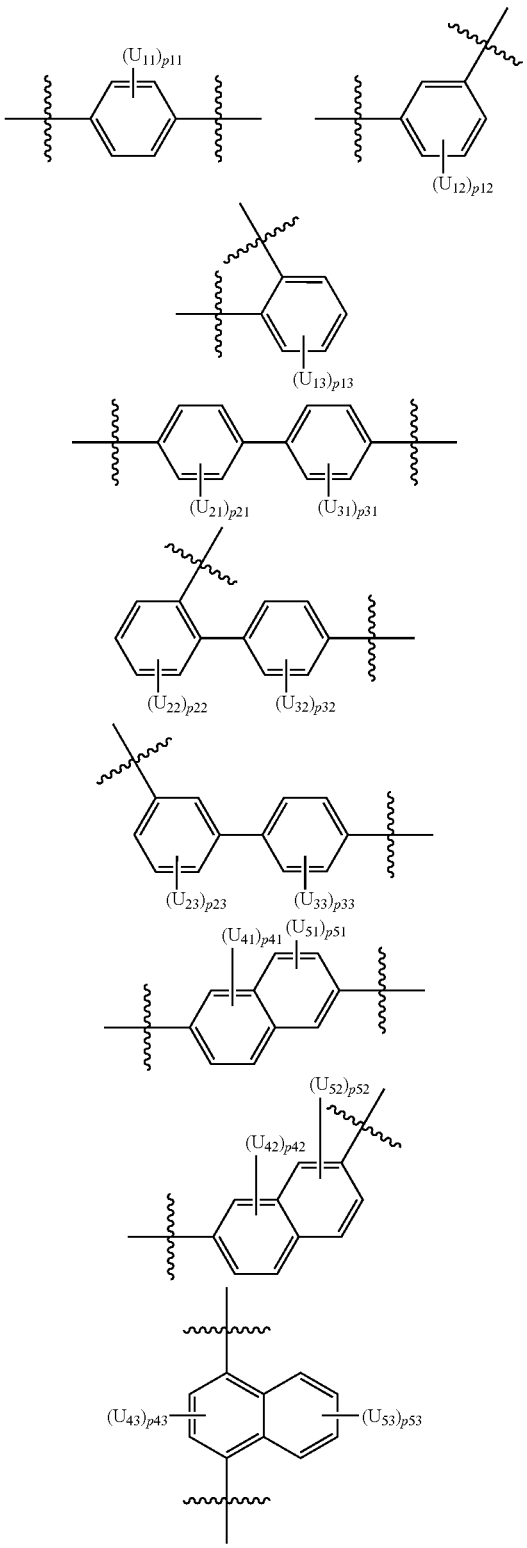

In the structural formulae, $U_{11}$ to $U_{13}$, $U_{21}$ to $U_{23}$, $U_{31}$ to $U_{33}$, $U_{41}$ to $U_{43}$ and $U_{51}$ to $U_{53}$ are the same as or different from each other, and each independently have the same definition as $U_1$ to $U_5$ described above, p11 to p13, p21 to p23, p31 to p33 and p53 are an integer of 0 to 4, p41, p42, p51 and p52 are an integer of 0 to 3, p43 is an integer of 0 to 2, when p11 is 2 or greater, $U_{11}$s are the same as or different from each other, when p12 is 2 or greater, $U_{12}$s are the same as or different from each other, when p13 is 2 or greater, $U_{13}$s are the same as or different from each other, when p21 is 2 or greater, $U_{21}$s are the same as or different from each other, when p22 is 2 or greater, $U_{22}$s are the same as or different from each other, when p23 is 2 or greater, $U_{23}$s are the same as or different from each other, when p31 is 2 or greater, $U_{31}$s are the same as or different from each other, when p32 is 2 or greater, $U_{32}$s are the same as or different from each other, when p33 is 2 or greater, $U_{33}$s are the same as or different from each other, when p41 is 2 or greater, $U_{41}$s are the same as or different from each other, when p42 is 2 or greater, $U_{42}$s are the same as or different from each other, when p43 is 2 or greater, $U_{43}$s are the same as or different from each other, when p51 is 2 or greater, $U_{51}$s are the same as or different from each other, when p52 is 2 or greater, $U_{52}$s are the same as or different from each other, and when p53 is 2 or greater, $U_{53}$s are the same as or different from each other.

According to one embodiment of the present specification, L1 is a direct bond or a phenylene group.

According to one embodiment of the present specification, L1 is a direct bond.

In one embodiment of the present disclosure, Ar1 is hydrogen; deuterium; a halogen group; a nitrile group; a nitro group; a hydroxyl group; a carbonyl group; an ester group; an imide group; an amino group; a substituted or unsubstituted silyl group; a substituted or unsubstituted boron group; a substituted or unsubstituted alkyl group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylphosphine group; a substituted or unsubstituted phosphine oxide group; a substituted or unsubstituted aryl group; or a substituted or unsubstituted heterocyclic group.

In one embodiment of the present disclosure, Ar1 is hydrogen; deuterium; a halogen group; a nitrile group; a carbonyl group; a substituted or unsubstituted silyl group; a substituted or unsubstituted alkyl group; a substituted or unsubstituted alkylaryl group; a substituted or unsubstituted heteroarylamine group; a substituted or unsubstituted arylamine group; a substituted or unsubstituted arylphosphine group; a substituted or unsubstituted phosphine oxide group; a substituted or unsubstituted aryl group; or a substituted or unsubstituted heterocyclic group.

According to one embodiment of the present specification, Ar1 is selected from the group consisting of hydrogen; a monocyclic or multicyclic substituted or unsubstituted aryl group having 6 to 60 carbon atoms; a monocyclic or multicyclic substituted or unsubstituted arylamine group having 6 to 60 carbon atoms; and a monocyclic or multicyclic substituted or unsubstituted heteroring having 2 to 60 carbon atoms.

According to one embodiment of the present specification, Ar1 is hydrogen; a monocyclic or multicyclic substituted or unsubstituted aryl group having 6 to 30 carbon atoms; a primary, secondary or tertiary substituted or unsubstituted arylamine group having 6 to 30 carbon atoms; or a substituted or unsubstituted heterocyclic group having 2 to 40 carbon atoms.

In one embodiment of the present disclosure, Ar1 may be hydrogen; an aryl group such as a phenyl group, a biphenyl group, a terphenyl group, a quaterphenyl group, a naphthyl group, an anthracenyl group, a phenanthrenyl group, a fluorenyl group, a pyridinyl group, a phenanthridinyl group, a dibenzothiophene group, a carbazolyl group and a phenanthrolinyl group; an arylamine group such as a diphenylamine group, a phenylbiphenylamine group, a dibiphenylamine group, a phenylnaphthylamine group, a triphenylamine group, an N-phenylfluoreneamine group and an N-biphenylfluoreneamine group; or heteroaryl such as a pyridyl group, a pyrrole group, a pyrimidyl group, a pyridazinyl group, a furanyl group, a thiophene group, an imidazole group, a pyrazole group, an oxazole group, an isoxazole group, a triazole group, an isothiazole group, a triazole group, a pyrazinyl group, a triazine group, a quinolinyl group, an isoquinolinyl group, a quinazolinyl group, a quinoxalinyl group, a naphthyridinyl group, an acridyl group, a xanthenyl group, a phenanthridinyl group, a diazanaphthalenyl group, a triazaindenyl group, an indole group, an indolinyl group, an indolizinyl group, a phthalazinyl group, a pyridopyrimidinyl group, a pyridopyrazinyl group, a pyrazinopyrazinyl group, a carbazole group, a benzothiophene group, a benzofuranyl group, a benzimidazole group, a benzothiazole group, a benzoxazole group, a benzocarbazole group, a dibenzothiophene group, a dibenzofuranyl group, a dibenzocarbazole group, an indolocarbazole group, an indenocarbazole group, a phenanthroline group, a phenazinyl group, a phenoxazinyl group, a phenothiazinyl group, an imidazopyridinyl group, an imidazophenanthridine group, a benzimidazoquinazolinyl group and a benzimidazophenanthridinyl group, and these may be further substituted.

Specifically, Ar1 may be unsubstituted or substituted with one or more substituents selected from the group consisting of deuterium; a halogen group; a nitrile group; a nitro group; a hydroxyl group; a carbonyl group; an ester group; an imide group; an amine group; a phosphine oxide group; an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylheteroarylamine group; an arylphosphine group; and a heterocyclic group.

According to one embodiment of the present specification, Ar1 in Chemical Formula 1 is a substituted or unsubstituted phenyl group; a substituted or unsubstituted biphenyl group; a substituted or unsubstituted naphthyl group; a substituted or unsubstituted anthracenyl group; a substituted or unsubstituted terphenyl group; a substituted or unsubstituted triphenylenyl group; a substituted or unsubstituted phenanthrolinyl group; a substituted or unsubstituted diphenylamine group, a substituted or unsubstituted phenylbiphenylamine group, a substituted or unsubstituted dibiphenylamine group, a substituted or unsubstituted phenylnaphthylamine group, a substituted or unsubstituted triphenylamine group, a substituted or unsubstituted N-phenylfluoreneamine group, a substituted or unsubstituted N-biphenylfluoreneamine group; a substituted or unsubstituted phenanthrenyl group; a substituted or unsubstituted pyridyl group; a substituted or unsubstituted pyrimidinyl group; a substituted or unsubstituted triazinyl group; a substituted or unsubstituted quinolinyl group; a substituted or unsubstituted quinazolinyl group; a substituted or unsubstituted carbazole group; a substituted or unsubstituted dibenzofuranyl group; a substituted or unsubstituted dibenzothiophenyl group; a substituted or unsubstituted imidazopyridine group; a substituted or unsubstituted imidazophenanthridine group; a substituted or unsubstituted benzimidazoquinazoline group; or a substituted or unsubstituted benzimidazophenanthridine group.

According to one embodiment of the present specification, Ar1 may be hydrogen or selected from among the following structures.

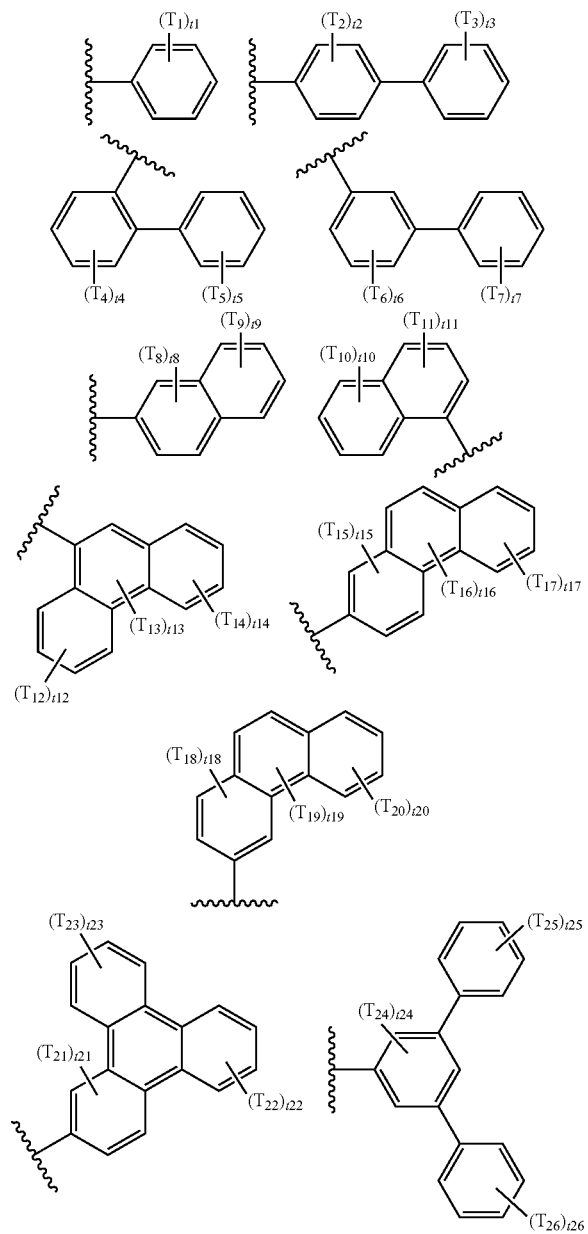

In the structural formulae, $T_1$ to $T_{26}$ are the same as or different from each other, and each independently hydrogen; deuterium; a halogen group; a substituted or unsubstituted alkyl group; a substituted or unsubstituted cycloalkyl group; a substituted or unsubstituted alkenyl group; a substituted or unsubstituted aryl group; a substituted or unsubstituted heterocyclic group; a substituted or unsubstituted alkylamine group; a substituted or unsubstituted heteroarylamine group; or a substituted or unsubstituted arylamine group, or adjacent two or more substituents bond to each other to form a ring, t1, t3, t5 t7, t25 and t26 are the same as or different from each other, and each independently an integer of 0 to 5, t2, t4, t6, t9, t10, t12, t14, t17, t20, t22 and t23 are the same as or different from each other, and each independently an integer of 0 to 4, t8, t11, t15, t18, t21 and t24 are the same as or different from each other, and each independently an integer of 0 to 3, t13 is an integer of 0 or 1, t16 and t19 are the same as or different from each other, and each independently an integer of 0 to 2, when t1 is 2 or greater, $T_1$s are the same as or different from each other, when t2 is 2 or greater, $T_2$s are the same as or different from each other, when t3 is 2 or greater, $T_1$s are the same as or different from each other, when t4 is 2 or greater, $T_4$s are the same as or different from each other, when t5 is 2 or greater, $T_5$s are the same as or different from each other, when t6 is 2 or greater, $T_6$s are the same as or different from each other, when t7 is 2 or greater, $T_7$s are the same as or different from each other, when t8 is 2 or greater, $T_8$s are the same as or different from each other, when t9 is 2 or greater, $T_9$s are the same as or different from each other, when t10 is 2 or greater, $T_{10}$s are the same as or different from each other, when t11 is 2 or greater, $T_{11}$s are the same as or different from each other, when t12 is 2 or greater, $T_{12}$s are the same as or different from each other, when t14 is 2 or greater, $T_{14}$s are the same as or different from each other, when t15 is 2 or greater, $T_{15}$s are the same as or different from each other, when t16 is 2, $T_{16}$s are the same as or different from each other, when t17 is 2 or greater, $T_{17}$s are the same as or different from each other, when t18 is 2 or greater, $T_{18}$s are the same as or different from each other, when t19 is 2, $T_{19}$s are the same as or different from each other, when t20 is 2 or greater, $T_{20}$s are the same as or different from each other, when t21 is 2 or greater, $T_{21}$s are the same as or different from each other, when t22 is 2 or greater, $T_{22}$s are the same as or different from each other, when t23 is 2 or greater, $T_{23}$s are the same as or different from each other, when t24 is 2 or greater, $T_{24}$s are the same as or different from each other, when t25 is 2 or greater, $T_{25}$s are the same as or different from each other, and when t26 is 2 or greater, $T_{26}$s are the same as or different from each other.

According to one embodiment of the present specification, Ar1 in Chemical Formula 1 may be represented by the following Chemical Formula 9.

[Chemical Formula 9]

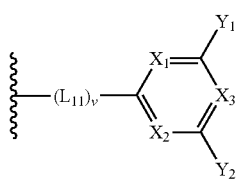

In Chemical Formula 9, $X_1$ to $X_3$ are the same as or different from each other, and each independently CR or N, at least one or more of $X_1$ to $X_3$ are N, Rs are the same as or different from each other, and each independently hydrogen; deuterium; a halogen group; a substituted or unsubstituted alkyl group; a substituted or unsubstituted cycloalkyl group; a substituted or unsubstituted alkenyl group; a substituted or unsubstituted aryl group; a substituted or unsubstituted heterocyclic group; a substituted or unsubstituted alkylamine group; a substituted or unsubstituted heteroarylamine group; or a substituted or unsubstituted arylamine group, or adjacent two or more substituents bond to each other to form a substituted or unsubstituted ring, $Y_1$ and $Y_2$ are the same as or different from each other, and each independently a substituted or unsubstituted aryl group, $L_{11}$ is a direct bond; substituted or unsubstituted arylene; or a substituted or unsubstituted heteroarylene group, and v is an integer of 0 to 5, and when v is 2 or greater, $L_{11}$s are the same as or different from each other.

According to one embodiment of the present specification, $Y_1$ and $Y_2$ in Chemical Formula 9 are a substituted or unsubstituted phenyl group; a substituted or unsubstituted biphenyl group; a substituted or unsubstituted naphthyl group; a substituted or unsubstituted anthracenyl group; a substituted or unsubstituted phenanthryl group; a substituted or unsubstituted terphenyl group or a substituted or unsubstituted triphenylene group.

According to one embodiment of the present specification, $Y_1$ and $Y_2$ in Chemical Formula 9 are hydrogen or may be selected from among the following structures.

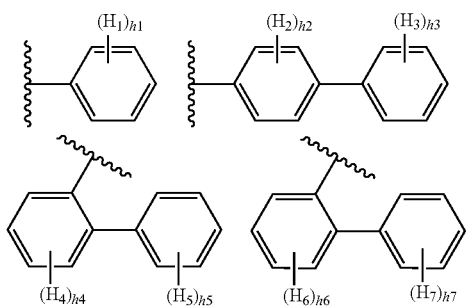

-continued

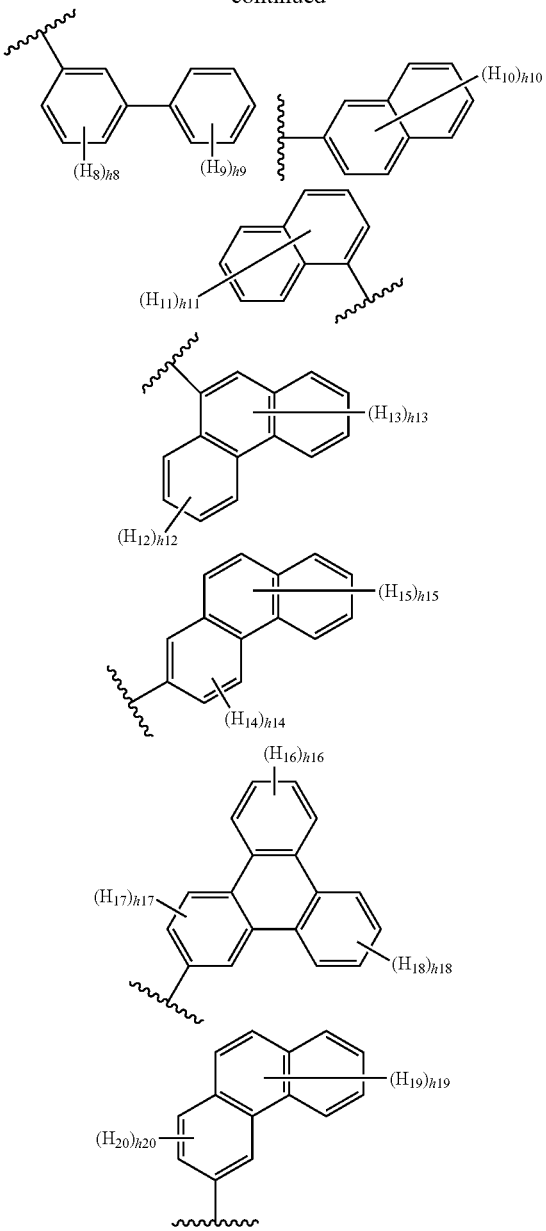

In the structural formulae, $H_1$ to $H_{20}$ are the same as or different from each other, and each independently hydrogen; deuterium; a halogen group; a substituted or unsubstituted alkyl group; a substituted or unsubstituted cycloalkyl group; a substituted or unsubstituted alkenyl group; a substituted or unsubstituted aryl group; a substituted or unsubstituted heterocyclic group; a substituted or unsubstituted alkylamine group; a substituted or unsubstituted heteroarylamine group; or a substituted or unsubstituted arylamine group, or adjacent two or more substituents bond to each other to form a ring, h1, h3, h5, h7, h9 and h13 are the same as or different from each other, and each independently an integer of 0 to 5, h2, h4, h6, h8, h12, h16 and h18 are the same as or different from each other, and each independently an integer of 0 to 4, h10 and h11 are the same as or different from each other, and each independently an integer of 0 to 7, h15 and h19 are the same as or different from each other, and each independently an integer of 0 to 6, h14, h17 and h20 are the same as or different from each other, and each independently an integer of 0 to 3, when h1 is 2 or greater, $H_1$s are the same as or different from each other, when h2 is 2 or greater, $H_2$s are the same as or different from each other, when h3 is 2 or greater, $H_3$s are the same as or different from each other, when h4 is 2 or greater, $H_4$s are the same as or different from each other, when h5 is 2 or greater, $H_5$s are the same as or different from each other, when h6 is 2 or greater, $H_6$s are the same as or different from each other, when h7 is 2 or greater, $H_7$s are the same as or different from each other, when h8 is 2 or greater, $H_8$s are the same as or different from each other, when h9 is 2 or greater, $H_9$s are the same as or different from each other, when h10 is 2 or greater, $H_{10}$s are the same as or different from each other, when h11 is 2 or greater, $H_{11}$s are the same as or different from each other, when h12 is 2 or greater, $H_{12}$s are the same as or different from each other, when h13 is 2 or greater, $H_{13}$s are the same as or different from each other, when h14 is 2 or greater, $H_{14}$s are the same as or different from each other, when h15 is 2 or greater, $H_{15}$s are the same as or different from each other, when h16 is 2 or greater, $H_{16}$s are the same as or different from each other, when h17 is 2 or greater, $H_{17}$s are the same as or different from each other, when h18 is 2 or greater, $H_{18}$s are the same as or different from each other, when h19 is 2 or greater, $H_{19}$s are the same as or different from each other, and when h20 is 2 or greater, $H_{20}$s are the same as or different from each other.

According to one embodiment of the present specification, Chemical Formula 9 may be selected from among the following structures, and the following structures may be each independently substituted with hydrogen; deuterium; a halogen group; a substituted or unsubstituted alkyl group; a substituted or unsubstituted cycloalkyl group; a substituted or unsubstituted alkenyl group; a substituted or unsubstituted aryl group; a substituted or unsubstituted heterocyclic group; a substituted or unsubstituted alkylamine group; a substituted or unsubstituted heteroarylamine group; or a substituted or unsubstituted arylamine group, or adjacent two or more substituents bond to each other to form a ring.

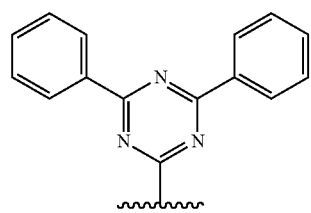

-continued

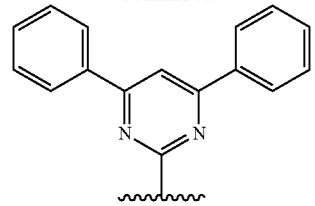

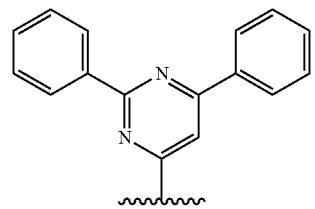

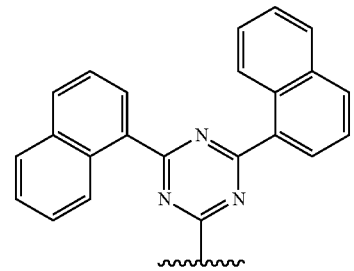

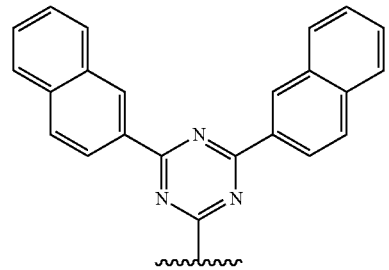

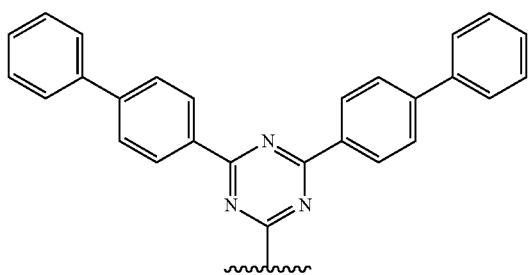

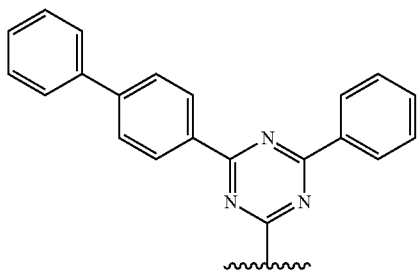

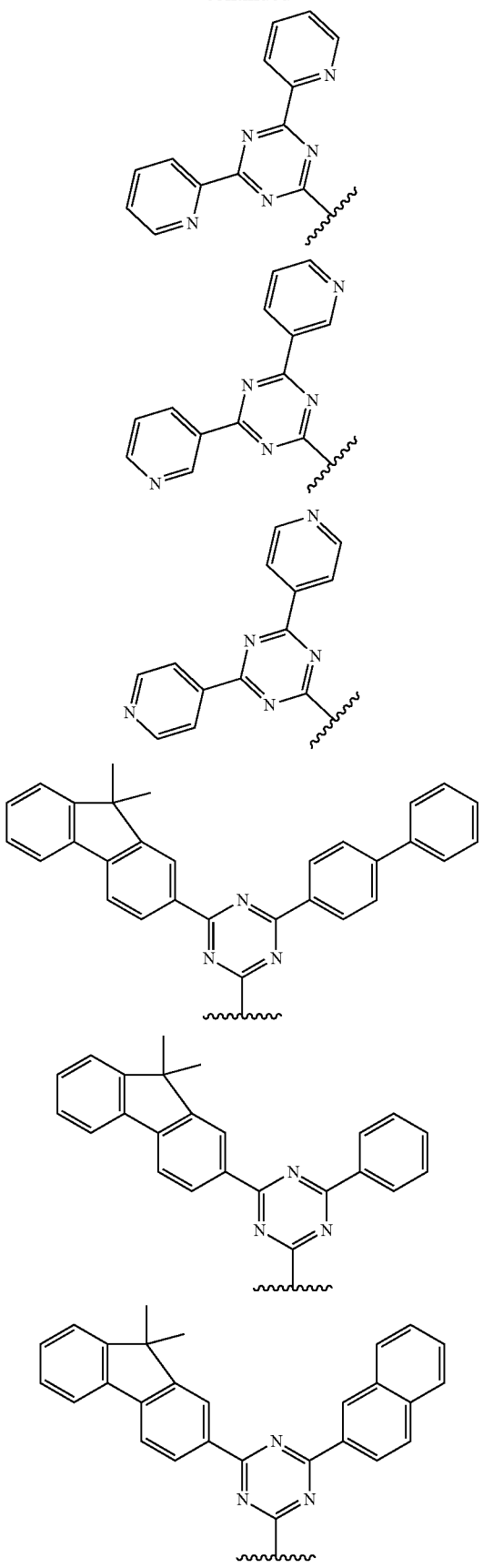

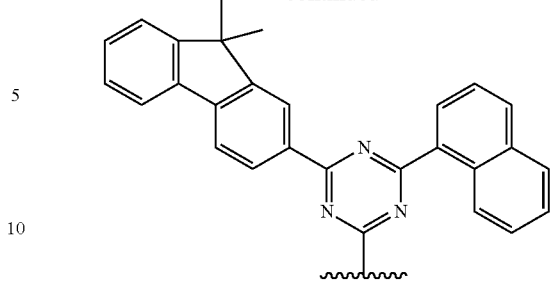

According to one embodiment of the present specification, Ar1 in Chemical Formula 1 may be represented by the following Chemical Formula 10.

[Chemical Formula 10]

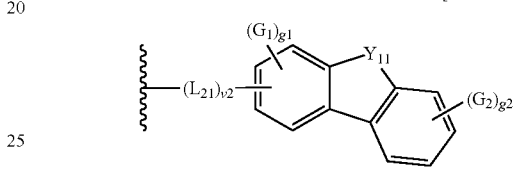

In Chemical Formula 10, $Y_{11}$ is $CR_aR_b$, $NR_c$, S or O, $R_a$ and $R_b$ are the same as or different from each other, and each independently hydrogen; deuterium; a halogen group; a substituted or unsubstituted alkyl group; a substituted or unsubstituted cycloalkyl group; a substituted or unsubstituted alkenyl group; a substituted or unsubstituted aryl group; a substituted or unsubstituted heterocyclic group; a substituted or unsubstituted alkylamine group; a substituted or unsubstituted heteroarylamine group; or a substituted or unsubstituted arylamine group, or adjacent substituents bond to each other to form a substituted or unsubstituted ring, $R_c$ is hydrogen; deuterium; a halogen group; a substituted or unsubstituted alkyl group; a substituted or unsubstituted cycloalkyl group; a substituted or unsubstituted alkenyl group; a substituted or unsubstituted aryl group; a substituted or unsubstituted heterocyclic group; a substituted or unsubstituted alkylamine group; a substituted or unsubstituted heteroarylamine group; or a substituted or unsubstituted arylamine group, or bonds to adjacent substituents to form a substituted or unsubstituted ring, $L_{21}$ is a direct bond; a substituted or unsubstituted arylene group; or substituted or unsubstituted heteroarylene, $G_1$ and $G_2$ are the same as or different from each other, and each independently hydrogen; deuterium; a halogen group; a substituted or unsubstituted alkyl group; a substituted or unsubstituted cycloalkyl group; a substituted or unsubstituted alkenyl group; a substituted or unsubstituted aryl group; a substituted or unsubstituted heterocyclic group; a substituted or unsubstituted alkylamine group; a substituted or unsubstituted heteroarylamine group; or a substituted or unsubstituted arylamine group, or adjacent two or more substituents bond to each other to form a ring, g1 is an integer of 0 to 3, g2 is an integer of 0 to 4 and v2 is an integer of 0 to 5, when g1 is 2 or greater, $G_1$s are the same as or different from each other, when g2 is 2 or greater, $G_2$s are the same as or different from each other, and when v2 is 2 or greater, $L_{21}$s are the same as or different from each other.

According to one embodiment of the present specification,

Chemical Formula 10 may be selected from among the following structures.

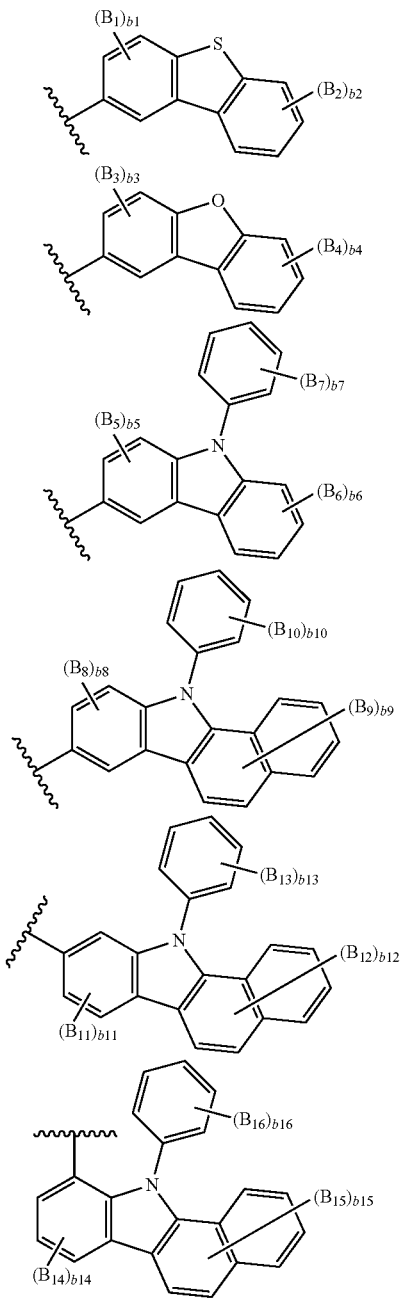

In the structural formulae, $B_1$ to $B_{21}$ are the same as or different from each other, and each independently hydrogen; deuterium; a halogen group; a substituted or unsubstituted alkyl group; a substituted or unsubstituted cycloalkyl group; a substituted or unsubstituted alkenyl group; a substituted or unsubstituted aryl group; a substituted or unsubstituted heterocyclic group; a substituted or unsubstituted alkylamine group; a substituted or unsubstituted heteroarylamine group; or a substituted or unsubstituted arylamine group, or adjacent two or more substituents bond to each other to form a ring, $R_a$ and $R_b$ are the same as or different from each other, and each independently hydrogen; deuterium; a halogen group; a substituted or unsubstituted alkyl group; a substituted or unsubstituted cycloalkyl group; a substituted or unsubstituted alkenyl group; a substituted or unsubstituted aryl group; a substituted or unsubstituted heterocyclic group; a substituted or unsubstituted alkylamine group; a substituted or unsubstituted heteroarylamine group; or a substituted or unsubstituted arylamine group, or adjacent substituents bond to each other to form a substituted or unsubstituted ring, b1, b3, b5, b8, b17 and b20 are the same as or different from each other, and each independently an integer of 0 to 3, b2, b4, b6 and b21 are the same as or different from each other, and each independently an integer of 0 to 4, b7, b10 and b19 are the same as or different from each other, and each independently an integer of 0 to 5, b9 and b18 are the same as or different from each other, and each independently an integer of 0 to 6, when b1 is 2 or greater, $B_1$s are the same as or different from each other, when b2 is 2 or greater, $B_2$s are the same as or different from each other, when b3 is 2 or greater, $B_3$s are the same as or different from each other, when b4 is 2 or greater, $B_4$s are the same as or different from each other, when b5 is 2 or greater, $B_5$s are the same as or different from each other, when b6 is 2 or greater, $B_6$s are the same as or different from each other, when b7 is 2 or greater, $B_7$s are the same as or different from each other, when b8 is 2 or greater, $B_8$s are the same as or different from each other, when b9 is 2 or greater, $B_9$s are the same as or different from each other, when b10 is 2 or greater, $B_{10}$s are the same as or different from each other, when b17 is 2 or greater, $B_{17}$s are the same as or different from each other, when b18 is 2 or greater, $B_{18}$s are the same as or different from each other, when b19 is 2 or greater, $B_{19}$s are the same as or different from each other, when b20 is 2 or greater, $B_{20}$s are the same as or different from each other, and when b21 is 2 or greater, $B_{21}$s are the same as or different from each other.

According to one embodiment of the present disclosure, Chemical Formula 10 may be selected from among the following structures.

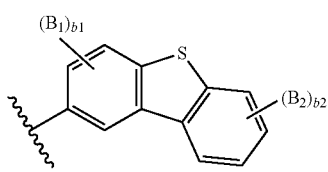

-continued

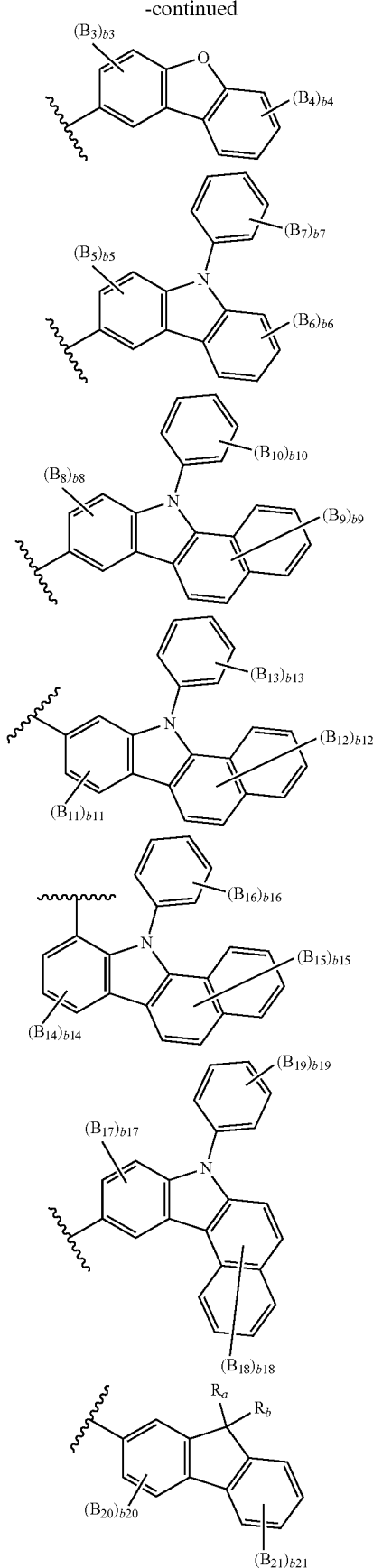

In the structural formulae, $B_1$ to $B_{21}$, $R_a$, $R_b$, b1 to b10 and b17 to b21 have the same definitions as described above, b11 and b14 are the same as or different from each other, and each independently an integer of 0 to 3, b13 and b16 are the same as or different from each other, and each independently an integer of 0 to 5, b12 and b15 are the same as or different from each other, and each independently an integer of 0 to 6, when b11 is 2 or greater, $B_{11}$s are the same as or different from each other, when b12 is 2 or greater, $B_{12}$s are the same as or different from each other, when b13 is 2 or greater, $B_{13}$s are the same as or different from each other, when b14 is 2 or greater, $B_{14}$s are the same as or different from each other, when b15 is 2 or greater, $B_{15}$s are the same as or different from each other, and when b16 is 2 or greater, $B_{16}$s are the same as or different from each other.

According to one embodiment of the present specification, Chemical Formula 10 may be selected from among the following structures, and the following structures may be each independently substituted with hydrogen; deuterium; a halogen group; a substituted or unsubstituted alkyl group; a substituted or unsubstituted cycloalkyl group; a substituted or unsubstituted alkenyl group; a substituted or unsubstituted aryl group; a substituted or unsubstituted heterocyclic group; a substituted or unsubstituted alkylamine group; a substituted or unsubstituted heteroarylamine group; or a substituted or unsubstituted arylamine group, or adjacent two or more substituents bond to each other to form a ring.

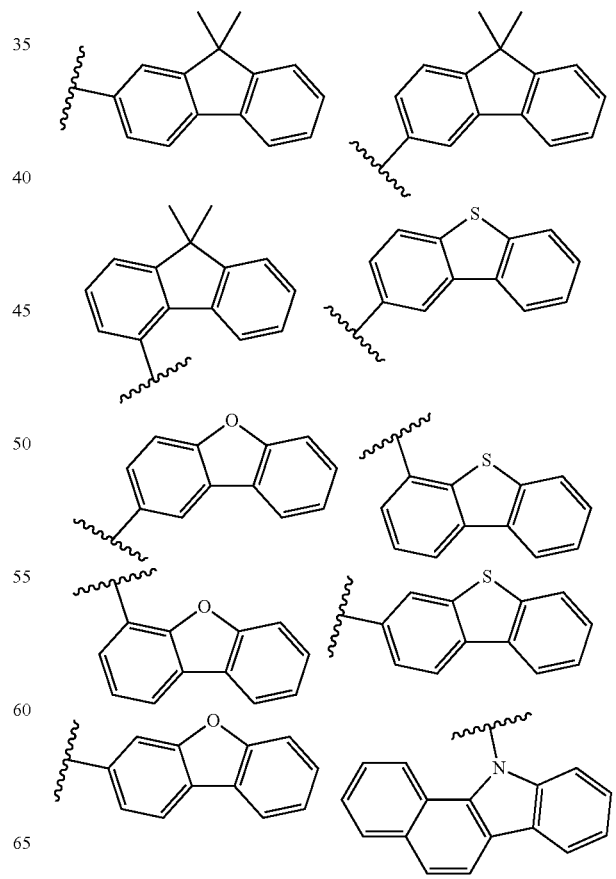

-continued

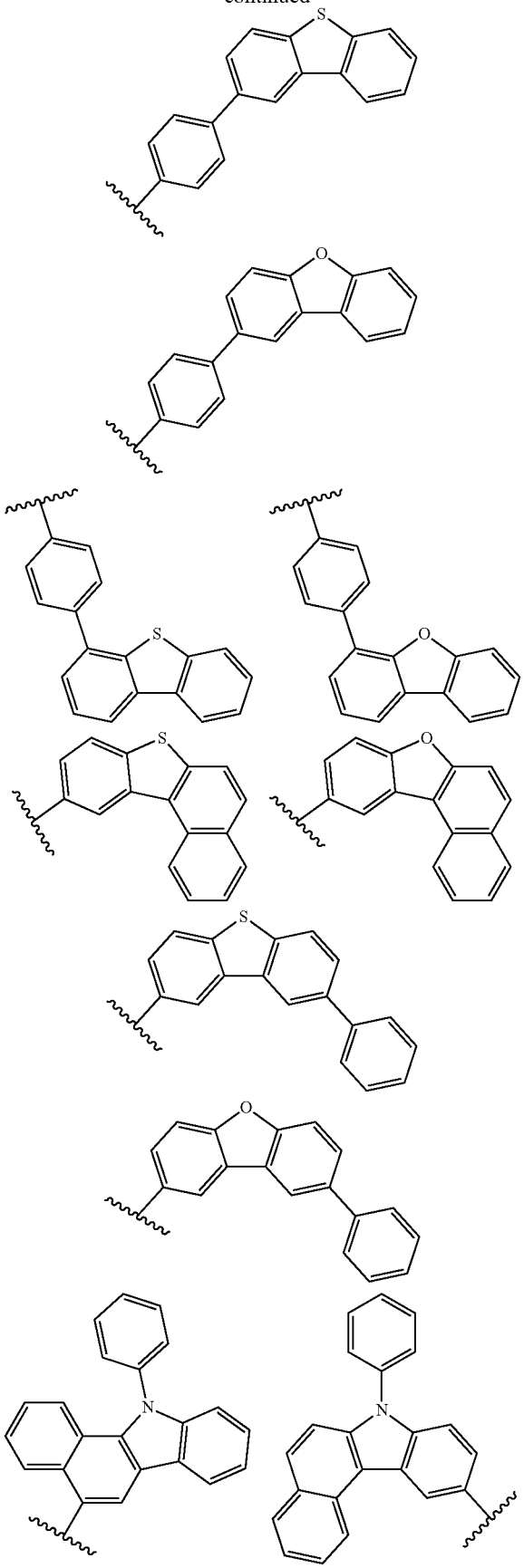

-continued

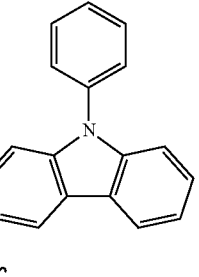 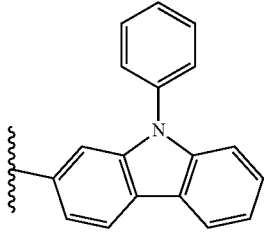

According to one embodiment of the present specification, Ar1 in Chemical Formula 1 may be represented by the following Chemical Formula 11.

[Chemical Formula 11]

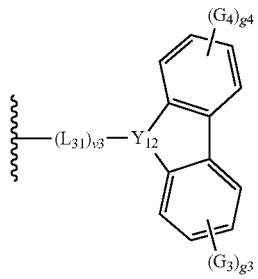

In Chemical Formula 11, $Y_{12}$ is $CR_e$ or N, $R_e$ is hydrogen; deuterium; a halogen group; a substituted or unsubstituted alkyl group; a substituted or unsubstituted cycloalkyl group; a substituted or unsubstituted alkenyl group; a substituted or unsubstituted aryl group; a substituted or unsubstituted heterocyclic group; a substituted or unsubstituted alkylamine group; a substituted or unsubstituted heteroarylamine group, $L_{31}$ is a direct bond; substituted or unsubstituted arylene; or substituted or unsubstituted heteroarylene, $G_3$ and $G_4$ are the same as or different from each other, and each independently hydrogen; deuterium; a halogen group; a substituted or unsubstituted alkyl group; a substituted or unsubstituted cycloalkyl group; a substituted or unsubstituted alkenyl group; a substituted or unsubstituted aryl group; a substituted or unsubstituted heterocyclic group; a substituted or unsubstituted alkylamine group; a substituted or unsubstituted heteroarylamine group; or a substituted or unsubstituted arylamine group, or adjacent two or more substituents bond to each other to form a ring, g3 and g4 are the same as or different from each other, and each independently an integer of 0 to 4, v3 is an integer of 0 to 5, when g3 is 2 or greater, $G_3$s are the same as or different from each other, when g4 is 2 or greater, $G_4$s are the same as or different from each other, and when v3 is 2 or greater, $L_{31}$s are the same as or different from each other.

According to one embodiment of the present specification, Chemical Formula 11 may be selected from among the following structures.

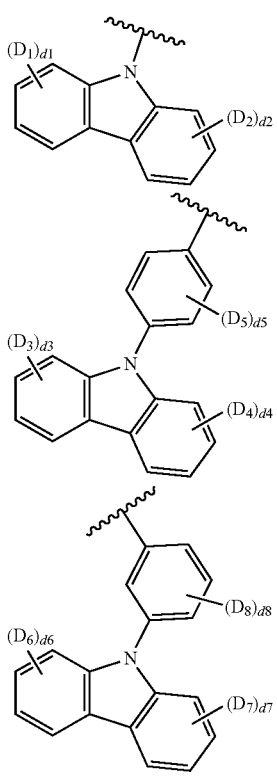

In the structural formulae, $D_1$ to $D_8$ are the same as or different from each other, and each independently hydrogen; deuterium; a halogen group; a substituted or unsubstituted alkyl group; a substituted or unsubstituted cycloalkyl group; a substituted or unsubstituted alkenyl group; a substituted or unsubstituted aryl group; a substituted or unsubstituted heterocyclic group; a substituted or unsubstituted alkylamine group; a substituted or unsubstituted heteroarylamine group; or a substituted or unsubstituted arylamine group, or adjacent two or more substituents bond to each other to form a ring, d1 to d8 are the same as or different from each other, and each independently an integer of 0 to 4, when d1 is 2 or greater, $D_1$s are the same as or different from each other, when d2 is 2 or greater, $D_2$s are the same as or different from each other, when d3 is 2 or greater, $D_3$s are the same as or different from each other, when d4 is 2 or greater, $D_4$s are the same as or different from each other, when d5 is 2 or greater, $D_5$s are the same as or different from each other, when d6 is 2 or greater, $D_6$s are the same as or different from each other, when d7 is 2 or greater, $D_7$s are the same as or different from each other, and when d8 is 2 or greater, $D_8$s are the same as or different from each other.

According to one embodiment of the present specification, Chemical Formula 11 may be selected from among the following structures, and the following structures may be each independently substituted with hydrogen; deuterium; a halogen group; a substituted or unsubstituted alkyl group; a substituted or unsubstituted cycloalkyl group; a substituted or unsubstituted alkenyl group; a substituted or unsubstituted aryl group; a substituted or unsubstituted heterocyclic group; a substituted or unsubstituted alkylamine group; a substituted or unsubstituted heteroarylamine group; or a substituted or unsubstituted arylamine group, or adjacent two or more substituents bond to each other to form a ring.

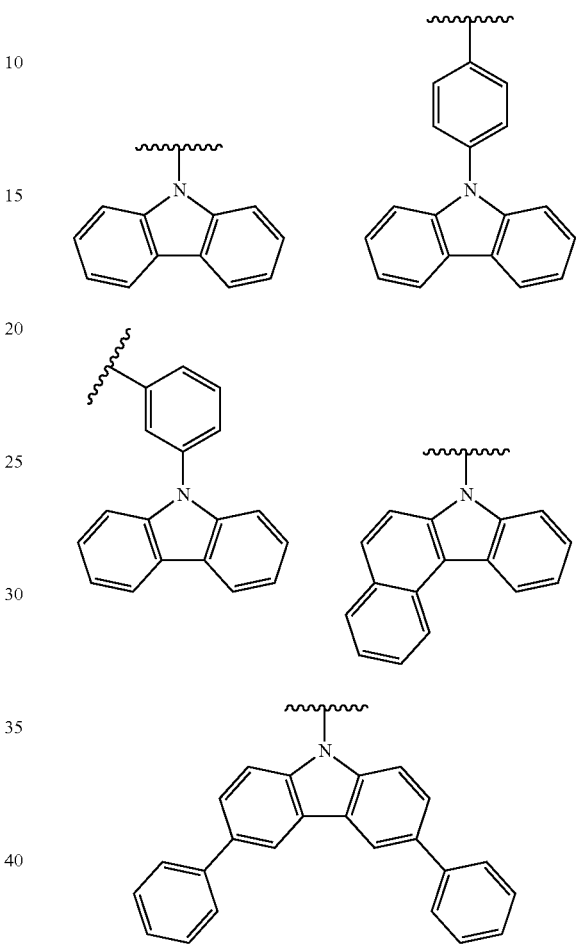

According to one embodiment of the present specification, Ar1 in Chemical Formula 1 may be represented by the following Chemical Formula 12-a or Chemical Formula 12-b.

[Chemical Formula 12-a]

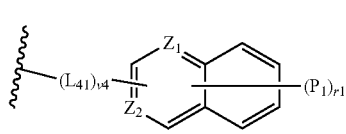

[Chemical Formula 12-b]

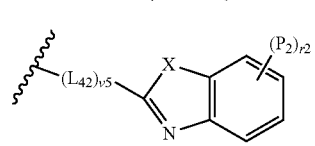

In Chemical Formula 12-a and Chemical Formula 12-b, $Z_1$ and $Z_2$ are the same as or different from each other, and each independently N or $CR_f$, $R_f$ is hydrogen; deuterium; a halogen group; a substituted or unsubstituted alkyl group; a substituted or unsubstituted cycloalkyl group; a substituted or unsubstituted alkenyl group; a substituted or unsubstituted aryl group; a substituted or unsubstituted heterocyclic group; a substituted or unsubstituted alkylamine group; a substituted or unsubstituted heteroarylamine group; or a substituted or unsubstituted arylamine group, or adjacent substituents bond to each other to form a substituted or unsubstituted ring, $L_{41}$ is a direct bond; substituted or unsubstituted arylene; or substituted or unsubstituted heteroarylene, X is an O atom, an S atom or $NR_g$, $R_g$ is hydrogen; deuterium; a halogen group; a substituted or unsubstituted alkyl group; a substituted or unsubstituted cycloalkyl group; a substituted or unsubstituted alkenyl group; a substituted or unsubstituted aryl group; a substituted or unsubstituted heterocyclic group; a substituted or unsubstituted alkylamine group; a substituted or unsubstituted heteroarylamine group; or a substituted or unsubstituted arylamine group, or adjacent substituents bond to each other to form a substituted or unsubstituted ring, $P_1$ and $P_2$ are hydrogen; deuterium; a halogen group; a substituted or unsubstituted alkyl group; a substituted or unsubstituted cycloalkyl group; a substituted or unsubstituted alkenyl group; a substituted or unsubstituted aryl group; a substituted or unsubstituted heterocyclic group; a substituted or unsubstituted alkylamine group; a substituted or unsubstituted heteroarylamine group; or a substituted or unsubstituted arylamine group, or adjacent two or more substituents bond to each other to form a ring, r1 is an integer of 0 to 5, r2 is an integer of 0 to 4, v4 and v5 are the same as or different from each other, and each independently an integer of 0 to 5, when r1 is 2 or greater, $P_1$s are the same as or different from each other, when r2 is 2 or greater, $P_2$s are the same as or different from each other, when v4 is 2 or greater, $L_{41}$s are the same as or different from each other, and when v5 is 2 or greater, $L_{42}$s are the same as or different from each other.

According to one embodiment of the present specification, Chemical Formula 12-a or Chemical Formula 12-b may be selected from among the following structures, and the following structures may be each independently substituted with hydrogen; deuterium; a halogen group; a substituted or unsubstituted alkyl group; a substituted or unsubstituted cycloalkyl group; a substituted or unsubstituted alkenyl group; a substituted or unsubstituted aryl group; a substituted or unsubstituted heterocyclic group; a substituted or unsubstituted alkylamine group; a substituted or unsubstituted heteroarylamine group; or a substituted or unsubstituted arylamine group, or adjacent two or more substituents bond to each other to form a ring.

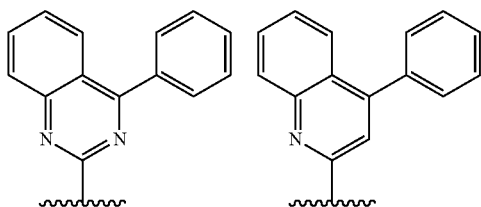

-continued

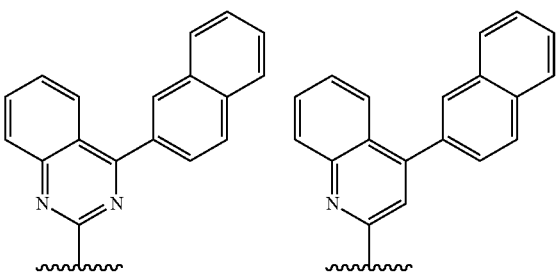

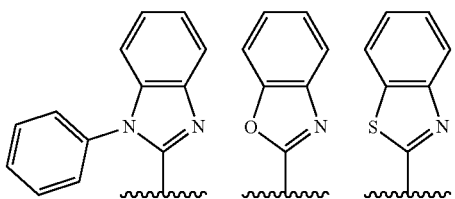

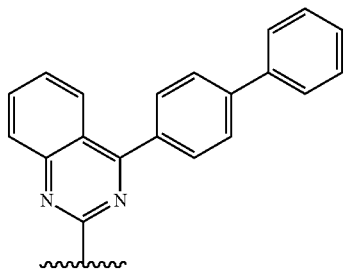

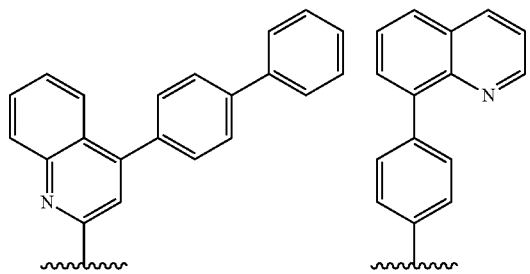

According to one embodiment of the present specification, Ar1 in Chemical Formula 1 may be represented by the following Chemical Formula 13.

[Chemical Formula 13]

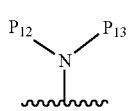

In Chemical Formula 13, $P_{12}$ and $P_{13}$ are the same as or different from each other, and each independently a substituted or unsubstituted aryl group; or a substituted or unsubstituted heterocyclic group.

According to one embodiment of the present specification, Chemical Formula 13 may be selected from among the following structures.

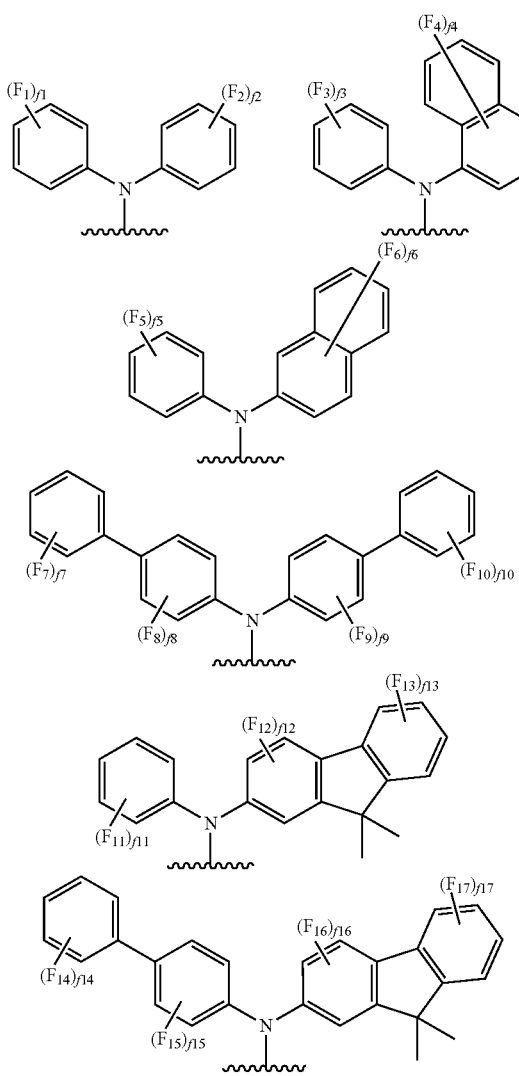

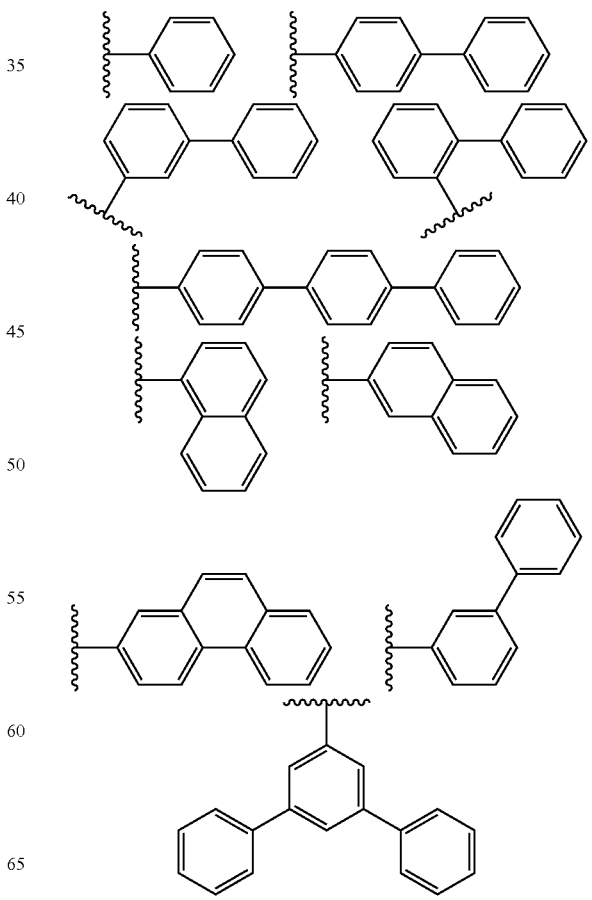

In the structural formulae, $F_1$ to $F_{17}$ are the same as or different from each other, each independently the same as or different from each other, and each independently hydrogen; deuterium; a halogen group; a substituted or unsubstituted alkyl group; a substituted or unsubstituted cycloalkyl group; a substituted or unsubstituted alkenyl group; a substituted or unsubstituted aryl group; a substituted or unsubstituted heterocyclic group; a substituted or unsubstituted alkylamine group; a substituted or unsubstituted heteroarylamine group; or a substituted or unsubstituted arylamine group, or adjacent two or more substituents bond to each other to form a ring, f1, f2, f3, f5, f7, f10, f11 and f14 are an integer of 0 to 5, f4 and f6 are an integer of 0 to 7, f8, f9, f13, f15 and f17 are an integer of 0 to 4, f12 and f16 are an integer of 0 to 3, when f1 is 2 or greater, $F_1$s are the same as or different from each other, when f2 is 2 or greater, $F_e$s are the same as or different from each other, when f3 is 2 or greater, $F_3$s are the same as or different from each other, when f4 is 2 or greater, $F_4$s are the same as or different from each other, when f5 is 2 or greater, $F_5$s are the same as or different from each other, when f6 is 2 or greater, $F_6$s are the same as or different from each other, when f7 is 2 or greater, $F_7$s are the same as or different from each other, when f8 is 2 or greater, $F_8$s are the same as or different from each other, when f9 is 2 or greater, $F_9$s are the same as or different from each other, when f10 is 2 or greater, $F_{10}$s are the same as or different from each other, when f11 is 2 or greater, $F_{11}$s are the same as or different from each other, when f12 is 2 or greater, $F_{12}$s are the same as or different from each other, when f13 is 2 or greater, $F_{13}$s are the same as or different from each other, when f14 is 2 or greater, $F_{14}$s are the same as or different from each other, when f15 is 2 or greater, $F_{15}$s are the same as or different from each other, when f16 is 2 or greater, $F_{16}$s are the same as or different from each other, and when f17 is 2 or greater, $F_{17}$s are the same as or different from each other.

According to one embodiment of the present specification, Ar1 may be hydrogen or any one selected from among the following structures.

-continued
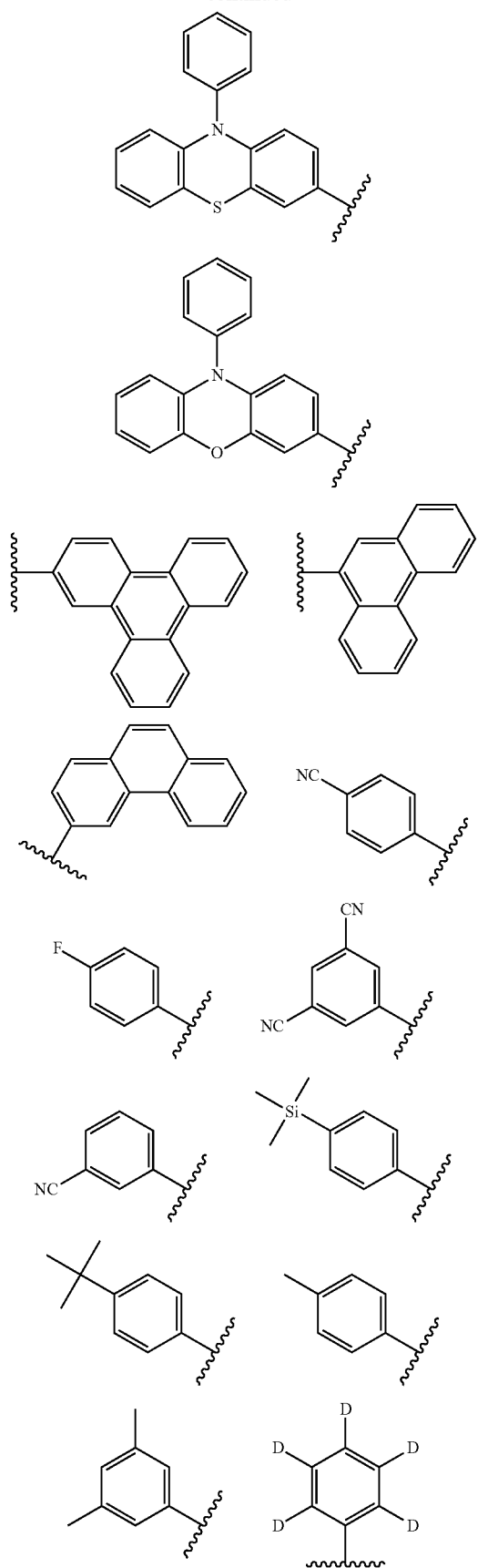
-continued
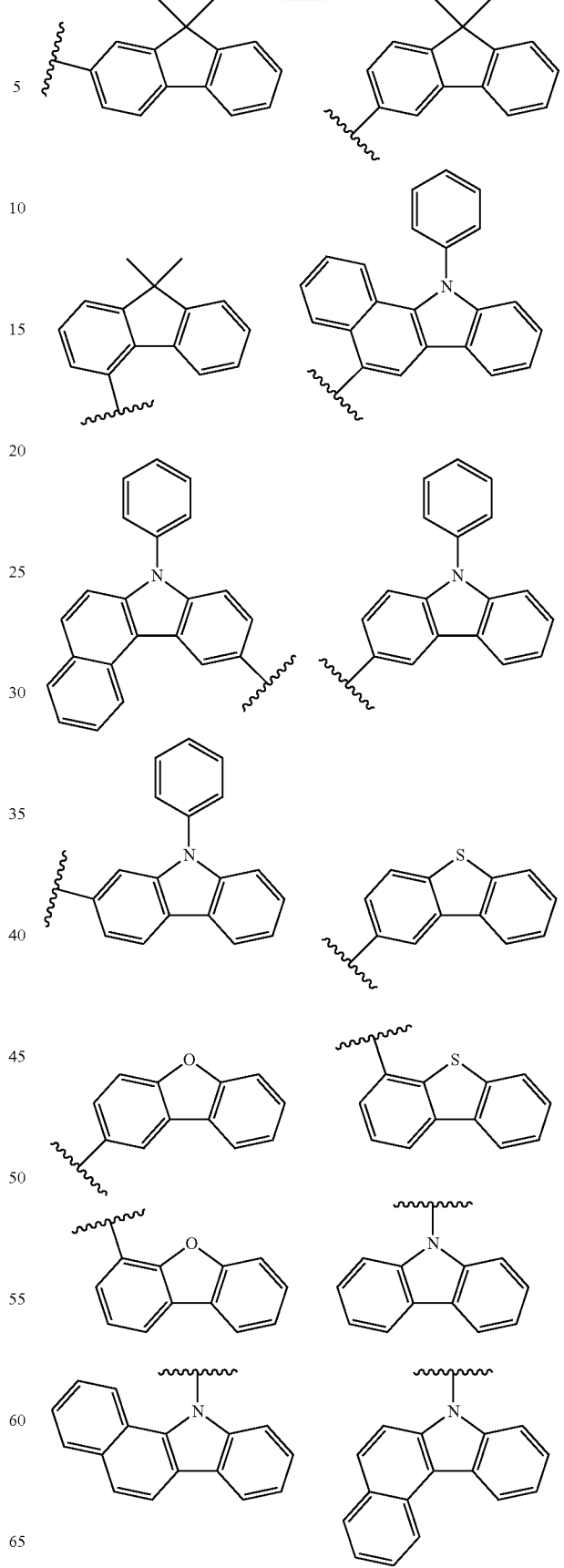

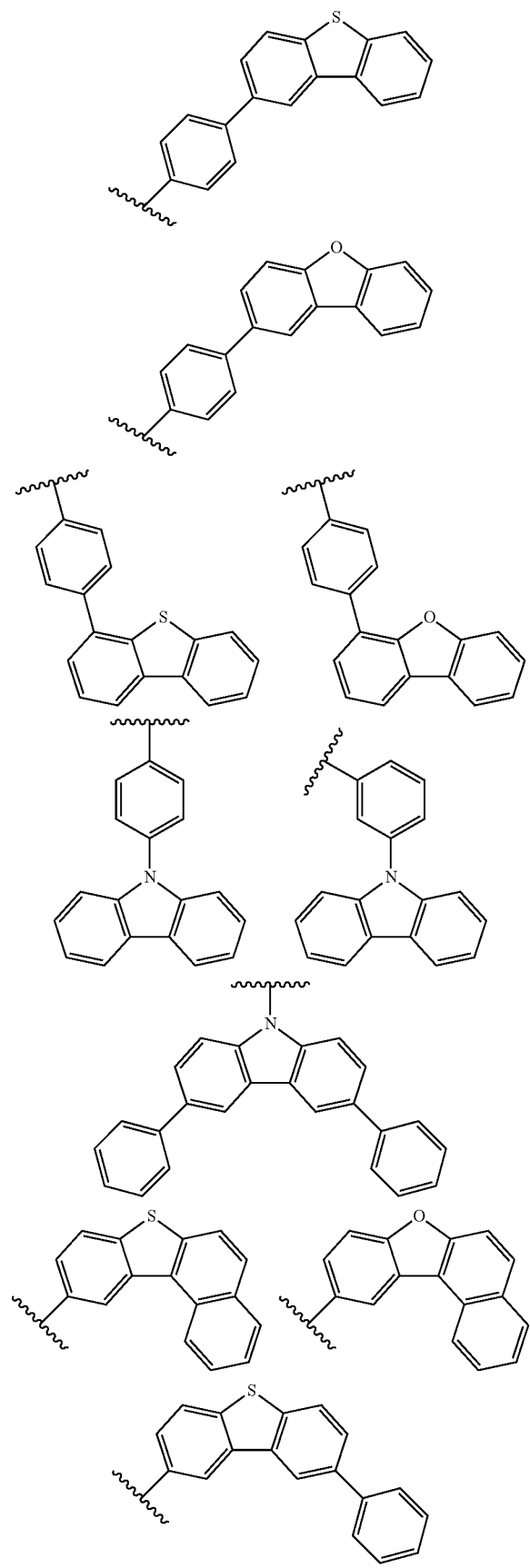

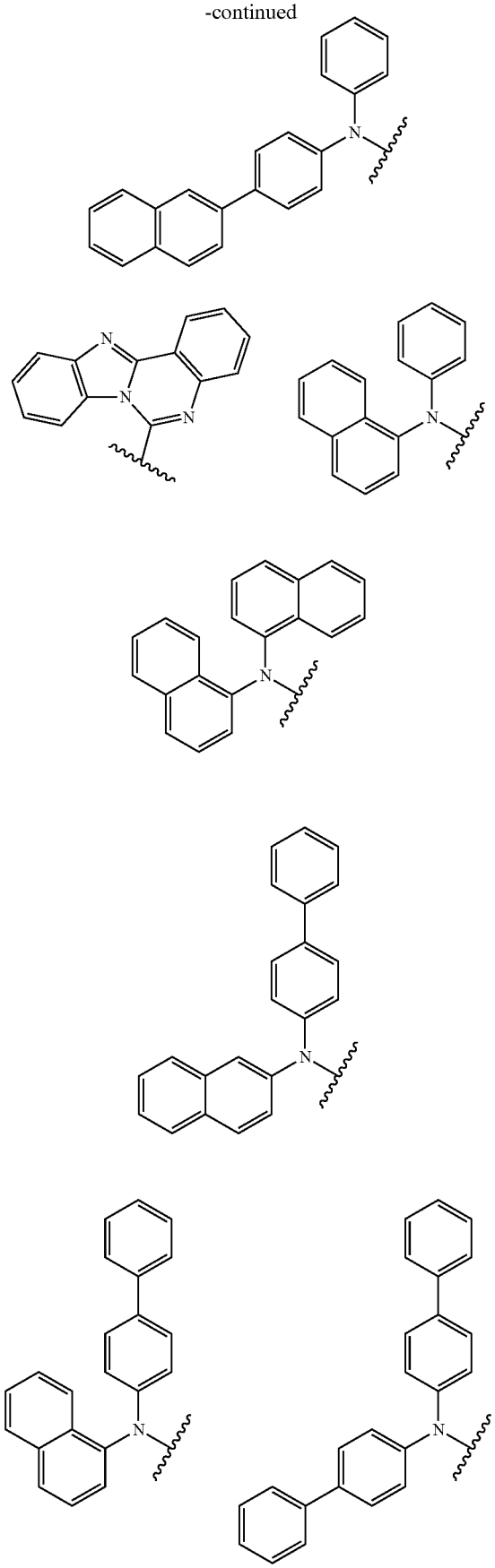
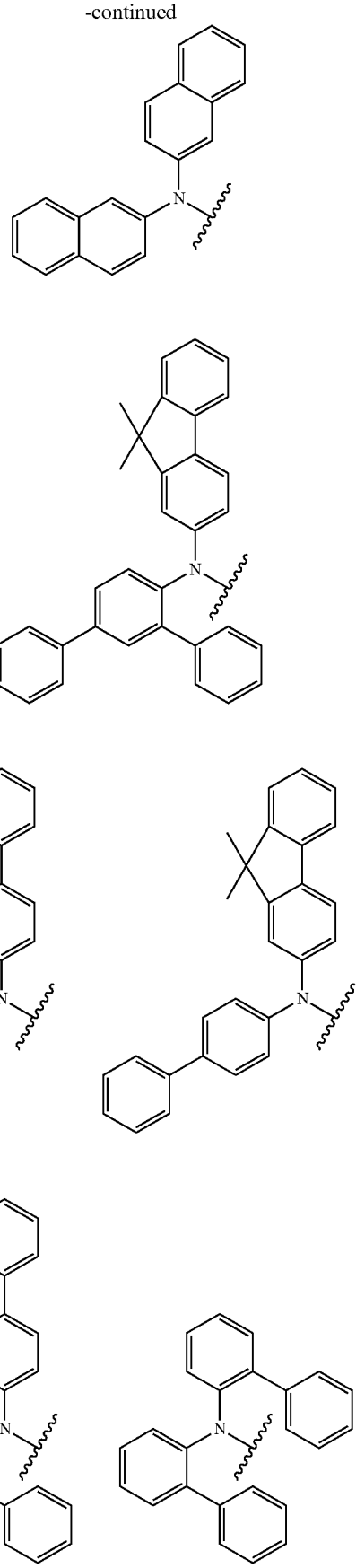

-continued
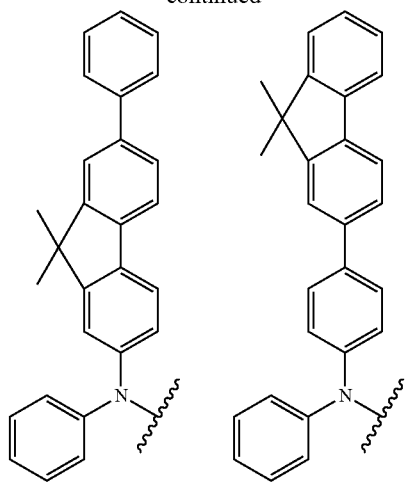
-continued
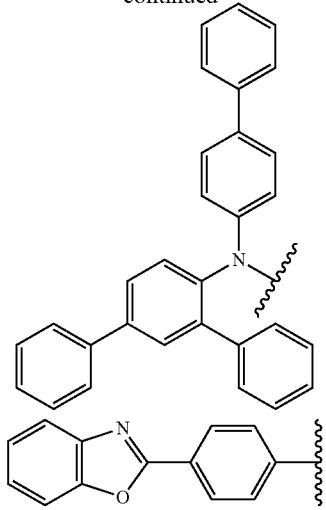
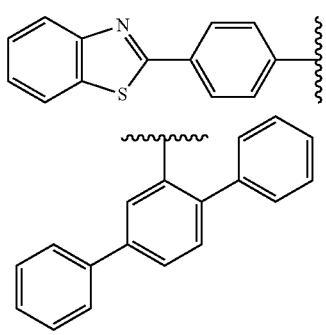
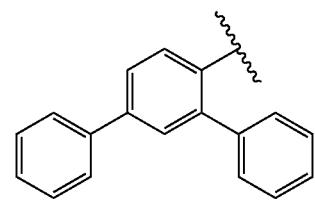
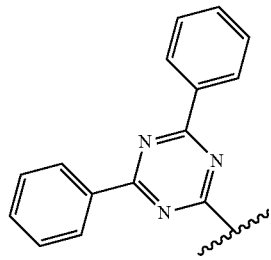
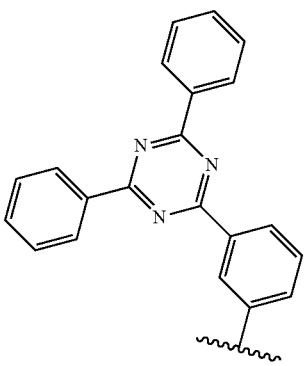

-continued
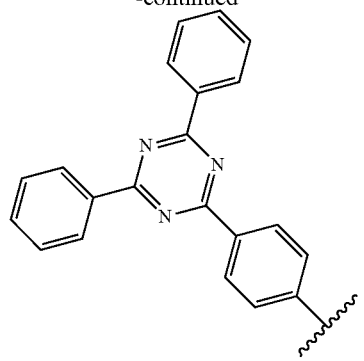
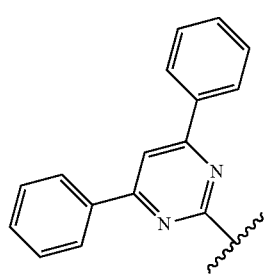
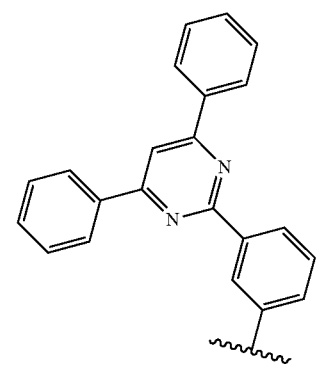
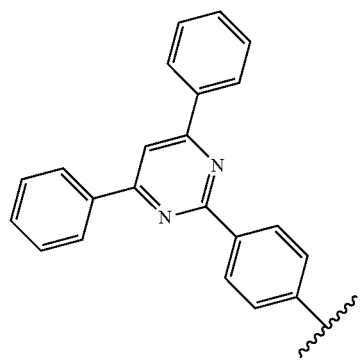
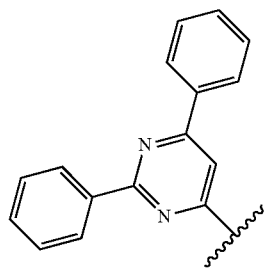
-continued
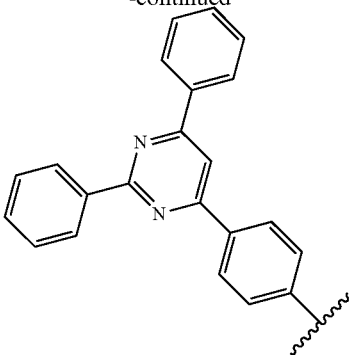
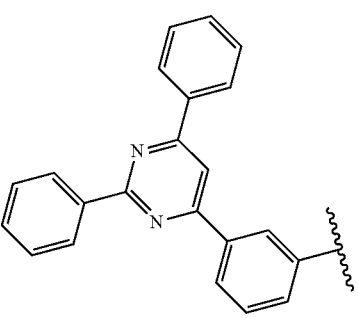
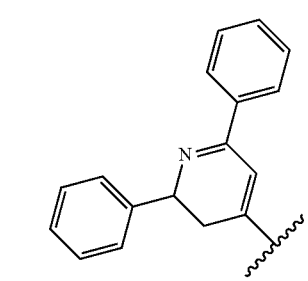
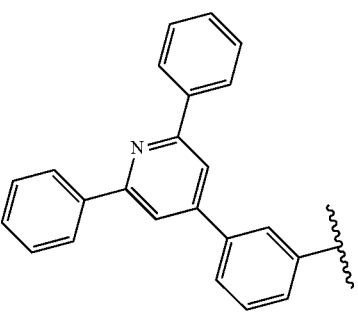
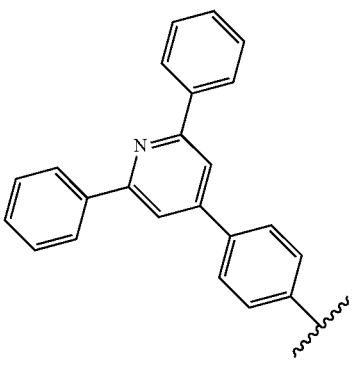

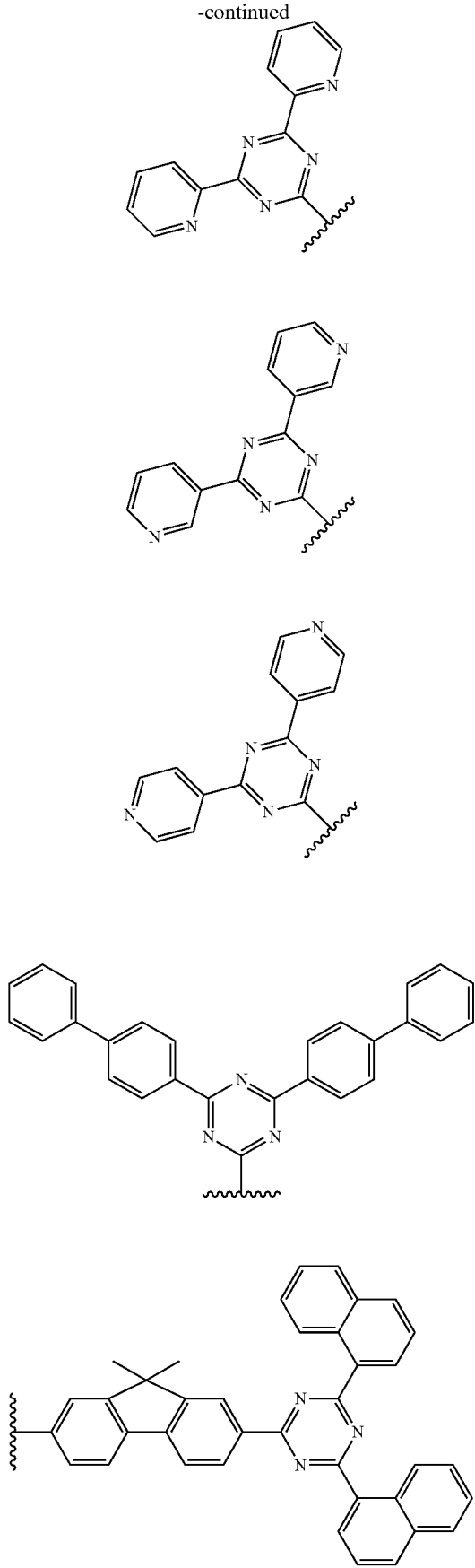

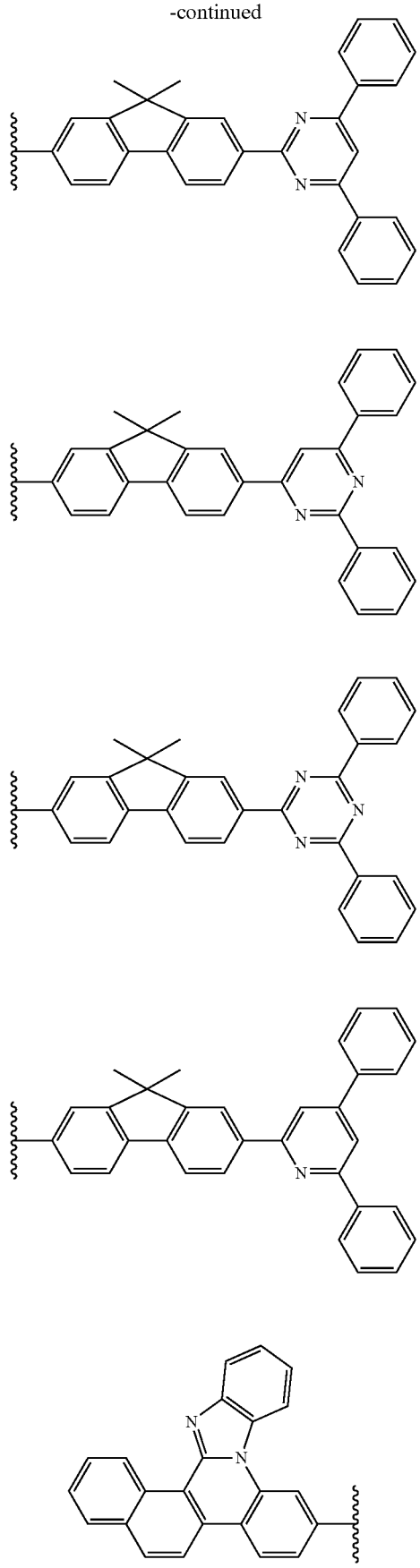

-continued
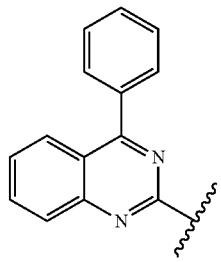 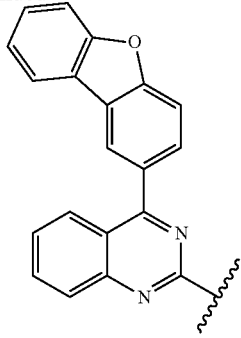
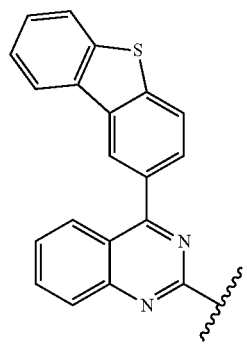 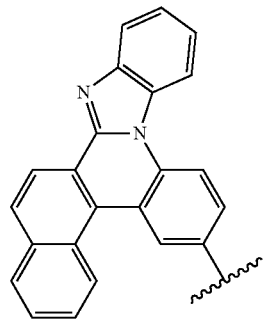
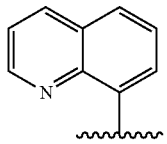 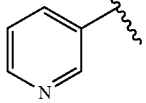 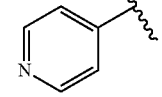
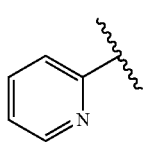 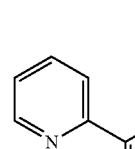
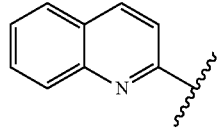
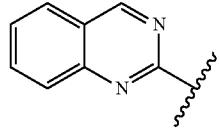
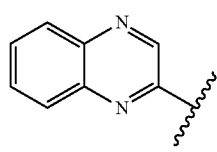
-continued
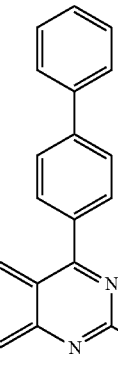 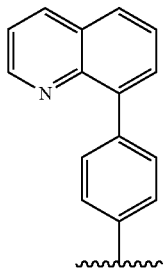
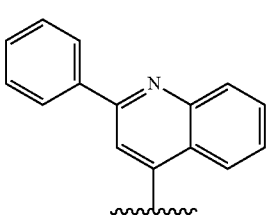 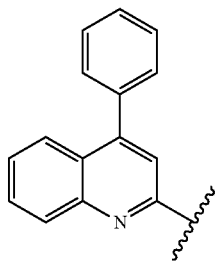
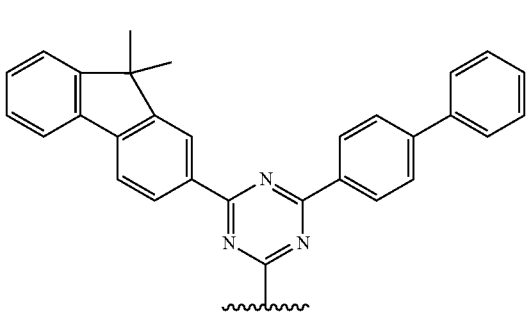
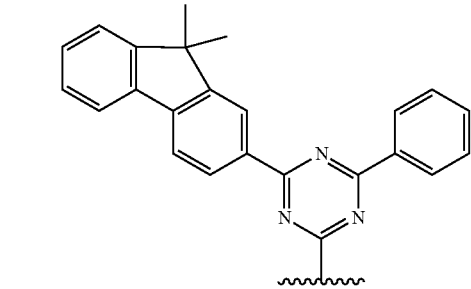
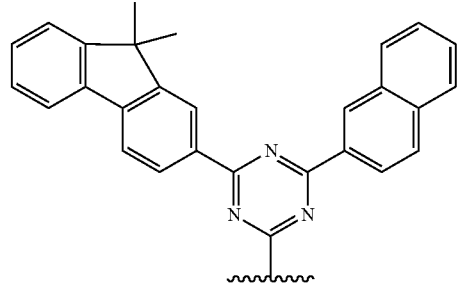

-continued

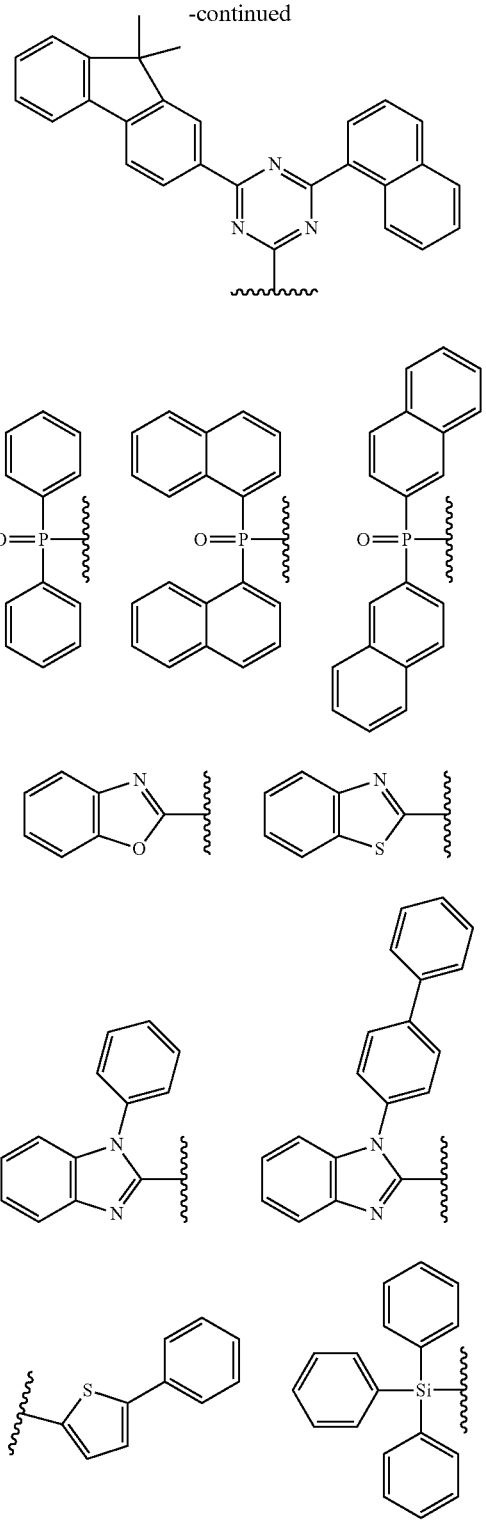

The structures may be unsubstituted or substituted with one or more substituents selected from the group consisting of deuterium; a halogen group; a nitrile group; a nitro group; a hydroxyl group; a carbonyl group; an ester group; an imide group; an amine group; a phosphine oxide group; an alkoxy group; an aryloxy group; an alkylthioxy group; an arylthioxy group; an alkylsulfoxy group; a silyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylheteroarylamine group; an arylphosphine group; and a heterocyclic group.

According to one embodiment of the present specification, Ar1 in Chemical Formula 1 is a phenyl group; a biphenyl group; a naphthyl group; an anthracenyl group; a terphenyl group; a triphenylenyl group; a phenanthrolinyl group; a diphenylamine group, a phenylbiphenylamine group, a dibiphenylamine group, a phenylnaphthylamine group, a triphenylamine group, an N-phenylfluoreneamine group, an N-biphenylfluoreneamine group; an N,N-diphenylfluoreneamine group; a phenanthrenyl group; a pyridyl group; a pyrimidinyl group; a triazinyl group; a quinolinyl group; a quinazolinyl group; a carbazole group; a dibenzofuranyl group; a dibenzothiophenyl group; a imidazopyridine group; an imidazophenanthridine group; a benzimidazoquinazoline group; or a benzimidazophenanthridine group, and these may be further substituted.

Specifically, Ar1 may be unsubstituted or substituted with one or more substituents selected from the group consisting of deuterium; a halogen group; a nitrile group; a nitro group; a hydroxyl group; a carbonyl group; an ester group; an imide group; an amine group; a phosphine oxide group; an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylheteroarylamine group; an arylphosphine group; and a heterocyclic group.

According to one embodiment of the present disclosure, when L1 is phenylene, Ar1 may be hydrogen, deuterium, a phenyl group, a nitrile group, a trimethylsilyl group, a naphthyl group, a diphenylamine group, a phenylbiphenylamine group, a phenylnaphthylamine group, a dibiphenylamine group, an N-phenylfluoreneamine group, an N-biphenylfluoreneamine group, an N,N-diphenylfluoreneamine group, a triphenylamine group, a pyrrolyl group, a pyridyl group, a pyrimidinyl group, a triazinyl group, a quinolinyl group, a quinazolinyl group, a benzimidazole group, a benzoxazole group, a benzothiazole group, a carbazole group, a dibenzofuranyl group, a phenanthrolyl group; a dibenzothiophene group, a 9,9-dimethylfluorenyl group, or a diphenylphosphine oxide group, and these may be further substituted.

According to one embodiment of the present disclosure, when L1 is a quinolinyl group, Ar1 may be hydrogen, a phenyl group, a biphenyl group or a naphthyl group.

According to one embodiment of the present disclosure, when L1 is a quinazolinyl group, Ar1 may be hydrogen, a phenyl group, a biphenyl group or a naphthyl group.

According to one embodiment of the present disclosure, when L1 is a carbazole group, Ar1 is a phenyl group.

According to one embodiment of the present disclosure, R1 to R3, R11 and R12 are the same as or different from each other, and each independently hydrogen; deuterium; a halogen group; a nitrile group; a nitro group; a hydroxyl group; a carbonyl group; an ester group; an imide group; an amino group; a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylheteroarylamine group; a substituted or unsubstituted arylphosphine group; a substituted or unsubstituted phosphine oxide group; a substituted or unsubstituted aryl group; or a substituted or unsubstituted heterocyclic group, or may bond to adjacent groups to form a substituted or unsubstituted ring.

According to one embodiment of the present disclosure, the substituted or unsubstituted ring formed by R1 to R3, R11 and R12 bonding to adjacent groups may be substituted or unsubstituted benzene, substituted or unsubstituted biphenyl, substituted or unsubstituted naphthalene, substituted or unsubstituted anthracene, substituted or unsubstituted phenanthrene, substituted or unsubstituted fluorene, substituted or unsubstituted pyridine, substituted or unsubstituted phenanthridine, substituted or unsubstituted dibenzothiophene, or substituted or unsubstituted carbazole, but is not limited thereto.

According to one embodiment of the present disclosure, R1 to R3, R11 and R12 are the same as or different from each other, and each independently selected from the group consisting of hydrogen, halogen, linear or branched substituted or unsubstituted alkyl having 1 to 60 carbon atoms, linear or branched substituted or unsubstituted alkenyl having 2 to 60 carbon atoms, linear or branched substituted or unsubstituted alkynyl having 2 to 60 carbon atoms, monocyclic or multicyclic substituted or unsubstituted cycloalkyl having 3 to 60 carbon atoms, monocyclic or multicyclic substituted or unsubstituted heterocycloalkyl having 2 to 60 carbon atoms, monocyclic or multicyclic substituted or unsubstituted aryl having 6 to 60 carbon atoms, and monocyclic or multicyclic substituted or unsubstituted heteroaryl having 2 to 60 carbon atoms.

According to one embodiment of the present disclosure, R1 to R3, R11 and R12 are the same as or different from each other, and each independently selected from the group consisting of hydrogen, monocyclic or multicyclic substituted or unsubstituted aryl having 6 to 60 carbon atoms and monocyclic or multicyclic substituted or unsubstituted heteroaryl having 2 to 60 carbon atoms.

According to one embodiment of the present disclosure, R1 to R3, R11 and R12 are the same as or different from each other, and may be each independently an aryl group such as a phenyl group, a biphenylyl group, a naphthyl group, an anthryl group, a chrysenyl group, a phenanthrenyl group, a triphenylenyl group, a pyrenyl group, a tetracenyl group, a pentacenyl group or a fluorenyl group, or a heterocyclic group such as a pyridyl group, a pyrrole group, a pyridyl group, a pyridazinyl group, a furanyl group, a thiophene group, an imidazole group, a pyrazole group, an oxazole group, an isoxazole group, a triazole group, an isothiazole group, a triazole group, a pyrazinyl group, a triazine group, a quinolinyl group, an isoquinolinyl group, a quinazoline group, a quinoxalinyl group, a naphthyridinyl group, an acridyl group, a xanthenyl group, a phenanthridinyl group, a diazanaphthalenyl group, a triazaindenyl group, an indole group, an indolinyl group, an indolizinyl group, a phthalazinyl group, a pyridopyrimidinyl group, a pyridopyrazinyl group, a pyrazinopyrazinyl group, a carbazole group, a benzothiophene group, a benzofuranyl group, a benzimidazole group, a benzothiazole group, a benzoxazole group, a benzocarbazole group, a dibenzothiophene group, a dibenzofuranyl group, a dibenzocarbazole group, an indolocarbazole group, an indenocarbazole group, a phenanthroline group, a phenazinyl group, a phenoxazinyl group, a phenothiazinyl group, an imidazopyridinyl group, an imidazophenanthridine group, a benzimidazoquinazolinyl group or benzimidazophenanthridinyl group, and these may be further substituted.

More specifically, R1 to R3, R11 and R12 may be a substituted or unsubstituted phenyl group; a substituted or unsubstituted biphenyl group; a substituted or unsubstituted naphthyl group; a substituted or unsubstituted anthracenyl group; a substituted or unsubstituted phenanthrenyl group; a substituted or unsubstituted fluorenyl group; a substituted or unsubstituted pyridinyl group; a substituted or unsubstituted phenanthridinyl group; a substituted or unsubstituted dibenzothiophene group; or a substituted or unsubstituted carbazolyl group.

According to one embodiment of the present disclosure, R1 to R3, R11 and R12 are hydrogen.

According to one embodiment of the present disclosure, R4 and R5 are the same as or different from each other, and each independently hydrogen; deuterium; a halogen group; a nitrile group; a nitro group; a hydroxyl group; a carbonyl group; an ester group; an imide group; an amino group; a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylheteroarylamine group; a substituted or unsubstituted arylphosphine group; or a substituted or unsubstituted phosphine oxide group.

According to one embodiment of the present disclosure, R4 and R5 are the same as or different from each other, and each independently hydrogen; deuterium; a halogen group;

a nitrile group; a nitro group; a substituted or unsubstituted alkyl group; a substituted or unsubstituted cycloalkyl group; a substituted or unsubstituted alkoxy group; a substituted or unsubstituted alkenyl group; or a substituted or unsubstituted phosphine oxide group.

According to one embodiment of the present disclosure, R4 and R5 are the same as or different from each other, and each independently hydrogen, deuterium, or a linear or branched alkyl group having 1 to 40 carbon atoms.

According to one embodiment of the present disclosure, R4 and R5 are the same as or different from each other, and may be hydrogen, methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohectylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 4-methylhexyl or 5-methylhexyl, and these may be further substituted.

According to one embodiment of the present disclosure, R4 and R5 are the same as or different from each other, and each independently hydrogen, methyl, ethyl, propyl, isopropyl, butyl or tert-butyl.

According to one embodiment of the present disclosure, R4 and R5 are methyl.

According to one embodiment of the present disclosure, R4 and R5 are hydrogen.

According to one embodiment of the present disclosure, the compound of Chemical Formula 1 may be any one selected from among the following compounds.

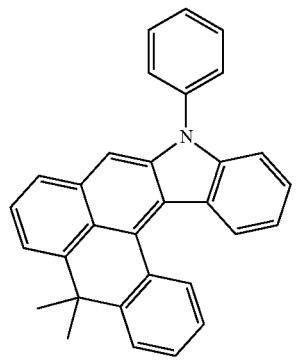

2-1-1

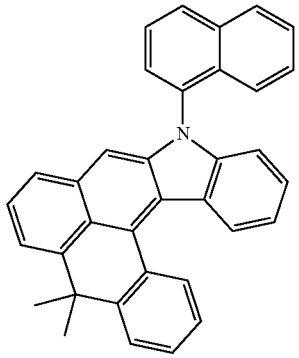

2-1-2

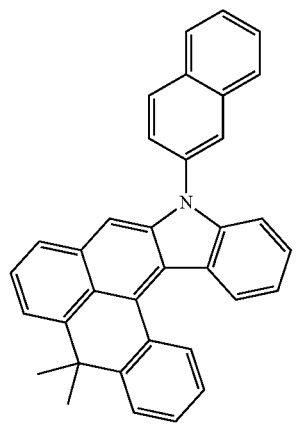

2-1-3

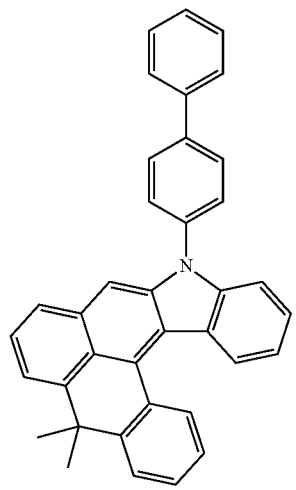

2-1-4

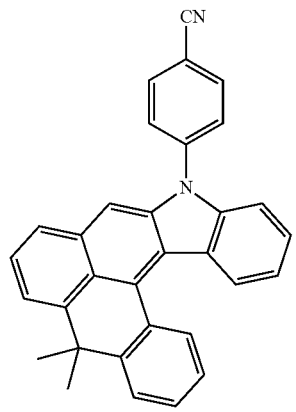

2-1-5

-continued
2-1-6
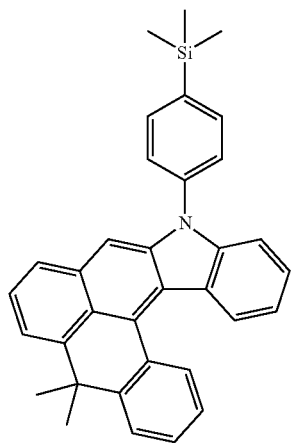
2-1-7
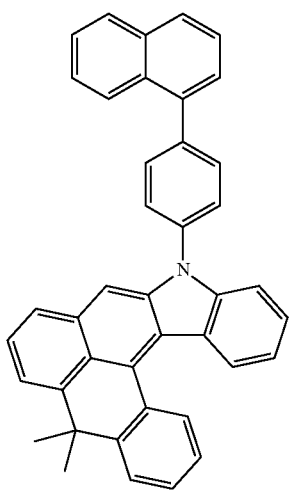
2-1-8
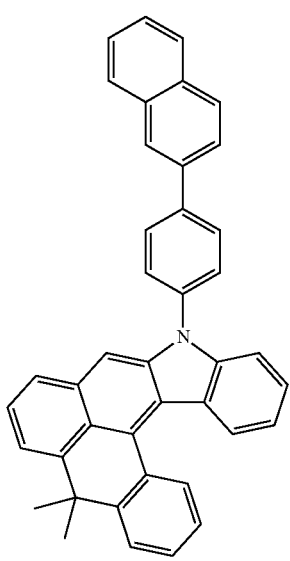
-continued
2-1-9
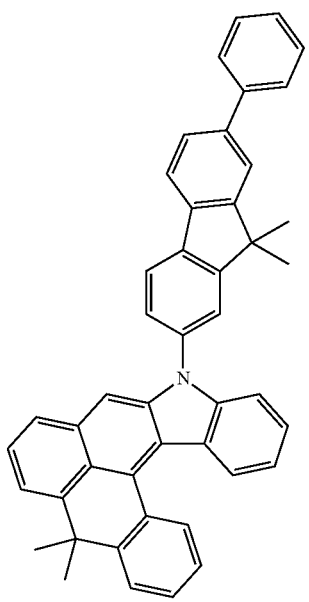
2-1-10
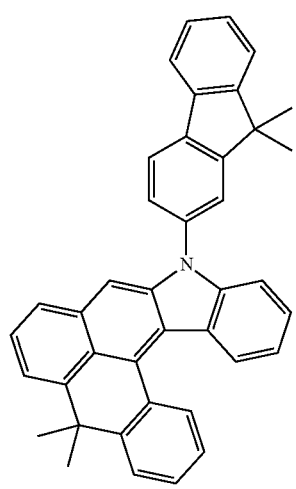
2-1-11
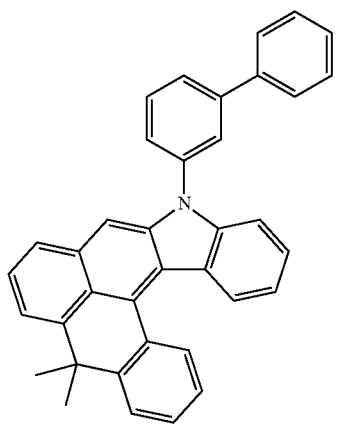

2-1-12
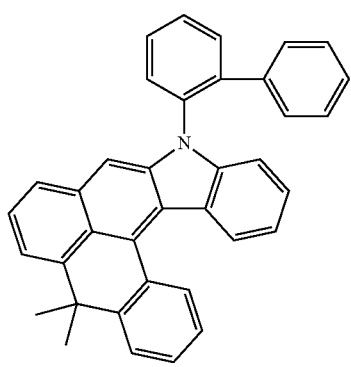
2-1-13
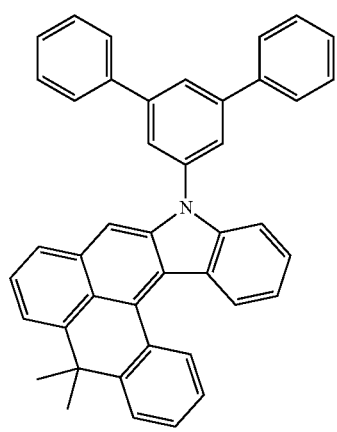
2-1-14
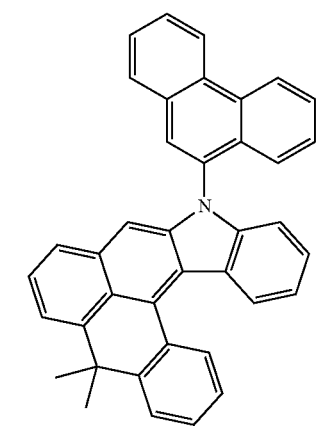
2-1-15
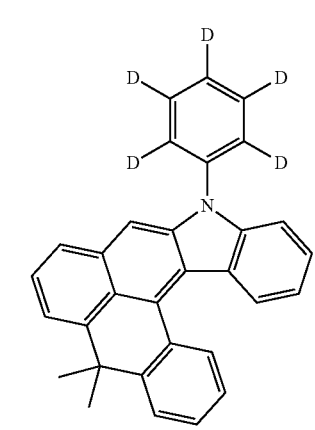
2-1-16
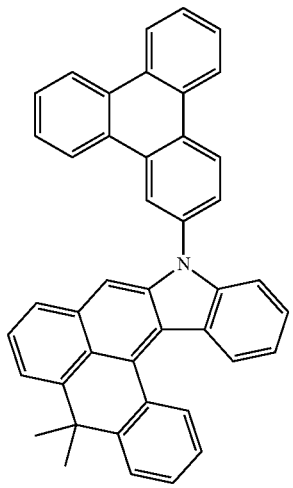
2-1-17
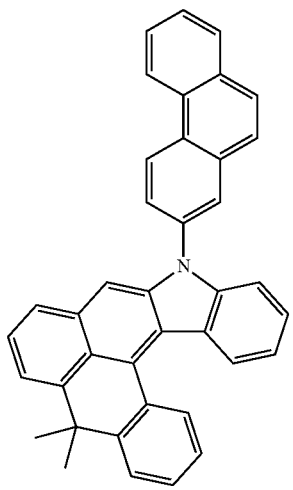
2-1-18
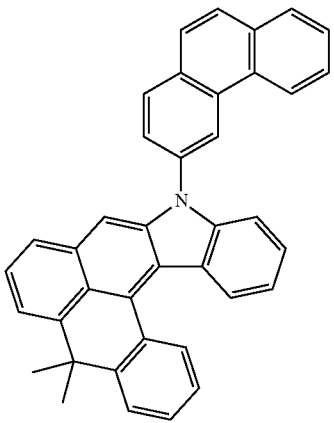

2-1-19
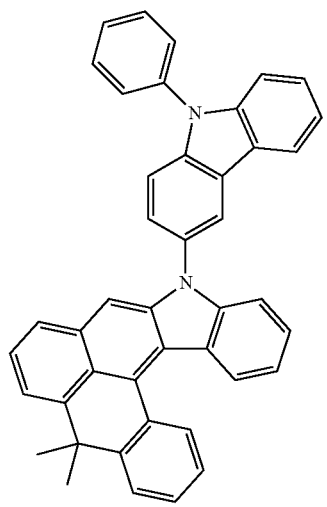
2-1-20
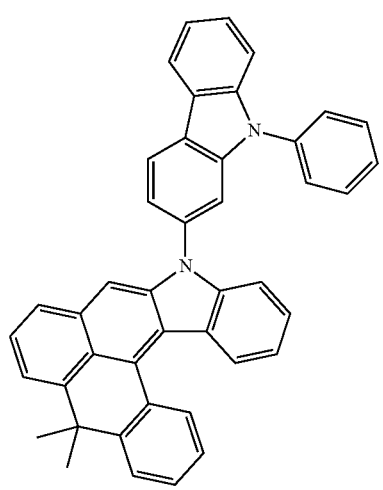
2-1-21
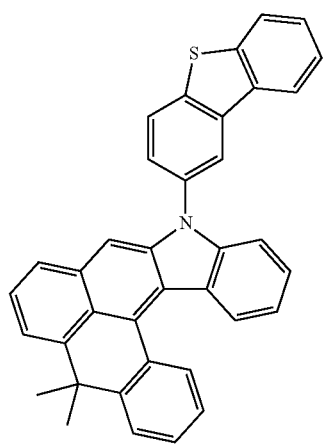
2-1-22
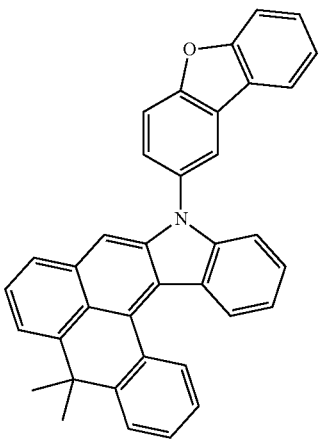
2-1-23
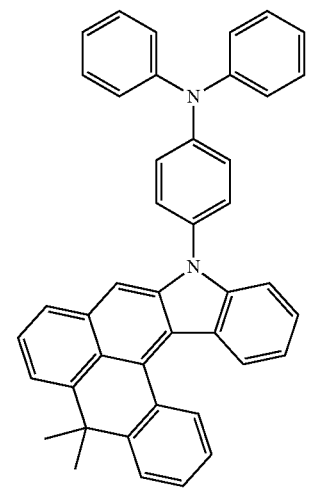
2-1-24
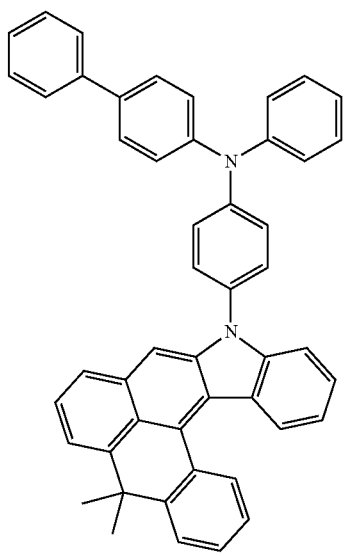

2-1-25
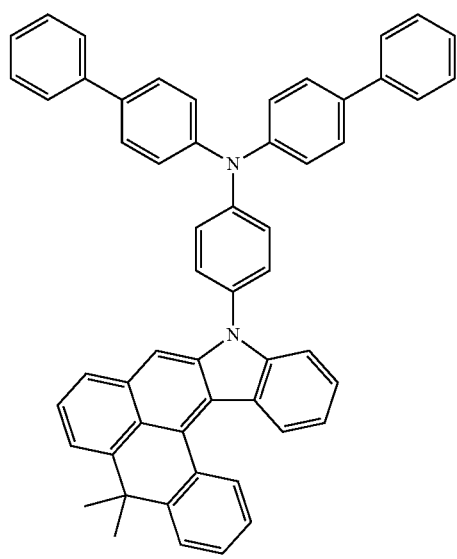
2-1-26
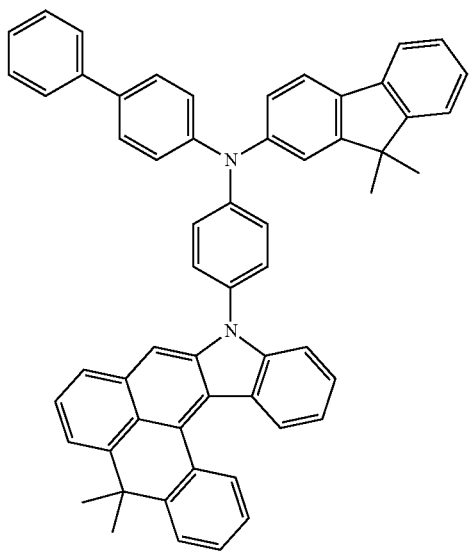
2-1-27
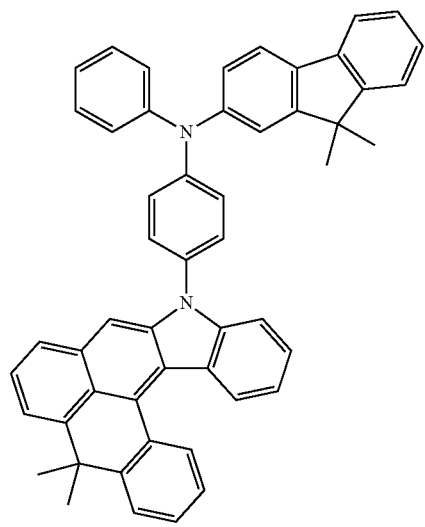
2-1-28
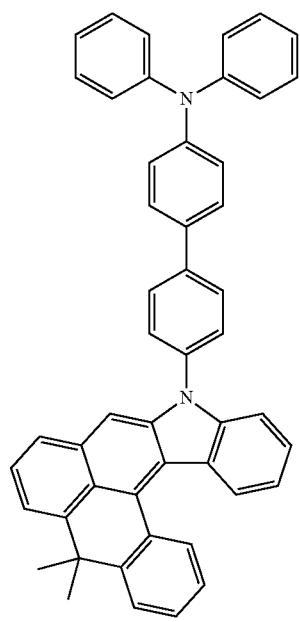
2-1-29
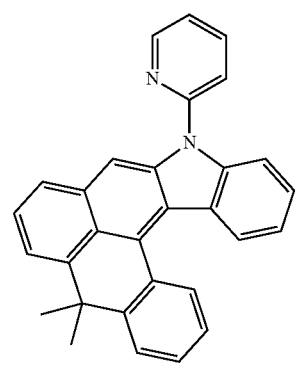
2-1-30
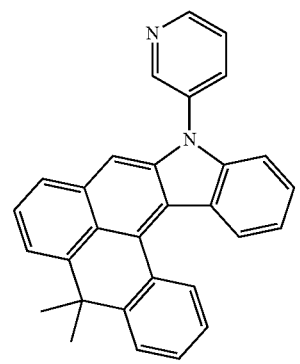

2-1-31
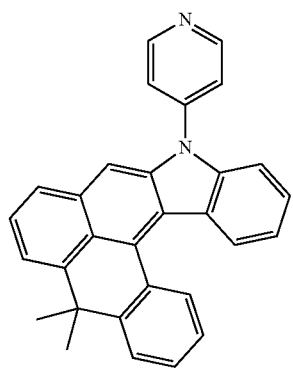
2-1-32
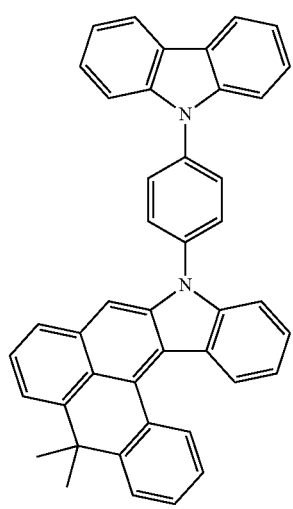
2-1-33
2-1-34
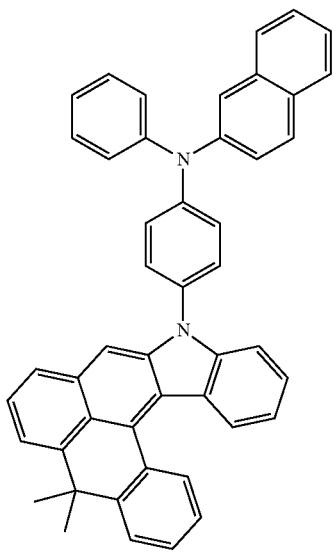
2-1-35
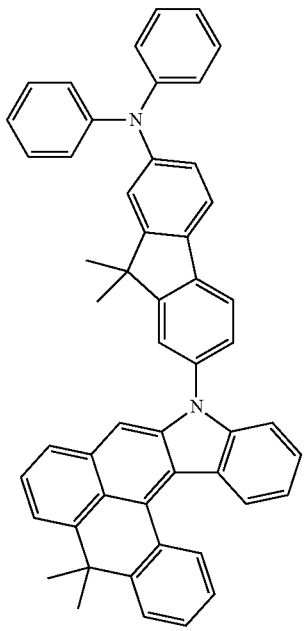

2-1-36
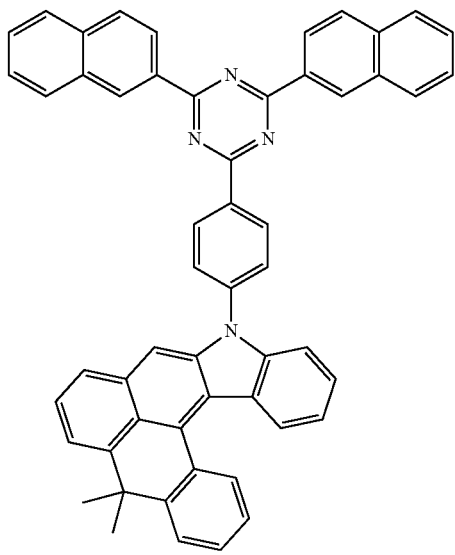
2-1-37
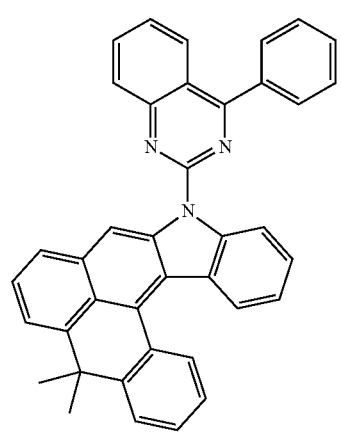
2-1-38
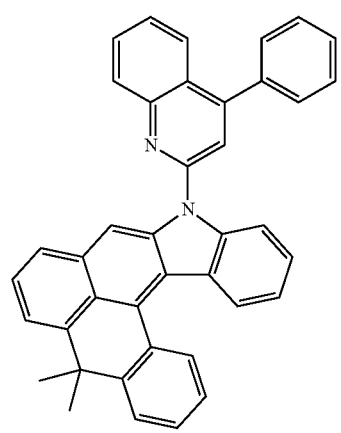
2-1-39
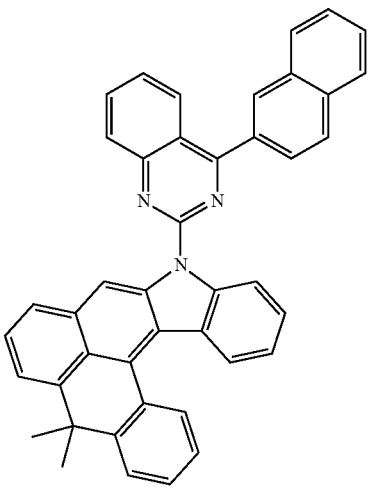
2-1-40
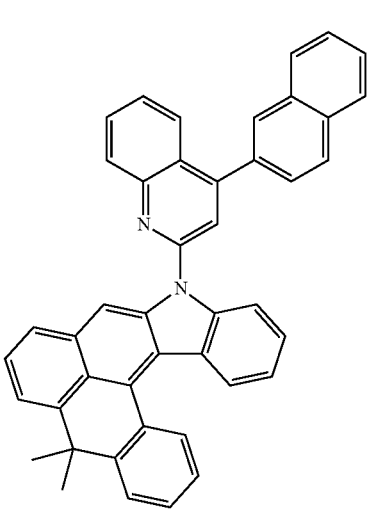
2-1-41
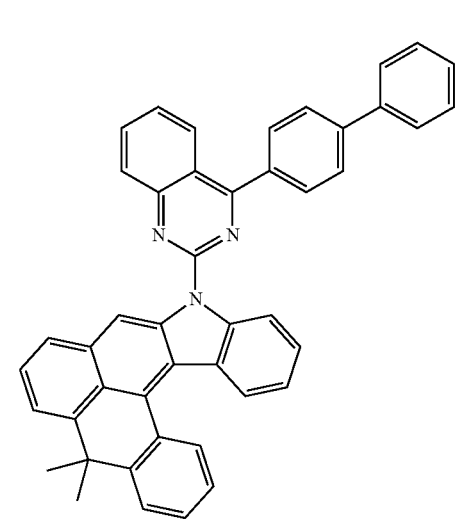

2-1-42
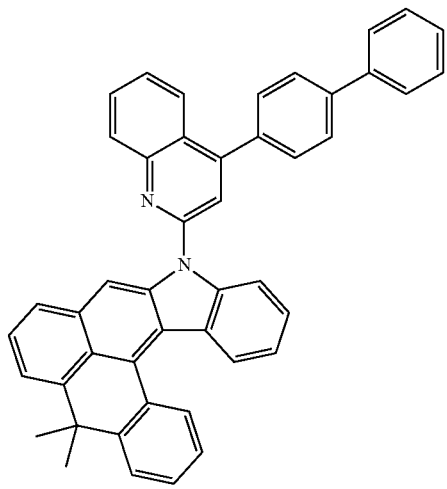
2-1-43
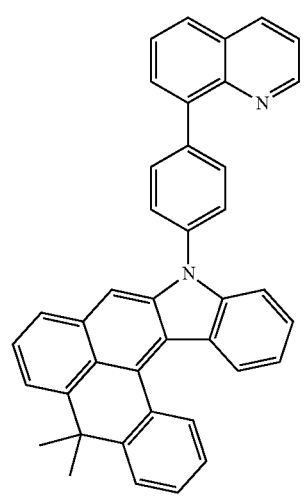
2-1-44
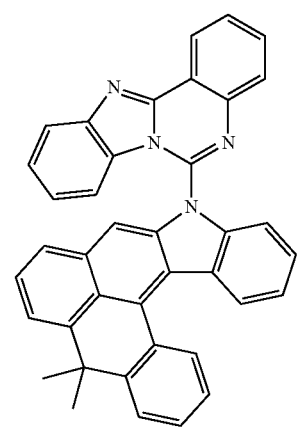
2-1-45
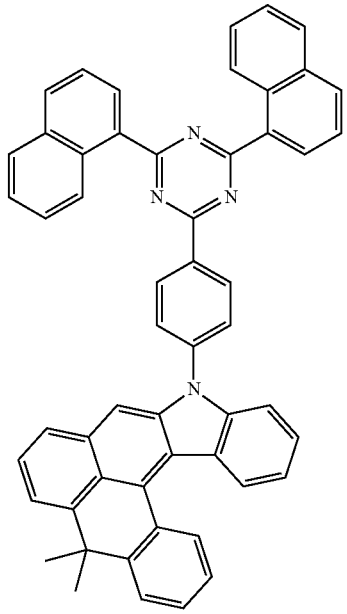
2-1-46
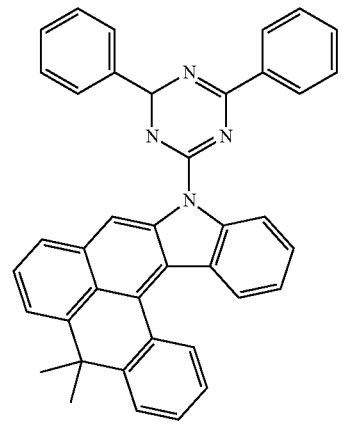
2-1-47

2-1-48
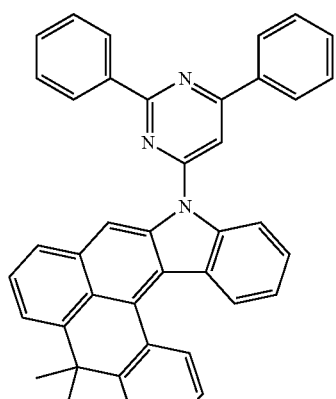
2-1-49
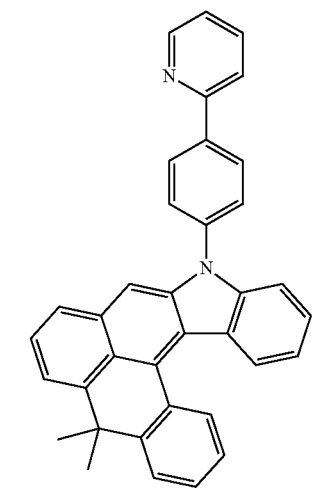
2-1-50
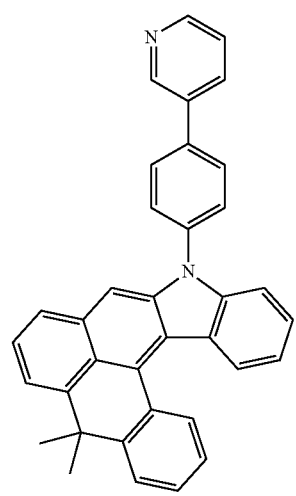
2-1-51
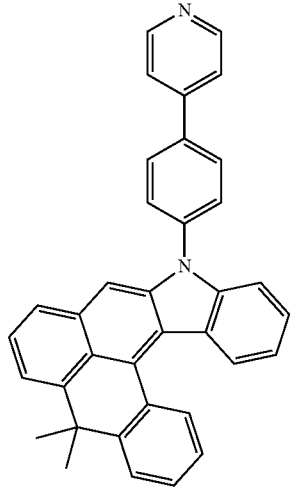
2-1-52
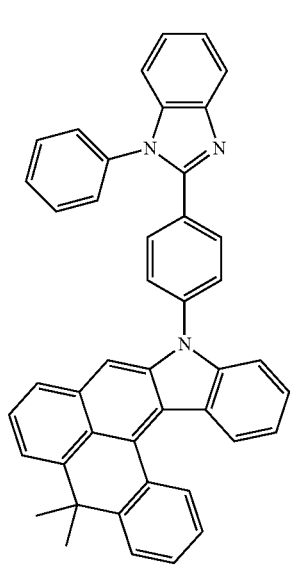
2-1-53
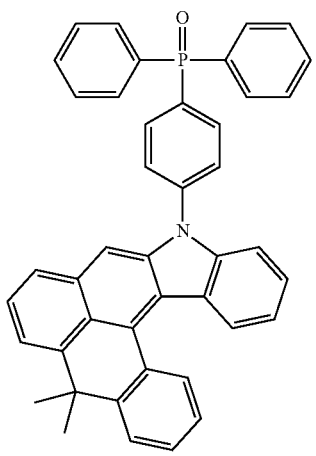

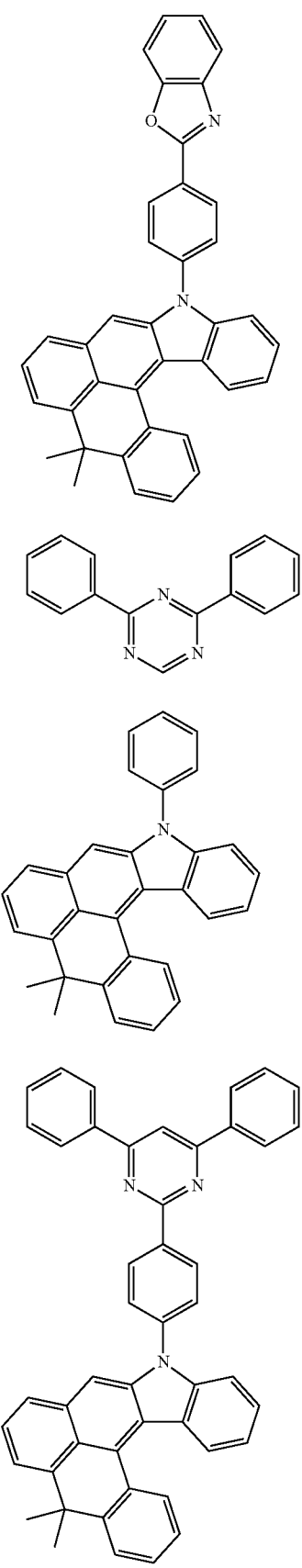
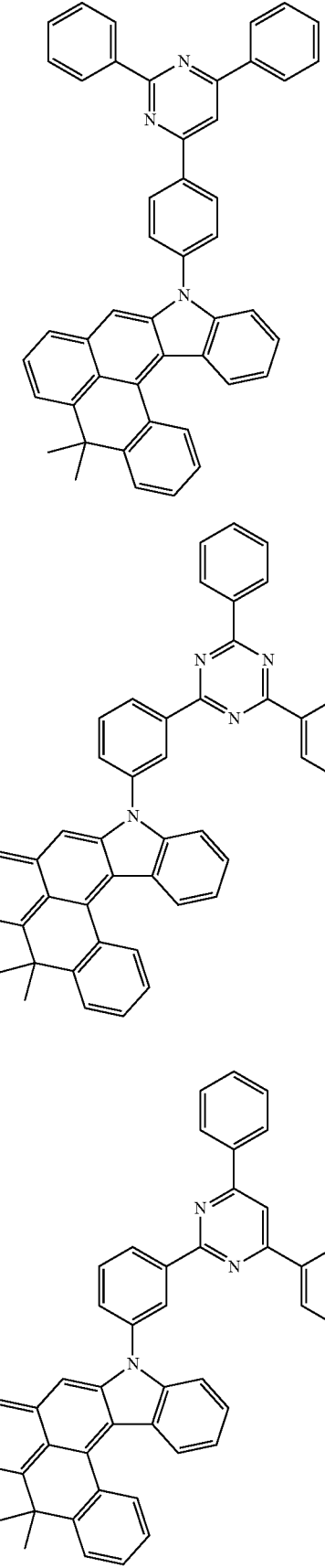

2-1-60
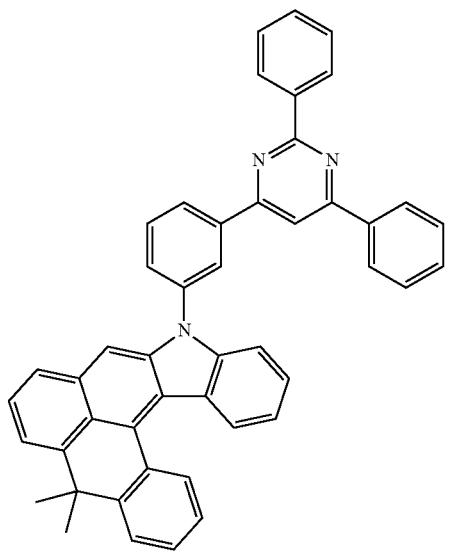
2-1-61
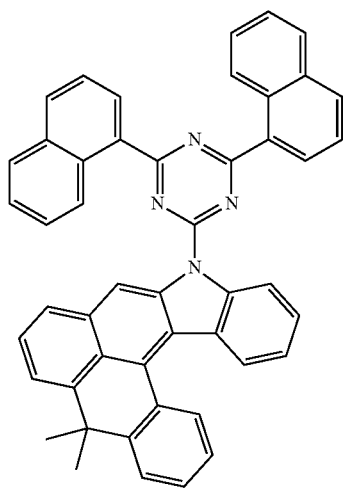
2-1-62
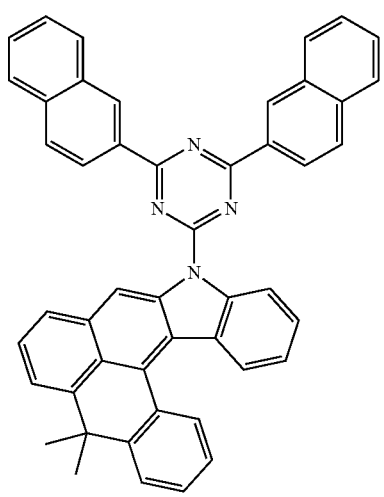
2-1-63
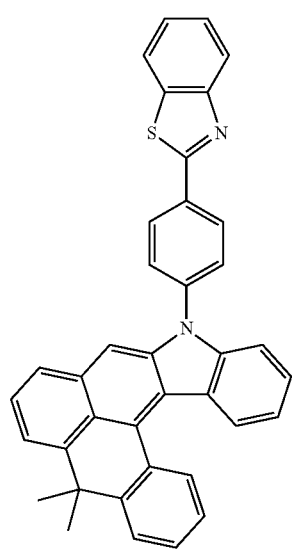
2-1-64
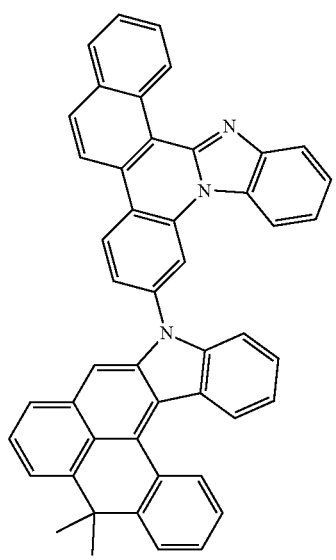
2-1-65
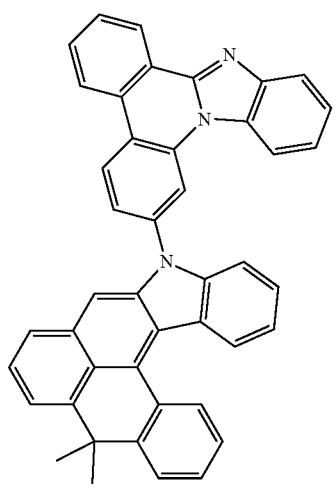

2-1-66
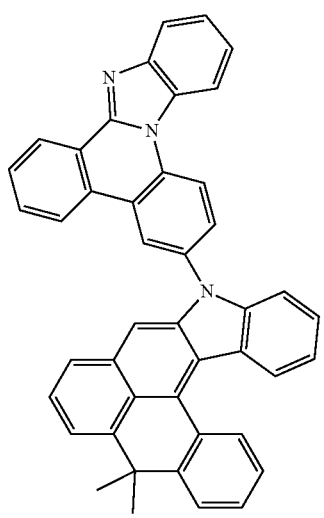
2-1-67
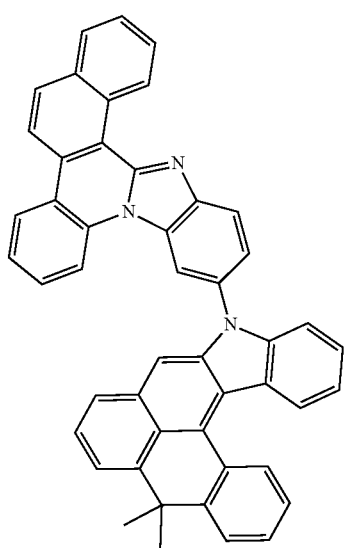
2-1-68
2-1-69
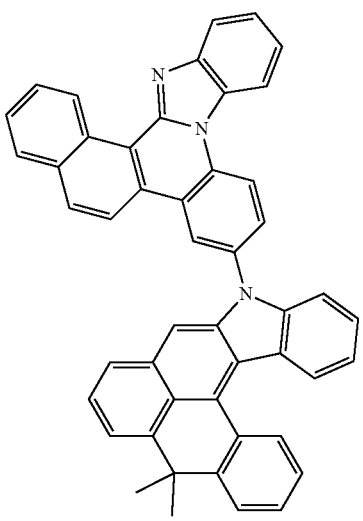
2-1-70
2-1-71
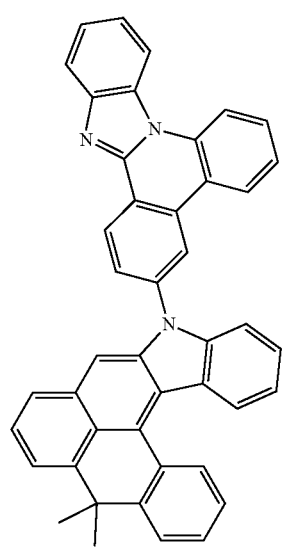

2-1-72
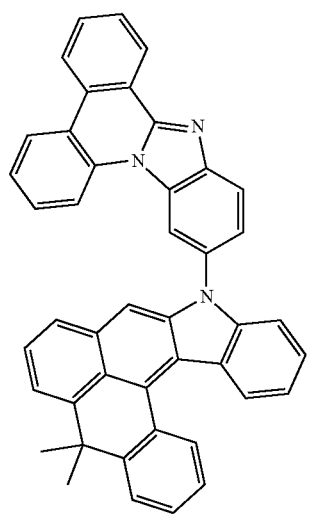
2-1-73
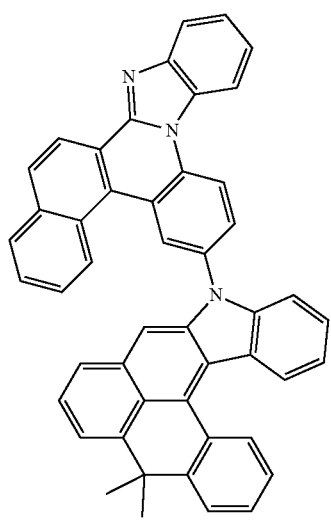
2-1-74
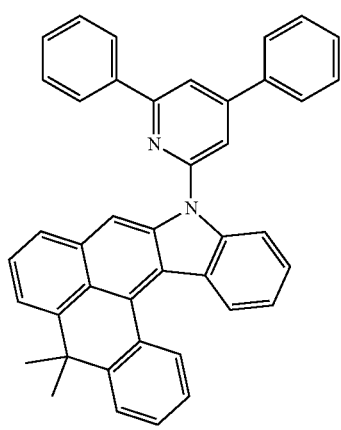
2-1-75
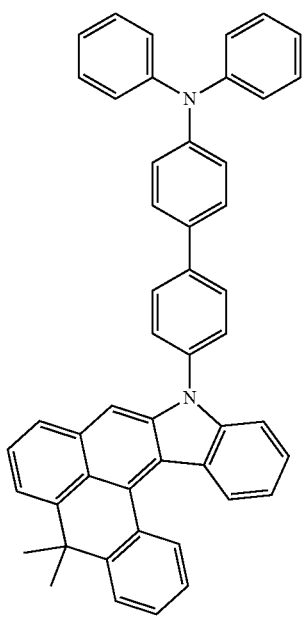
2-1-76
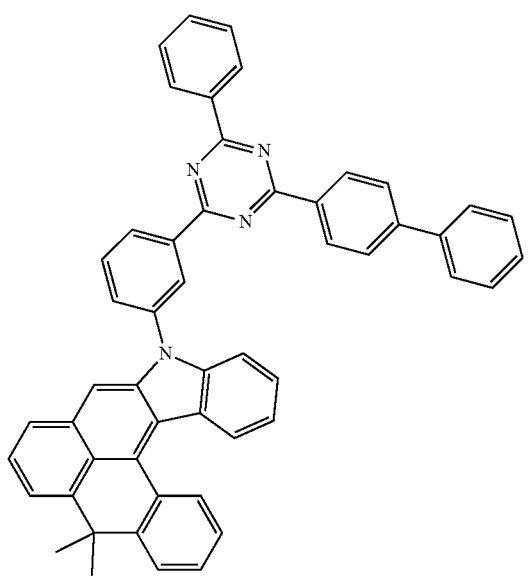

2-1-77
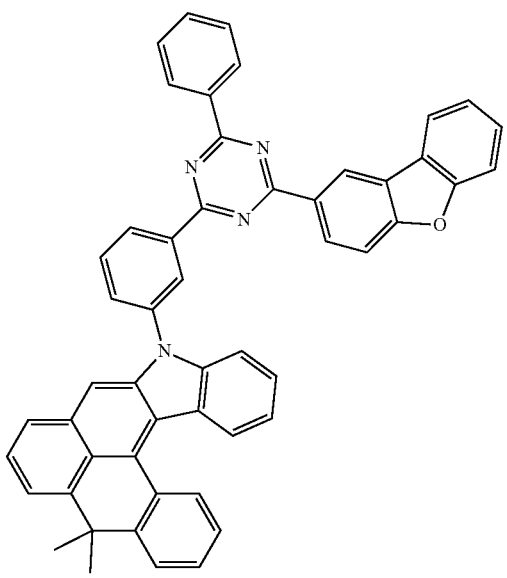
2-1-78
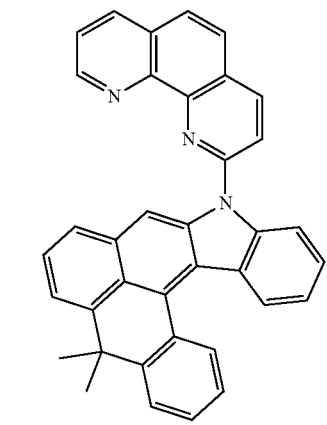
2-1-79
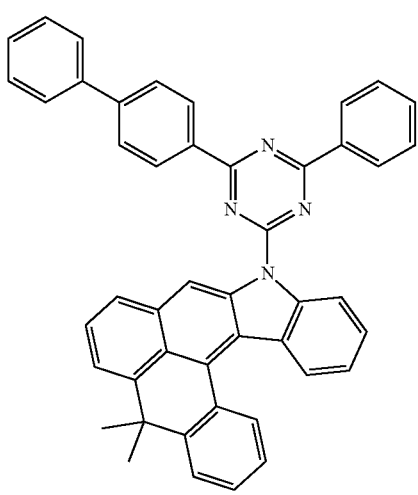
2-1-80
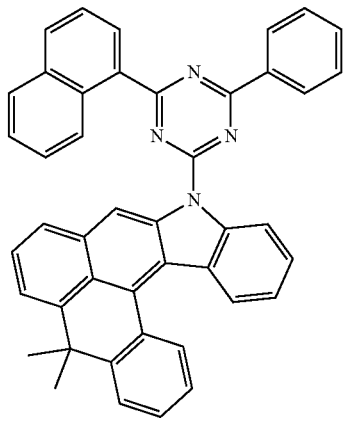
2-1-81
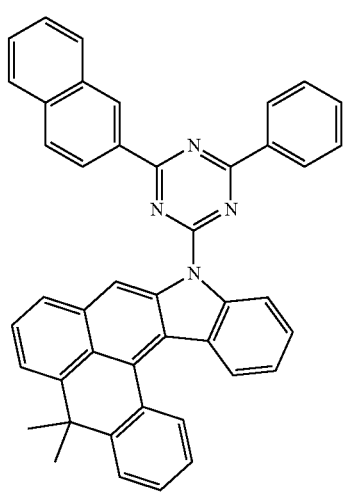
2-1-82
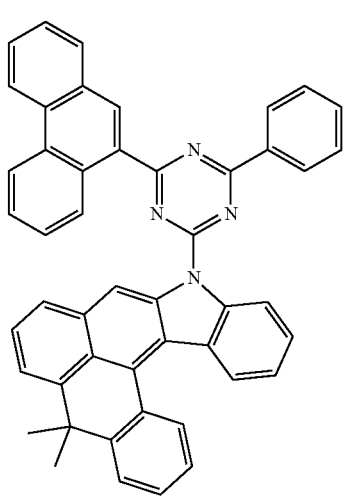

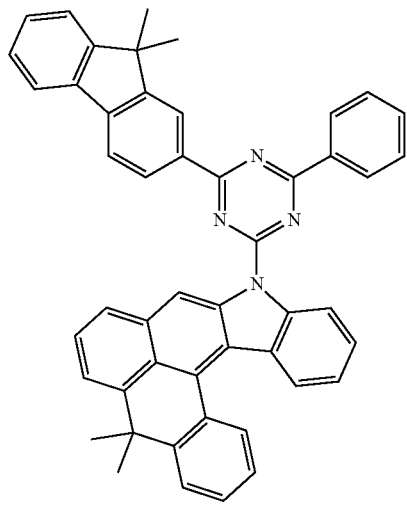
2-1-83
According to one embodiment of the present disclosure, the compound of Chemical Formula 1 may be any one selected from among the following compounds.
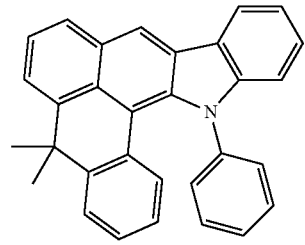
2-2-1
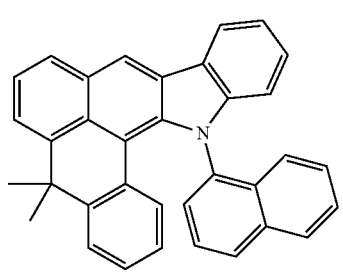
2-2-2
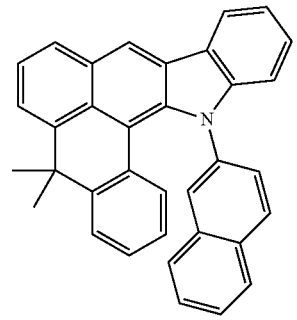
2-2-3
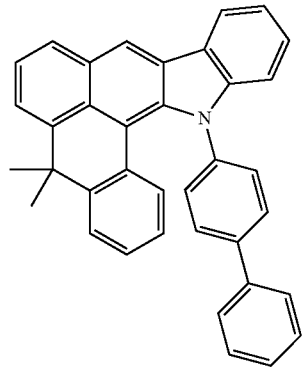
2-2-4
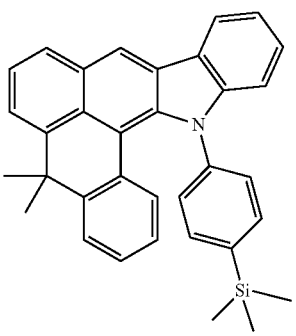
2-2-5
2-2-6
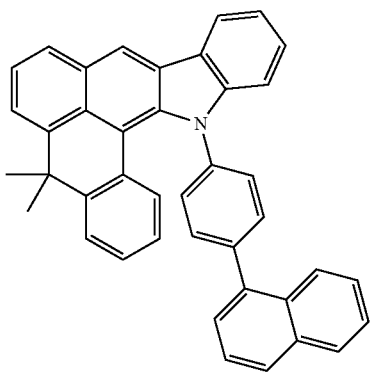
2-2-7

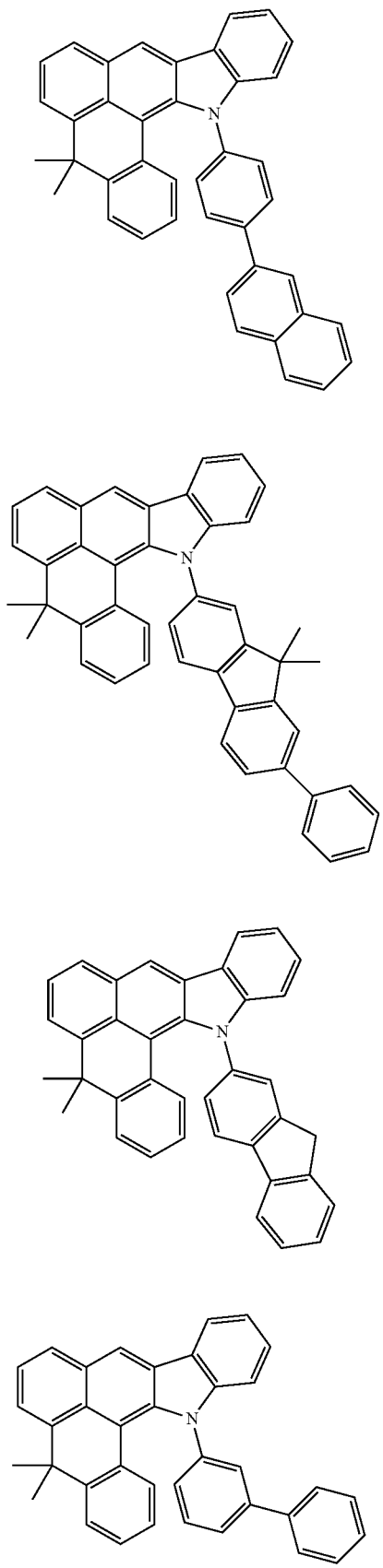
2-2-8
2-2-9
2-2-10
2-2-11
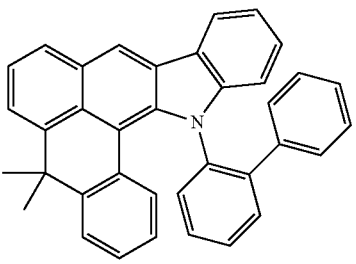
2-2-12
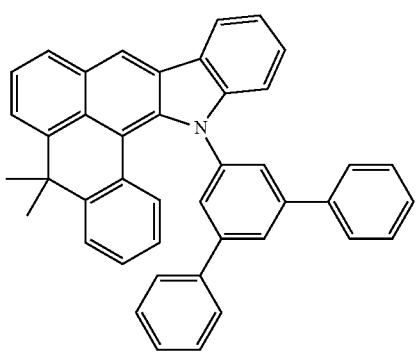
2-2-13
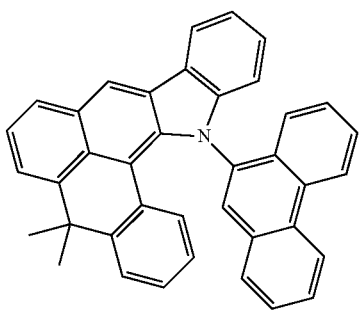
2-2-14
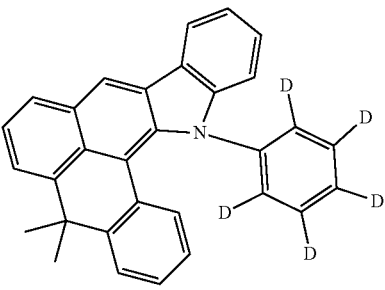
2-2-15
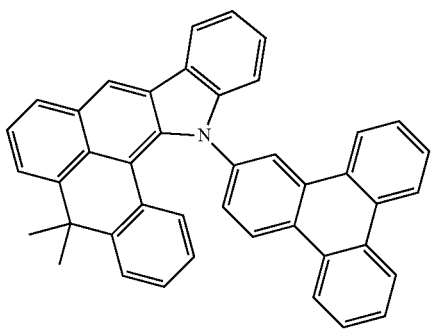
2-2-16

-continued
2-2-17
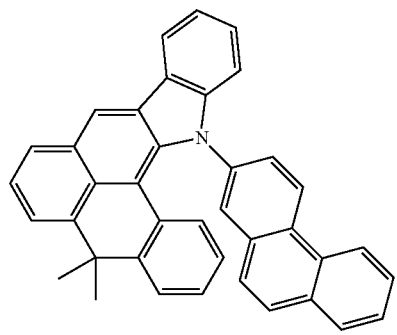
2-2-18
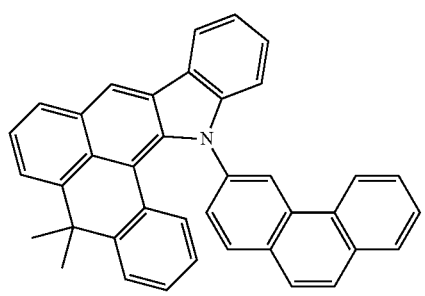
2-2-19
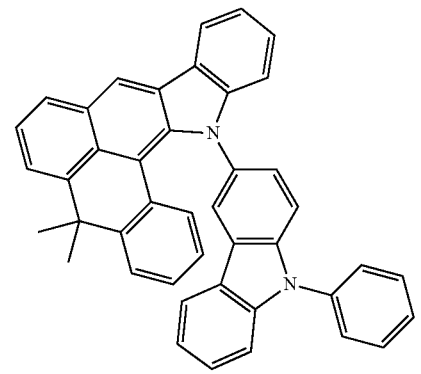
2-2-20
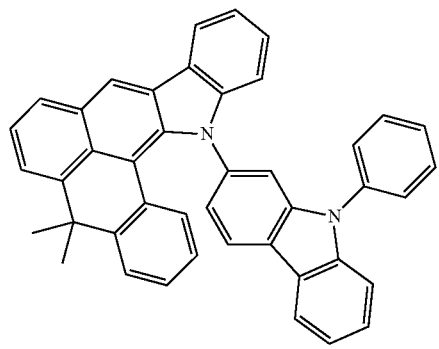
2-2-21
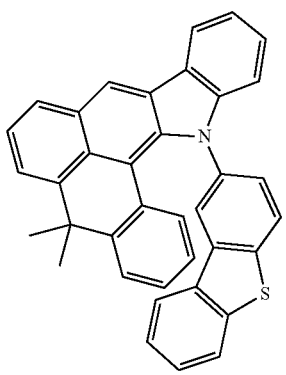
2-2-22
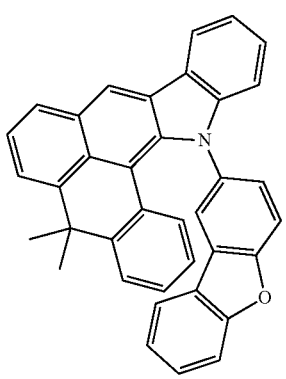
2-2-23
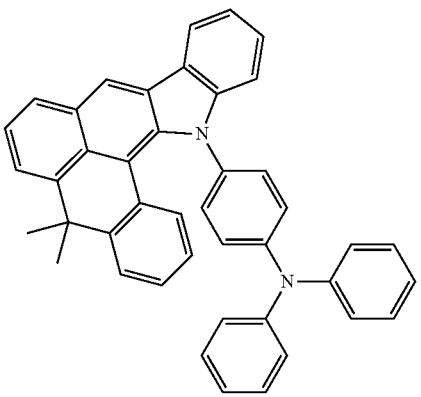
2-2-24
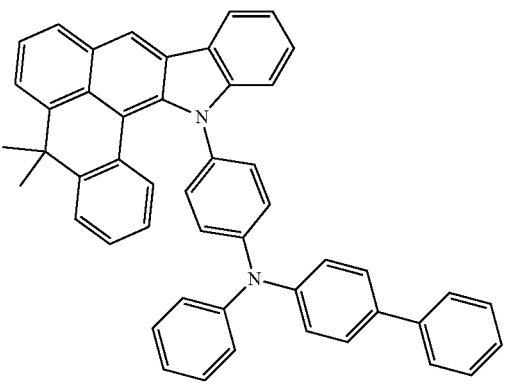

2-2-25
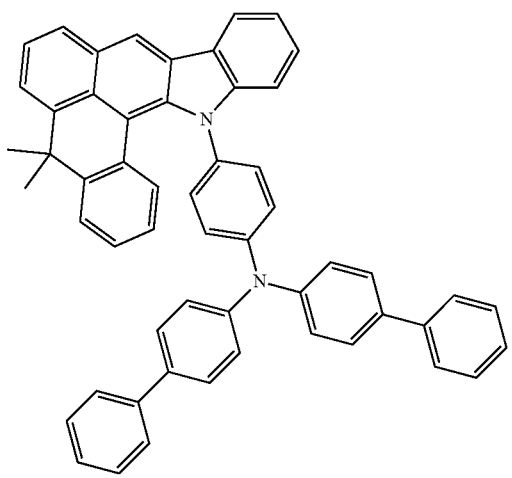
2-2-28
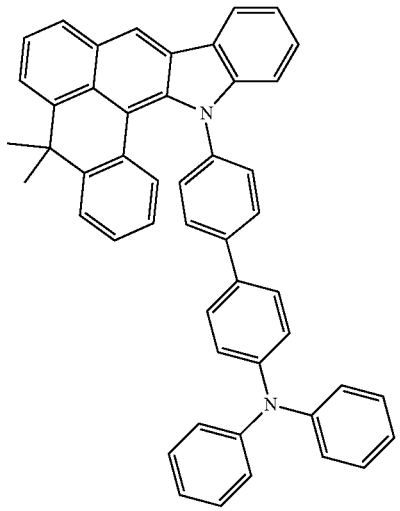
2-2-26
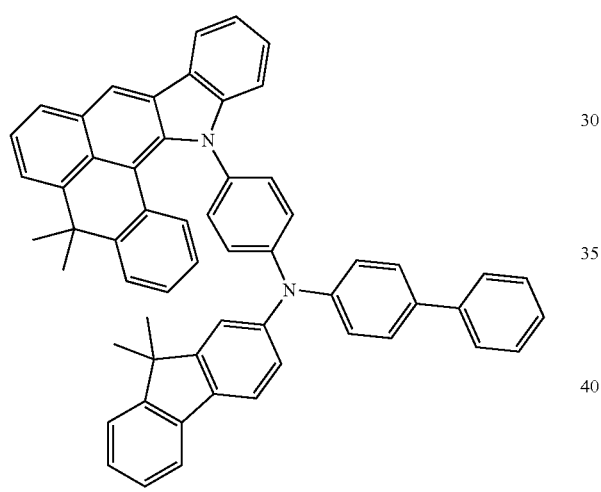
2-2-29
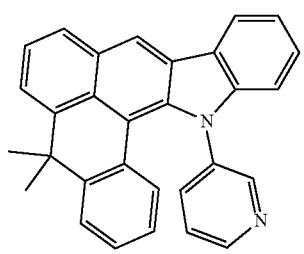
2-2-30
2-2-27
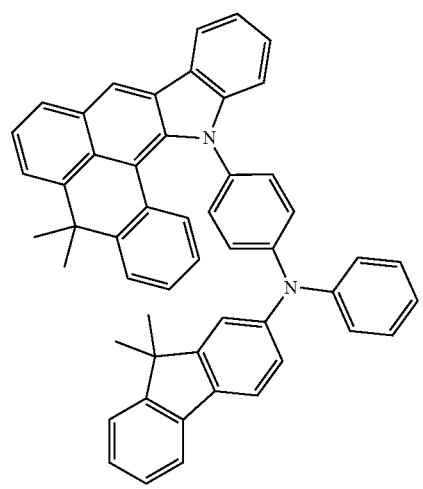
2-2-31
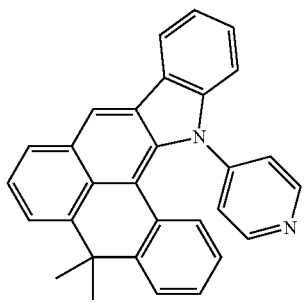

2-2-32 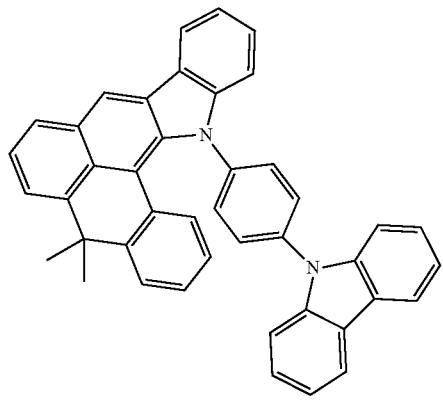
2-2-33 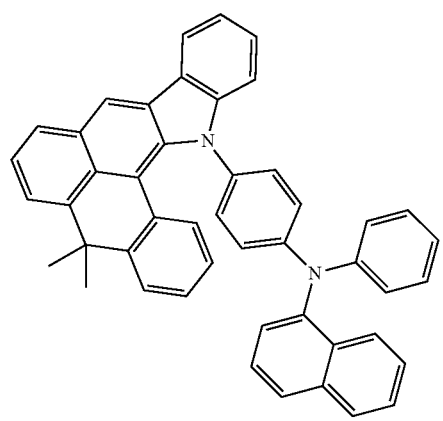
2-2-34 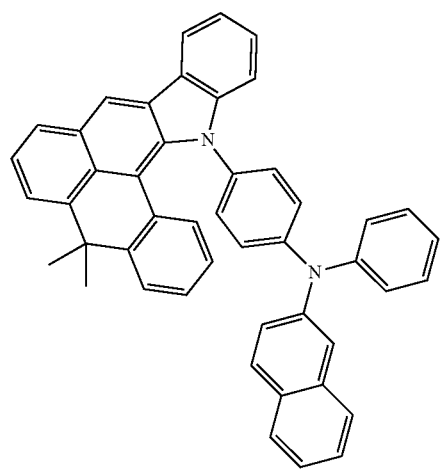
2-2-35 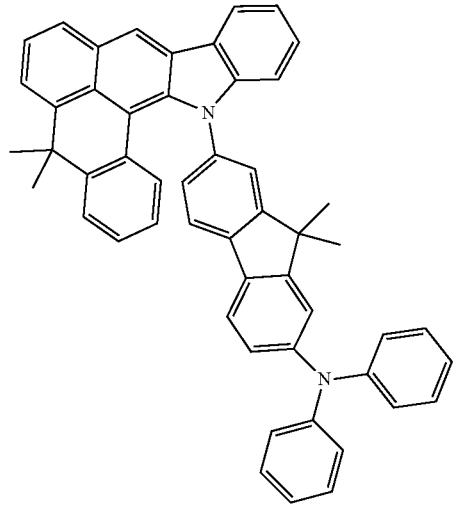
2-2-36 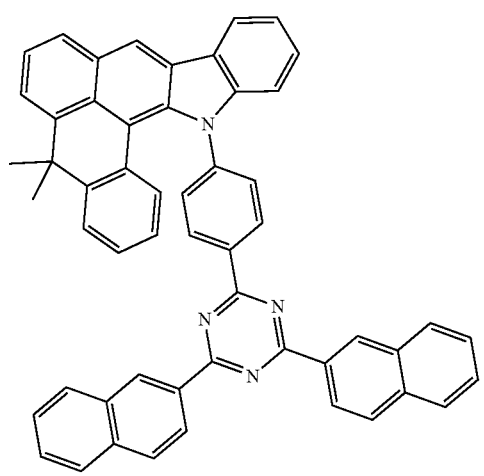
2-2-37 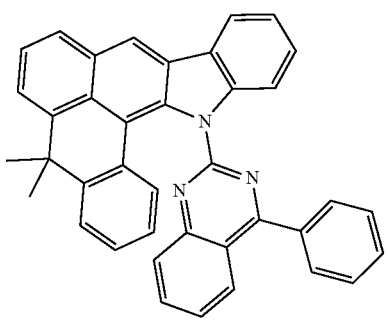
2-2-38 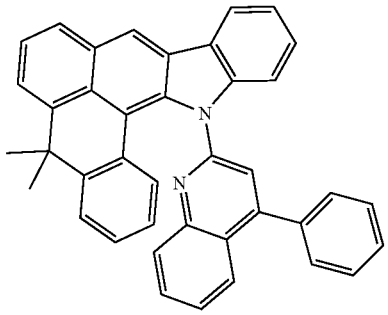

97
-continued
2-2-39
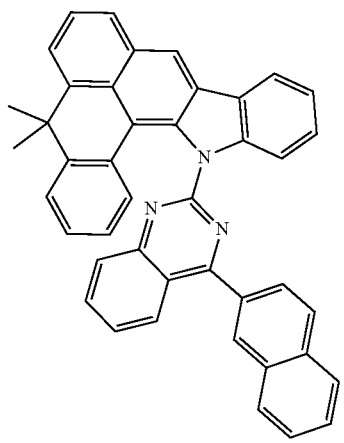
2-2-40
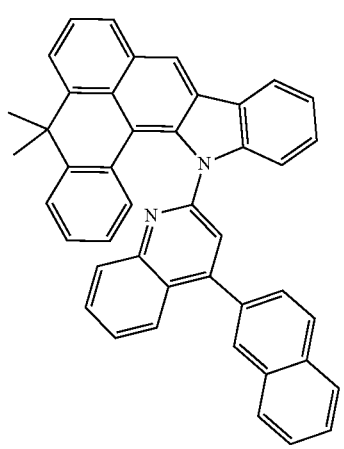
2-2-41
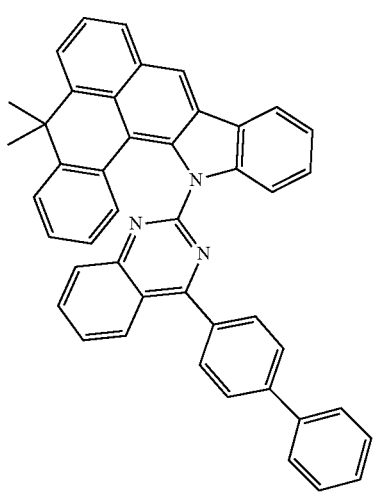
98
-continued
2-2-42
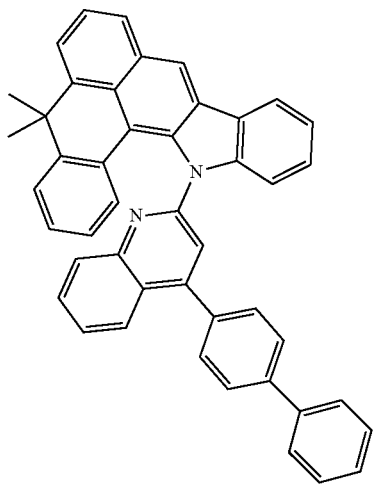
2-2-43
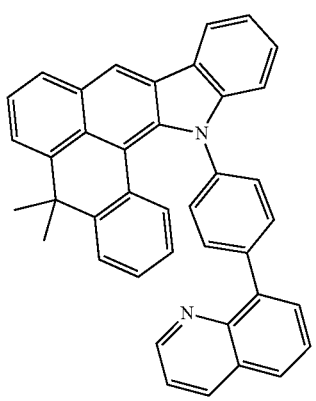
2-2-44
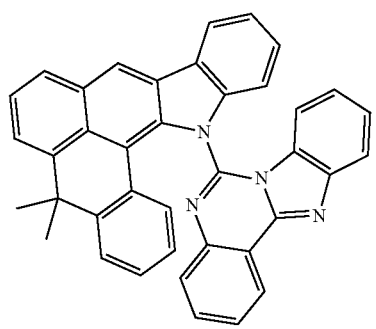

-continued
2-2-45
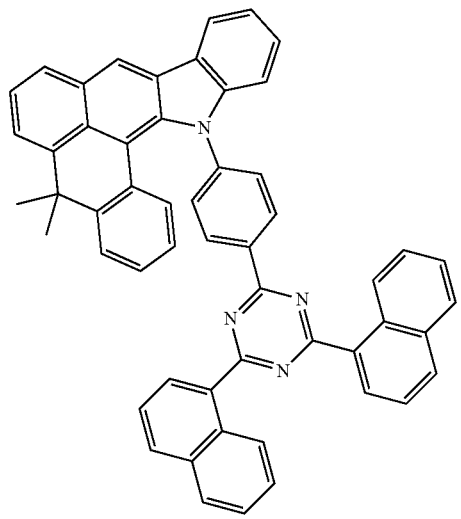
2-2-46
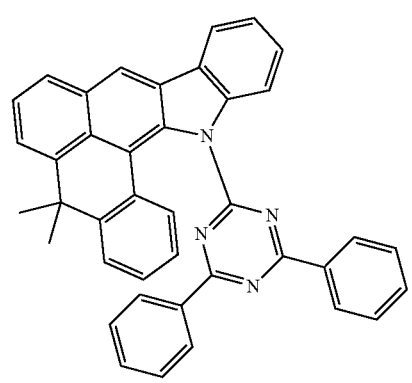
2-2-47
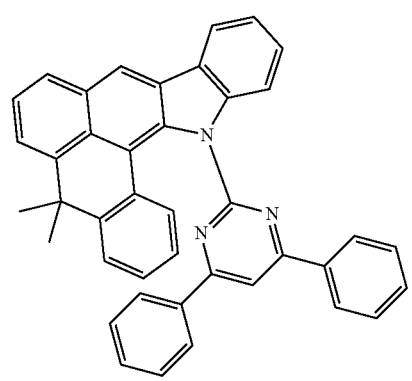
2-2-48
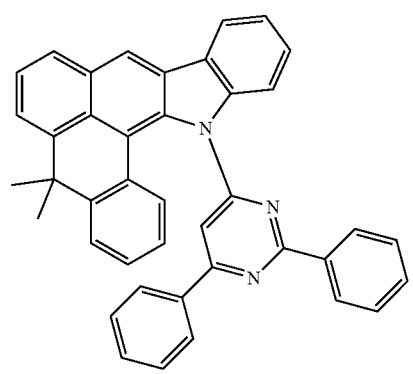
-continued
2-2-49
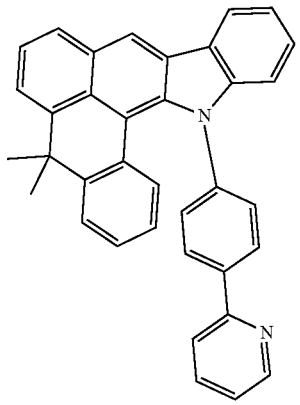
2-2-50
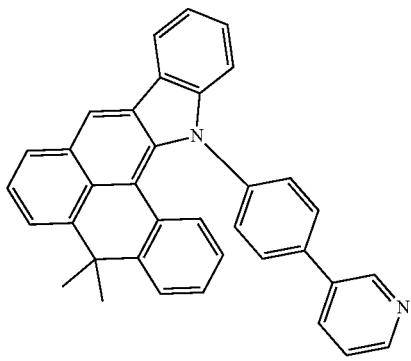
2-2-51
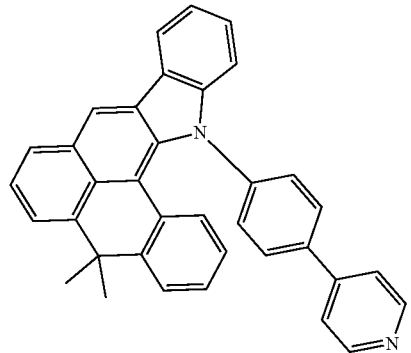
2-2-52
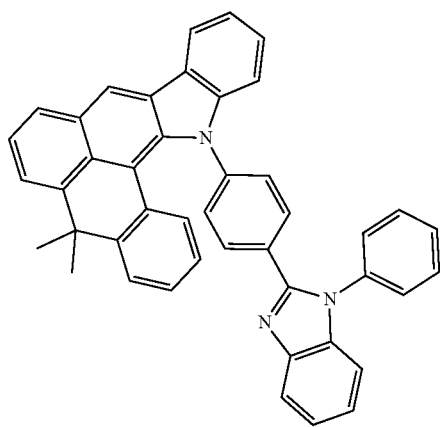

2-2-53
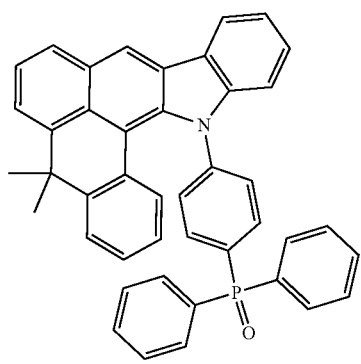
2-2-54
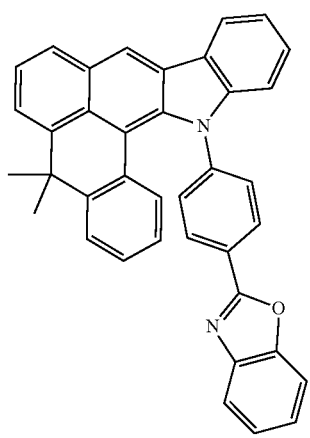
2-2-55
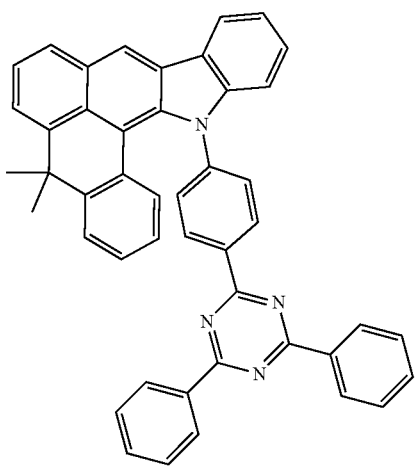
2-2-56
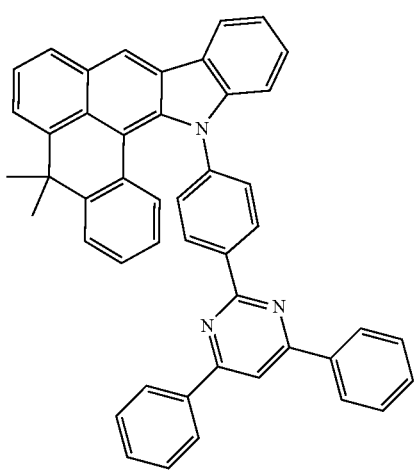
2-2-57
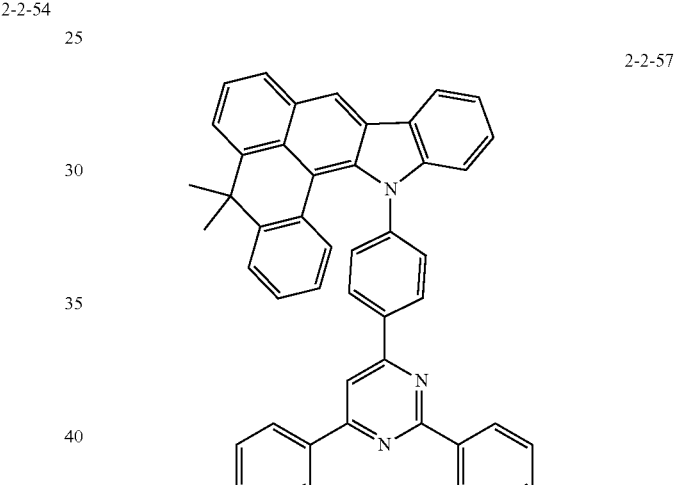
2-2-58
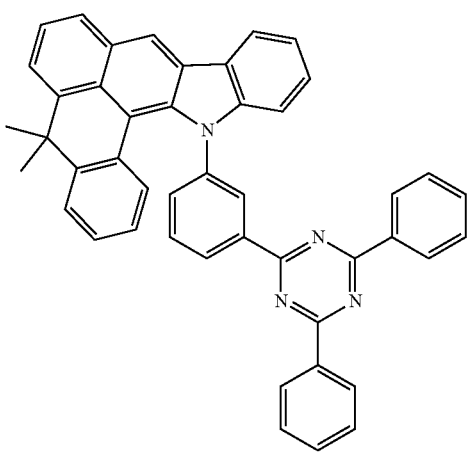

103
-continued
2-2-59
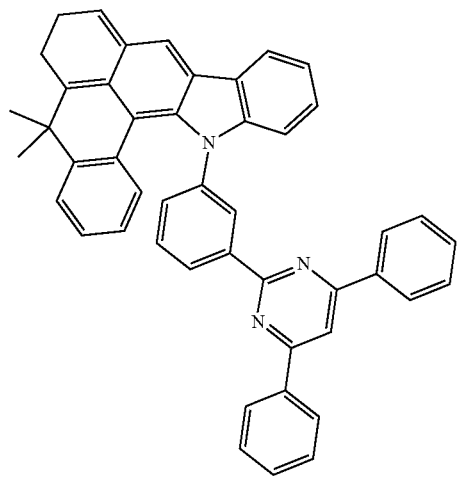
2-2-60
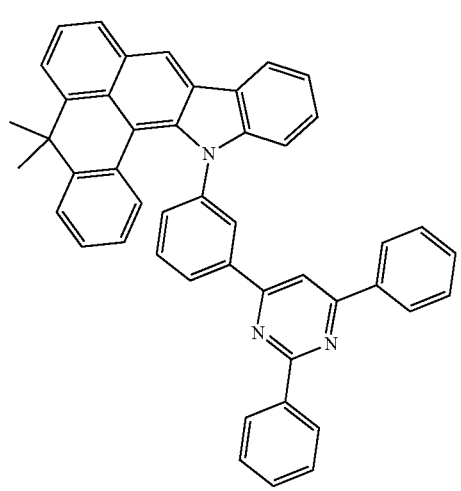
2-2-61
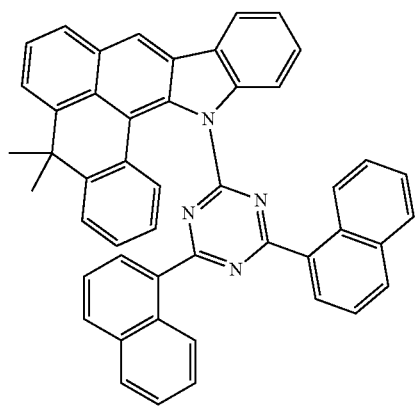
104
-continued
2-2-62
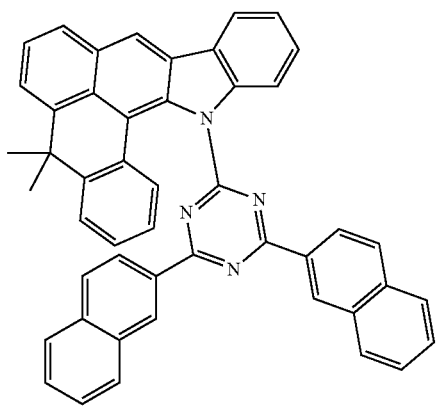
2-2-63
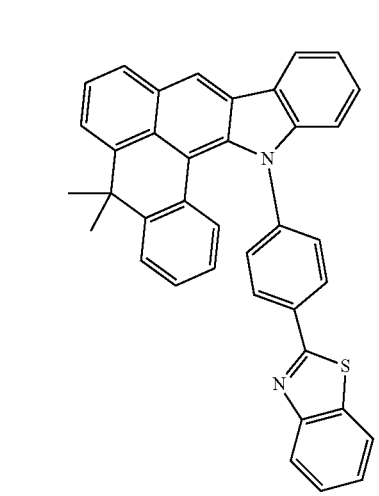
2-2-64
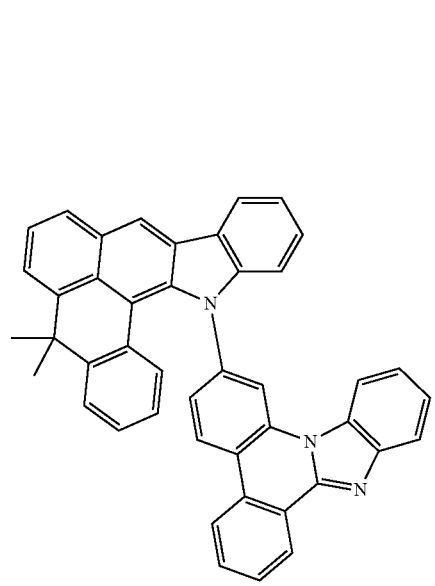

2-2-65
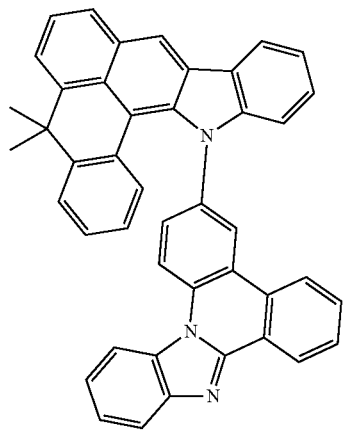
2-2-66
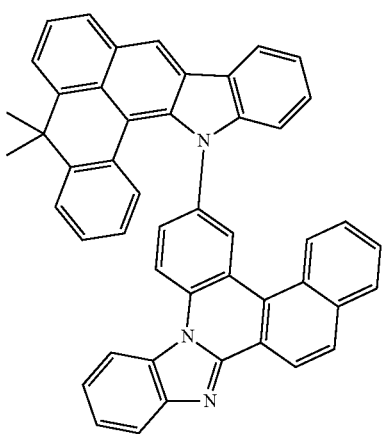
2-2-67
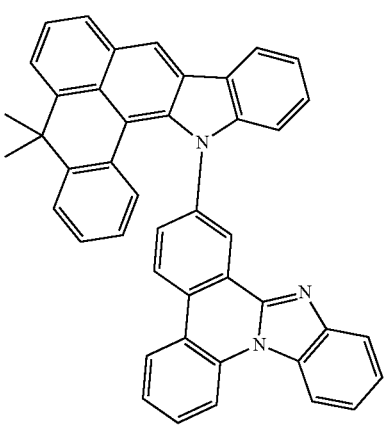
2-2-68
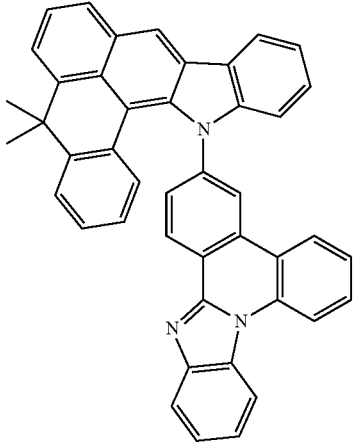
2-2-69
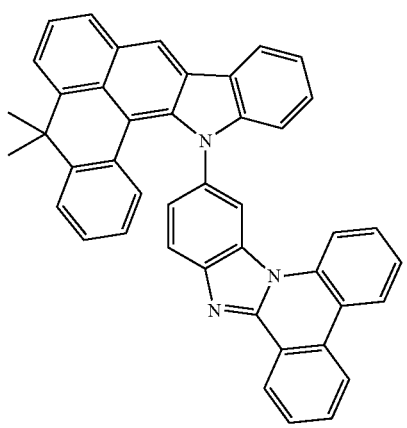
2-2-70
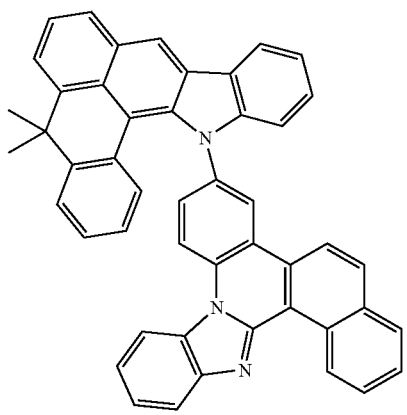

2-2-71
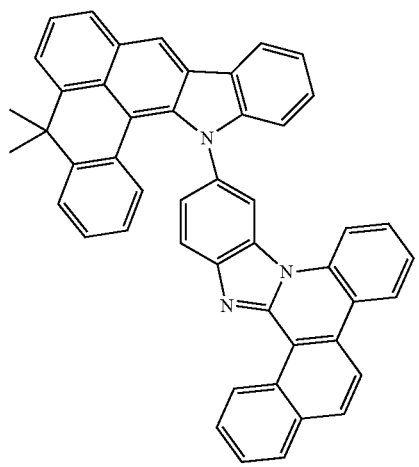
2-2-72
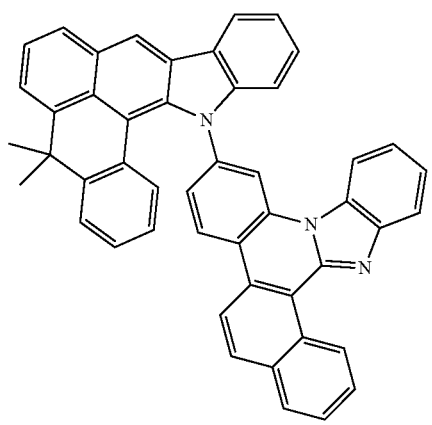
2-2-73
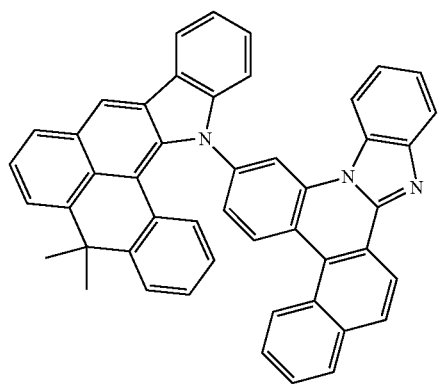
2-2-74
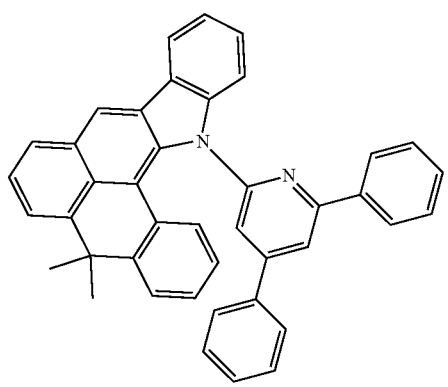
2-2-75
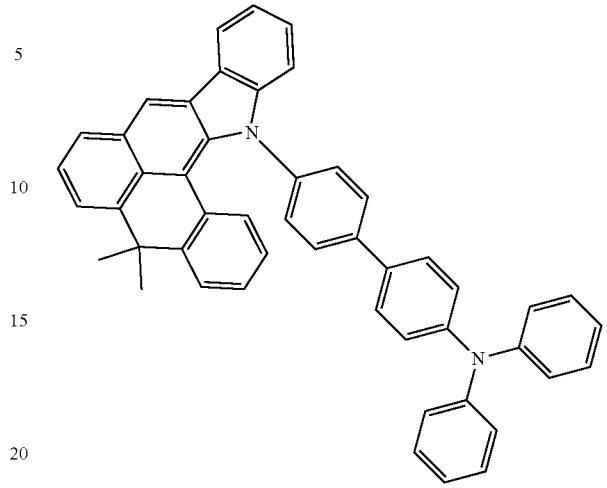
2-2-76
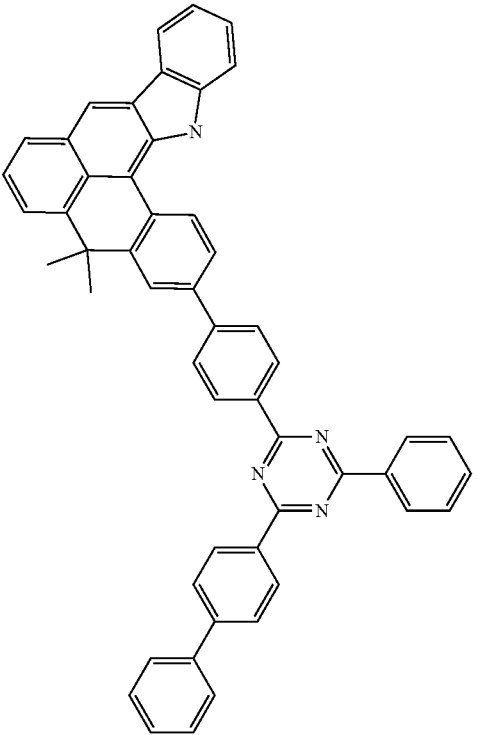

2-2-77
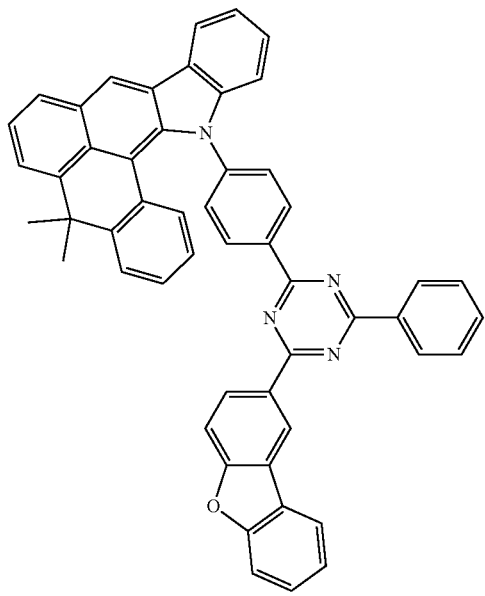
2-2-78
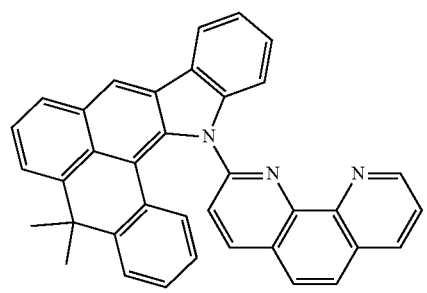
2-2-79
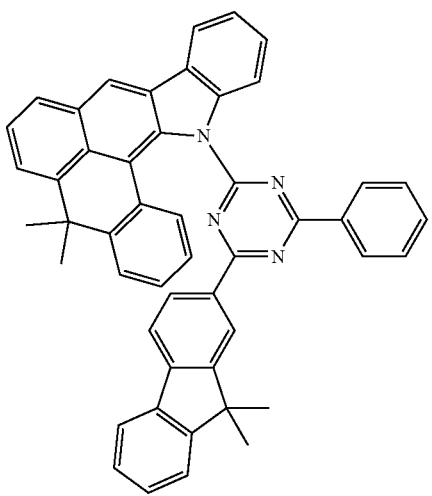
2-2-80
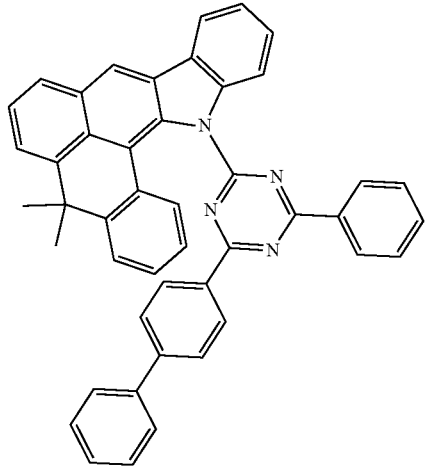
2-2-81
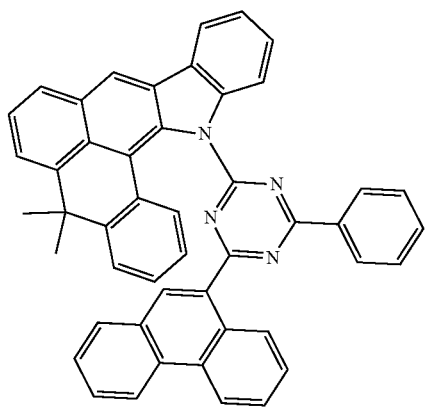
2-2-82
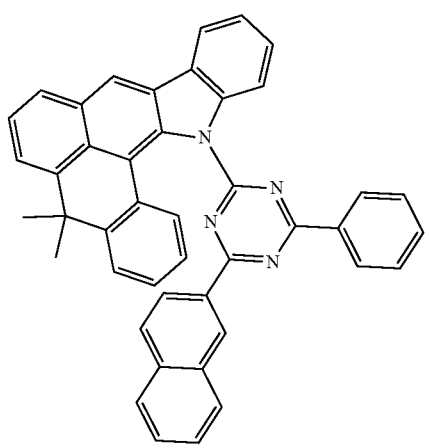

2-2-83
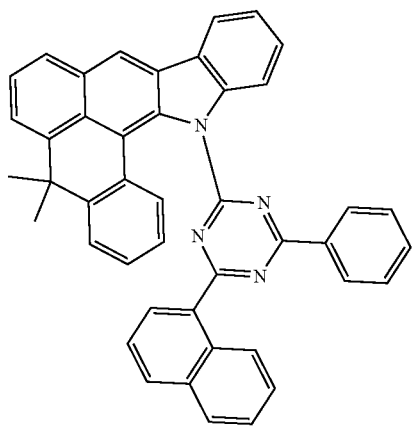
According to one embodiment of the present disclosure, the compound of Chemical Formula 1 may be any one selected from among the following compounds.
3-1
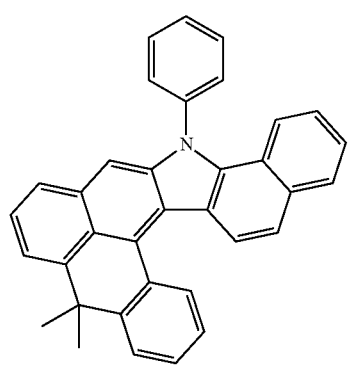
3-2
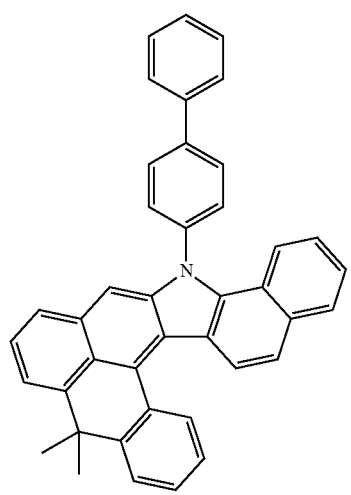
3-3
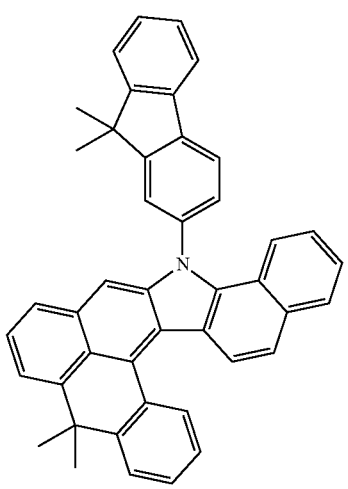
3-4
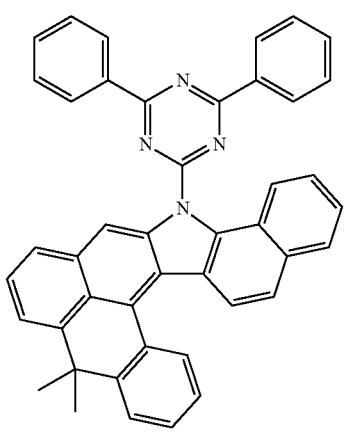
3-5
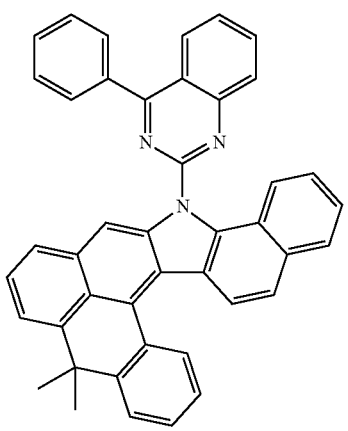

3-6
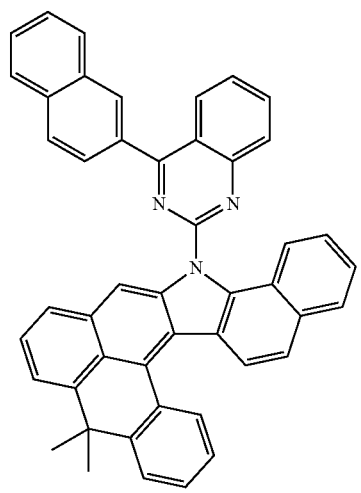
3-7
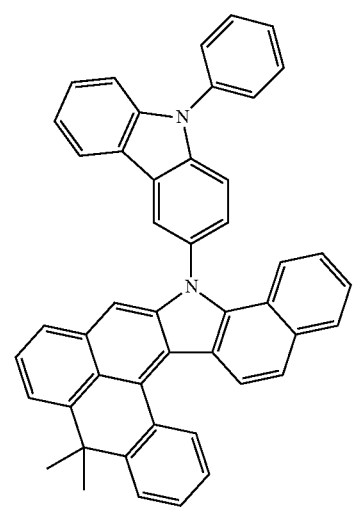
3-8
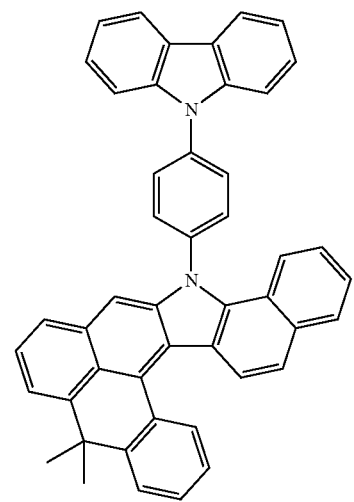
3-9
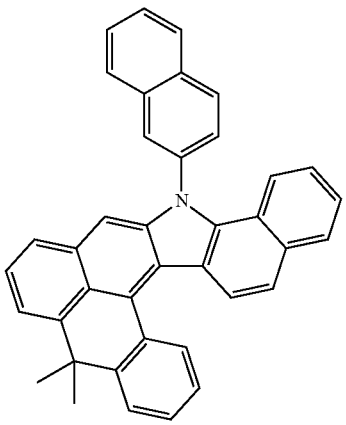
3-10
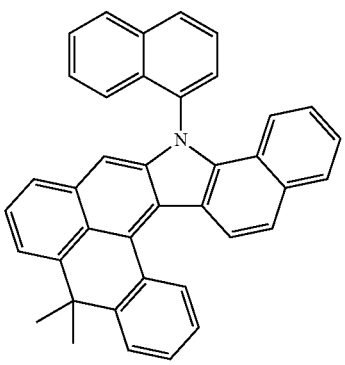
3-11
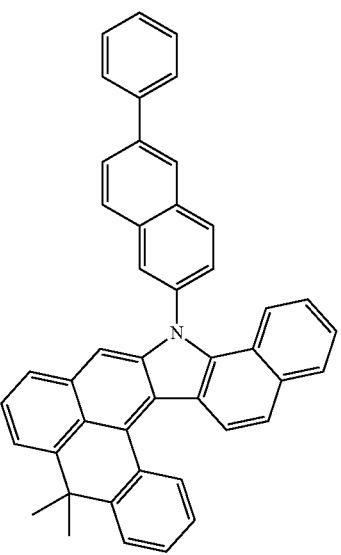

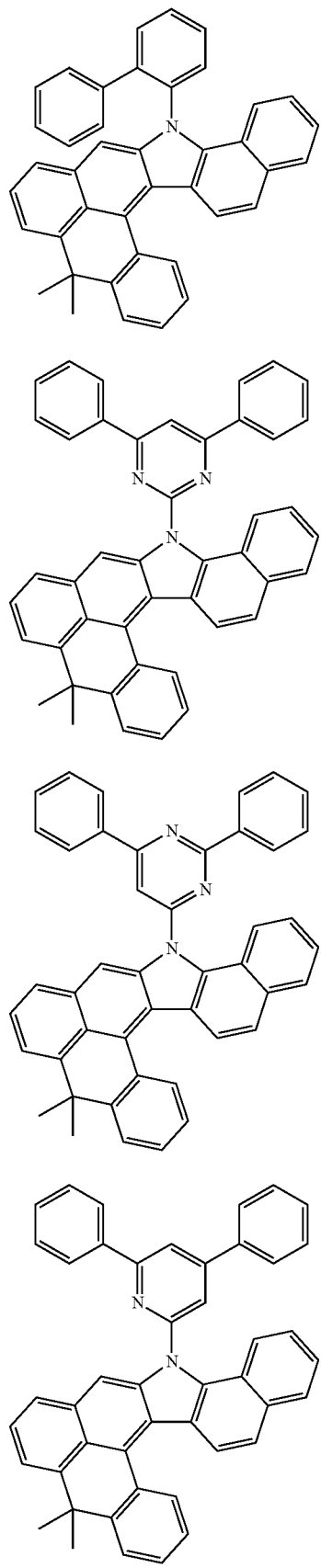
3-12
3-13
3-14
3-15
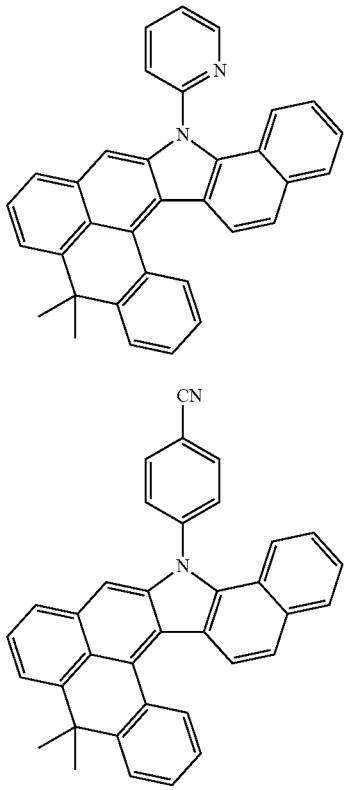
3-16
3-17
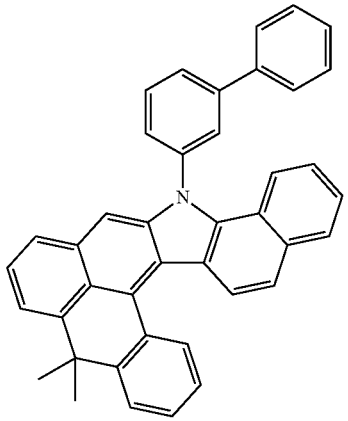
3-18
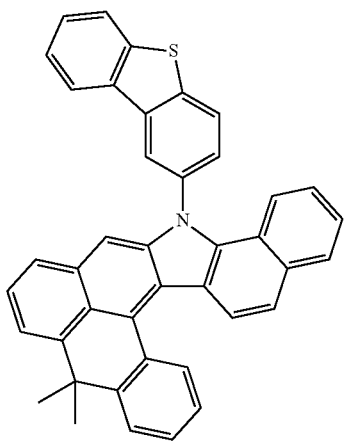
3-19

3-20
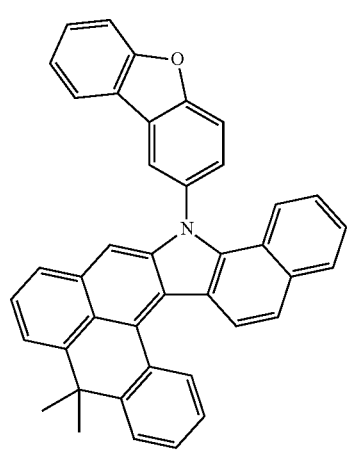
3-21
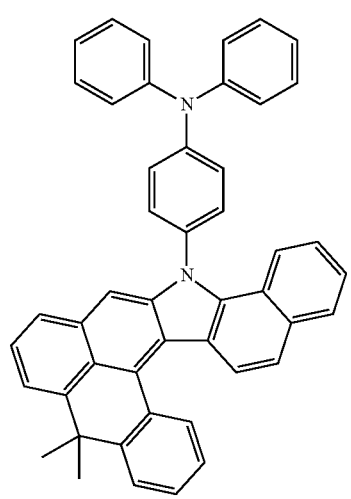
3-22
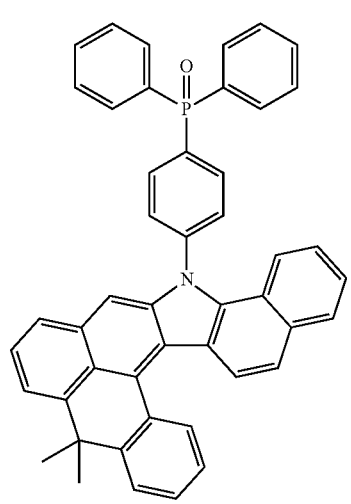
3-23
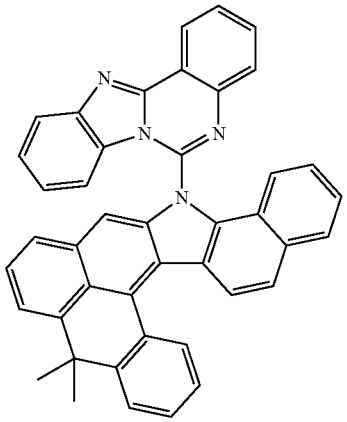
According to one embodiment of the present disclosure, the compound of Chemical Formula 1 may be any one selected from among the following compounds.
4-1
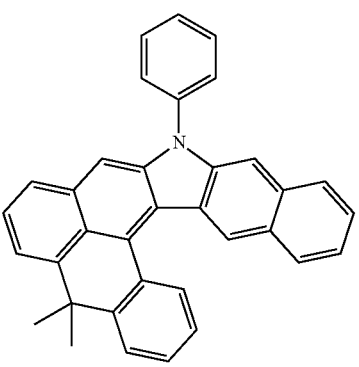
4-2
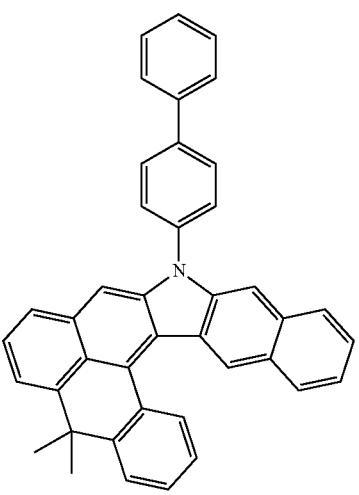

-continued
4-3
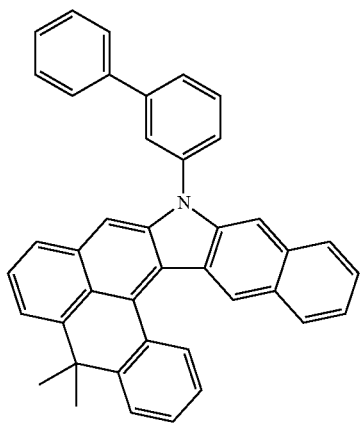
4-4
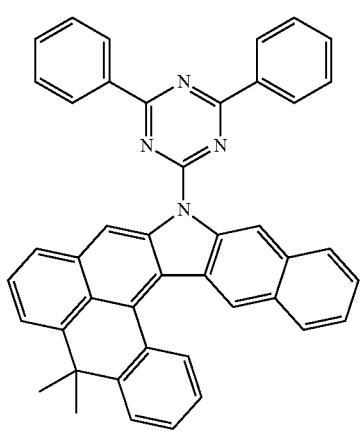
4-5
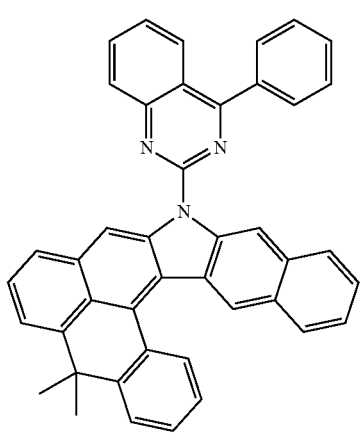
-continued
4-6
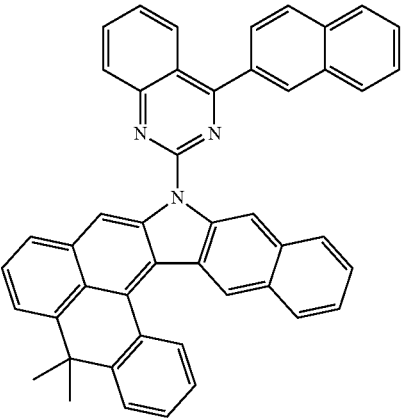
4-7
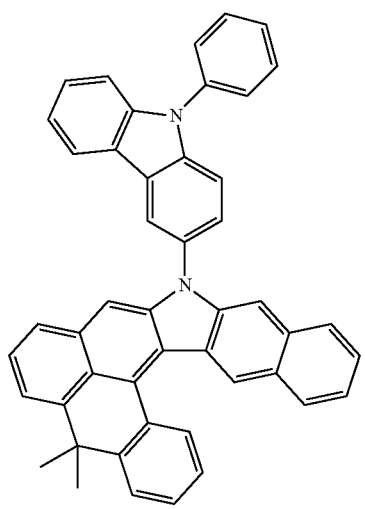
4-8
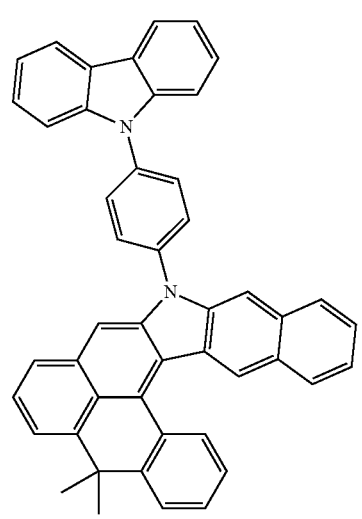

-continued
4-9
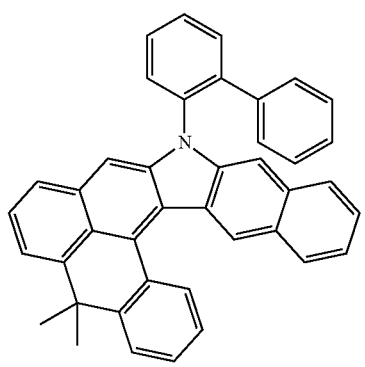
4-10
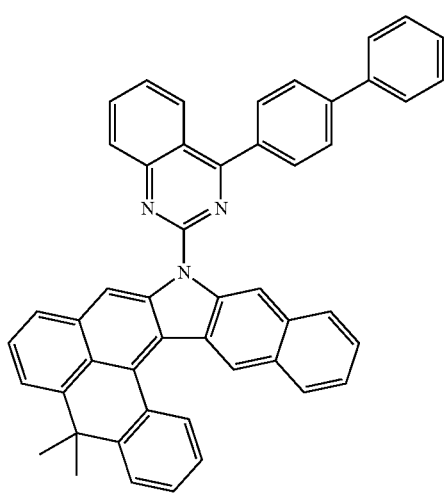
4-11
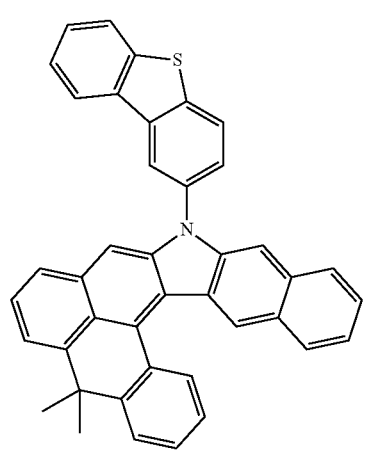
-continued
4-12
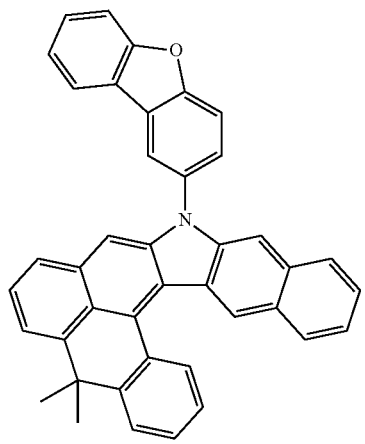
4-13
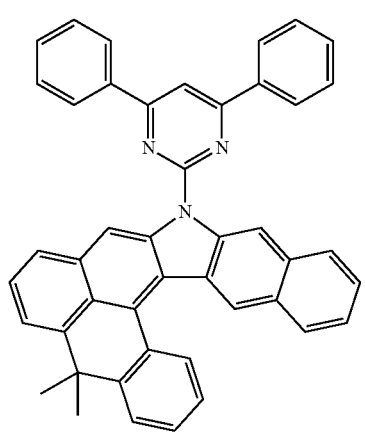
4-14
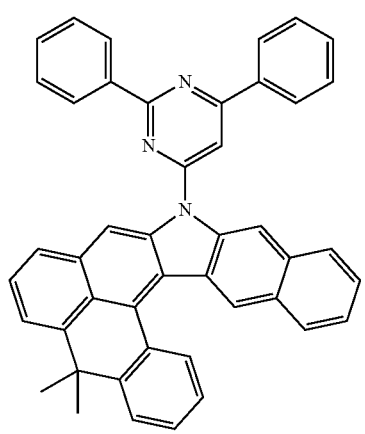

4-15
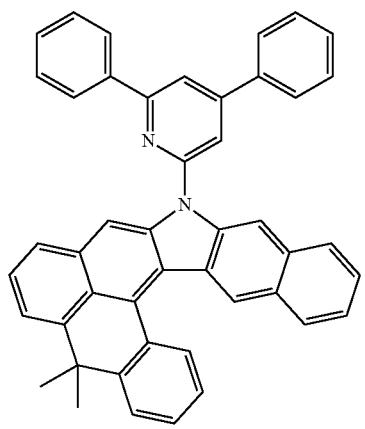
4-16
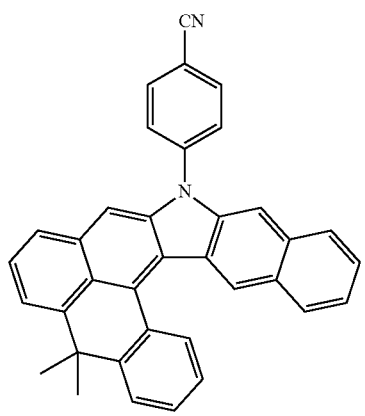
4-17
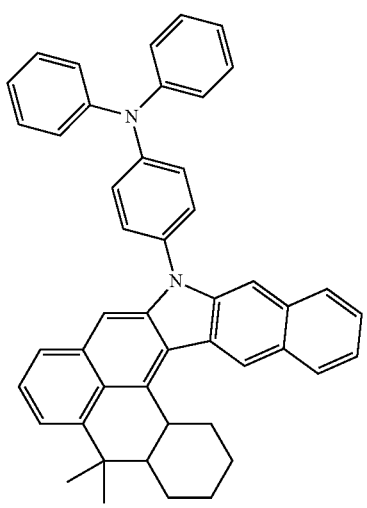
According to one embodiment of the present disclosure, the compound of Chemical Formula 1 may be any one selected from among the following compounds.
5-1
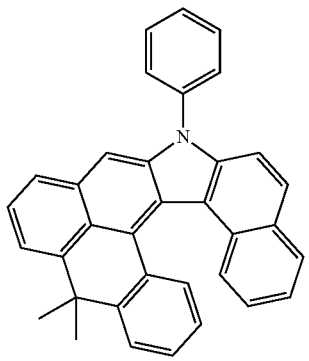
5-2
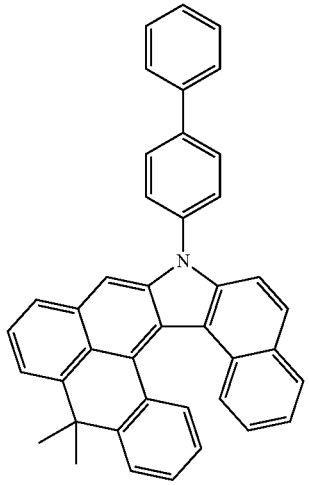
5-3
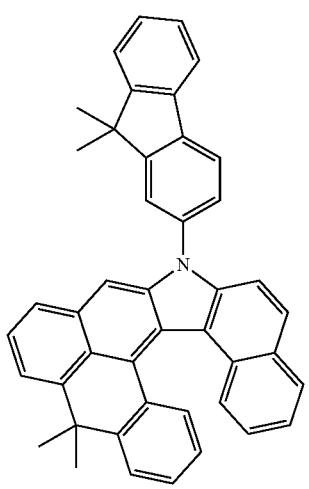

5-4
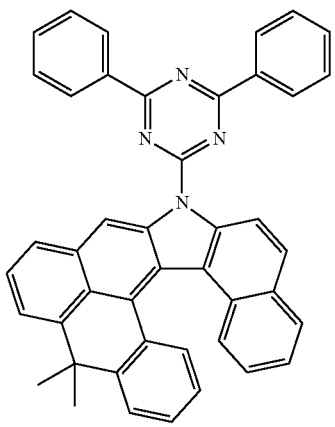
5-5
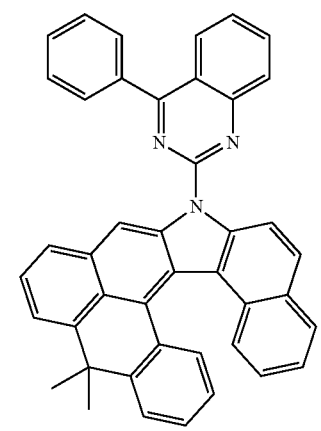
5-6
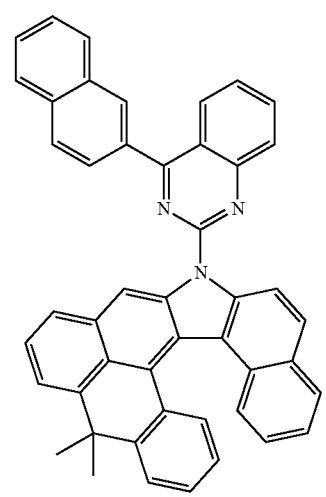
5-7
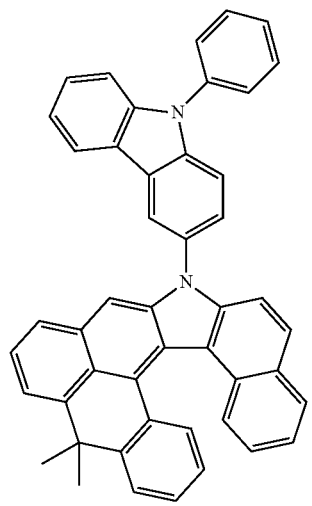
5-8
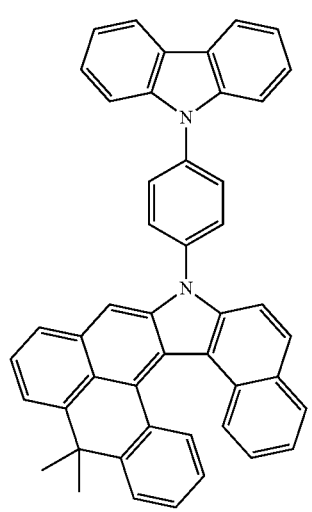
5-9
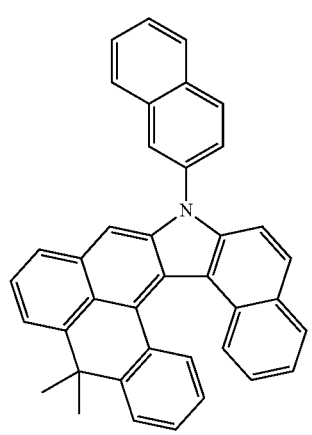

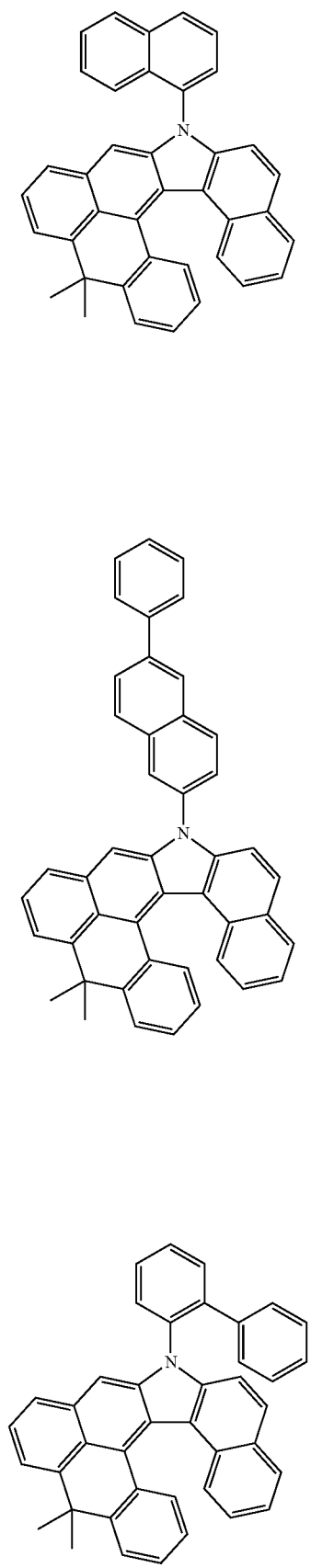
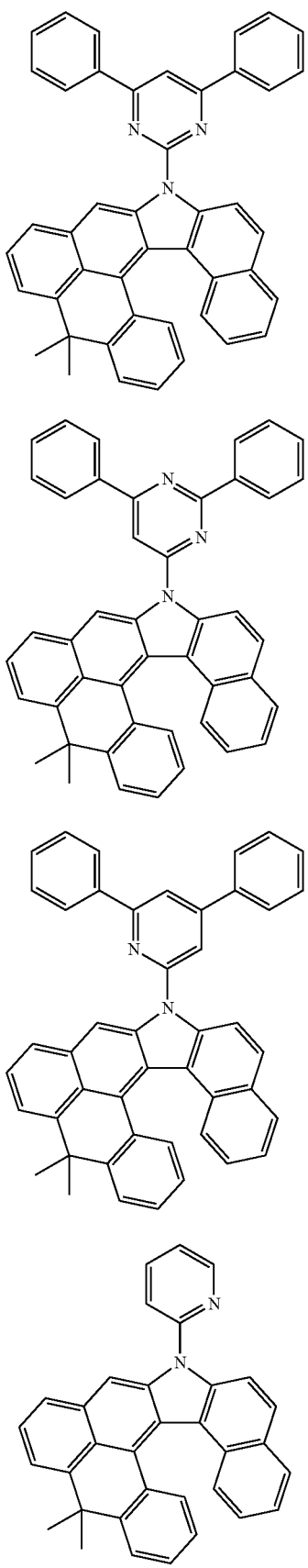

-continued
5-17
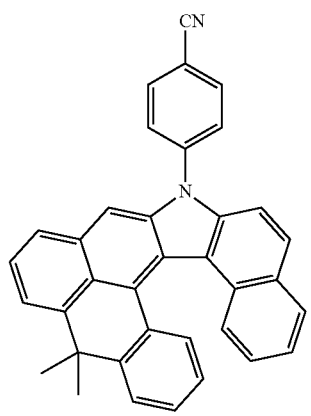
5-18
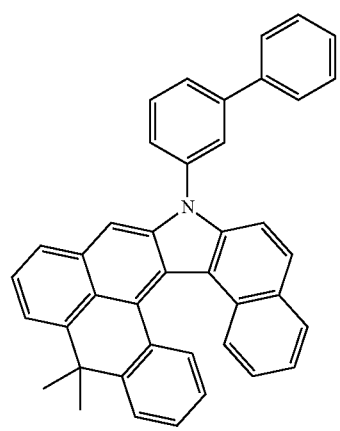
5-19
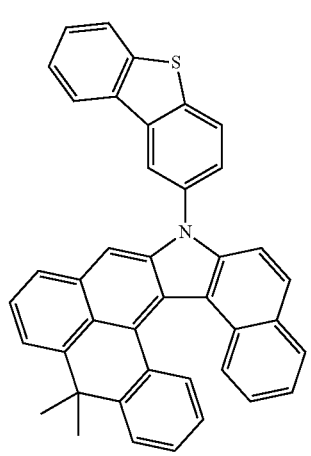
-continued
5-20
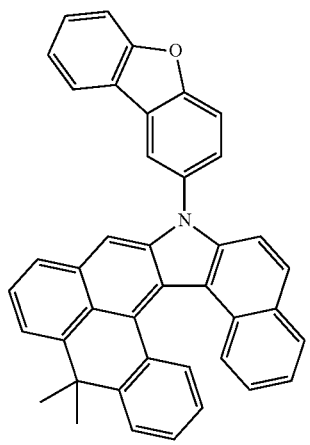
5-21
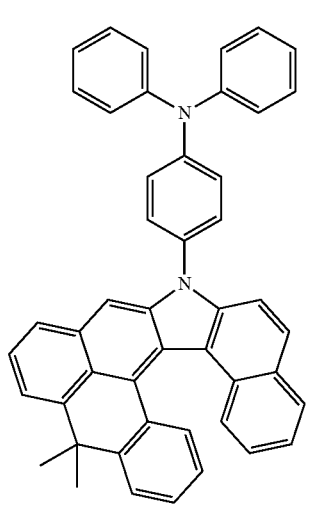
5-22
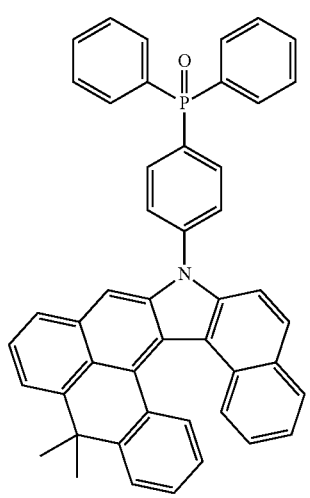

5-23
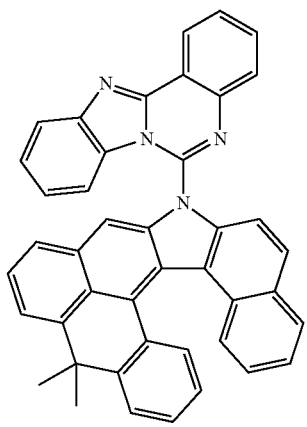
6-4
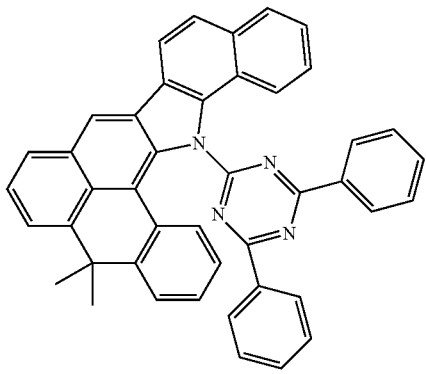
According to one embodiment of the present disclosure, the compound of Chemical Formula 1 may be any one selected from among the following compounds.
6-1
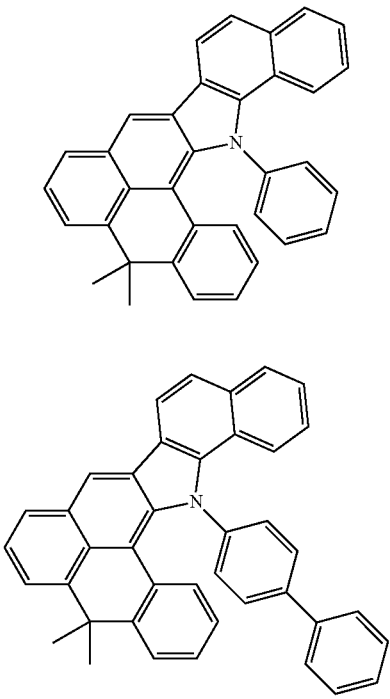
6-5
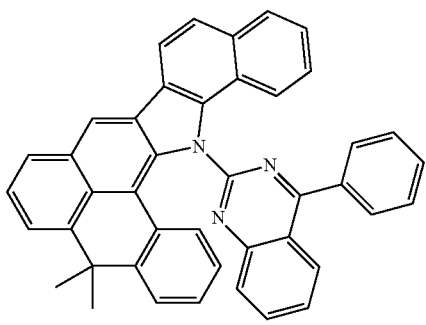
6-2
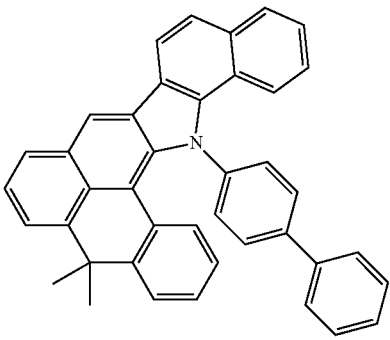
6-6
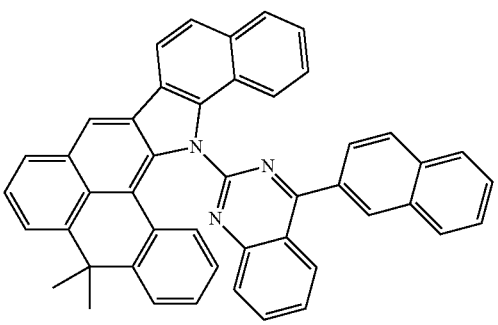
6-3
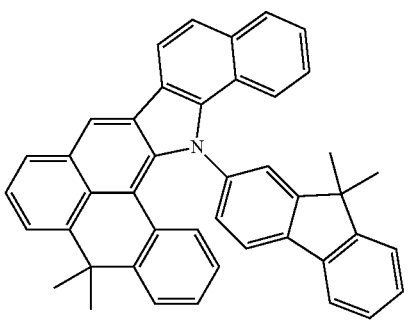
6-7
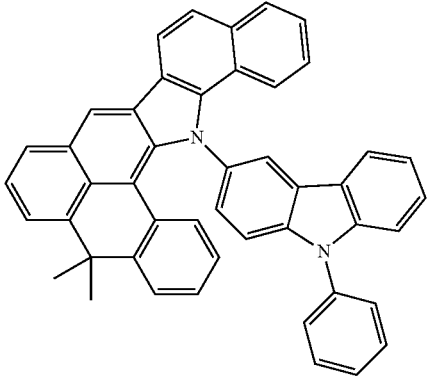

6-8
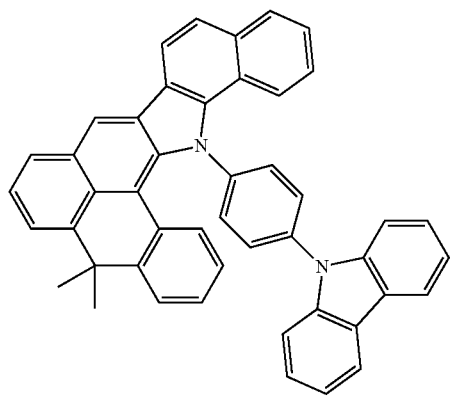
6-9
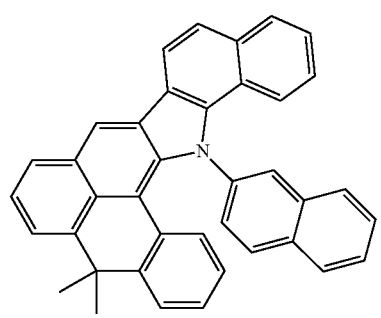
6-10
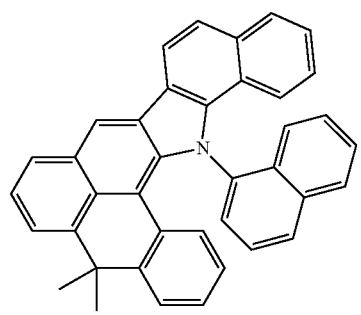
6-11
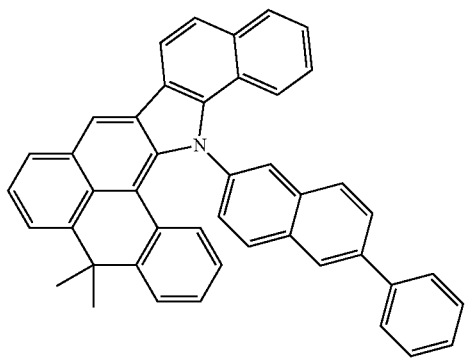
6-12
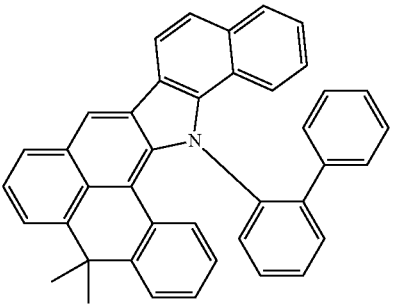
6-13
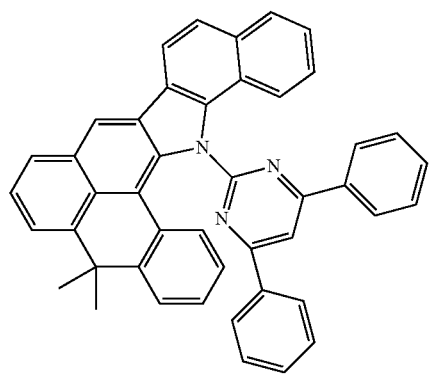
6-14
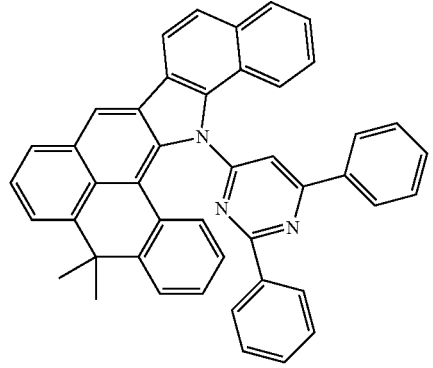
6-15
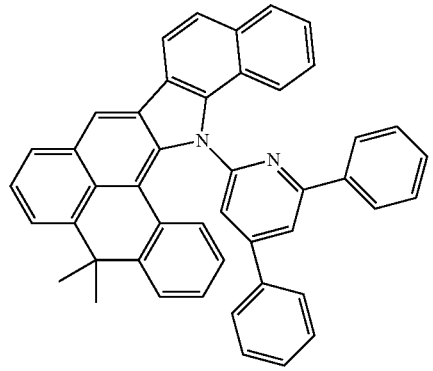

6-16
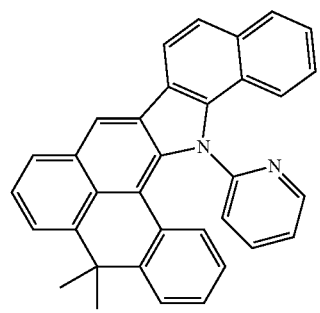
6-17
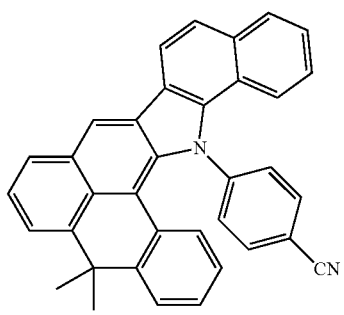
6-18
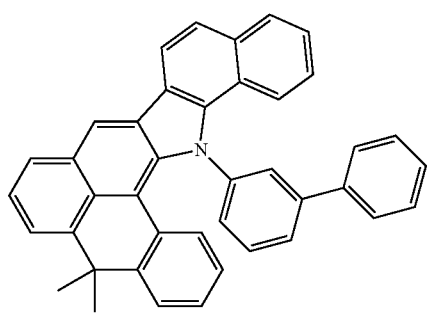
6-19
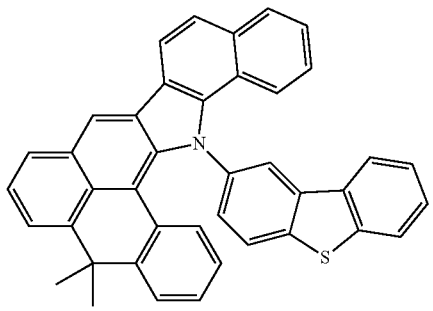
6-20
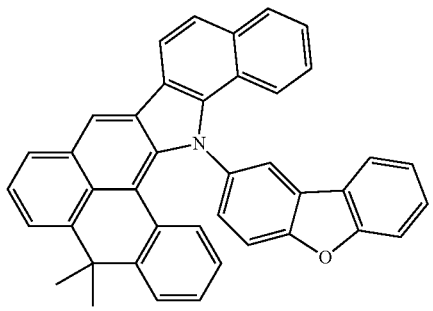
6-21
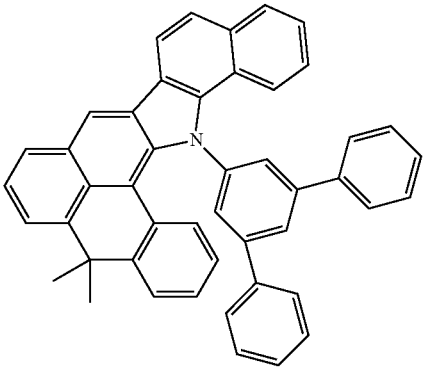
6-22
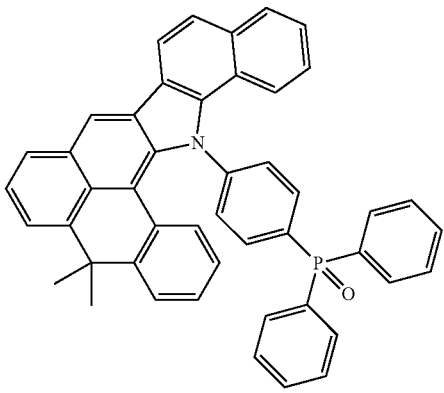
6-23
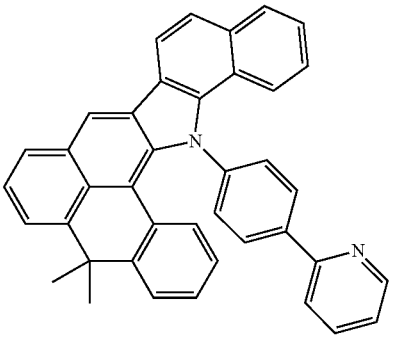
According to one embodiment of the present disclosure, the compound of Chemical Formula 1 may be any one selected from among the following compounds.
7-1
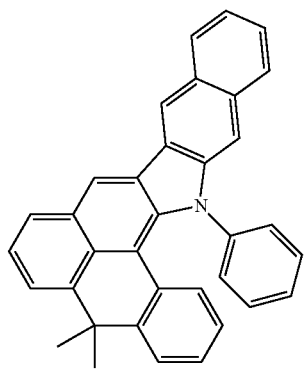

7-2
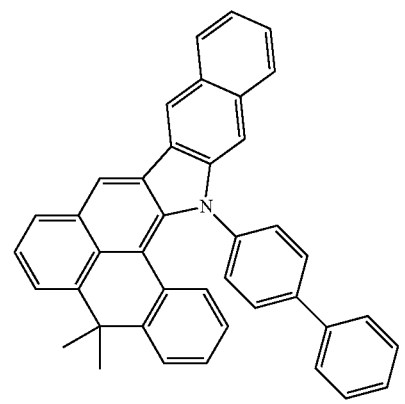
7-3
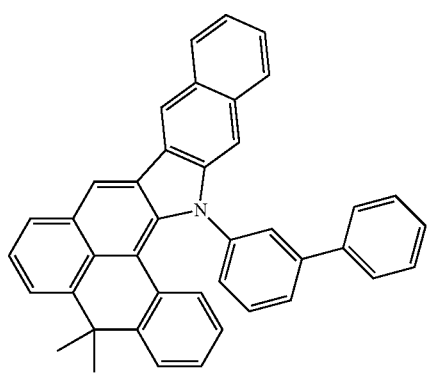
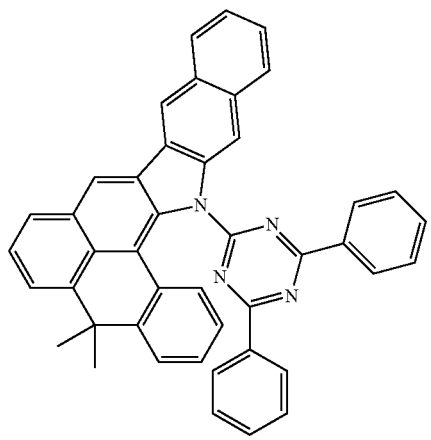
7-5
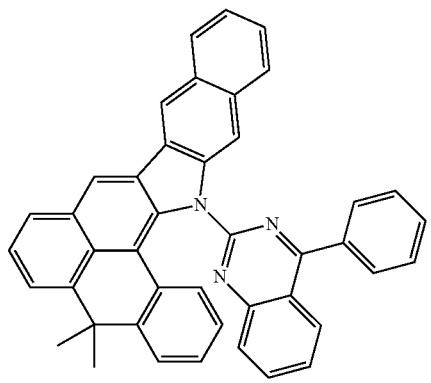
7-6
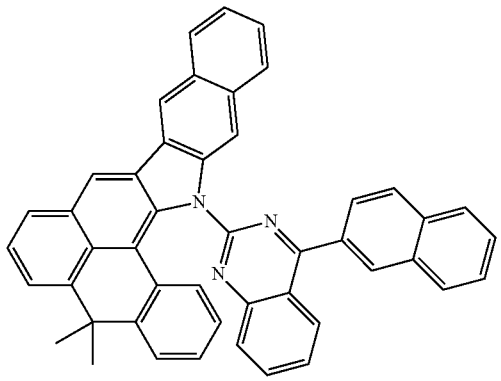
7-7
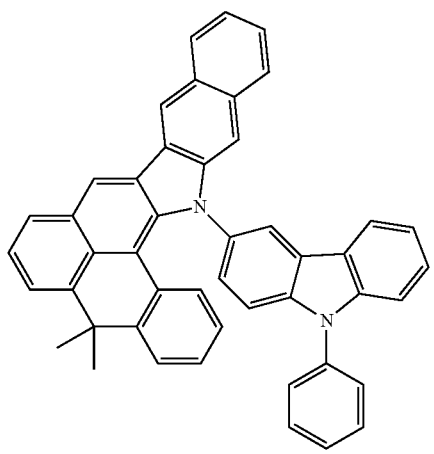
7-8
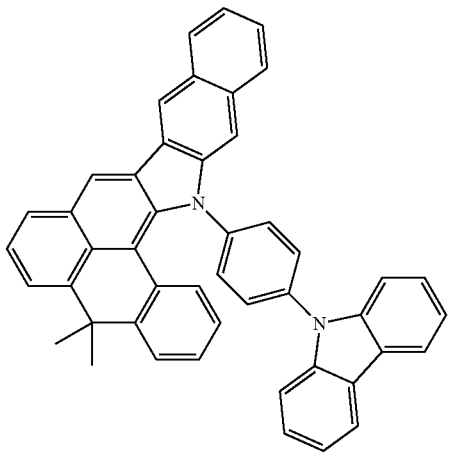
7-9
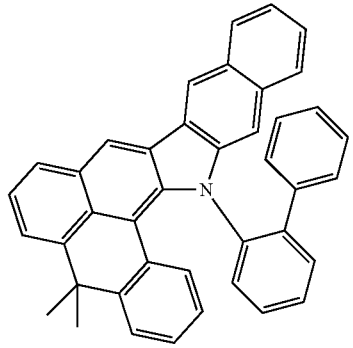

7-10
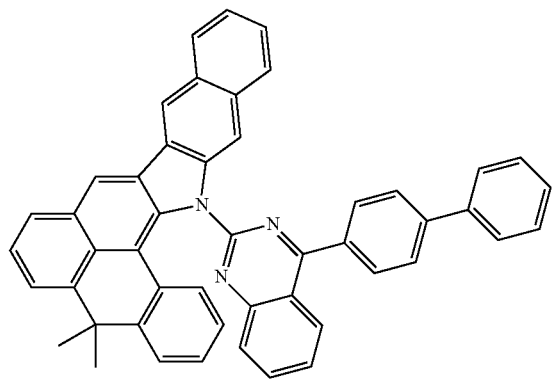
7-11
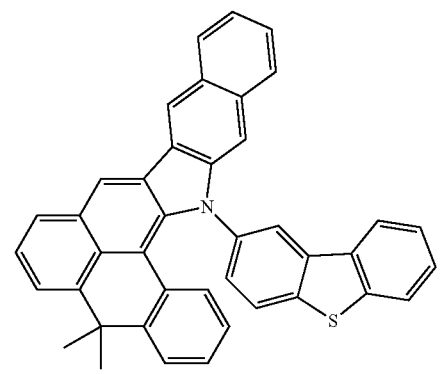
7-12
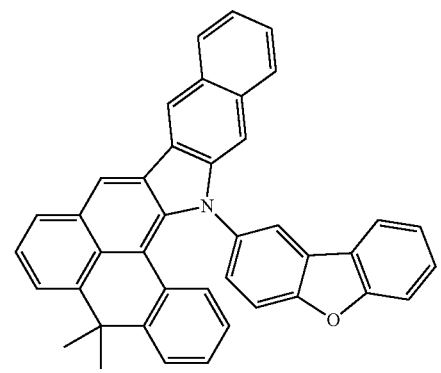
7-13
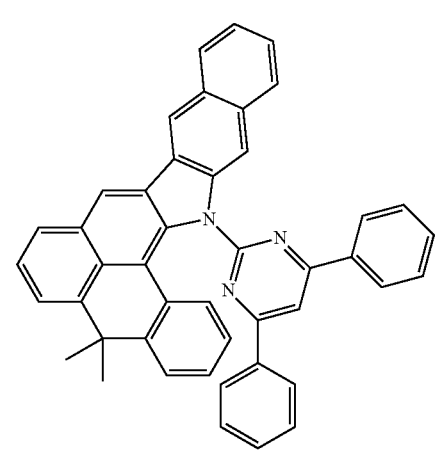
7-14
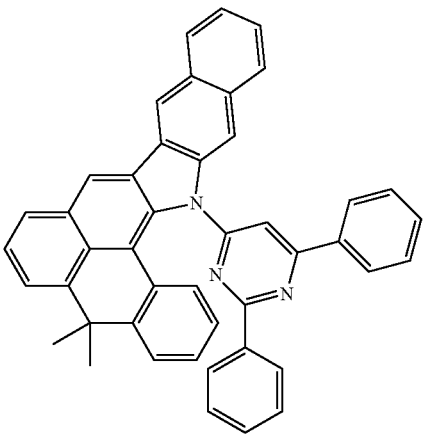
7-15
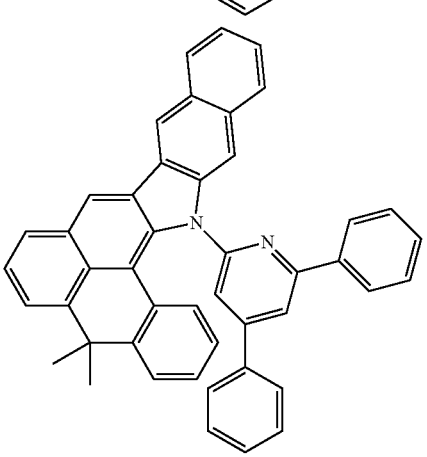
7-16
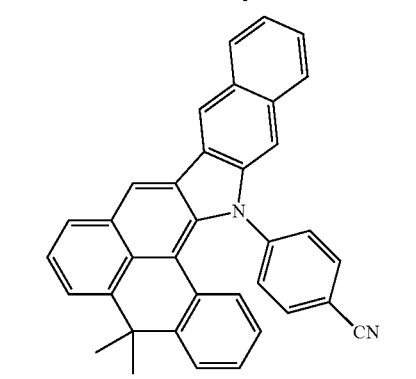
7-17
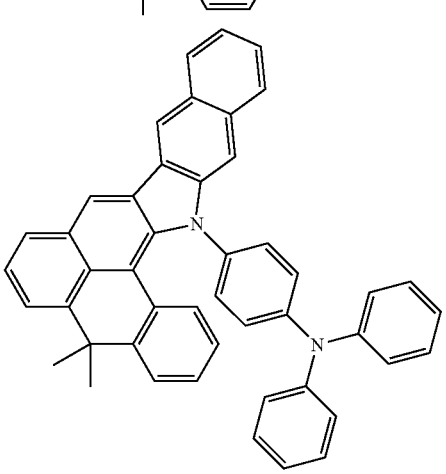

According to one embodiment of the present disclosure, the compound of Chemical Formula 1 may be any one selected from among the following compounds.
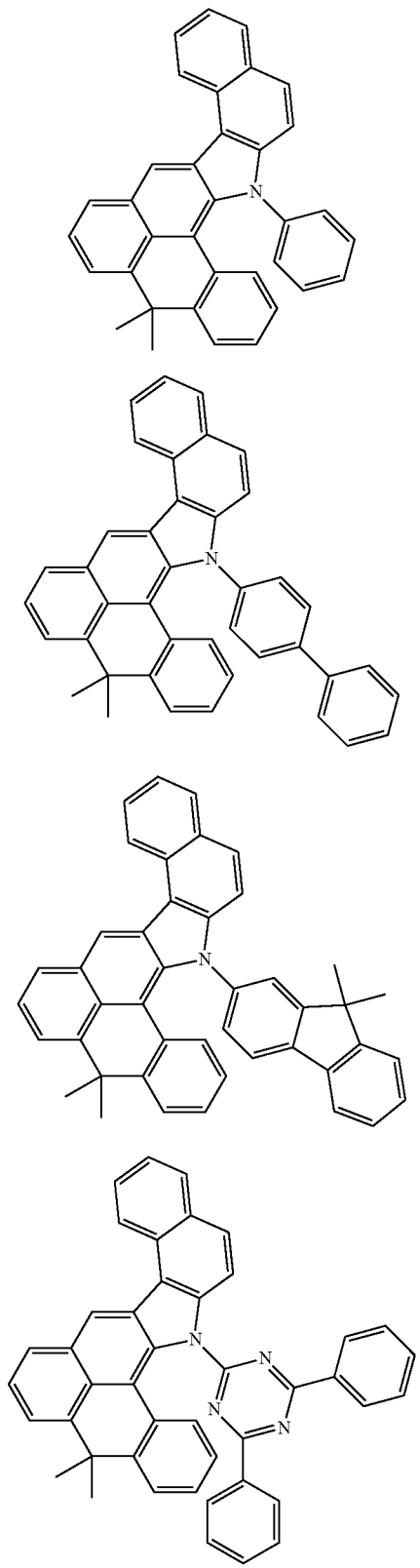
8-1
8-2
8-3
8-4
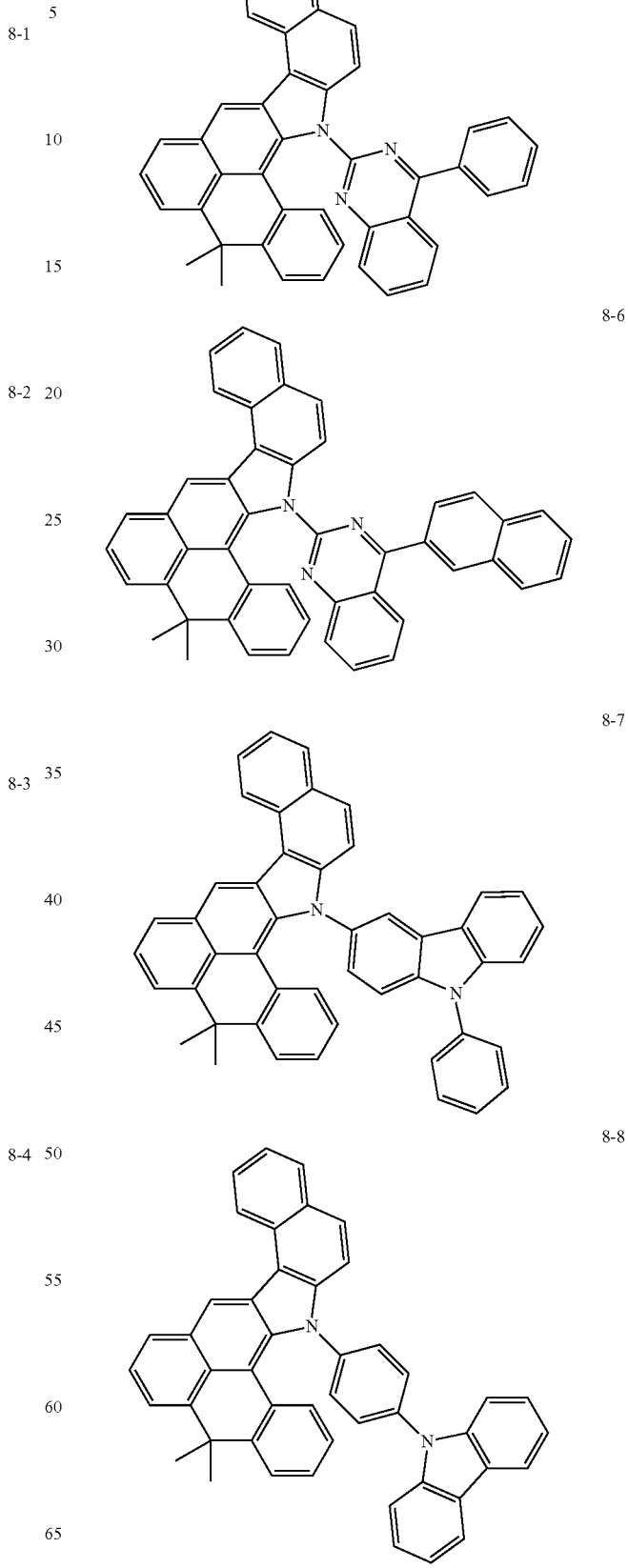
8-5
8-6
8-7
8-8

8-9
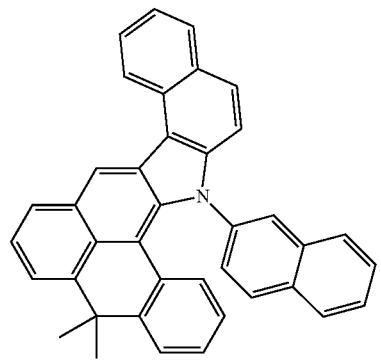
8-10
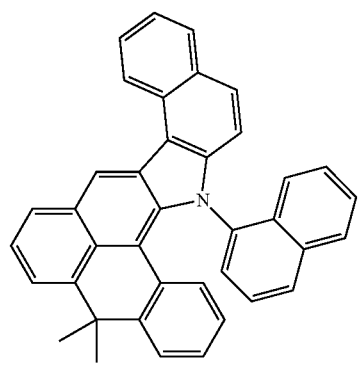
8-11
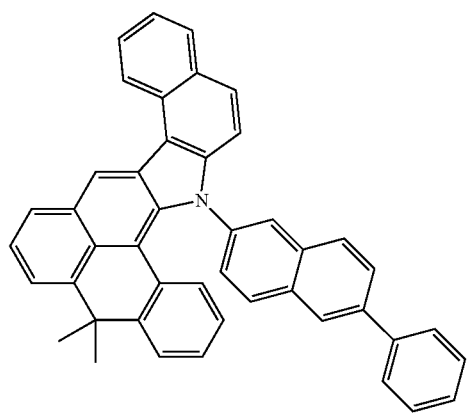
8-12
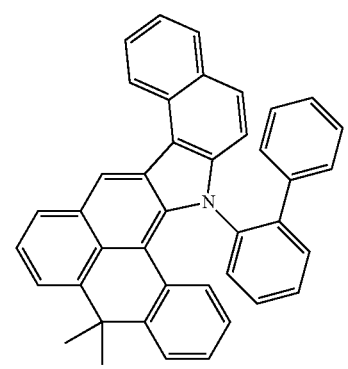
8-13
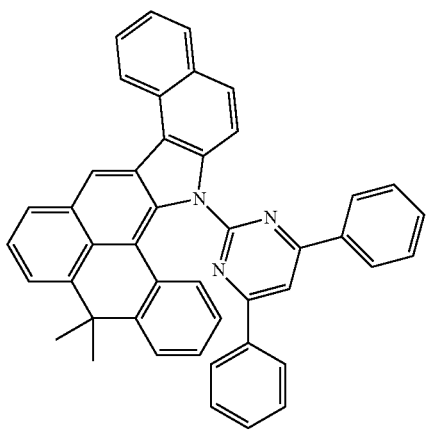
8-14
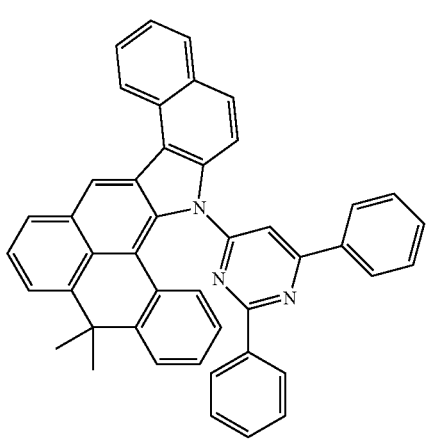
8-15
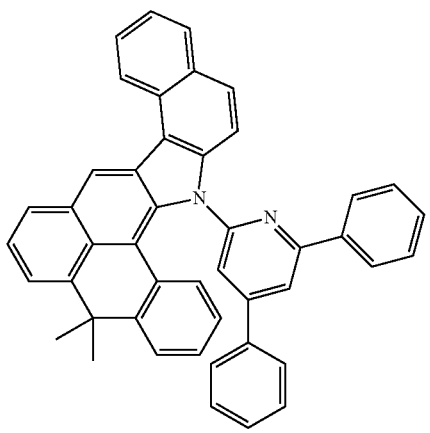
8-16
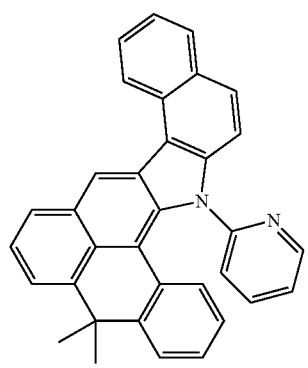

8-17
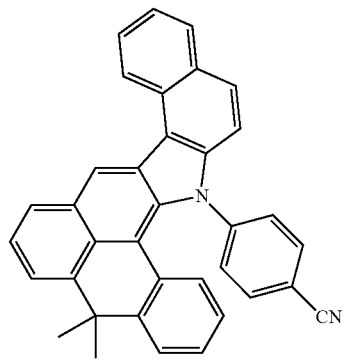

8-18
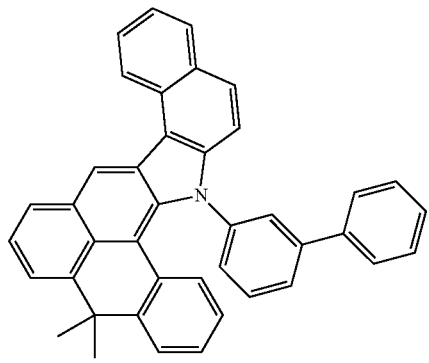

8-19
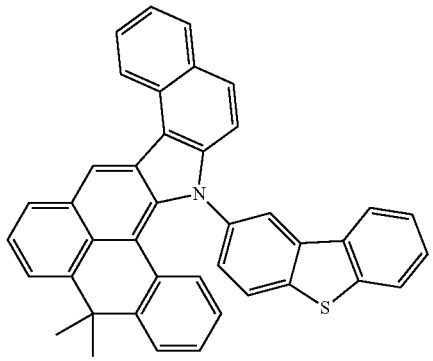

8-20
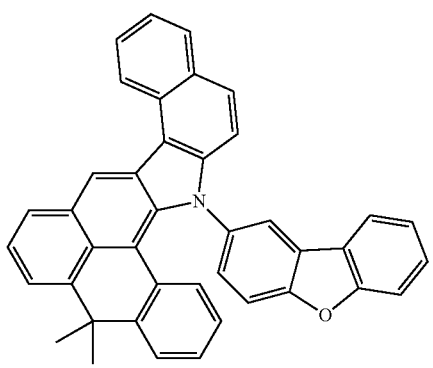

8-21
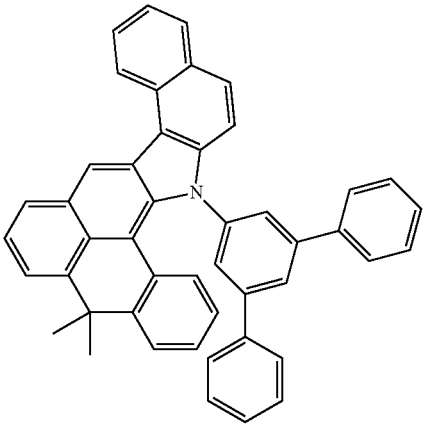

8-22
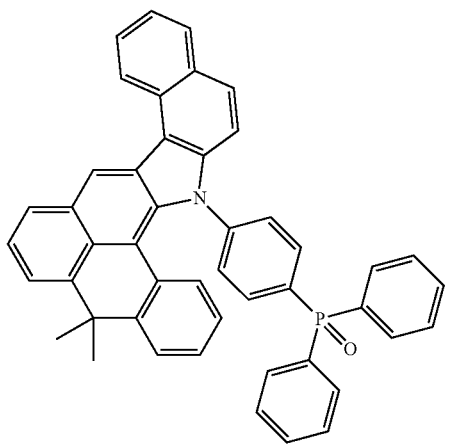

8-23
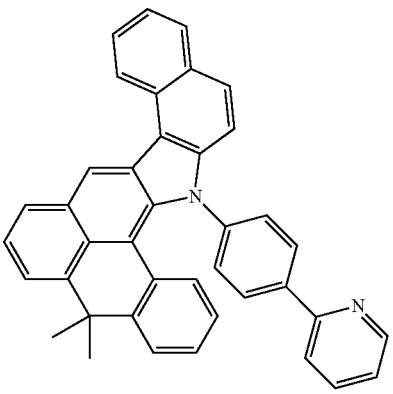

A conjugation length of a compound and an energy band gap thereof are closely related. Specifically, as a conjugation length of a compound increases, an energy band gap thereof decreases. As described above, the cores of the compounds include limited conjugation, and therefore, the energy bad gaps are large.

In the present disclosure, compounds having various energy band gaps may be synthesized by introducing various substituents to positions of Ar1, R1 to R4 of the core structure having a large energy band gap as above. Normally, an energy band gap is readily controlled by introducing substituents to a core structure having a large energy band gap, however, when a core structure has a small energy band gap, controlling the energy band gap to become large is difficult. In addition, in the present disclosure, HOMO and LUMO energy levels may be controlled as well by introducing various substituents to positions of Ar1, R1 to R4 of the core structure having structures as above.

Furthermore, by introducing various substituents to the core structure having structures as above, compounds having unique properties of the introduced substituents may be synthesized. For example, by introducing substituents normally used as hole injection layer materials, hole transfer layer materials, light emitting layer materials and electron transfer layer materials used for manufacturing an organic light emitting device to the core structure, materials satisfying needs required for each organic material layer may be synthesized.

In addition, an organic light emitting device according to one embodiment of the present disclosure comprises a first electrode, a second electrode, and one or more organic material layers disposed between the first electrode and the second electrode, and one or more layers of the organic material layers comprise the multicyclic compound.

The organic light emitting device of the present disclosure may be manufactured using common methods and materials used for manufacturing organic light emitting devices, except that one or more layers of the organic material layers are formed using the compound described above.

The compound may be formed into the organic material layer using a solution coating method as well as a vacuum deposition method when manufacturing an organic light emitting device. Herein, the solution coating method means spin coating, dip coating, ink jet printing, screen printing, a spray method, roll coating and the like, but is not limited thereto.

The organic material layer of the organic light emitting device of the present disclosure may be formed in a single layer structure, but may be formed in a multilayer structure in which two or more organic material layers are laminated. For example, the organic light emitting device of the present disclosure may have a structure comprising an electron blocking layer, a hole injection layer, a hole transfer layer, a light emitting layer, an electron transfer layer, an electron injection layer and the like as the organic material layer. However, the structure of the organic light emitting device is not limited thereto, and may include less numbers of organic material layers.

Accordingly, in the organic light emitting device of the present disclosure, the organic material layer may comprise one or more layers of a hole injection layer, a hole transfer layer, and a layer carrying out hole injection and hole transfer at the same time, and one or more layers of the layers may comprise the compound represented by Chemical Formula 1.

In one embodiment of the present disclosure, the organic material layer comprises an electron blocking layer, and the electron blocking layer comprises the compound represented by Chemical Formula 1.

In another embodiment, the organic material layer comprises a light emitting layer, and the light emitting layer comprises the compound represented by Chemical Formula 1. As one example, the compound represented by Chemical Formula 1 may be comprised as a phosphorescent host material of the light emitting layer.

As another example, the organic material layer comprising the compound represented by Chemical Formula 1 includes the compound represented by Chemical Formula 1 as a host, and comprises other organic compounds, metals or metal compounds as a dopant.

As another example, the organic material layer comprising the compound represented by Chemical Formula 1 comprises the compound represented by Chemical Formula 1 as a host, and the compound may be used together with an iridium (Ir)-based dopant.

In one embodiment of the present disclosure, the organic light emitting device is a green organic light emitting device in which the light emitting layer comprises the compound represented by Chemical Formula 1 as a host.

In one embodiment of the present disclosure, the organic light emitting device is a red organic light emitting device in which the light emitting layer comprises the compound represented by Chemical Formula 1 as a host.

In addition, the organic material layer may comprise one or more layers of an electron transfer layer, an electron injection layer, and a layer carrying out electron transfer and electron injection at the same time, and one or more layers of the layers may comprise the compound.

In another embodiment, the organic material layer of the organic electronic device comprises a hole transfer layer, and the hole transfer layer comprises the compound represented by Chemical Formula 1.

In another embodiment, the organic material layer comprises a hole transfer layer and an electron blocking layer, and at least one of the hole transfer layer and the electron blocking layer comprises the compound represented by Chemical Formula 1.

In such an organic material layer having a multilayer structure, the compound may be comprised in a light emitting layer, a layer carrying out hole injection/hole transfer and light emission at the same time, a layer carrying out hole transfer and light emission at the same time, or a layer carrying out electron transfer and light emission at the same time, and the like.

For example, the structure of the organic light emitting device of the present disclosure may have structures as shown in FIG. 1 and FIG. 2, however, the structure is not limited thereto.

FIG. 1 illustrates a structure of an organic light emitting device in which an anode (2), a light emitting layer (3) and a cathode (4) are consecutively laminated on a substrate (1). In such a structure, the compound may be included in the light emitting layer (3).

FIG. 2 illustrates a structure of an organic light emitting device in which an anode (2), a hole injection layer (5), a hole transfer layer (6), a light emitting layer (7), an electron transfer layer (8) and a cathode (4) are consecutively laminated on a substrate (1). In such a structure, the compound may be included in the hole injection layer (5), the hole transfer layer (6), the light emitting layer (7) or the electron transfer layer (8).

In addition, in the structures, an electron blocking layer may be additionally comprised, and according to one embodiment, the electron blocking layer may be laminated on the hole transfer layer, and the light emitting layer may be laminated thereon in the structures.

For example, the organic light emitting device according to the present disclosure may be manufactured by forming an anode on a substrate by depositing a metal, a metal oxide having conductivity, or an alloy thereof using a physical vapor deposition (PVD) method such as sputtering or e-beam evaporation, forming an organic material layer including a hole injection layer, a hole transfer layer, a light emitting layer and an electron transfer layer thereon, and then depositing a material capable of being used as a cathode thereon. In addition to such a method, the organic light emitting device may also be manufactured by consecutively depositing a cathode material, an organic material layer, and an anode material on a substrate.

The organic material layer may have a multilayer structure comprising a hole injection layer, a hole transfer layer, an electron blocking layer, a light emitting layer, an electron transfer layer and the like, but is not limited thereto, and may have a single layer structure. In addition, the organic material layer may be prepared into less numbers of layers using various polymer materials through a solvent process such as spin coating, dip coating, doctor blading, screen printing, ink jet printing or a thermal transfer method instead of a deposition method.

As the anode material, materials having large work function are normally preferred so that hole injection to an organic material layer is smooth. Specific examples of the anode material capable of being used in the present disclosure include metals such as vanadium, chromium, copper, zinc and gold, or alloys thereof; metal oxides such as zinc oxide, indium oxide, indium tin oxide (ITO) and indium zinc oxide (IZO); combinations of metals and oxides such as ZnO:Al or SnO$_2$:Sb; conductive polymers such as poly(3-methyl compound), poly[3,4-(ethylene-1,2-dioxy)compound] (PEDT), polypyrrole and polyaniline, but are not limited thereto.

As the cathode material, materials having small work function are normally preferred so that electron injection to an organic material layer is smooth. Specific examples of the cathode material include metals such as magnesium, calcium, sodium, potassium, titanium, indium, yttrium, lithium, gadolinium, aluminum, silver, tin and lead, or alloys thereof; multilayer structure materials such as LiF/Al or LiO$_2$/Al, and the like, but are not limited thereto.

As the hole injection material, materials having a highest occupied molecular orbital (HOMO) between the work function of an anode material and the HOMO of surrounding organic material layers are preferred as materials favorably receiving holes from an anode at a low voltage. Specific examples of the hole injection material include metal porphyrins, oligothiophene, arylamine-based organic materials, hexanitrile hexaazatriphenylene-based organic materials, quinacridone-based organic materials, perylene-based organic materials, anthraquinone, and polyaniline- and polycompound-based conductive polymers, and the like, but are not limited thereto.

As the hole transfer material, materials having high mobility for holes are suited as materials receiving holes from an anode or a hole injection layer and transfers the holes to a light emitting layer. Specific examples thereof include arylamine-based organic materials, conductive polymers, block copolymers having conjugated parts and non-conjugated parts together, and the like, but are not limited thereto.

As the light emitting material, materials having favorable quantum efficiency for fluorescence or phosphorescence are preferred as materials capable of emitting light in a visible light region by receiving holes and electrons from a hole transfer layer and an electron transfer layer, respectively, and binding the holes and the electrons. Specific examples thereof include 8-hydroxy-quinoline aluminum complexes (Alq$_3$); carbazole-based compounds; dimerized styryl compounds; BAlq; 10-hydroxybenzo quinoline-metal compounds; benzoxazole-, benzothiazole- and benzimidazole-based compounds; poly(p-phenylenevinylene) (PPV)-based polymers; spiro compounds; polyfluorene, rubrene, and the like, but are not limited thereto.

The organic material layer including the compound represented by Chemical Formula 1 includes the compound represented by Chemical Formula 1 as a host, and the compound may be used together with an iridium (Ir)-based dopant.

The iridium-based complex used as the dopant is as follows.

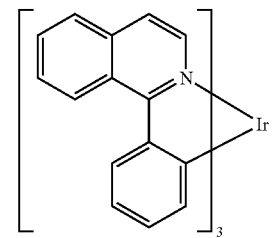

[Ir(piq)$_3$]

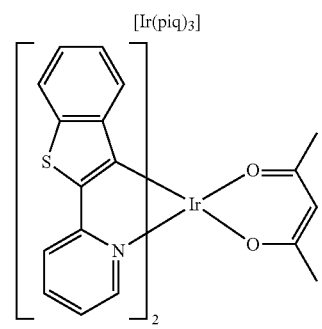

[Btp$_2$Ir(acac)]

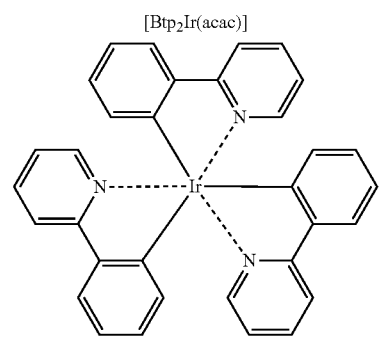

[Ir(ppy)$_3$]

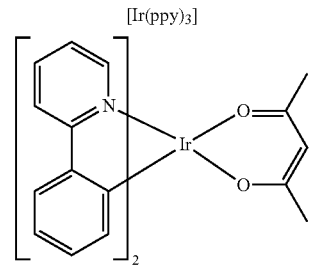

[Ir(ppy)$_2$(acac)]

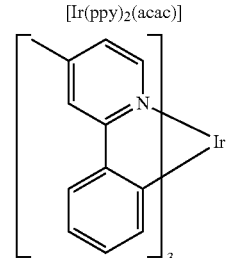

[Ir(mpyp)$_3$]

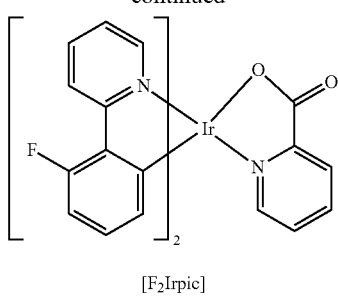

[F2Irpic]

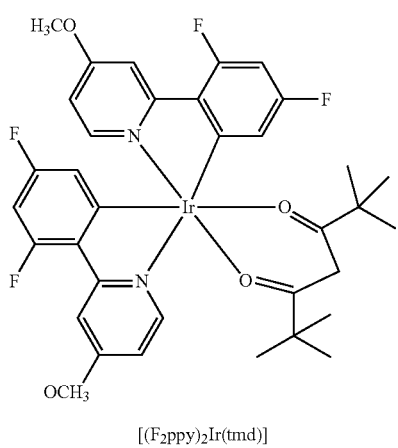

[(F2ppy)2Ir(tmd)]

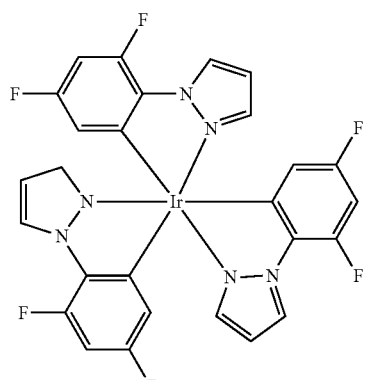

[Ir(dfppz)3]

As the electron transfer material, materials having high mobility for electrons are suited as materials favorably receiving electrons from a cathode and transferring the electrons to a light emitting layer. Specific examples thereof comprise Al complexes of 8-hydroxyquinoline; complexes including $Alq_3$; organic radical compounds; hydroxyflavon-metal complexes and the like, but are not limited thereto.

One embodiment of the present specification relates to an organic light emitting device comprising the compound represented by Chemical Formula 1 in one or more layers of the organic material layers, and comprising a compound of the following Chemical Formula 14 in the light emitting layer among the organic material layers.

[Chemical Formula 14]

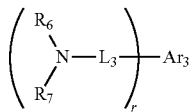

In Chemical Formula 14, $Ar_3$ is a benzofluorene skeleton, a fluoranthene skeleton, a pyrene skeleton or a chrysene skeleton, $L_3$ is a single bond, a $C_6$ to $C_{30}$ arylene group or a $C_5$ to $C_{30}$ divalent heterocyclic group, $R_6$ and $R_7$ are the same as or different from each other, and each independently selected from the group consisting of a substituted or unsubstituted $C_6$ to $C_{30}$ aryl group, a substituted or unsubstituted $C_5$ to $C_{30}$ heterocyclic group, a substituted or unsubstituted $C_1$ to $C_{30}$ alkyl group, and a substituted or unsubstituted $C_7$ to $C_{30}$ aralkyl group, and $R_6$ and $R_7$ may bond to each other to form a saturated or unsaturated ring, r is an integer of 1 or greater, and when r is 2 or greater, $R_6$s are the same as or different from each other, and $R_7$s are the same as or different from each other.

In one embodiment of the present specification, $L_3$ is a single bond or a $C_6$ to $C_{30}$ arylene group.

In another embodiment, $L_3$ is a single bond.

In one embodiment of the present specification, $Ar_3$ is a benzofluorene skeleton, a fluoranthene skeleton or a pyrene skeleton.

In another embodiment, $Ar_3$ is a pyrene skeleton.

In one embodiment of the present specification, $R_6$ and $R_7$ are the same as or different from each other, and each independently a substituted or unsubstituted $C_6$ to $C_{30}$ aryl group, a substituted or unsubstituted $C_5$ to $C_{30}$ heterocyclic group, or a substituted or unsubstituted $C_1$ to $C_{30}$ alkyl group.

In another embodiment, $R_6$ and $R_7$ are the same as or different from each other, and each independently a substituted or unsubstituted $C_6$ to $C_{30}$ aryl group.

In another embodiment, $R_6$ and $R_7$ are the same as or different from each other, and each independently a phenyl group unsubstituted or substituted with a germanium group.

In another embodiment, $R_6$ and $R_7$ are the same as or different from each other, and each independently a phenyl group unsubstituted or substituted with a trimethylgermanium group.

In one embodiment of the present specification, $Ar_3$ is a pyrene skeleton, $L_3$ is a single bond, $R_6$ and $R_7$ are the same as or different from each other, and each independently an aryl group unsubstituted or substituted with a germanium group, and r is 2 in the organic light emitting device.

In one embodiment of the present specification, $Ar_3$ is a pyrene skeleton, $L_3$ is a single bond, $R_6$ is a phenyl group, $R_7$ is a phenyl group substituted with a trimethylgermanium group, and r is 2 in the organic light emitting device.

In one embodiment of the present specification, the compound of Chemical Formula 14 may be comprised as a dopant of the light emitting layer.

One embodiment of the present specification relates to an organic light emitting device comprising the compound represented by Chemical Formula 1 in one or more layers of the organic material layers, and comprising a compound of the following Chemical Formula 15 in the light emitting layer among the organic material layers.

[Chemical Formula 15]

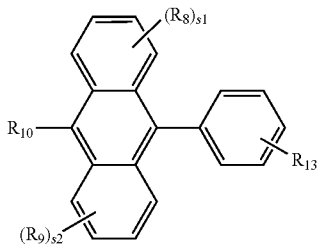

In Chemical Formula 15, $R_{10}$ is a substituted or unsubstituted 1-naphthyl group, a substituted or unsubstituted 2-naphthyl group, a substituted or unsubstituted 1-anthryl group, a substituted or unsubstituted 2-anthryl group, a substituted or unsubstituted 1-phenanthryl group, a substituted or unsubstituted 2-phenanthryl group, a substituted or unsubstituted 3-phenanthryl group, a substituted or unsubstituted 4-phenanthryl group, a substituted or unsubstituted 9-phenanthryl group, a substituted or unsubstituted 1-naphthacenyl group, a substituted or unsubstituted 2-naphthacenyl group, a substituted or unsubstituted 9-naphthacenyl group, a substituted or unsubstituted 1-pyrenyl group, a substituted or unsubstituted 2-pyrenyl group, a substituted or unsubstituted 4-pyrenyl group, a substituted or unsubstituted 3-methyl-2-naphthyl group, a substituted or unsubstituted 4-methyl-1-naphthyl group or the following structural formula

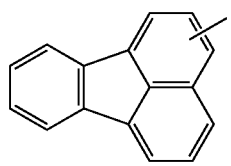

$R_{13}$ is a group selected from the group consisting of a phenyl group, a 1-naphthyl group, a 2-naphthyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 3-biphenylyl group, a 4-biphenylyl group, a p-terphenyl-4-yl group, a p-terphenyl-3-yl group, a p-terphenyl-2-yl group, an m-terphenyl-4-yl group, an m-terphenyl-3-yl group, an m-terphenyl-2-yl group, an o-tolyl group, an m-tolyl group, a p-tolyl group, a p-t-butylphenyl group, a p-(2-phenylpropyl)phenyl group, a 3-methyl-2-naphthyl group, a 4-methyl-1-naphthyl group, a 4-methyl-1-anthryl group, a 4'-methylbiphenylyl group, a 4"-t-butyl-p-terphenyl-4-yl group and a 3-fluoranthenyl group, $R_8$ and $R_9$ are the same as or different from each other, and each independently a substituted or unsubstituted aryl group having 6 to 50 carbon atoms, a substituted or unsubstituted heteroaryl group having 5 to 50 nuclear atoms, a substituted or unsubstituted alkyl group having 1 to 50 carbon atoms, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 nuclear atoms, a substituted or unsubstituted arylthio group having 5 to 50 nuclear atoms, a substituted or unsubstituted alkoxycarbonyl group having 1 to 50 carbon atoms, a carboxyl group, a halogen atom, a cyano group, a nitro group or a hydroxyl group, and s1 and s2 are each an integer of 0 to 4.

In one embodiment of the present specification, $R_{10}$ is a substituted or unsubstituted 1-naphthyl group or a substituted or unsubstituted 2-naphthyl group.

In another embodiment, $R_{10}$ is a substituted or unsubstituted 1-naphthyl group.

In another embodiment, $R_{10}$ is a 1-naphthyl group.

In one embodiment of the present specification, $R_{13}$ is a phenyl group, a 1-naphthyl group or a 2-naphthyl group.

In another embodiment, $R_{13}$ is a 2-naphthyl group.

In one embodiment of the present specification, $R_8$ and $R_9$ are the same as or different from each other, and each independently a substituted or unsubstituted aryl group having 6 to 50 carbon atoms, a substituted or unsubstituted heteroaryl group having 5 to 50 carbon atoms, or a substituted or unsubstituted alkyl group having 1 to 50 carbon atoms.

In one embodiment of the present specification, $R_8$ and $R_9$ are the same as or different from each other, and each independently a substituted or unsubstituted aryl group having 6 to 50 carbon atoms, or a substituted or unsubstituted heteroaryl group having 5 to 50 carbon atoms.

In one embodiment of the present specification, s1 and s2 are each an integer of 0 to 2.

In another embodiment, s1 and s2 are 0.

In one embodiment of the present specification, $R_{10}$ and $R_{13}$ are the same as or different from each other, and each independently a 1-naphthyl group or a 2-naphthyl group, and s1 and s2 are 0.

In another embodiment, $R_{10}$ is a 1-naphthyl group, $R_{13}$ is a 2-naphthyl group, and s1 and s2 are 0.

In one embodiment of the present specification, the compound of Chemical Formula 15 may be comprised as a host of the light emitting layer.

In one embodiment of the present specification, one or more layers of the organic material layers comprise the compound represented by Chemical Formula 1, and the compound of Chemical Formula 14 and the compound of Chemical Formula 15 are comprised in the light emitting layer among the organic material layers in the organic light emitting device.

Another embodiment relates to an organic light emitting device comprising the compound represented by Chemical Formula 1 in one or more layers of the organic material layers, comprising the compound of Chemical Formula 14 in which $Ar_3$ is a pyrene skeleton, $L_3$ is a single bond, $R_6$ and $R_7$ are an aryl group unsubstituted or substituted with a germanium group, and r is 2, and including the compound of Chemical Formula 15 in which $R_{10}$ and $R_{13}$ are the same as or different from each other, and each independently a 1-naphthyl group or a 2-naphthyl group, and s1 and s2 are 0, in the light emitting layer among the organic material layers.

The organic light emitting device according to the present specification may be a top-emission type, a bottom-emission type or a dual-emission type depending on the materials used.

The compound according to the present disclosure may also be used in organic electronic devices including organic solar cells, organic photo conductors, organic transistors and the like under a similar principle used in the organic light emitting device.

Mode for Disclosure

A method for preparing the compound of Chemical Formula 1 and manufacture of an organic light emitting device using the same will be described in detail in the following examples. However, the following examples are for illustrative purposes only, and the scope of the present disclosure is not limited thereto.

Synthesis Example

<Preparation Example A> Preparation of Compound of Chemical Formula 2-1

A compound of Chemical Formula 2-1 was prepared using the following reaction formula.

1) Synthesis of Intermediate A

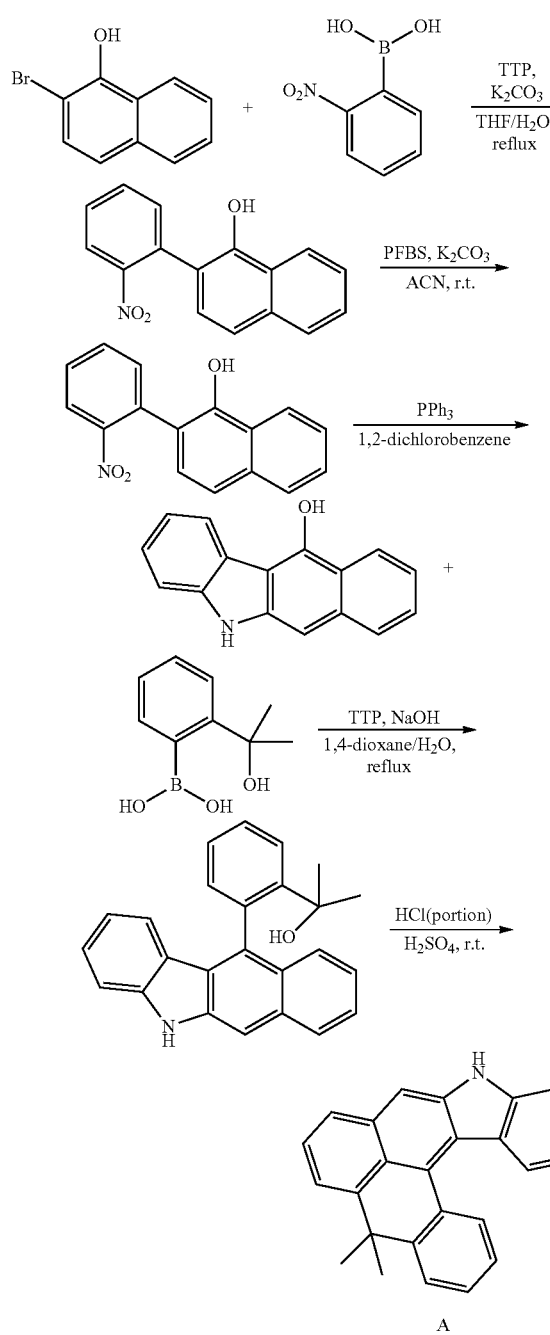

2) Synthesis of Compound of Chemical Formula 2-1

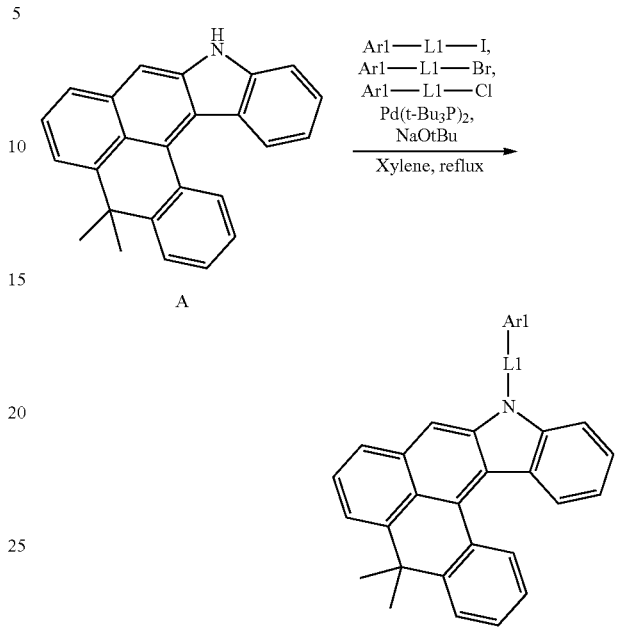

<Preparation Example B> Preparation of Compound of Chemical Formula 2-2

A compound of Chemical Formula 2-2 was prepared using the following reaction formula.

1) Synthesis of Intermediate B

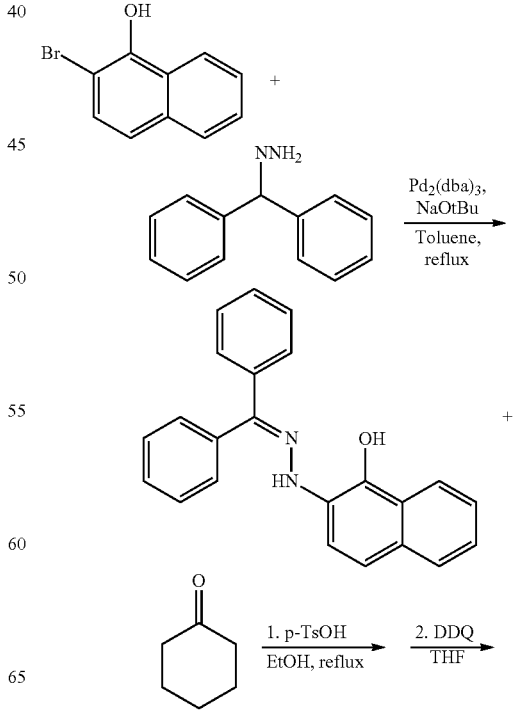

-continued

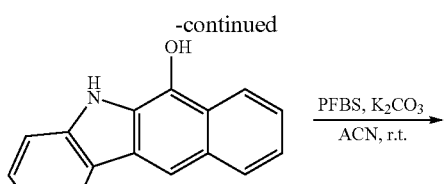

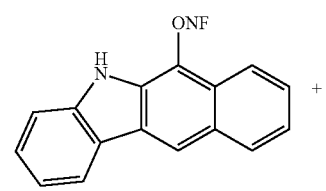

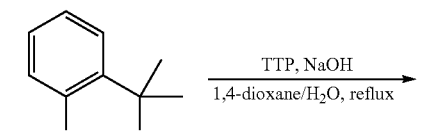

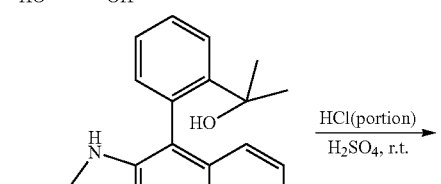

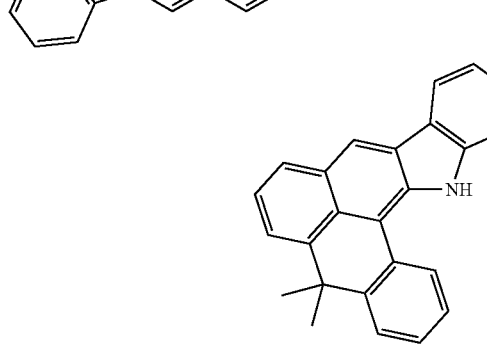

2) Synthesis of Compound of Chemical Formula 2-2

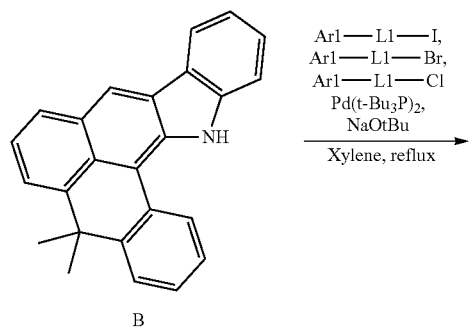

-continued

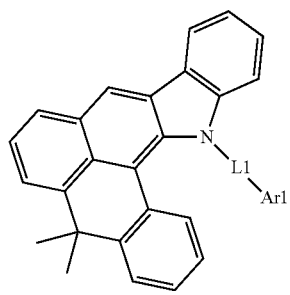

In the present specification, a reaction in which both R4 and R5 of Chemical Formula 1 are a methyl group is illustrated as in A and B, however, those skilled in the art may substitute R4 and R5 of Chemical Formula 1 with other examples using compounds (starting materials), reaction methods and reaction conditions known in the art.

<Preparation Example 1> Preparation of Compound 1-1 (Compound of Chemical Formula 2-1-1)

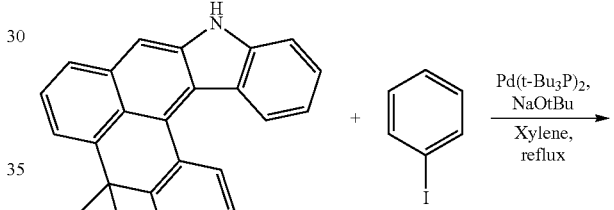

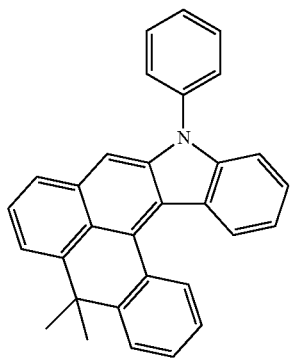

After completely dissolving Compound A (15.0 g, 45.02 mmol) and iodobenzene (10.10 g, 49.53 mmol) in 150 ml of xylene in a 500 ml round bottom flask under nitrogen atmosphere, sodium tert-butoxide (5.62 g, 58.53 mmol) and then bis(tri-tert-butylphosphine) palladium(0) (0.12 g, 0.23 mmol) were added thereto, and the result was heated and stirred for 3 hours. The result was cooled to room temperature and filtered to remove salts, then xylene was vacuum concentrated, and the result was columned using tetrahydrofuran:hexane=1:10 to prepare Compound 1-1 (11.51 g, yield: 94%).

MS[M+H]$^+$=410

<Preparation Example 2> Preparation of Compound 1-2 (Compound of Chemical Formula 2-1-4)

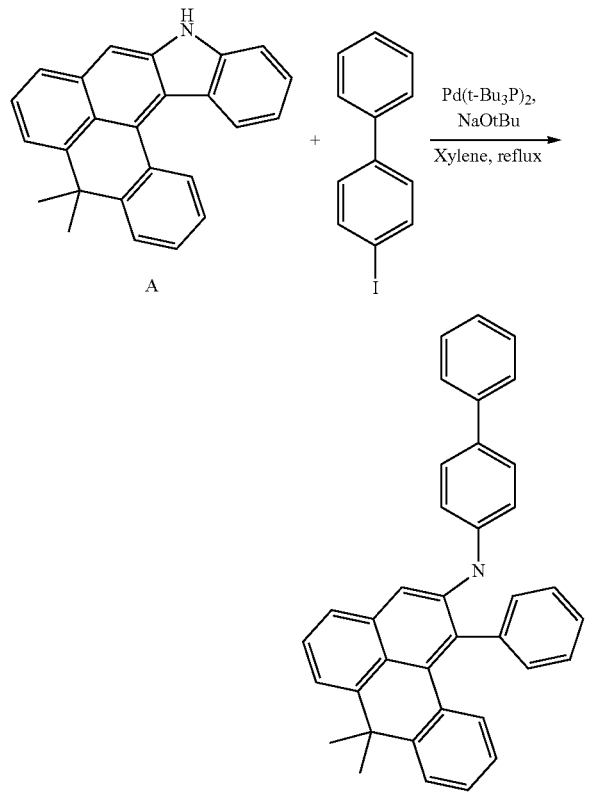

After completely dissolving Compound A (15.0 g, 45.02 mmol) and 4-iodobiphenyl (13.87 g, 49.53 mmol) in 190 ml of xylene in a 500 ml round bottom flask under nitrogen atmosphere, sodium tert-butoxide (5.62 g, 58.53 mmol) and then bis(tri-tert-butylphosphine) palladium(0) (0.12 g, 0.23 mmol) were added thereto, and the result was heated and stirred for 5 hours. The result was cooled to room temperature and filtered to remove salts, then xylene was vacuum concentrated, and the result was columned using tetrahydrofuran:hexane=1:8 to prepare Compound 1-2 (12.54 g, yield: 80%).

MS[M+H]$^+$=486

<Preparation Example 3> Preparation of Compound 1-3 (Compound of Chemical Formula 2-1-10)

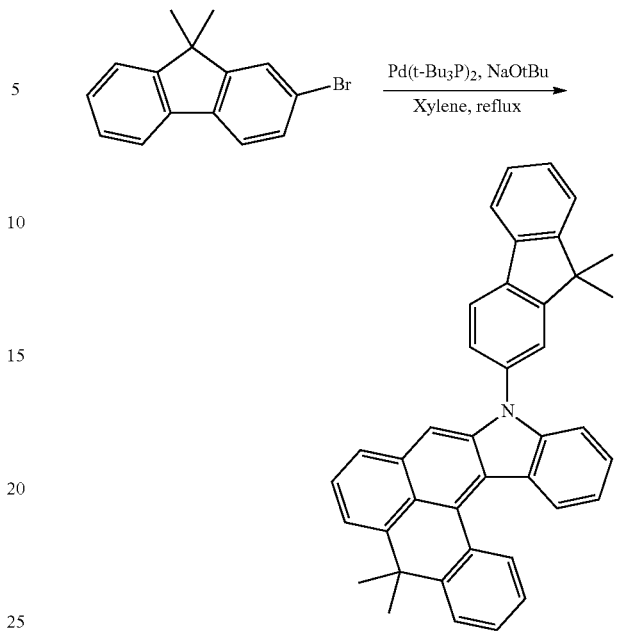

After completely dissolving Compound A (15.0 g, 45.02 mmol) and 2-bromo-9,9-dimethyl-9H-fluorene (13.47 g, 49.53 mmol) in 180 ml of xylene in a 500 ml round bottom flask under nitrogen atmosphere, sodium tert-butoxide (5.62 g, 58.53 mmol) and then bis(tri-tert-butylphosphine) palladium(0) (0.12 g, 0.23 mmol) were added thereto, and the result was heated and stirred for 5 hours. The result was cooled to room temperature and filtered to remove salts, then xylene was vacuum concentrated, and the result was columned using tetrahydrofuran:hexane=1:15 to prepare Compound 1-3 (12.42 g, yield: 79%).

MS[M+H]$^+$=526

<Preparation Example 4> Preparation of Compound of Compound 1-4 (Compound of Chemical Formula 2-1-46)

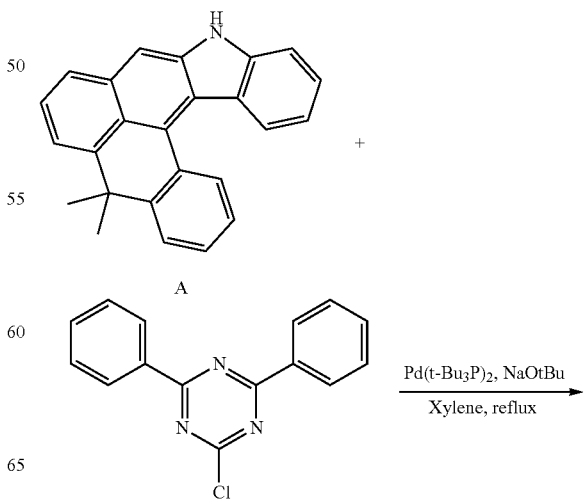

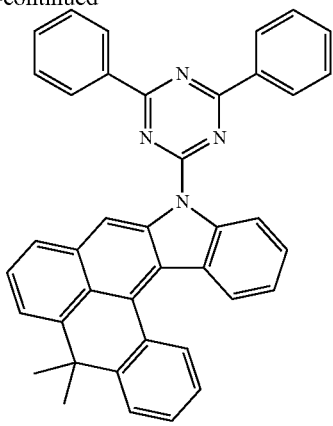

After completely dissolving Compound A (15.0 g, 45.02 mmol) and 2-chloro-4,6-diphenyl-1,3,5-triazine (15.41 g, 49.53 mmol) in 210 ml of xylene in a 500 ml round bottom flask under nitrogen atmosphere, sodium tert-butoxide (5.62 g, 58.53 mmol) and then bis(tri-tert-butylphosphine) palladium(0) (0.12 g, 0.23 mmol) were added thereto, and the result was heated and stirred for 5 hours. The result was cooled to room temperature and filtered to remove salts, then xylene was vacuum concentrated, and the result was columned using tetrahydrofuran:hexane=1:7 to prepare Compound 1-4 (14.92 g, yield: 88%).

MS[M+H]$^+$=565

<Preparation Example 5> Preparation of Compound 1-5 (Compound of Chemical Formula 2-1-47)

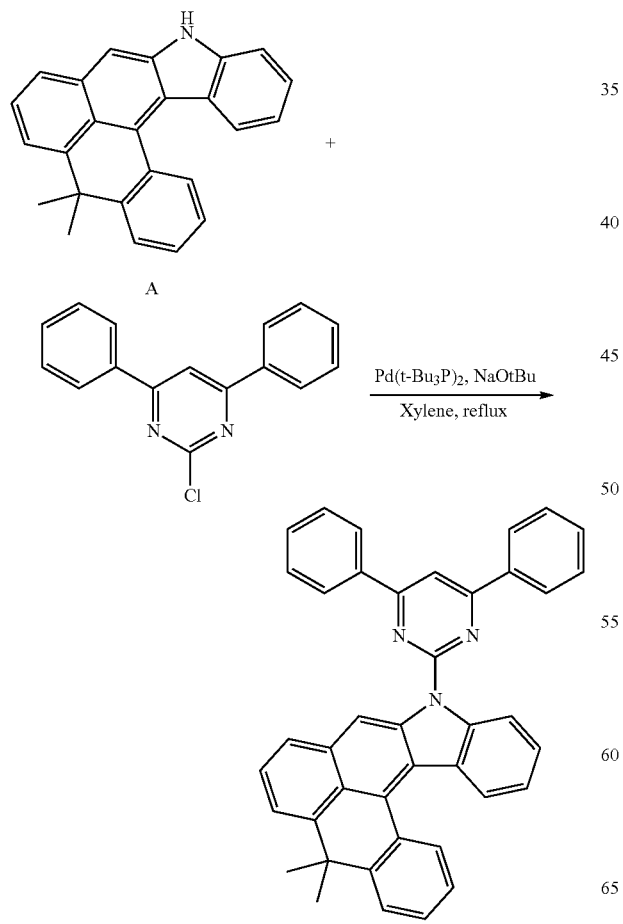

After completely dissolving Compound A (15.0 g, 45.02 mmol) and 2-chloro-4,6-diphenylpyrimidine (15.40 g, 49.53 mmol) in 220 ml of xylene in a 500 ml round bottom flask under nitrogen atmosphere, sodium tert-butoxide (5.62 g, 58.53 mmol) and then bis(tri-tert-butylphosphine) palladium(0) (0.12 g, 0.23 mmol) were added thereto, and the result was heated and stirred for 5 hours. The result was cooled to room temperature and filtered to remove salts, then xylene was vacuum concentrated, and the result was columned using tetrahydrofuran:hexane=1:7 to prepare Compound 1-5 (13.43 g, yield: 84%).

MS[M+H]$^+$=564

<Preparation Example 6> Preparation of Compound 1-6 (Compound of Chemical Formula 2-1-48)

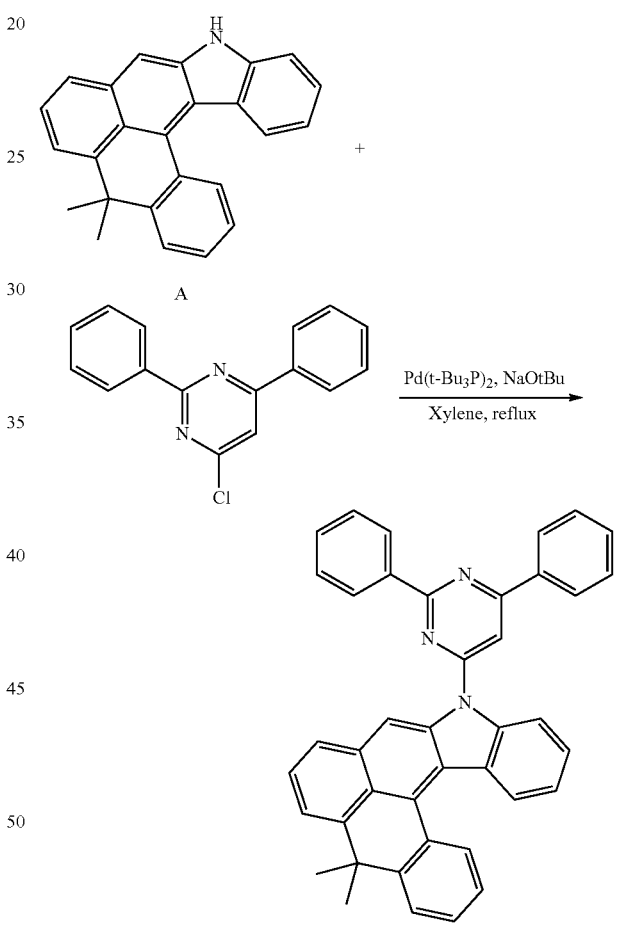

After completely dissolving Compound A (15.0 g, 45.02 mmol) and 4-chloro-2,6-diphenylpyrimidine (15.40 g, 49.53 mmol) in 220 ml of xylene in a 500 ml round bottom flask under nitrogen atmosphere, sodium tert-butoxide (5.62 g, 58.53 mmol) and then bis(tri-tert-butylphosphine) palladium(0) (0.12 g, 0.23 mmol) were added thereto, and the result was heated and stirred for 5 hours. The result was cooled to room temperature and filtered to remove salts, then xylene was vacuum concentrated, and the result was columned using tetrahydrofuran:hexane=1:7 to prepare Compound 1-6 (12.36 g, yield: 79%).

MS[M+H]$^+$=564

<Preparation Example 7> Preparation of Compound 1-7 (Compound of Chemical Formula 2-1-74)

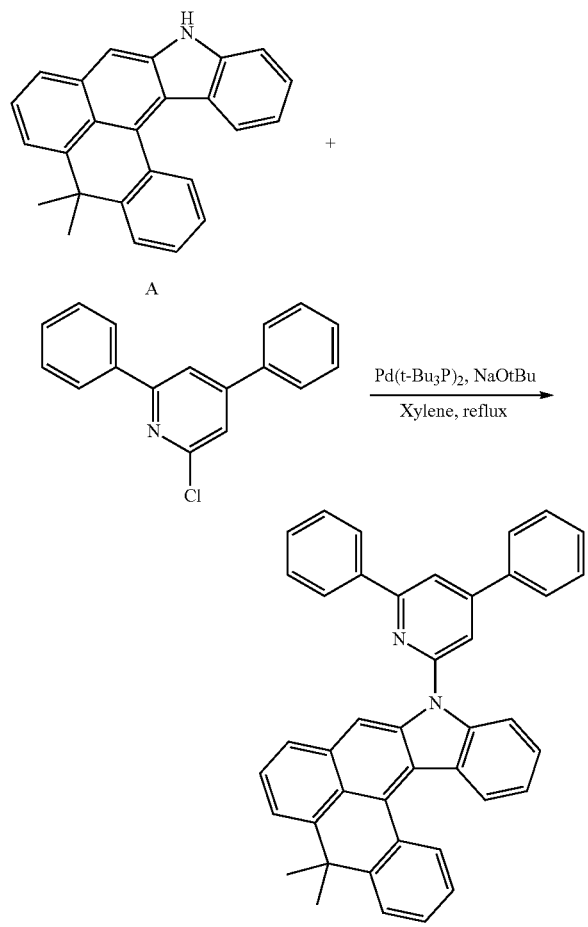

After completely dissolving Compound A (15.0 g, 45.02 mmol) and 2-chloro-4,6-diphenylpyridine (15.40 g, 49.53 mmol) in 210 ml of xylene in a 500 ml round bottom flask under nitrogen atmosphere, sodium tert-butoxide (5.62 g, 58.53 mmol) and then bis(tri-tert-butylphosphine) palladium (0) (0.12 g, 0.23 mmol) were added thereto, and the result was heated and stirred for 5 hours. The result was cooled to room temperature and filtered to remove salts, then xylene was vacuum concentrated, and the result was columned using tetrahydrofuran:hexane=1:7 to prepare Compound 1-7 (11.84 g, yield: 73%).
MS[M+H]⁺=563

<Preparation Example 8> Preparation of Compound 1-8 (Compound of Chemical Formula 2-1-37)

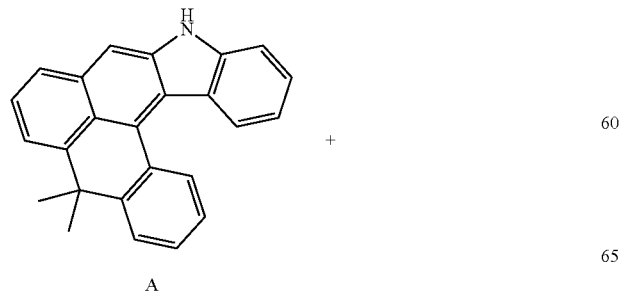

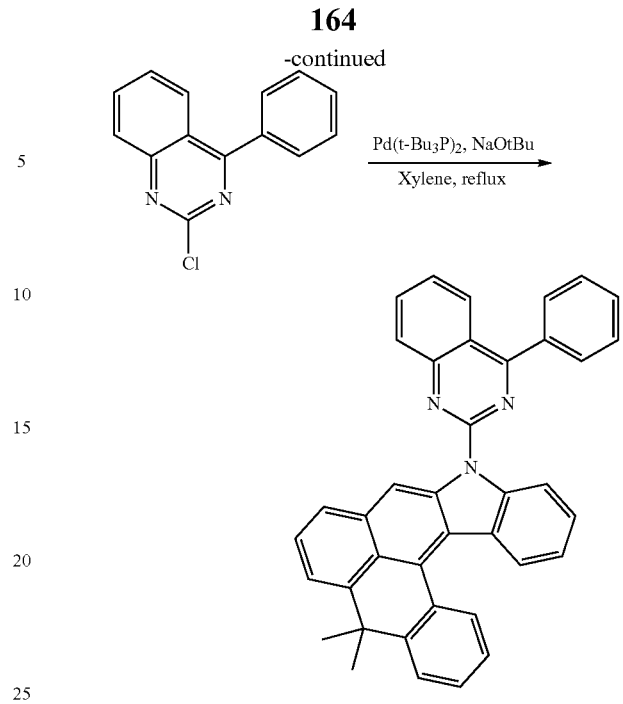

After completely dissolving Compound A (15.0 g, 45.02 mmol) and 2-chloro-4-phenylquinazoline (11.39 g, 49.53 mmol) in 220 ml of xylene in a 500 ml round bottom flask under nitrogen atmosphere, sodium tert-butoxide (5.62 g, 58.53 mmol) and then bis(tri-tert-butylphosphine) palladium (0) (0.12 g, 0.23 mmol) were added thereto, and the result was heated and stirred for 5 hours. The result was cooled to room temperature and filtered to remove salts, then xylene was vacuum concentrated, and the result was columned using tetrahydrofuran:hexane=1:5 to prepare Compound 1-8 (13.43 g, yield: 84%).
MS[M+H]⁺=538

<Preparation Example 9> Preparation of Compound 1-9 (Compound of Chemical Formula 2-1-39)

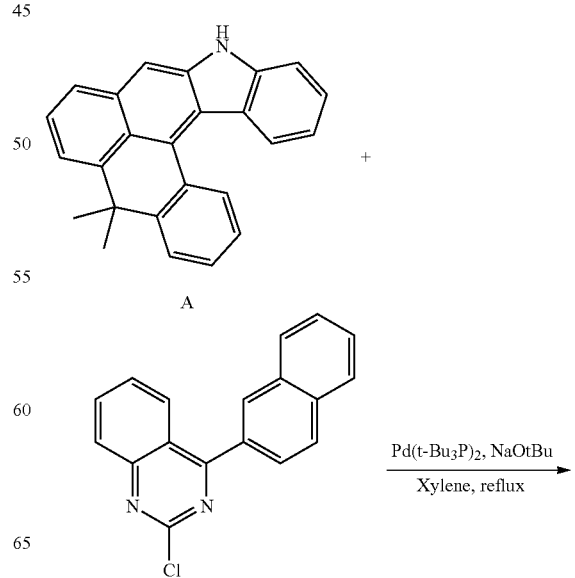

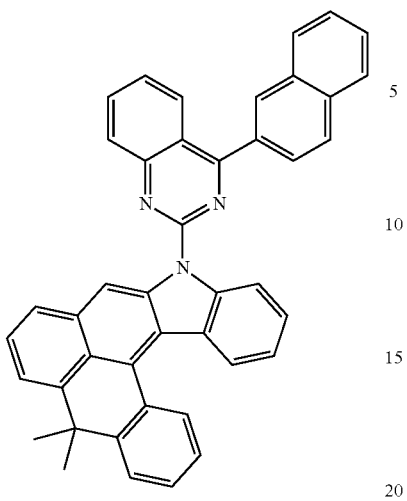

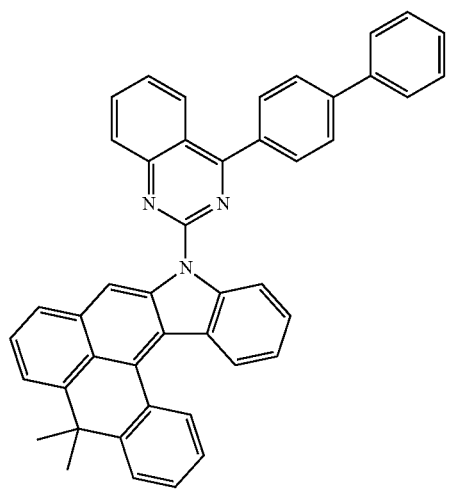

After completely dissolving Compound A (15.0 g, 45.02 mmol) and 2-chloro-4-(naphthalen-2-yl)quinazoline (14.36 g, 49.53 mmol) in 240 ml of xylene in a 500 ml round bottom flask under nitrogen atmosphere, sodium tert-butoxide (5.62 g, 58.53 mmol) and then bis(tri-tert-butylphosphine) palladium(0) (0.12 g, 0.23 mmol) were added thereto, and the result was heated and stirred for 3 hours. The result was cooled to room temperature and filtered to remove salts, then xylene was vacuum concentrated, and the result was columned using tetrahydrofuran:hexane=1:5 to prepare Compound 1-9 (11.55 g, yield: 65%).

MS[M+H]$^+$=588

After completely dissolving Compound A (15.0 g, 45.02 mmol) and 4-([1,1'-biphenyl]-4-yl)-2-chloroquinazoline (14.35 g, 49.53 mmol) in 240 ml of xylene in a 500 ml round bottom flask under nitrogen atmosphere, sodium tert-butoxide (5.62 g, 58.53 mmol) and then bis(tri-tert-butylphosphine) palladium(0) (0.12 g, 0.23 mmol) were added thereto, and the result was heated and stirred for 5 hours. The result was cooled to room temperature and filtered to remove salts, then xylene was vacuum concentrated, and the result was columned using tetrahydrofuran:hexane=1:5 to prepare Compound 1-10 (17.51 g, yield: 93%).

MS[M+H]$^+$=614

<Preparation Example 10> Preparation of Compound 1-10 (Chemical Formula 2-1-41)

<Preparation Example 11> Preparation of Compound 1-11 (Compound of Chemical Formula 2-1-19)

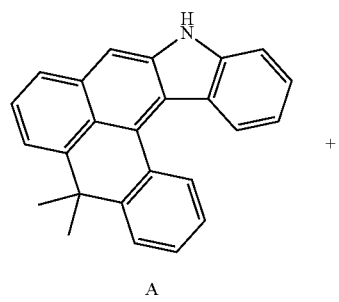

A

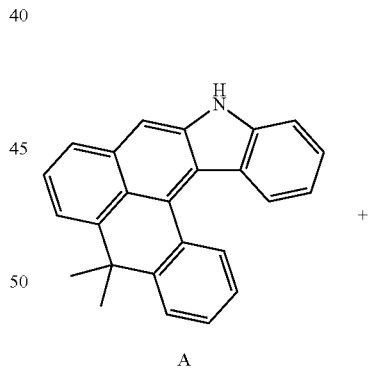

A

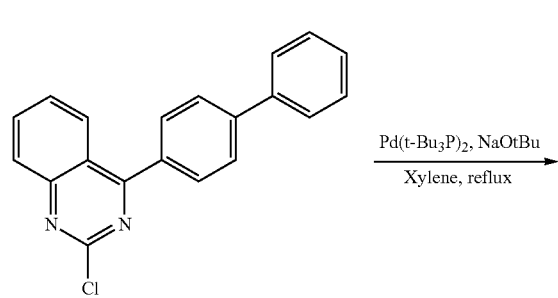

Pd(t-Bu$_3$P)$_2$, NaOtBu
Xylene, reflux

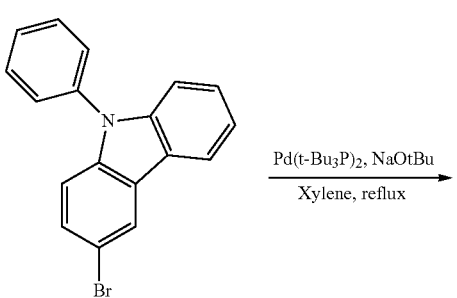

Pd(t-Bu$_3$P)$_2$, NaOtBu
Xylene, reflux

-continued

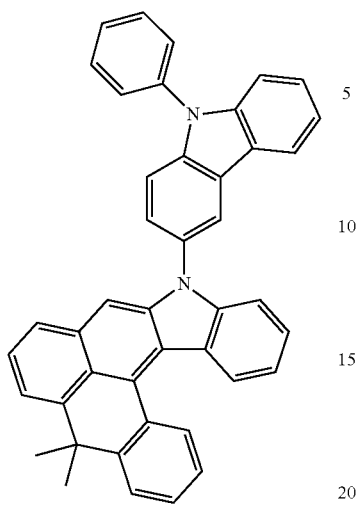

After completely dissolving Compound A (15.0 g, 45.02 mmol) and 3-bromo-9-phenyl-9H-carbazole (15.90 g, 49.53 mmol) in 200 ml of xylene in a 500 ml round bottom flask under nitrogen atmosphere, sodium tert-butoxide (5.62 g, 58.53 mmol) and then bis(tri-tert-butylphosphine) palladium (0) (0.12 g, 0.23 mmol) were added thereto, and the result was heated and stirred for 5 hours. The result was cooled to room temperature and filtered to remove salts, then xylene was vacuum concentrated, and the result was columned using tetrahydrofuran:hexane=1:6 to prepare Compound 1-11 (13.15 g, yield: 82%).

MS[M+H]$^+$=575

<Preparation Example 12> Preparation of Compound 1-12 (Compound of Chemical Formula 2-1-32)

-continued

After completely dissolving Compound A (15.0 g, 45.02 mmol) and 3-bromo-9-phenyl-9H-carbazole (15.90 g, 49.53 mmol) in 230 ml of xylene in a 500 ml round bottom flask under nitrogen atmosphere, sodium tert-butoxide (5.62 g, 58.53 mmol) and then bis(tri-tert-butylphosphine) palladium (0) (0.12 g, 0.23 mmol) were added thereto, and the result was heated and stirred for 5 hours. The result was cooled to room temperature and filtered to remove salts, then xylene was vacuum concentrated, and the result was columned using tetrahydrofuran:hexane=1:6 to prepare Compound 1-12 (14.95 g, yield: 87%).

MS[M+H]$^+$=575

<Preparation Example 13> Preparation of Compound 1-13 (Compound of Chemical Formula 2-1-20)

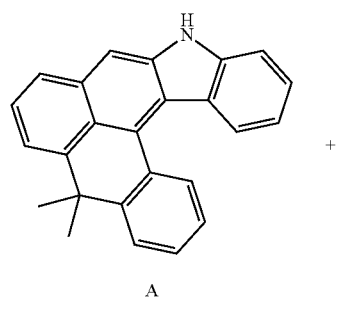

A

+

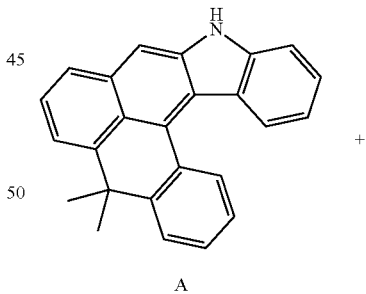

A

+

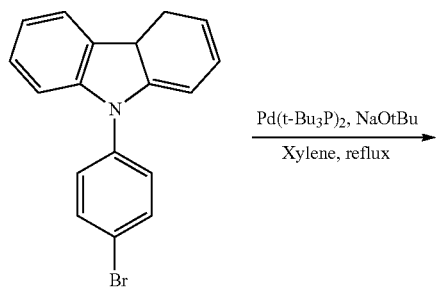

Pd(t-Bu$_3$P)$_2$, NaOtBu
────────────────
Xylene, reflux

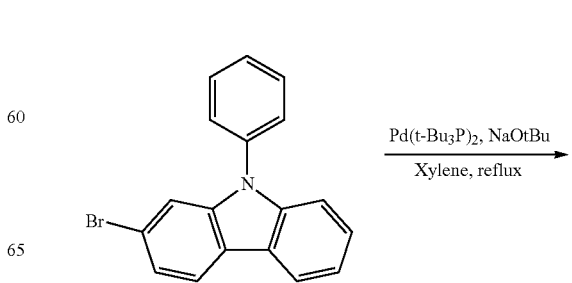

Pd(t-Bu$_3$P)$_2$, NaOtBu
────────────────
Xylene, reflux

-continued

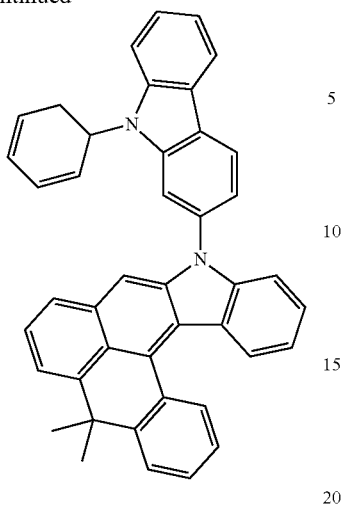

After completely dissolving Compound A (15.0 g, 45.02 mmol) and 2-bromo-9-phenyl-9H-carbazole (15.90 g, 49.53 mmol) in 230 ml of xylene in a 500 ml round bottom flask under nitrogen atmosphere, sodium tert-butoxide (5.62 g, 58.53 mmol) and then bis(tri-tert-butylphosphine) palladium (0) (0.12 g, 0.23 mmol) were added thereto, and the result was heated and stirred for 5 hours. The result was cooled to room temperature and filtered to remove salts, then xylene was vacuum concentrated, and the result was columned using tetrahydrofuran:hexane=1:6 to prepare Compound 1-13 (12.02 g, yield: 76%).

MS[M+H]$^+$=575

<Preparation Example 14> Preparation of Compound 1-14 (Compound of Chemical Formula 2-1-23)

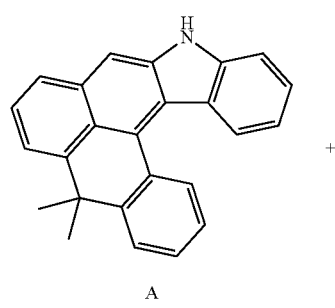

A

+

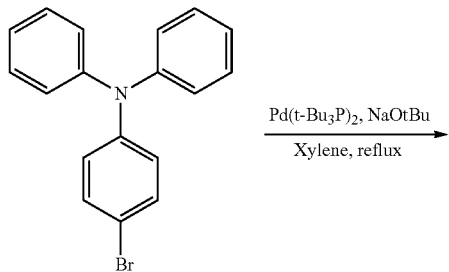

Pd(t-Bu$_3$P)$_2$, NaOtBu
Xylene, reflux
→

-continued

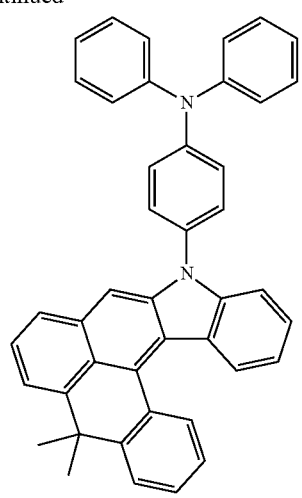

After completely dissolving Compound A (15.0 g, 45.02 mmol) and 4-bromo-N,N-diphenylaniline (15.92 g, 49.53 mmol) in 190 ml of xylene in a 500 ml round bottom flask under nitrogen atmosphere, sodium tert-butoxide (5.62 g, 58.53 mmol) and then bis(tri-tert-butylphosphine) palladium (0) (0.12 g, 0.23 mmol) were added thereto, and the result was heated and stirred for 5 hours. The result was cooled to room temperature and filtered to remove salts, then xylene was vacuum concentrated, and the result was columned using tetrahydrofuran:hexane=1:10 to prepare Compound 1-14 (11.01 g, yield: 64%).

MS[M+H]$^+$=577

<Preparation Example 15> Preparation of Compound 1-15 (Compound of Chemical Formula 2-1-25)

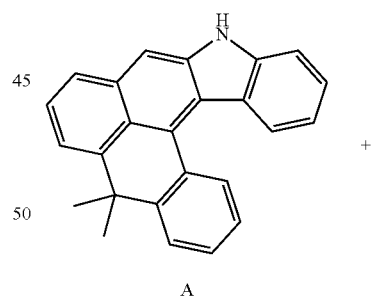

A

+

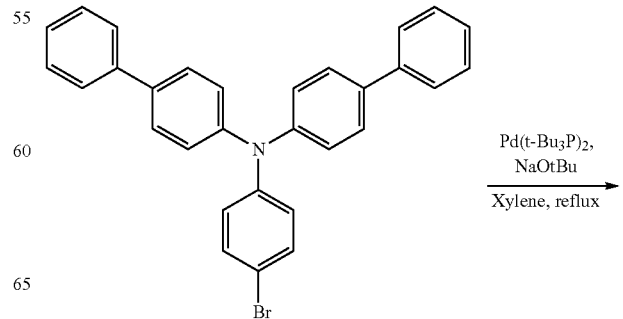

Pd(t-Bu$_3$P)$_2$, NaOtBu
Xylene, reflux
→

-continued

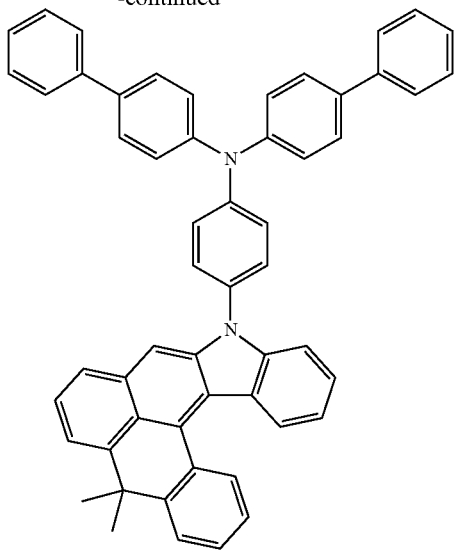

After completely dissolving Compound A (15.0 g, 45.02 mmol) and N-([1,1'-biphenyl]-4-yl)-N-(4-bromophenyl)-[1,1'-biphenyl]-4-amine (21.81 g, 49.53 mmol) in 210 ml of xylene in a 500 ml round bottom flask under nitrogen atmosphere, sodium tert-butoxide (5.62 g, 58.53 mmol) and then bis(tri-tert-butylphosphine) palladium(0) (0.12 g, 0.23 mmol) were added thereto, and the result was heated and stirred for 5 hours. The result was cooled to room temperature and filtered to remove salts, then xylene was vacuum concentrated, and the result was columned using tetrahydrofuran:hexane=1:7 to prepare Compound 1-15 (18.54 g, yield: 85%).

MS[M+H]$^+$=729

<Preparation Example 16> Preparation of Compound 1-16 (Compound of Chemical Formula 2-1-26)

-continued

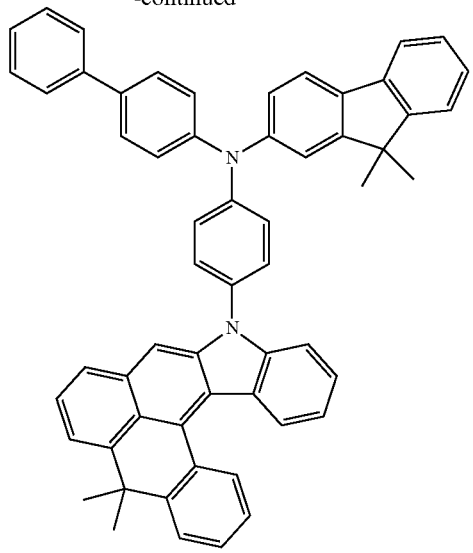

After completely dissolving Compound A (15.0 g, 45.02 mmol) and N-([1,1'-biphenyl]-4-yl)-N-(4-bromophenyl)-9,9-dimethyl-9H-fluoren-2-amine (22.05 g, 49.53 mmol) in 210 ml of xylene in a 500 ml round bottom flask under nitrogen atmosphere, sodium tert-butoxide (5.62 g, 58.53 mmol) and then bis(tri-tert-butylphosphine) palladium(0) (0.12 g, 0.23 mmol) were added thereto, and the result was heated and stirred for 5 hours. The result was cooled to room temperature and filtered to remove salts, then xylene was vacuum concentrated, and the result was columned using tetrahydrofuran:hexane=1:7 to prepare Compound 1-16 (19.66 g, yield: 87%).

MS[M+H]$^+$=769

<Preparation Example 17> Preparation of Compound 1-17 (Compound of Chemical Formula 2-1-28)

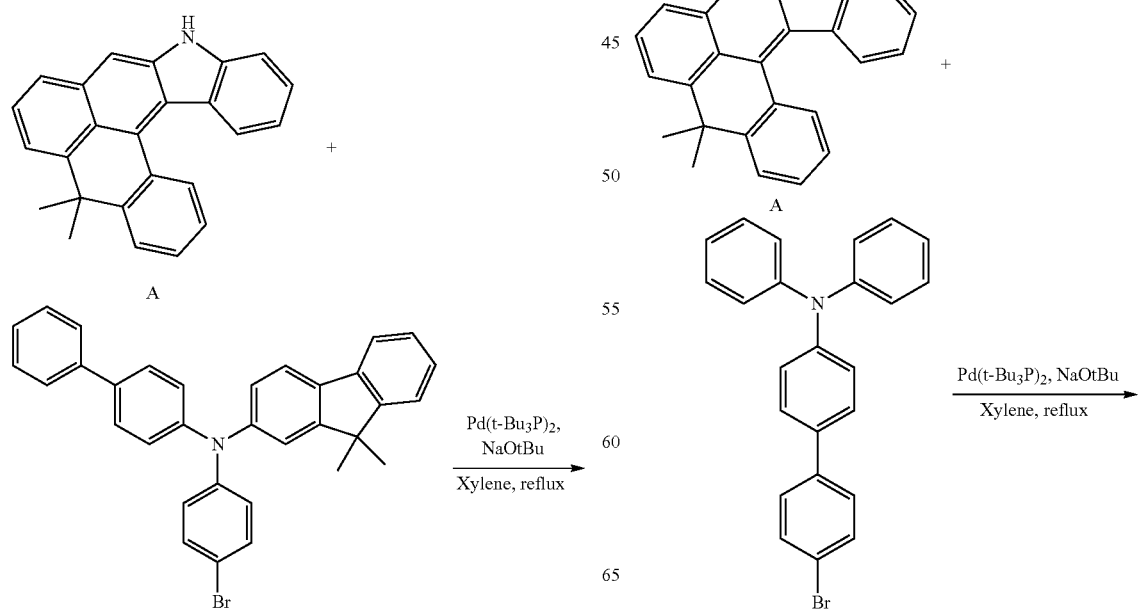

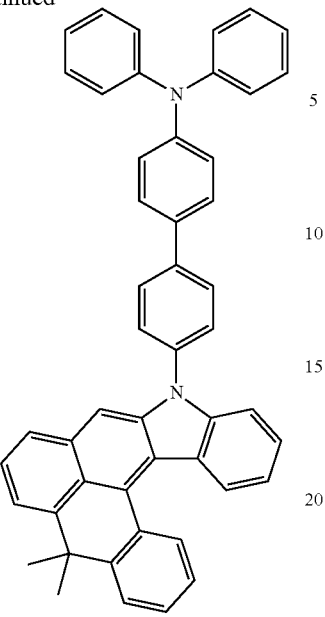

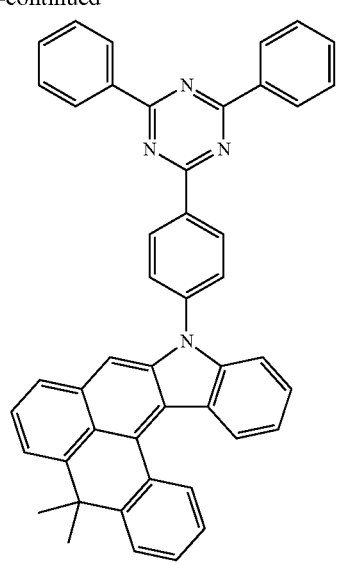

After completely dissolving Compound A (15.0 g, 45.02 mmol) and 4'-bromo-N,N-diphenyl-[1,1'-biphenyl]-4-amine (19.82 g, 49.53 mmol) in 210 ml of xylene in a 500 ml round bottom flask under nitrogen atmosphere, sodium tert-butoxide (5.62 g, 58.53 mmol) and then bis(tri-tert-butylphosphine) palladium(0) (0.12 g, 0.23 mmol) were added thereto, and the result was heated and stirred for 5 hours. The result was cooled to room temperature and filtered to remove salts, then xylene was vacuum concentrated, and the result was columned using tetrahydrofuran:hexane=1:6 to prepare Compound 1-17 (17.44 g, yield: 89%).

MS[M+H]$^+$=653

<Preparation Example 18> Preparation of Compound 1-18 (Compound of Chemical Formula 2-1-46)

After completely dissolving Compound A (15.0 g, 45.02 mmol) and 2-(4-bromophenyl)-4,6-diphenyl-1,3,5-triazine (19.17 g, 49.53 mmol) in 290 ml of xylene in a 500 ml round bottom flask under nitrogen atmosphere, sodium tert-butoxide (5.62 g, 58.53 mmol) and then bis(tri-tert-butylphosphine) palladium(0) (0.12 g, 0.23 mmol) were added thereto, and the result was heated and stirred for 5 hours. The result was cooled to room temperature and filtered to remove salts, then xylene was vacuum concentrated, and the result was columned using tetrahydrofuran:hexane=1:7 to prepare Compound 1-18 (17.88 g, yield: 87%).

MS[M+H]$^+$=641

<Preparation Example 19> Preparation of Compound 1-19 (Compound of Chemical Formula 2-1-76)

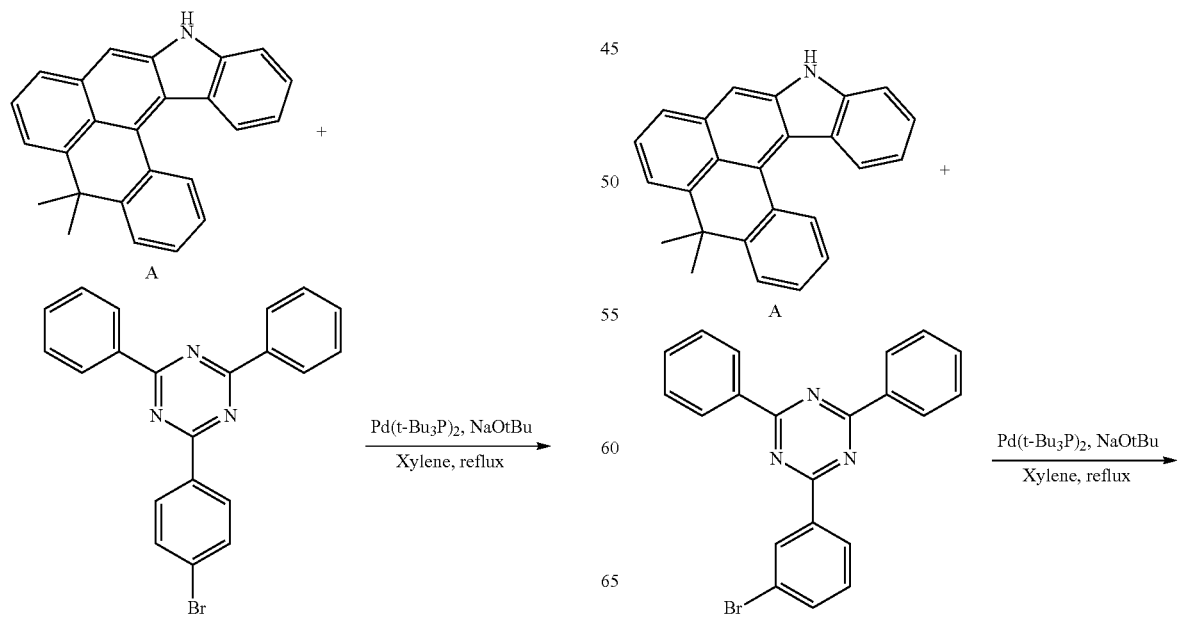

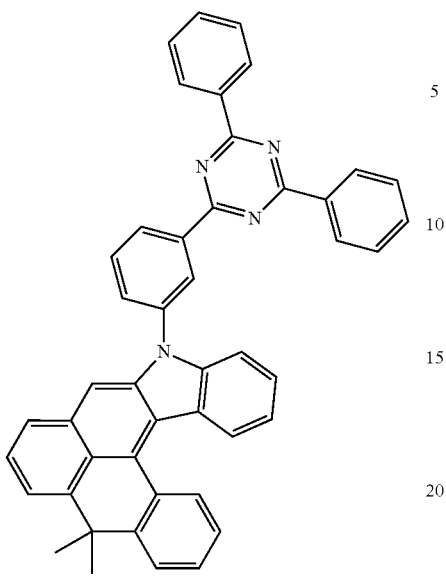

After completely dissolving Compound A (15.0 g, 45.02 mmol) and 2-(3-bromophenyl)-4,6-diphenyl-1,3,5-triazine (19.17 g, 49.53 mmol) in 240 ml of xylene in a 500 ml round bottom flask under nitrogen atmosphere, sodium tert-butoxide (5.62 g, 58.53 mmol) and then bis(tri-tert-butylphosphine) palladium(0) (0.12 g, 0.23 mmol) were added thereto, and the result was heated and stirred for 5 hours. The result was cooled to room temperature and filtered to remove salts, then xylene was vacuum concentrated, and the result was columned using tetrahydrofuran:hexane=1:7 to prepare Compound 1-19 (15.41 g, yield: 76%).

MS[M+H]$^+$=641

<Preparation Example 20> Preparation of Compound 1-20 (Compound of Chemical Formula 2-1-53)

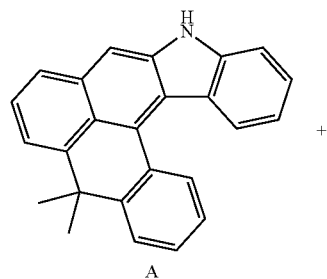

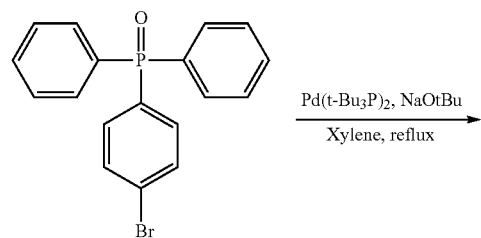

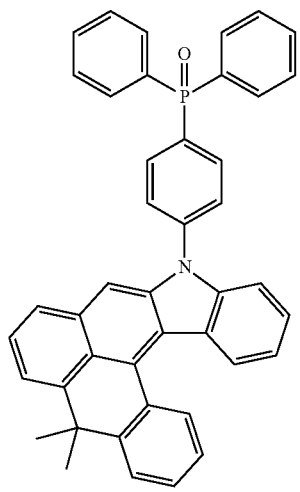

After completely dissolving Compound A (15.0 g, 45.02 mmol) and (4-bromophenyl)diphenylphosphine oxide (16.35 g, 49.53 mmol) in 280 ml of xylene in a 500 ml round bottom flask under nitrogen atmosphere, sodium tert-butoxide (5.62 g, 58.53 mmol) and then bis(tri-tert-butylphosphine) palladium(0) (0.12 g, 0.23 mmol) were added thereto, and the result was heated and stirred for 5 hours. The result was cooled to room temperature and filtered to remove salts, then xylene was vacuum concentrated, and the result was columned using tetrahydrofuran:hexane=1:8 to prepare Compound 1-20 (11.01 g, yield: 64%).

MS[M+H]$^+$=610

<Preparation Example 21> Preparation of Compound 1-21 (Compound of Chemical Formula 2-1-52)

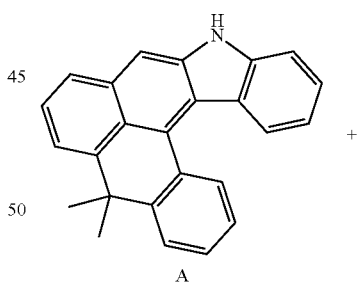

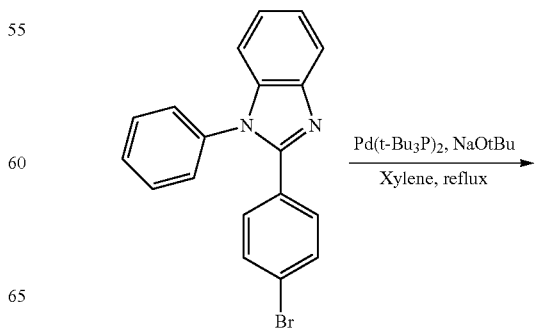

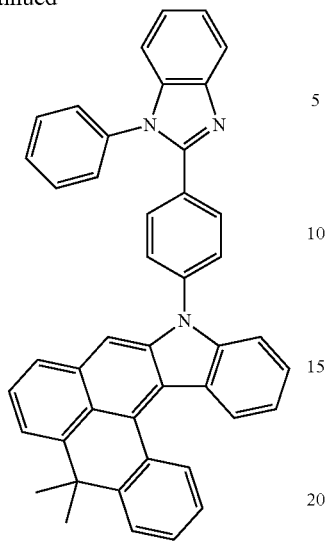

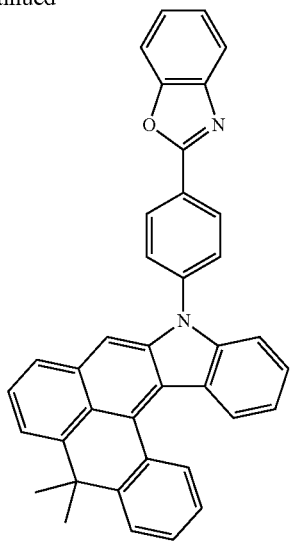

After completely dissolving Compound A (15.0 g, 45.02 mmol) and 2-(4-bromophenyl)-1-phenyl-1H-benzo[d]imidazole (17.24 g, 49.53 mmol) in 210 ml of xylene in a 500 ml round bottom flask under nitrogen atmosphere, sodium tert-butoxide (5.62 g, 58.53 mmol) and then bis(tri-tert-butylphosphine) palladium(0) (0.12 g, 0.23 mmol) were added thereto, and the result was heated and stirred for 5 hours. The result was cooled to room temperature and filtered to remove salts, then xylene was vacuum concentrated, and the result was columned using tetrahydrofuran:hexane=1:11 to prepare Compound 1-21 (16.12 g, yield: 89%).

MS[M+H]$^+$=602

After completely dissolving Compound A (15.0 g, 45.02 mmol) and 2-(4-bromophenyl)benzo[d]oxazole (13.52 g, 49.53 mmol) in 210 ml of xylene in a 500 ml round bottom flask under nitrogen atmosphere, sodium tert-butoxide (5.62 g, 58.53 mmol) and then bis(tri-tert-butylphosphine) palladium(0) (0.12 g, 0.23 mmol) were added thereto, and the result was heated and stirred for 5 hours. The result was cooled to room temperature and filtered to remove salts, then xylene was vacuum concentrated, and the result was columned using tetrahydrofuran:hexane=1:8 to prepare Compound 1-22 (12.16 g, yield: 77%).

MS[M+H]$^+$=527

<Preparation Example 22> Preparation of Compound 1-22 (Compound of Chemical Formula 2-1-54)

<Preparation Example 23> Preparation of Compound 1-23 (Compound of Chemical Formula 2-1-63)

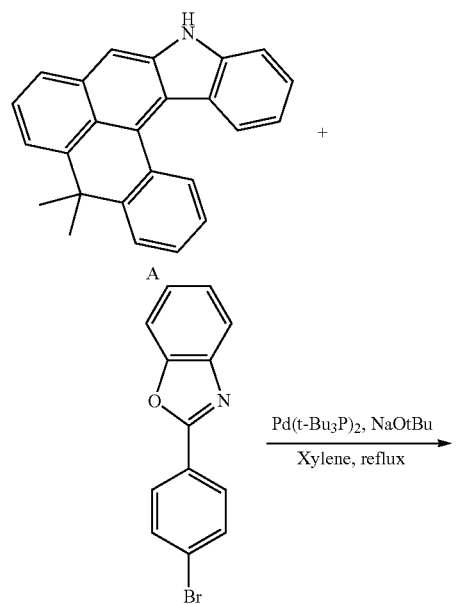

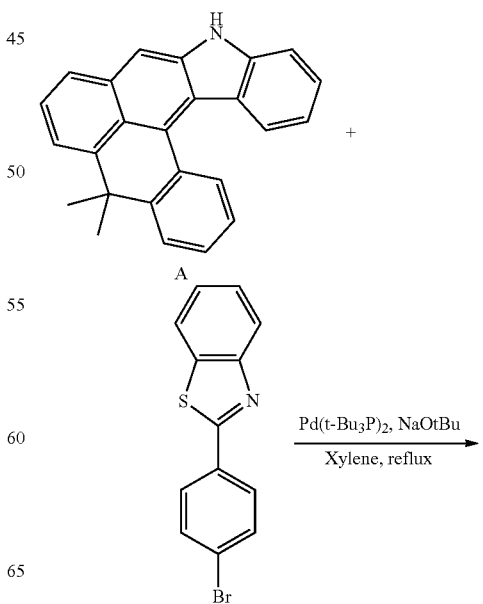

-continued

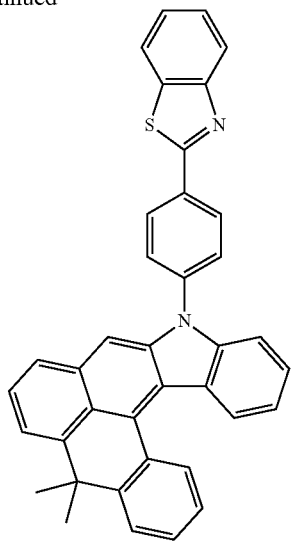

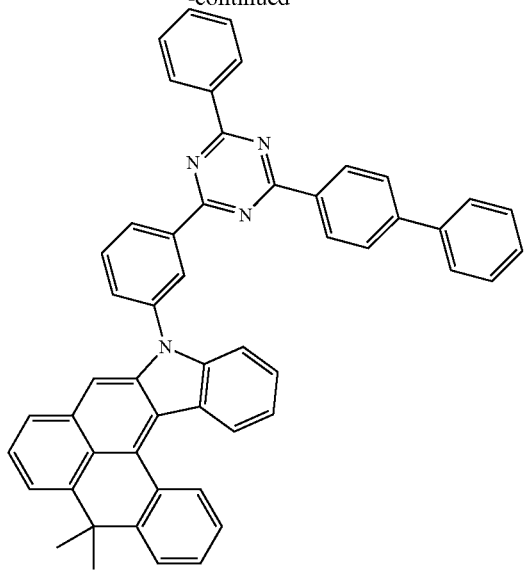

After completely dissolving Compound A (15.0 g, 45.02 mmol) and 2-(4-bromophenyl)benzo[d]thiazole (14.31 g, 49.53 mmol) in 210 ml of xylene in a 500 ml round bottom flask under nitrogen atmosphere, sodium tert-butoxide (5.62 g, 58.53 mmol) and then bis(tri-tert-butylphosphine) palladium(0) (0.12 g, 0.23 mmol) were added thereto, and the result was heated and stirred for 5 hours. The result was cooled to room temperature and filtered to remove salts, then xylene was vacuum concentrated, and the result was columned using tetrahydrofuran:hexane=1:8 to prepare Compound 1-23 (14.19 g, yield: 87%).

MS[M+H]$^+$=543

<Preparation Example 24> Preparation of Compound 1-24 (Compound of Chemical Formula 2-1-76)

After completely dissolving Compound A (15.0 g, 45.02 mmol) and 2-([1,1'-biphenyl]-4-yl)-4-(3-bromophenyl)-6-phenyl-1,3,5-triazine (19.17 g, 49.53 mmol) in 300 ml of xylene in a 500 ml round bottom flask under nitrogen atmosphere, sodium tert-butoxide (5.62 g, 58.53 mmol) and then bis(tri-tert-butylphosphine) palladium(0) (0.12 g, 0.23 mmol) were added thereto, and the result was heated and stirred for 5 hours. The result was cooled to room temperature and filtered to remove salts, then xylene was vacuum concentrated, and the result was columned using tetrahydrofuran:hexane=1:4 to prepare Compound 1-24 (18.91 g, yield: 88%).

MS[M+H]$^+$=717

<Preparation Example 25> Preparation of Compound 1-25 (Compound of Chemical Formula 2-1-77)

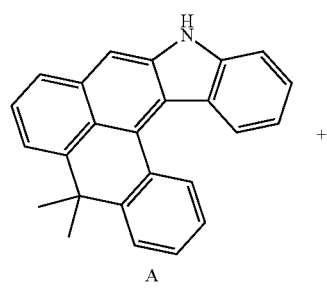

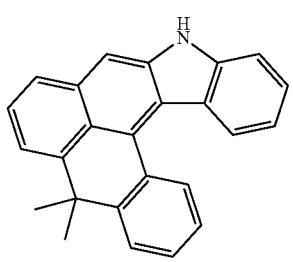

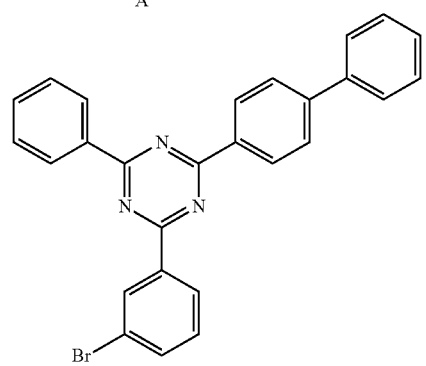

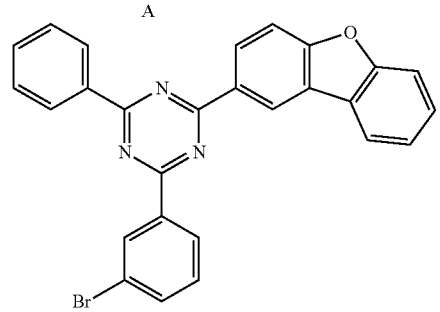

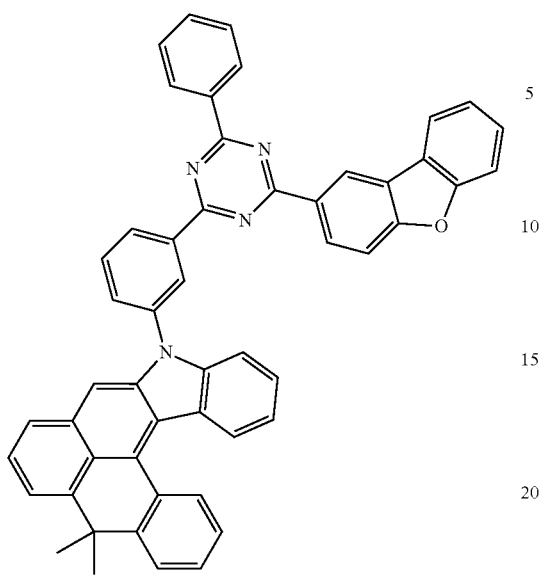

After completely dissolving Compound A (15.0 g, 45.02 mmol) and 2-(3-bromophenyl)-4-(dibenzo[b,d]furan-2-yl)-6-phenyl-1,3,5-triazine (19.17 g, 49.53 mmol) in 300 ml of xylene in a 500 ml round bottom flask under nitrogen atmosphere, sodium tert-butoxide (5.62 g, 58.53 mmol) and then bis(tri-tert-butylphosphine) palladium(0) (0.12 g, 0.23 mmol) were added thereto, and the result was heated and stirred for 4 hours. The result was cooled to room temperature and filtered to remove salts, then xylene was vacuum concentrated, and the result was columned using tetrahydrofuran:hexane=1:5 to prepare Compound 1-25 (17.42 g, yield: 79%).

MS[M+H]$^+$=731

<Preparation Example 26> Preparation of Compound 1-26 (Compound of Chemical Formula 2-1-64)

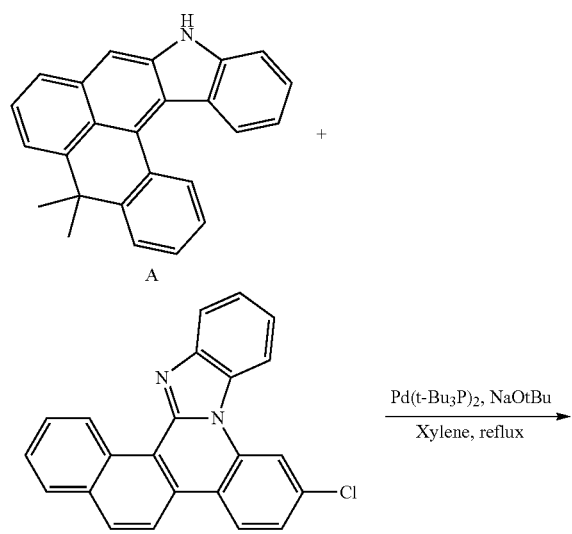

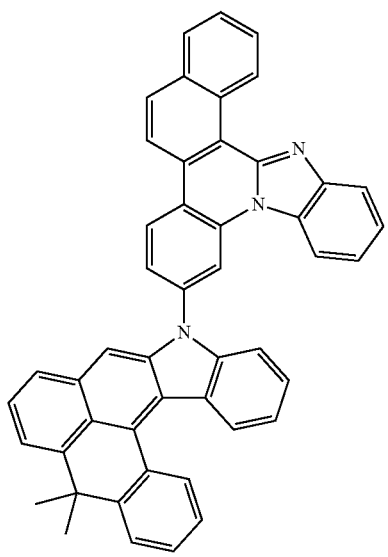

After completely dissolving Compound A (15.0 g, 45.02 mmol) and 9-chlorobenzo[i]benzo[4,5]imidazo[1,2-f]phenanthridine (17.43 g, 49.53 mmol) in 300 ml of xylene in a 500 ml round bottom flask under nitrogen atmosphere, sodium tert-butoxide (5.62 g, 58.53 mmol) and then bis(tri-tert-butylphosphine) palladium(0) (0.12 g, 0.23 mmol) were added thereto, and the result was heated and stirred for 12 hours. The result was cooled to room temperature and filtered to remove salts, then xylene was vacuum concentrated, and the result was columned using tetrahydrofuran:hexane=1:3 to prepare Compound 1-26 (17.09 g, yield: 87%).

MS[M+H]$^+$=650

<Preparation Example 27> Preparation of Compound 1-27 (Compound of Chemical Formula 2-1-78)

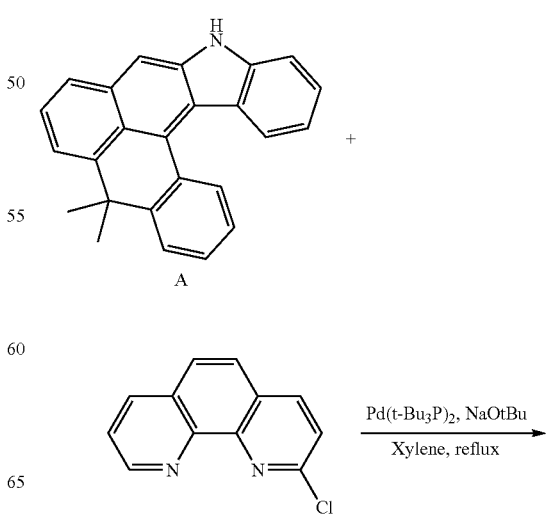

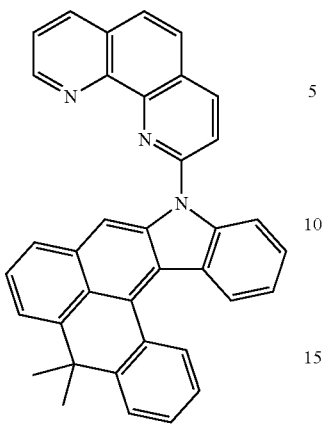

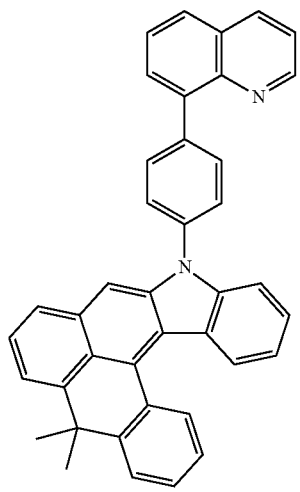

After completely dissolving Compound A (15.0 g, 45.02 mmol) and 2-bromo-1,10-phenanthroline (12.78 g, 49.53 mmol) in 300 ml of xylene in a 500 ml round bottom flask under nitrogen atmosphere, sodium tert-butoxide (5.62 g, 58.53 mmol) and then bis(tri-tert-butylphosphine) palladium (0) (0.12 g, 0.23 mmol) were added thereto, and the result was heated and stirred for 5 hours. The result was cooled to room temperature and filtered to remove salts, then xylene was vacuum concentrated, and the result was columned using tetrahydrofuran:hexane=1:7 to prepare Compound 1-27 (12.44 g, yield: 78%).

MS[M+H]$^+$=512

After completely dissolving Compound A (15.0 g, 45.02 mmol) and 8-(4-bromophenyl)quinolone (10.10 g, 49.53 mmol) in 150 ml of xylene in a 500 ml round bottom flask under nitrogen atmosphere, sodium tert-butoxide (5.62 g, 58.53 mmol) and then bis(tri-tert-butylphosphine) palladium (0) (0.12 g, 0.23 mmol) were added thereto, and the result was heated and stirred for 2 hours. The result was cooled to room temperature and filtered to remove salts, then xylene was vacuum concentrated, and the result was columned using tetrahydrofuran:hexane=1:10 to prepare Compound 1-28 (12.64 g, yield: 82%).

MS[M+H]$^+$=537

<Preparation Example 28> Preparation of Compound 1-28 (Compound of Chemical Formula 2-1-43)

<Preparation Example 29> Preparation of Compound 1-29 (Compound of Chemical Formula 2-1-44)

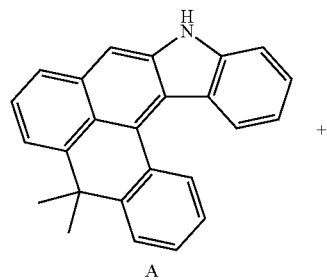

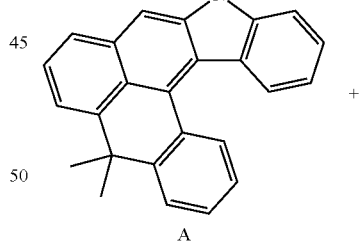

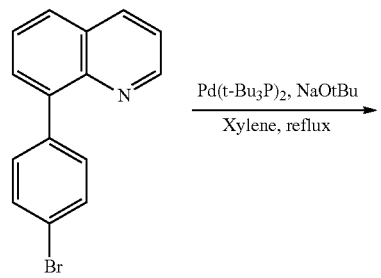

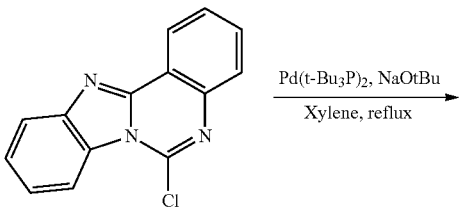

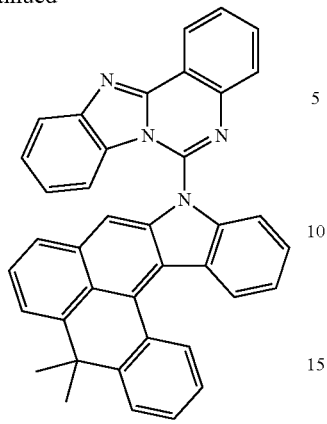

After completely dissolving Compound A (15.0 g, 45.02 mmol) and 6-chlorobenzo[4,5]imidazo[1,2-c]quinazoline (12.53 g, 49.53 mmol) in 150 ml of xylene in a 500 ml round bottom flask under nitrogen atmosphere, sodium tert-butoxide (5.62 g, 58.53 mmol) and then bis(tri-tert-butylphosphine) palladium(0) (0.12 g, 0.23 mmol) were added thereto, and the result was heated and stirred for 5 hours. The result was cooled to room temperature and filtered to remove salts, then xylene was vacuum concentrated, and the result was columned using tetrahydrofuran:hexane=1:6 to prepare Compound 1-29 (14.22 g, yield: 86%).

MS[M+H]$^+$=551

<Preparation Example 30> Compound Synthesis of Following Compounds 1-30 to 1-58

1-30

<image ignored>

1-31

<image ignored>

1-32

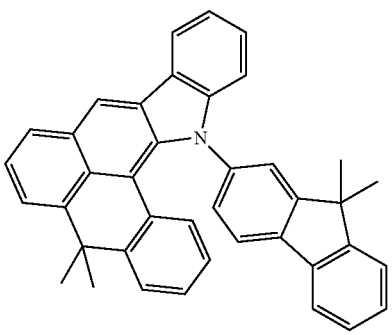

1-33

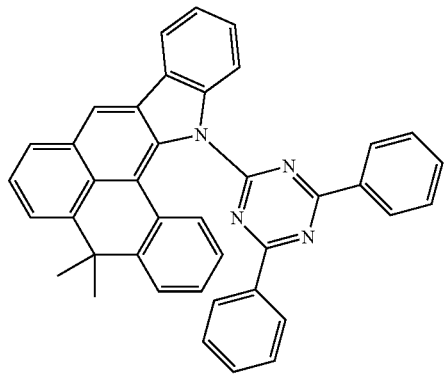

1-34

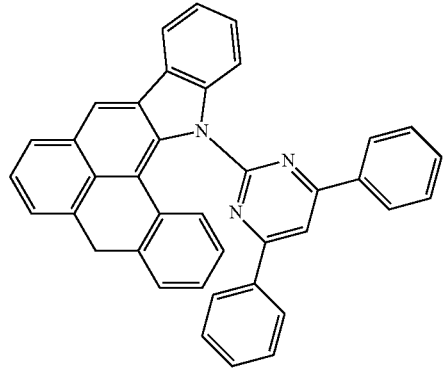

1-35

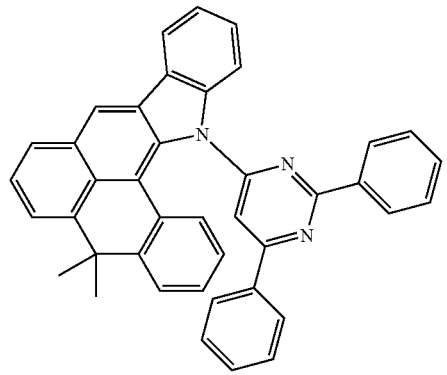

1-36
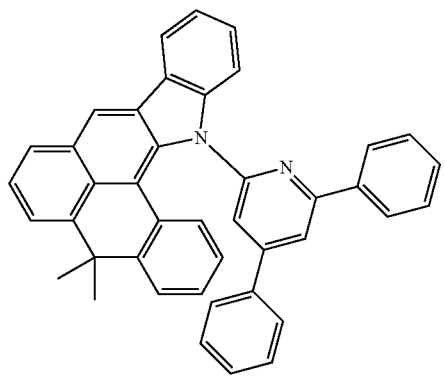
1-37
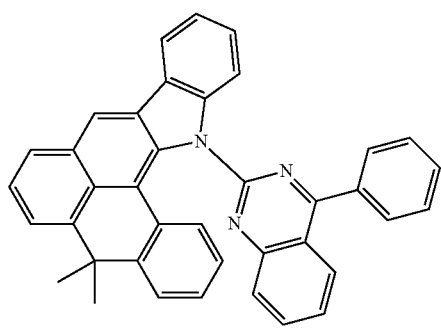
1-38
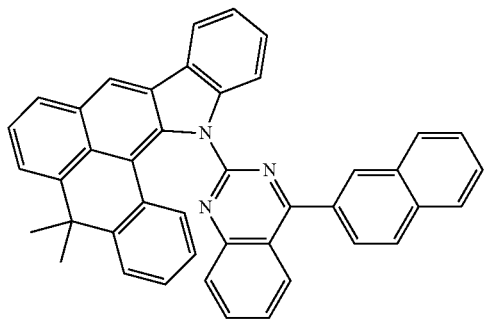
1-39
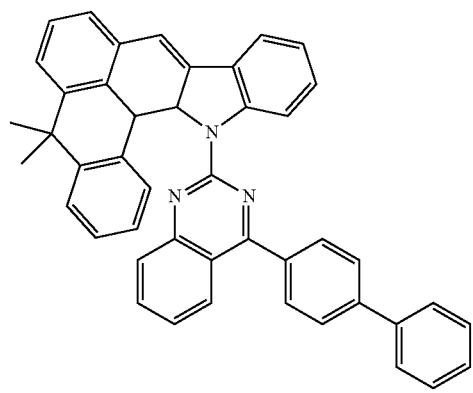
1-40
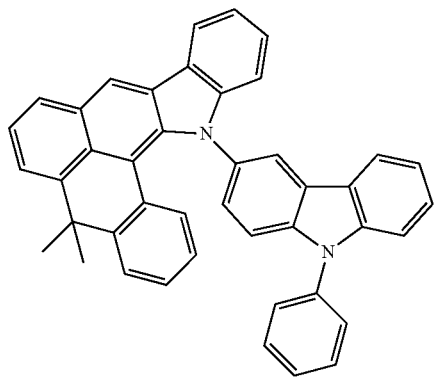
1-41
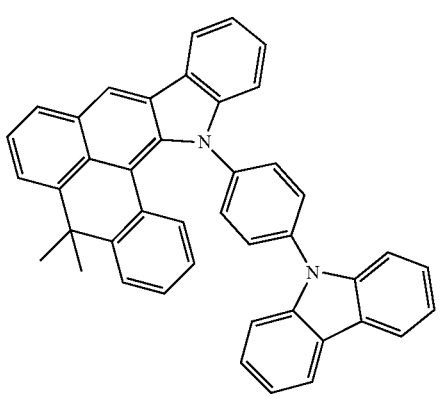
1-42
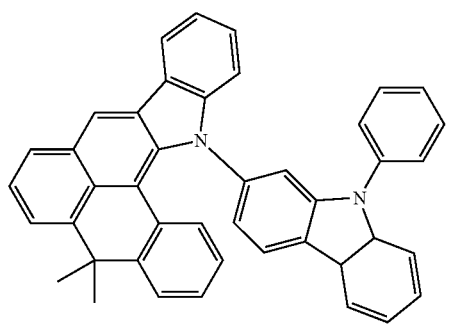
1-43
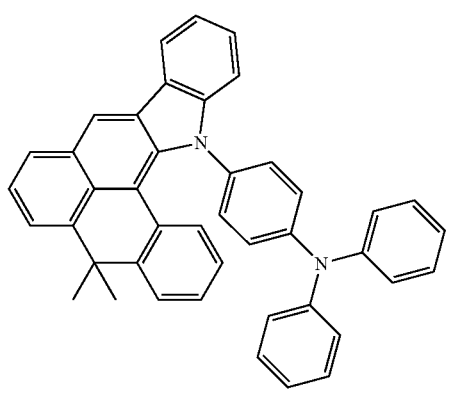

1-44
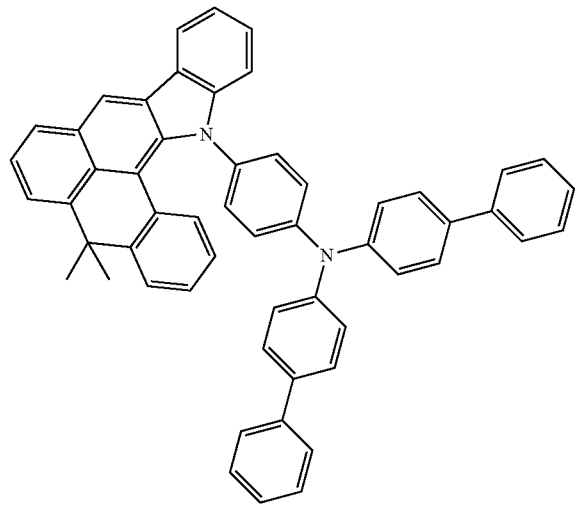
1-45
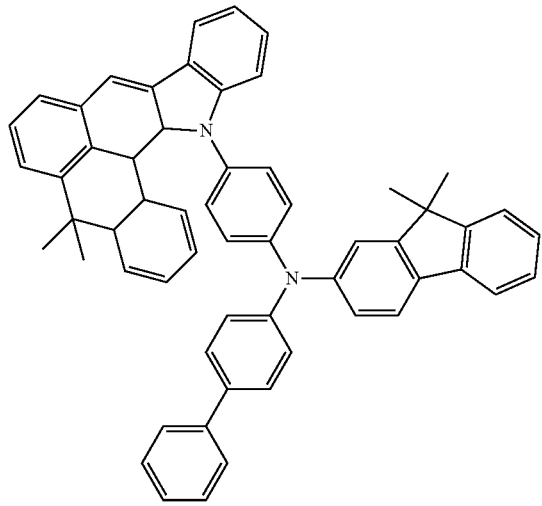
1-46
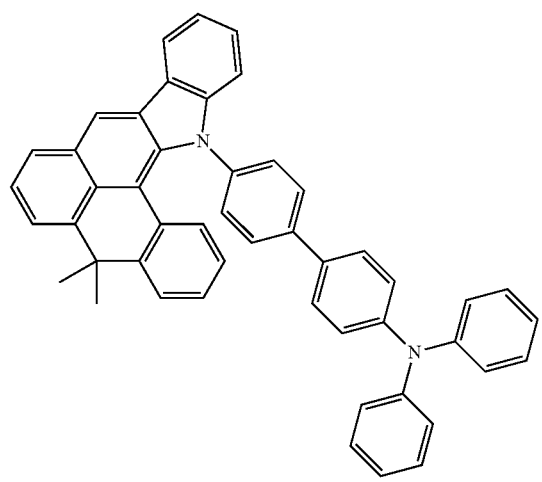
1-47
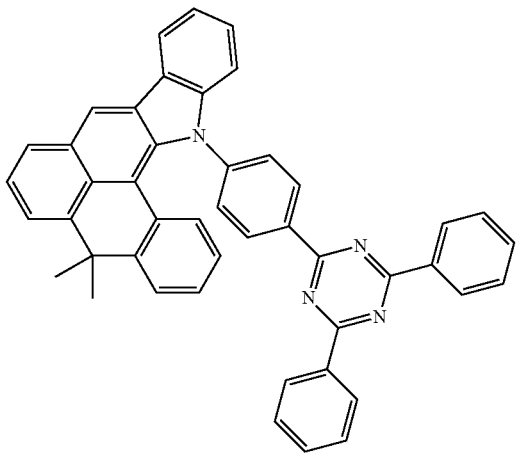
1-48
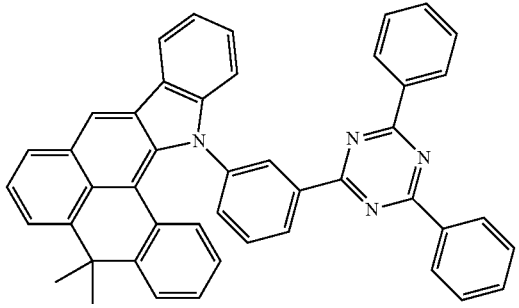
1-49
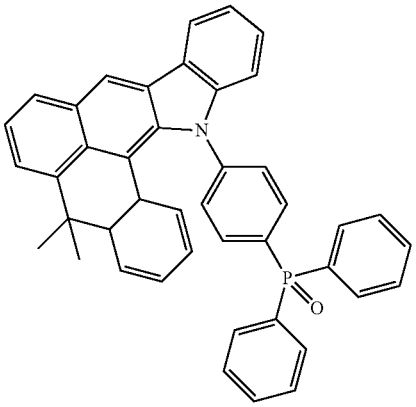
1-50
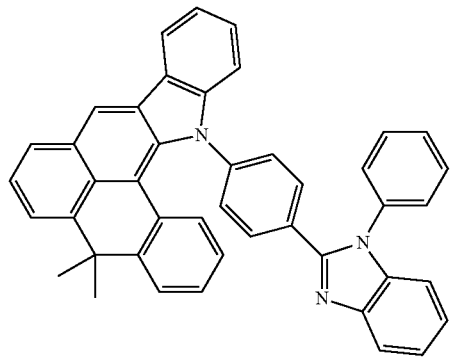

1-51

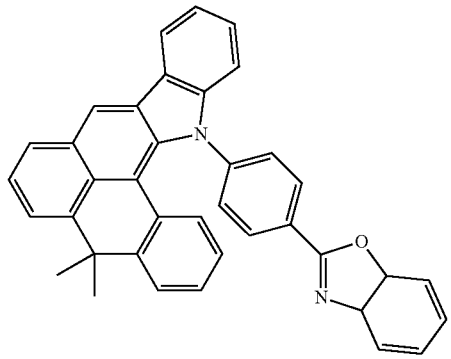

1-52

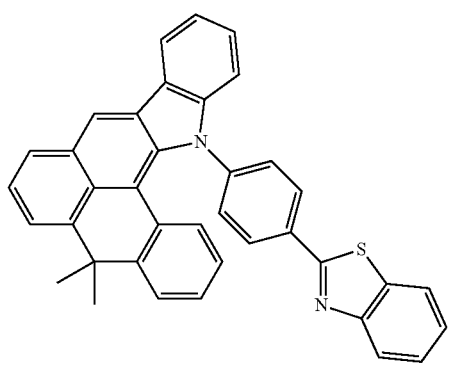

1-53

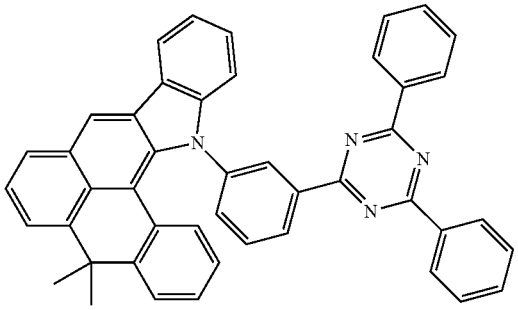

1-54

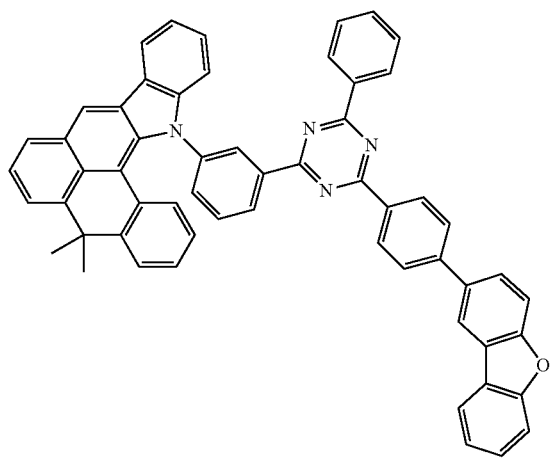

1-55

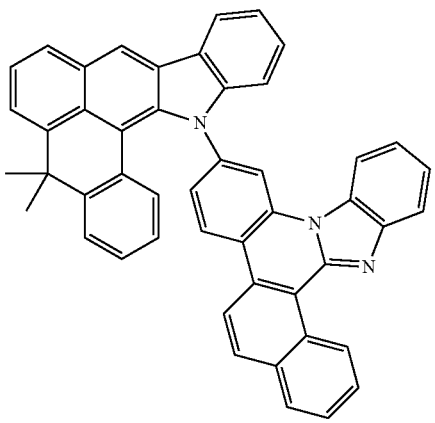

1-56

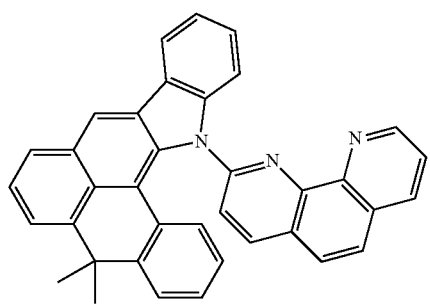

1-57

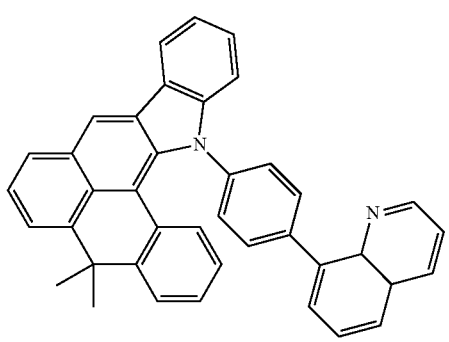

1-58

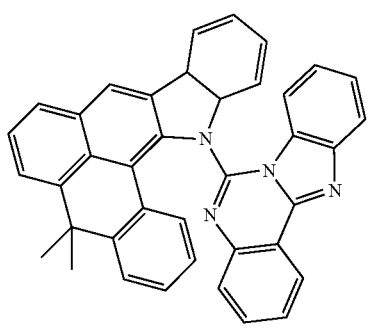

Compounds 1-30 to 1-58 were prepared in the same manner as in Preparation Examples 1 to 29, the methods of preparing Compounds 1-1 to 1-29, except that Compound B was used instead of Compound A as the starting material.

Example 1-1

A glass substrate on which indium tin oxide (ITO) was coated as a thin film to a thickness of 1,000 Å was placed in detergent-dissolved distilled water and ultrasonic cleaned. Herein, a product of Fischer Co. was used as the detergent, and as the distilled water, distilled water filtered twice with a filter manufactured by Millipore Co. was used. After the ITO was cleaned for 30 minutes, ultrasonic cleaning was repeated twice using distilled water for 10 minutes. After the cleaning with distilled water was finished, the substrate was ultrasonic cleaned with solvents of isopropyl alcohol, acetone and methanol, then dried, and then transferred to a plasma cleaner. In addition, the substrate was cleaned for 5 minutes using oxygen plasma, and then transferred to a vacuum depositor.

On the transparent ITO electrode prepared as above, a hole injection layer was formed by thermal vacuum depositing hexanitrile hexaazatriphenylene (HAT) of the following chemical formula to a thickness of 500 Å.

[HAT]

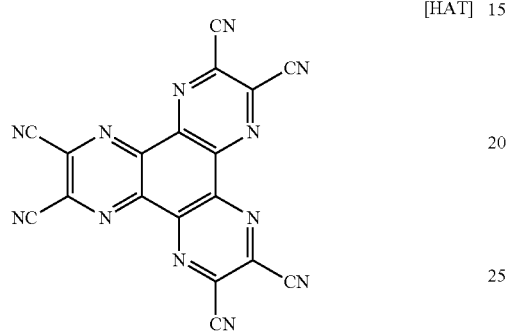

A hole transfer layer was formed on the hole injection layer by vacuum depositing the following compound 4-4'-bis[N-(1-naphthyl)-N-phenylamino]biphenyl (NPB) (300 Å), a material transferring holes.

[NPB]

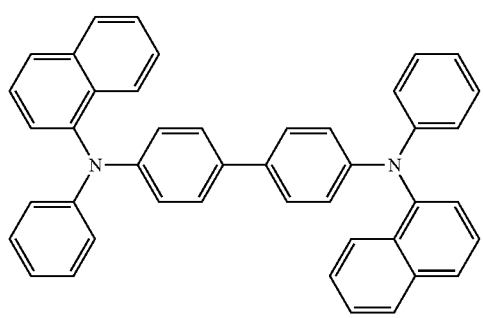

Subsequently, an electron blocking layer was formed on the hole transfer layer by vacuum depositing Compound 1-1 (compound of the following Chemical Formula 2-1-1) to a film thickness of 100 Å.

[Chemical Formula 2-2-1]

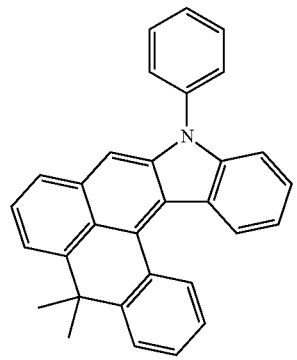

Subsequently, a light emitting layer was formed on the electron blocking layer to a film thickness of 300 Å by vacuum depositing BH and BD as follows in a weight ratio of 25:1.

[BH]

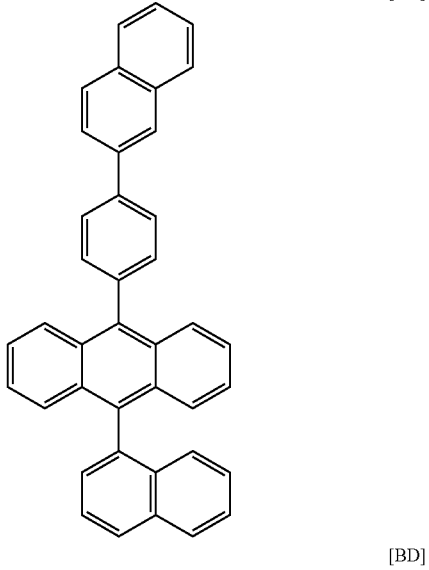

[BD]

[ET1]

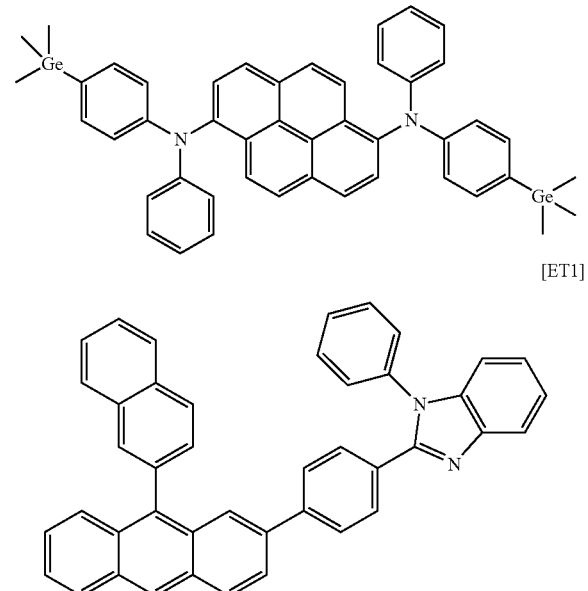

[LiQ]

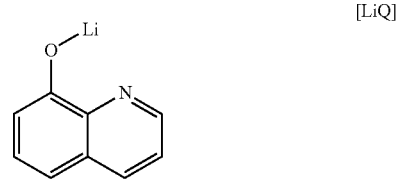

On the light emitting layer, an electron injection and transfer layer was formed to a thickness of 300 Å by vacuum depositing Compound ET1 and the lithium quinolate (LiQ) compound in a weight ratio of 1:1. A cathode was formed on the electron injection and transfer layer by depositing lithium fluoride (LiF) to a thickness of 12 Å and aluminum to a thickness of 2,000 Å in consecutive order.

An organic light emitting device was manufactured by maintaining, in the above-mentioned processes, the deposition rates of the organic materials at 0.4 Å/sec to 0.7 Å/sec, the deposition rates of the lithium fluoride and the aluminum of the cathode at 0.3 Å/sec and 2 Å/sec, respectively, and the degree of vacuum during the deposition at $2 \times 10^{-7}$ torr to $5 \times 10^{-6}$ torr.

Example 1-2

An organic light emitting device was manufactured in the same manner as in Example 1-1 except that Compound 1-2 was used instead of Compound 1-1.

Example 1-3

An organic light emitting device was manufactured in the same manner as in Example 1-1 except that Compound 1-3 was used instead of Compound 1-1.

Example 1-4

An organic light emitting device was manufactured in the same manner as in Example 1-1 except that Compound 1-11 was used instead of Compound 1-1.

Example 1-5

An organic light emitting device was manufactured in the same manner as in Example 1-1 except that Compound 1-12 was used instead of Compound 1-1.

Example 1-6

An organic light emitting device was manufactured in the same manner as in Example 1-1 except that Compound 1-13 was used instead of Compound 1-1.

Example 1-7

An organic light emitting device was manufactured in the same manner as in Example 1-1 except that Compound 1-14 was used instead of Compound 1-1.

Example 1-8

An organic light emitting device was manufactured in the same manner as in Example 1-1 except that Compound 1-15 was used instead of Compound 1-1.

Example 1-9

An organic light emitting device was manufactured in the same manner as in Example 1-1 except that Compound 1-16 was used instead of Compound 1-1.

Example 1-10

An organic light emitting device was manufactured in the same manner as in Example 1-1 except that Compound 1-17 was used instead of Compound 1-1.

Example 1-11

An organic light emitting device was manufactured in the same manner as in Example 1-1 except that Compound 1-30 was used instead of Compound 1-1.

Example 1-12

An organic light emitting device was manufactured in the same manner as in Example 1-1 except that Compound 1-31 was used instead of Compound 1-1.

Example 1-13

An organic light emitting device was manufactured in the same manner as in Example 1-1 except that Compound 1-32 was used instead of Compound 1-1.

Example 1-14

An organic light emitting device was manufactured in the same manner as in Example 1-1 except that Compound 1-40 was used instead of Compound 1-1.

Example 1-15

An organic light emitting device was manufactured in the same manner as in Example 1-1 except that Compound 1-41 was used instead of Compound 1-1.

Example 1-16

An organic light emitting device was manufactured in the same manner as in Example 1-1 except that Compound 1-42 was used instead of Compound 1-1.

Example 1-17

An organic light emitting device was manufactured in the same manner as in Example 1-1 except that Compound 1-43 was used instead of Compound 1-1.

Example 1-18

An organic light emitting device was manufactured in the same manner as in Example 1-1 except that Compound 1-44 was used instead of Compound 1-1.

Example 1-19

An organic light emitting device was manufactured in the same manner as in Example 1-1 except that Compound 1-45 was used instead of Compound 1-1.

Example 1-20

An organic light emitting device was manufactured in the same manner as in Example 1-1 except that Compound 1-46 was used instead of Compound 1-1.

Comparative Example 1

An organic light emitting device was manufactured in the same manner as in Example 1-1 except that the following Compound EB1 was used instead of Compound 1-1.

[EB1]

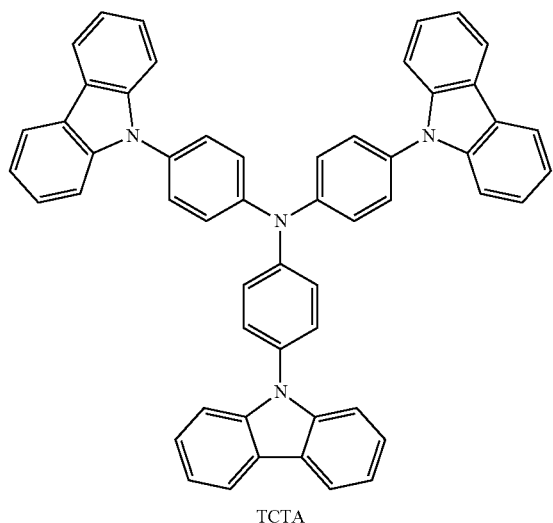

TCTA

When a current was applied to the organic light emitting devices manufactured in Examples 1-1 to 1-20 and Comparative Example 1, results of Table 1 were obtained.

TABLE 1

| | Compound (Electron Blocking Layer) | Voltage (V@10 mA/cm$^2$) | Efficiency (cd/A@10 mA/cm$^2$) | Color Coordinate (x, y) |
|---|---|---|---|---|
| Example 1-1 | Compound 1-1 | 3.79 | 6.65 | (0.138, 0.127) |
| Example 1-2 | Compound 1-2 | 3.64 | 6.75 | (0.139, 0.122) |
| Example 1-3 | Compound 1-3 | 3.75 | 6.66 | (0.138, 0.126) |
| Example 1-4 | Compound 1-11 | 3.96 | 6.31 | (0.138, 0.127) |
| Example 1-5 | Compound 1-12 | 3.93 | 6.42 | (0.137, 0.125) |
| Example 1-6 | Compound 1-13 | 3.82 | 6.47 | (0.136, 0.125) |
| Example 1-7 | Compound 1-14 | 3.80 | 6.51 | (0.136, 0.127) |
| Example 1-8 | Compound 1-15 | 3.87 | 6.35 | (0.136, 0.125) |
| Example 1-9 | Compound 1-16 | 3.86 | 6.34 | (0.137, 0.125) |
| Example 1-10 | Compound 1-17 | 3.85 | 6.31 | (0.138, 0.125) |
| Example 1-11 | Compound 1-30 | 3.85 | 6.33 | (0.136, 0.125) |
| Example 1-12 | Compound 1-31 | 3.81 | 6.32 | (0.137, 0.125) |
| Example 1-13 | Compound 1-32 | 3.89 | 6.30 | (0.136, 0.125) |
| Example 1-14 | Compound 1-40 | 3.89 | 6.50 | (0.138, 0.126) |
| Example 1-15 | Compound 1-41 | 3.84 | 6.52 | (0.137, 0.125) |
| Example 1-16 | Compound 1-42 | 3.80 | 6.50 | (0.136, 0.127) |
| Example 1-17 | Compound 1-43 | 3.81 | 6.55 | (0.135, 0.127) |
| Example 1-18 | Compound 1-44 | 3.84 | 6.51 | (0.138, 0.127) |
| Example 1-19 | Compound 1-45 | 3.78 | 6.59 | (0.137, 0.125) |
| Example 1-20 | Compound 1-46 | 3.84 | 6.46 | (0.137, 0.125) |
| Comparative Example 1 | EB1 (TCTA) | 4.53 | 5.01 | (0.136, 0.127) |

As shown in Table 1, the organic light emitting device manufactured using the compound of the present disclosure as an electron blocking layer exhibited excellent properties in terms of efficiency, driving voltage and/or stability of the organic light emitting device when compared to an existing organic light emitting device using TCTA since the compound of the present disclosure performed a role of blocking electrons.

Based on the results of Table 1, it was identified that the compound according to the present disclosure had an excellent electron blocking ability and was capable of being used in an organic light emitting device.

<Example 2-1> to <Example 2-20>

Experiments were carried out in the same manner as in Example 1-1 except that the compounds of Examples 1-1 to 1-20 were used as the hole transfer layer instead of NPB.

Comparative Example 2-1

An organic light emitting device was manufactured in the same manner as in Example 2-1 except that the following compound of HT1 (NPB) was used instead of Compound 1-1.

[HT1]

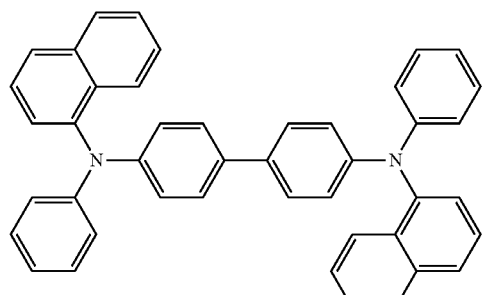

Comparative Example 2-2

An organic light emitting device was manufactured in the same manner as in Example 2-1 except that the following compound of HT2 (TCTA) was used instead of Compound 1-1.

[HT2]

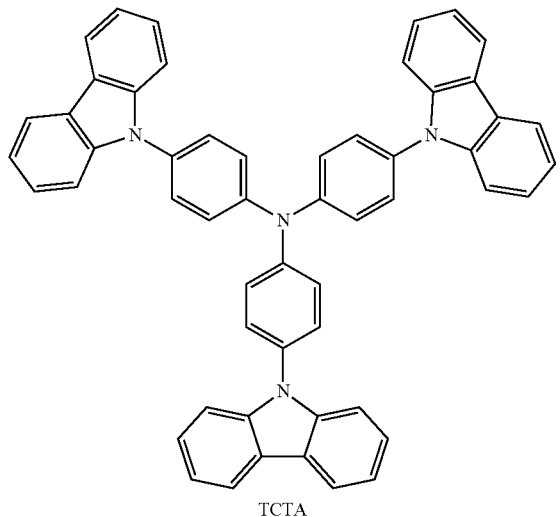

TCTA

When a current was applied to the organic light emitting devices manufactured in Examples 2-1 to 2-20, and Comparative Example 2-1 and Comparative Example 2-2, results of Table 2 were obtained.

TABLE 2

| | Compound (Hole Transfer Layer) | Voltage (V@10 mA/cm$^2$) | Efficiency (cd/A@10 mA/cm$^2$) | Color Coordinate (x, y) |
|---|---|---|---|---|
| Example 2-1 | Compound 1-1 | 4.35 | 5.65 | (0.138, 0.127) |
| Example 2-2 | Compound 1-2 | 4.22 | 5.55 | (0.139, 0.122) |
| Example 2-3 | Compound 1-3 | 4.38 | 5.66 | (0.138, 0.126) |
| Example 2-4 | Compound 1-11 | 4.59 | 5.39 | (0.138, 0.127) |
| Example 2-5 | Compound 1-12 | 4.55 | 5.42 | (0.137, 0.125) |
| Example 2-6 | Compound 1-13 | 4.46 | 5.47 | (0.136, 0.125) |
| Example 2-7 | Compound 1-14 | 4.48 | 5.51 | (0.136, 0.127) |
| Example 2-8 | Compound 1-15 | 4.53 | 5.35 | (0.136, 0.125) |
| Example 2-9 | Compound 1-16 | 4.49 | 5.34 | (0.137, 0.125) |
| Example 2-10 | Compound 1-17 | 4.52 | 5.38 | (0.138, 0.125) |
| Example 2-11 | Compound 1-30 | 4.54 | 5.46 | (0.136, 0.125) |
| Example 2-12 | Compound 1-31 | 4.46 | 5.36 | (0.137, 0.125) |
| Example 2-13 | Compound 1-32 | 4.41 | 5.31 | (0.136, 0.125) |
| Example 2-14 | Compound 1-40 | 4.50 | 5.50 | (0.138, 0.126) |
| Example 2-15 | Compound 1-41 | 4.43 | 5.52 | (0.137, 0.125) |
| Example 2-16 | Compound 1-42 | 4.57 | 5.58 | (0.136, 0.127) |
| Example 2-17 | Compound 1-43 | 4.56 | 5.55 | (0.135, 0.127) |
| Example 2-18 | Compound 1-44 | 4.44 | 5.51 | (0.138, 0.127) |
| Example 2-19 | Compound 1-45 | 4.41 | 5.59 | (0.137, 0.125) |
| Example 2-20 | Compound 1-46 | 4.58 | 5.46 | (0.137, 0.125) |
| Comparative Example 2-1 | HT1 (NPB) | 5.46 | 4.71 | (0.136, 0.127) |
| Comparative Example 2-2 | HT2 (TCTA) | 5.21 | 4.95 | (0.136, 0.127) |

As shown in Table 2, the organic light emitting device manufactured using the compound of the present disclosure as a hole transfer layer exhibited excellent properties in terms of efficiency, driving voltage and/or stability of the organic light emitting device when compared to Comparative Examples 2-1 and 2-2 using TCTA and NPB.

Based on the results of Table 2, it was identified that the compound according to the present disclosure had an excellent hole transfer ability and was capable of being used in an organic light emitting device.

Based on the results of Tables 1 and 2, it was identified that the compound according to the present disclosure had an excellent hole transfer ability as well as an excellent electron blocking ability, and was capable of being used in an organic light emitting device.

Comparative Example 3

A glass substrate on which indium tin oxide (ITO) was coated as a thin film to a thickness of 1,000 Å was placed in detergent-dissolved distilled water and ultrasonic cleaned. Herein, a product of Fischer Co. was used as the detergent, and as the distilled water, distilled water filtered twice with a filter manufactured by Millipore Co. was used. After the ITO was cleaned for 30 minutes, ultrasonic cleaning was repeated twice using distilled water for 10 minutes. After the cleaning with distilled water was finished, the substrate was ultrasonic cleaned with solvents of isopropyl alcohol, acetone and methanol, then dried, and then transferred to a plasma cleaner. In addition, the substrate was cleaned for 5 minutes using oxygen plasma, and then transferred to a vacuum depositor.

An organic EL device was manufactured by forming a light emitting element in the order of m-MTDATA (60 nm)/TCTA (80 nm)/CBP+10% Ir(ppy)$_3$ (300 nm)/BCP (10 nm)/Alq$_3$ (30 nm)/LiF (1 nm)/Al (200 nm) on the transparent ITO electrode prepared as above using CBP as a host.

Structures of the m-MTDATA, the TCTA, the Ir(ppy)$_3$, the CBP and the BCP are each as follows.

m-MTDATA

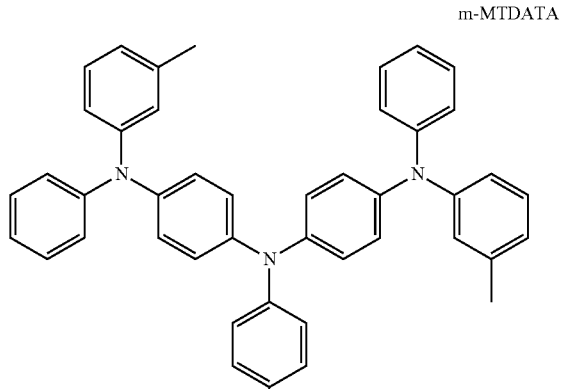

TCTA

Ir(ppy)₃

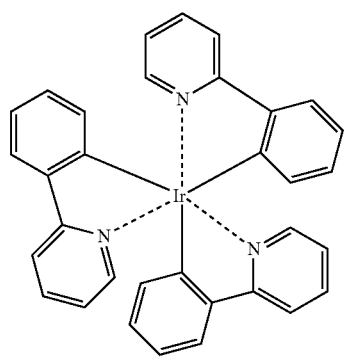

BCP

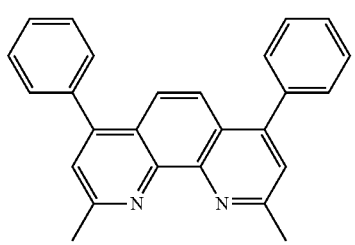

CBP

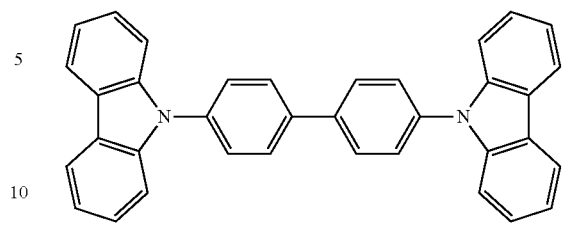

The compounds synthesized in the synthesis examples were high-purity sublimation purified using commonly known methods, and then a green organic light emitting device was manufactured using a method as below.

Example 3-1

An organic light emitting device was manufactured in the same manner as in Comparative Example 3 except that Compound 1-4 was used instead of CBP.

Example 3-2

An organic light emitting device was manufactured in the same manner as in Comparative Example 3 except that Compound 1-5 was used instead of Compound CBP.

Example 3-3

An organic light emitting device was manufactured in the same manner as in Comparative Example 3 except that Compound 1-6 was used instead of Compound CBP.

Example 3-4

An organic light emitting device was manufactured in the same manner as in Comparative Example 3 except that Compound 1-7 was used instead of Compound CBP.

Example 3-5

An organic light emitting device was manufactured in the same manner as in Comparative Example 3 except that Compound 1-11 was used instead of Compound CBP.

Example 3-6

An organic light emitting device was manufactured in the same manner as in Comparative Example 3 except that Compound 1-12 was used instead of Compound CBP.

Example 3-7

An organic light emitting device was manufactured in the same manner as in Comparative Example 3 except that Compound 1-13 was used instead of Compound CBP.

Example 3-8

An organic light emitting device was manufactured in the same manner as in Comparative Example 3 except that Compound 1-18 was used instead of Compound CBP.

Example 3-9

An organic light emitting device was manufactured in the same manner as in Comparative Example 3 except that Compound 1-19 was used instead of Compound CBP.

Example 3-10

An organic light emitting device was manufactured in the same manner as in Comparative Example 3 except that Compound 1-24 was used instead of Compound CBP.

Example 3-11

An organic light emitting device was manufactured in the same manner as in Comparative Example 3 except that Compound 1-25 was used instead of Compound CBP.

Example 3-12

An organic light emitting device was manufactured in the same manner as in Comparative Example 3 except that Compound 1-26 was used instead of Compound CBP.

Example 3-13

An organic light emitting device was manufactured in the same manner as in Comparative Example 3 except that Compound 1-33 was used instead of Compound CBP.

Example 3-14

An organic light emitting device was manufactured in the same manner as in Comparative Example 3 except that Compound 1-34 was used instead of Compound CBP.

Example 3-15

An organic light emitting device was manufactured in the same manner as in Comparative Example 3 except that Compound 1-35 was used instead of Compound CBP.

Example 3-16

An organic light emitting device was manufactured in the same manner as in Comparative Example 3 except that Compound 1-36 was used instead of Compound CBP.

Example 3-17

An organic light emitting device was manufactured in the same manner as in Comparative Example 3 except that Compound 1-40 was used instead of Compound CBP.

Example 3-18

An organic light emitting device was manufactured in the same manner as in Comparative Example 3 except that Compound 1-41 was used instead of Compound CBP.

Example 3-19

An organic light emitting device was manufactured in the same manner as in Comparative Example 3 except that Compound 1-42 was used instead of Compound CBP.

Example 3-20

An organic light emitting device was manufactured in the same manner as in Comparative Example 3 except that Compound 1-47 was used instead of Compound CBP.

Example 3-21

An organic light emitting device was manufactured in the same manner as in Comparative Example 3 except that Compound 1-48 was used instead of Compound CBP.

Example 3-22

An organic light emitting device was manufactured in the same manner as in Comparative Example 3 except that Compound 1-53 was used instead of Compound CBP.

Example 3-23

An organic light emitting device was manufactured in the same manner as in Comparative Example 3 except that Compound 1-54 was used instead of Compound CBP.

Example 3-24

An organic light emitting device was manufactured in the same manner as in Comparative Example 3 except that Compound 1-55 was used instead of Compound CBP.

When a current was applied to the organic light emitting devices manufactured in Comparative Example 3, and Examples 3-1 to 3-24, results of Table 3 were obtained.

TABLE 3

|  | Compound (Host) | Voltage (V@10 mA/cm$^2$) | Efficiency (cd/A@10 mA/cm$^2$) | EL Peak (nm) |
|---|---|---|---|---|
| Comparative Example 3 | CBP | 7.32 | 38.12 | 516 |
| Example 3-1 | Compound 1-4 | 6.40 | 46.33 | 517 |
| Example 3-2 | Compound 1-5 | 6.42 | 46.24 | 516 |
| Example 3-3 | Compound 1-6 | 6.41 | 45.72 | 517 |
| Example 3-4 | Compound 1-7 | 6.42 | 45.65 | 518 |

TABLE 3-continued

| | Compound (Host) | Voltage (V@10 mA/cm²) | Efficiency (cd/A@10 mA/cm²) | EL Peak (nm) |
|---|---|---|---|---|
| Example 3-5 | Compound 1-8 | 6.60 | 42.31 | 517 |
| Example 3-6 | Compound 1-9 | 6.53 | 42.63 | 517 |
| Example 3-7 | Compound 1-12 | 6.61 | 42.62 | 516 |
| Example 3-8 | Compound 1-16 | 6.62 | 42.64 | 517 |
| Example 3-9 | Compound 1-17 | 6.52 | 45.42 | 516 |
| Example 3-10 | Compound 1-18 | 6.41 | 46.30 | 518 |
| Example 3-11 | Compound 1-19 | 6.42 | 42.70 | 517 |
| Example 3-12 | Compound 1-20 | 6.63 | 42.76 | 516 |
| Example 3-13 | Compound 1-21 | 6.60 | 44.93 | 517 |
| Example 3-14 | Compound 1-24 | 6.44 | 45.84 | 516 |
| Example 3-15 | Compound 1-28 | 6.61 | 44.72 | 518 |
| Example 3-16 | Compound 1-29 | 6.59 | 44.65 | 517 |
| Example 3-17 | Compound 1-30 | 6.68 | 44.31 | 515 |
| Example 3-18 | Compound 1-31 | 6.53 | 44.63 | 516 |
| Example 3-19 | Compound 1-32 | 6.54 | 44.62 | 516 |
| Example 3-20 | Compound 1-33 | 6.57 | 44.64 | 517 |
| Example 3-21 | Compound 1-36 | 6.54 | 45.08 | 518 |
| Example 3-22 | Compound 1-40 | 6.66 | 44.72 | 517 |
| Example 3-23 | Compound 1-41 | 6.52 | 44.70 | 517 |
| Example 3-24 | Compound 1-42 | 6.53 | 44.76 | 517 |

As a result of the tests, it was identified that the green organic light emitting devices of Examples 3-1 to 3-24 using the compound represented by Chemical Formula 1 according to the present disclosure as a host material of a light emitting layer exhibited excellent performance in terms of current efficiency and driving voltage when compared to the green organic light emitting device of Comparative Example 3 using existing CBP. It was seen that the compounds having triazine, pyrimidine, pyridine and the like as substituents are suited as a green light emitting organic device.

<Example 4-1> to <Example 4-16>

The compounds synthesized in the synthesis examples were high-purity sublimation purified using commonly known methods, and then a red organic light emitting device was manufactured using a method as below.

An ITO glass was patterned so that a light emitting area became a 2 mm×2 mm size, and then cleaned. After installing the substrate in a vacuum chamber, the base pressure was set at $1\times10^6$ torr, and as organic materials on the ITO, DNTPD (700 Å) and α-NPB (300 Å) were formed, 1-4, 1-5, 1-8, 1-9, 1-10, 1-26, 1-27, 1-29, 1-33, 1-34, 1-37, 1-38, 1-39, 1-55, 1-56 or 1-58 prepared by the present disclosure was used as a host (90 wt %), the following (pic)$_2$Ir(acac) (10 wt %) was vacuum deposited (300 Å) as a dopant, and Alq$_3$ (350 Å) LiF (5 Å) and Al (1,000 Å) were formed in a film form in this order, and measurements were carried out at 0.4 mA.

Structures of the DNTPD, the α-NPB, the (pic)$_2$Ir(acac) and the Alq$_3$ are as follows.

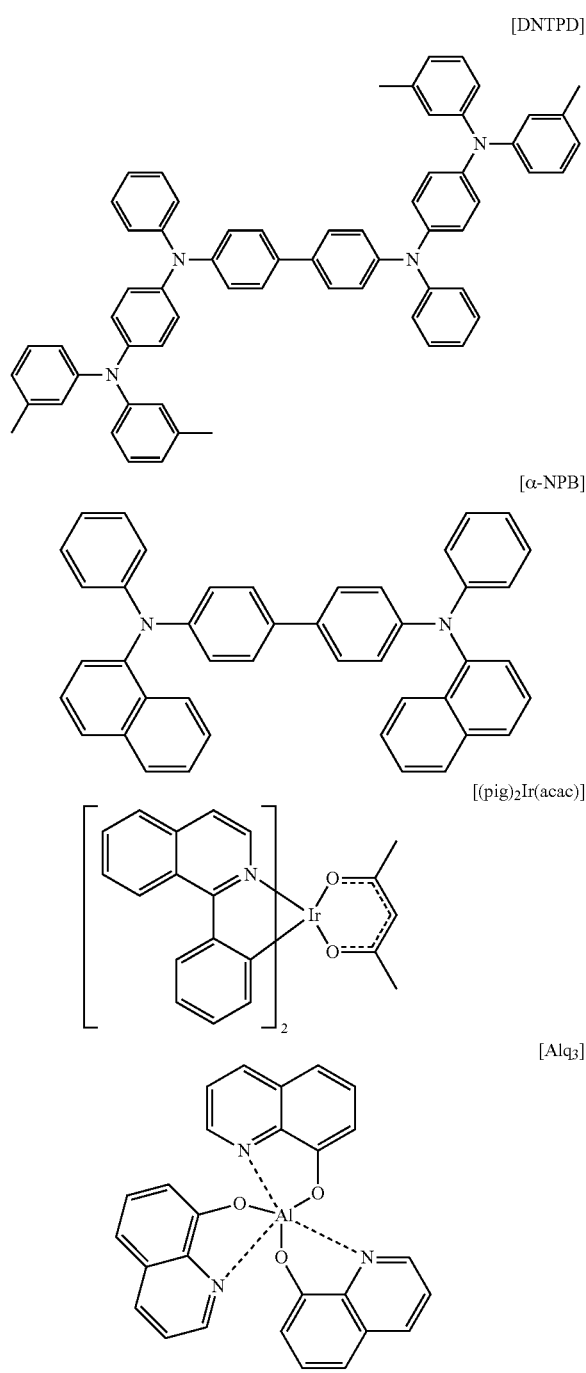

Comparative Example 4

An organic light emitting device for Comparative Example 4 was manufactured in the same manner as in the examples except that, in the device structure, CBP that is much used as a general phosphorescent host material was used as a host of the light emitting layer instead of the organic light emitting compounds prepared by the present disclosure.

For the organic electroluminescent devices manufactured according to Examples 4-1 to 4-16 and Comparative Example 4, a voltage, current density, luminance, a color coordinate and a lifespan were measured, and the results are shown in the following Table 4. T95 means time taken for the luminance decreasing to 95% of its initial luminance (5000 nit)

a filter manufactured by Millipore Co. was used. After the ITO was cleaned for 30 minutes, ultrasonic cleaning was repeated twice using distilled water for 10 minutes. After the cleaning with distilled water was finished, the substrate was ultrasonic cleaned with solvents of isopropyl alcohol, acetone and methanol, then dried, and then transferred to a plasma cleaner. In addition, the substrate was cleaned for 5 minutes using oxygen plasma, and then transferred to a vacuum depositor.

On the transparent ITO electrode prepared as above, a hole injection layer was formed by thermal vacuum depositing hexanitrile hexaazatriphenylene (HAT) of the following chemical formula to a thickness of 500 Å.

TABLE 4

| Category | Host | Dopant | Voltage (V@10 mA/cm2) | Luminance (V) | CIEx (cd/m$^2$) | CIEy | T95 (hr) |
|---|---|---|---|---|---|---|---|
| Example 4-1 | Compound 1-4 | [(piq)$_2$Ir (acac)] | 4.3 | 1860 | 0.670 | 0.329 | 465 |
| Example 4-2 | Compound 1-5 | [(piq)$_2$Ir (acac)] | 4.2 | 1850 | 0.674 | 0.325 | 415 |
| Example 4-3 | Compound 1-8 | [(piq)$_2$Ir (acac)] | 4.1 | 1900 | 0.672 | 0.327 | 440 |
| Example 4-4 | Compound 1-9 | [(piq)$_2$Ir (acac)] | 4.3 | 1840 | 0.673 | 0.335 | 435 |
| Example 4-5 | Compound 1-10 | [(piq)$_2$Ir (acac)] | 4.0 | 1790 | 0.675 | 0.333 | 405 |
| Example 4-6 | Compound 1-26 | [(piq)$_2$Ir (acac)] | 4.2 | 1810 | 0.670 | 0.339 | 420 |
| Example 4-7 | Compound 1-27 | [(piq)$_2$Ir (acac)] | 4.3 | 1970 | 0.671 | 0.338 | 445 |
| Example 4-8 | Compound 1-29 | [(piq)$_2$Ir (acac)] | 4.3 | 1860 | 0.668 | 0.329 | 465 |
| Example 4-9 | Compound 1-33 | [(piq)$_2$Ir (acac)] | 4.2 | 1950 | 0.673 | 0.325 | 415 |
| Example 4-10 | Compound 1-34 | [(piq)$_2$Ir (acac)] | 4.1 | 1900 | 0.670 | 0.327 | 440 |
| Example 4-11 | Compound 1-37 | [(piq)$_2$Ir (acac)] | 4.3 | 1940 | 0.671 | 0.335 | 435 |
| Example 4-12 | Compound 1-38 | [(piq)$_2$Ir (acac)] | 4.0 | 1990 | 0.674 | 0.333 | 405 |
| Example 4-13 | Compound 1-39 | [(piq)$_2$Ir (acac)] | 4.2 | 1910 | 0.675 | 0.339 | 420 |
| Example 4-14 | Compound 1-55 | [(piq)$_2$Ir (acac)] | 4.3 | 1970 | 0.671 | 0.338 | 445 |
| Example 4-15 | Compound 1-56 | [(piq)$_2$Ir (acac)] | 4.3 | 1960 | 0.668 | 0.329 | 465 |
| Example 4-16 | Compound 1-58 | [(piq)$_2$Ir (acac)] | 4.2 | 1950 | 0.674 | 0.325 | 415 |
| Comparative Example 4 | CBP | [(piq)$_2$Ir (acac)] | 7.5 | 820 | 0.679 | 0.339 | 160 |

As a result of the tests, it was identified that the red organic light emitting devices of Examples 4-1 to 4-16 using Compounds 1-4, 1-5, 1-8, 1-9, 1-10, 1-26, 1-27, 1-29, 1-33, 1-34, 1-37, 1-38, 1-39, 1-55, 1-56 and 1-58 prepared according to the present disclosure as a host material of a light emitting layer exhibited excellent performance in terms of current efficiency, driving voltage and lifespan when compared to the red organic light emitting device of Comparative Example 4 using existing CBP.

Example 5-1

A glass substrate on which indium tin oxide (ITO) was coated as a thin film to a thickness of 1,000 Å was placed in detergent-dissolved distilled water and ultrasonic cleaned. Herein, a product of Fischer Co. was used as the detergent, and as the distilled water, distilled water filtered twice with

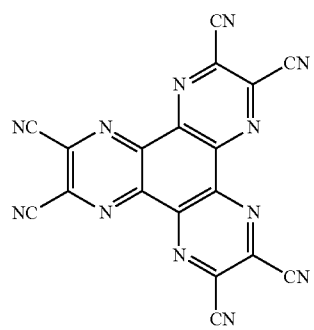
[HAT]

A hole transfer layer was formed on the hole injection layer by vacuum depositing the following compound 4-4'- bis[N-(1-naphthyl)-N-phenylamino]biphenyl (NPB) (400 Å), a material transferring holes.

[NPB]

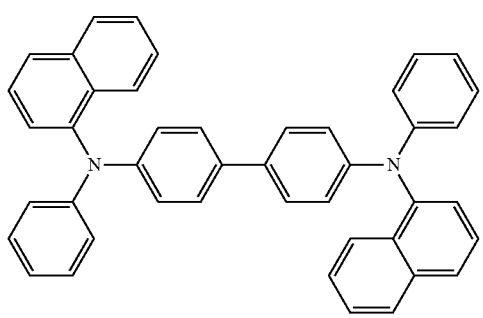

Subsequently, a light emitting layer was formed on the hole transfer layer to a film thickness of 300 Å by vacuum depositing BH and BD as follows in a weight ratio of 25:1.

[BH]

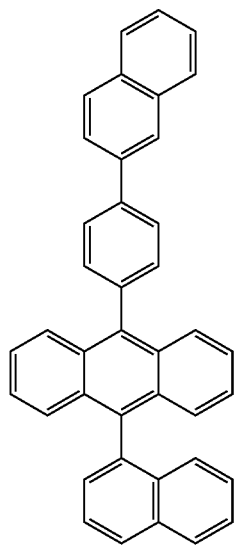

[BD]

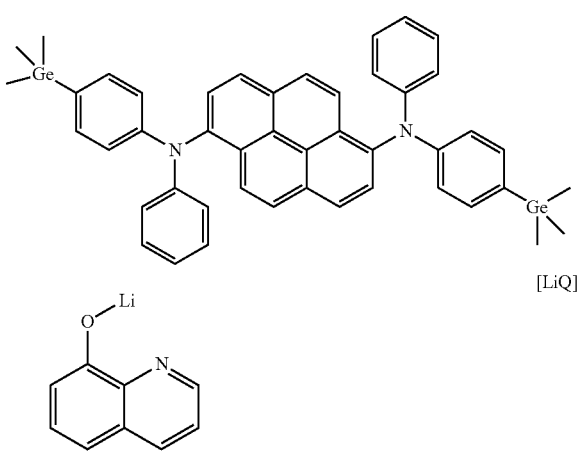

[LiQ]

On the light emitting layer, an electron injection and transfer layer was formed to a thickness of 300 Å by vacuum depositing Compound 1-4 prepared in Preparation Example 4 and the lithium quinolate (LiQ) compound in a weight ratio of 1:1. A cathode was formed on the electron injection and transfer layer by depositing lithium fluoride (LiF) to a thickness of 12 Å and aluminum to a thickness of 2,000 Å in consecutive order. An organic light emitting device was manufactured by maintaining, in the above-mentioned processes, the deposition rates of the organic materials at 0.4 Å/sec to 0.7 Å/sec, the deposition rates of the lithium fluoride and the aluminum of the cathode at 0.3 Å/sec and 2 Å/sec, respectively, and the degree of vacuum during the deposition at $2 \times 10^{-7}$ torr to $5 \times 10^{-6}$ torr.

Example 5-2

An experiment was carried out in the same manner as in Example 5-1 except that Compound 1-5 was used as the electron transfer layer instead of Compound 1-4.

Example 5-3

An experiment was carried out in the same manner as in Example 5-1 except that Compound 1-6 was used as the electron transfer layer instead of Compound 1-4.

Example 5-4

An experiment was carried out in the same manner as in Example 5-1 except that Compound 1-7 was used as the electron transfer layer instead of Compound 1-4.

Example 5-5

An experiment was carried out in the same manner as in Example 5-1 except that Compound 1-20 was used as the electron transfer layer instead of Compound 1-4.

Example 5-6

An experiment was carried out in the same manner as in Example 5-1 except that Compound 1-21 was used as the electron transfer layer instead of Compound 1-4.

Example 5-7

An experiment was carried out in the same manner as in Example 5-1 except that Compound 1-22 was used as the electron transfer layer instead of Compound 1-4.

Example 5-8

An experiment was carried out in the same manner as in Example 5-1 except that Compound 1-23 was used as the electron transfer layer instead of Compound 1-4.

Example 5-9

An experiment was carried out in the same manner as in Example 5-1 except that Compound 1-24 was used as the electron transfer layer instead of Compound 1-4.

Example 5-10

An experiment was carried out in the same manner as in Example 5-1 except that Compound 1-25 was used as the electron transfer layer instead of Compound 1-4.

Example 5-11

An experiment was carried out in the same manner as in Example 5-1 except that Compound 1-26 was used as the electron transfer layer instead of Compound 1-4.

Example 5-12

An experiment was carried out in the same manner as in Example 5-1 except that Compound 1-27 was used as the electron transfer layer instead of Compound 1-4.

Example 5-13

An experiment was carried out in the same manner as in Example 5-1 except that Compound 1-28 was used as the electron transfer layer instead of Compound 1-4.

Example 5-14

An experiment was carried out in the same manner as in Example 5-1 except that Compound 1-29 was used as the electron transfer layer instead of Compound 1-4.

Example 5-15

An experiment was carried out in the same manner as in Example 5-1 except that Compound 1-33 was used as the electron transfer layer instead of Compound 1-4.

Example 5-16

An experiment was carried out in the same manner as in Example 5-1 except that Compound 1-34 was used as the electron transfer layer instead of Compound 1-4.

Example 5-17

An experiment was carried out in the same manner as in Example 5-1 except that Compound 1-35 was used as the electron transfer layer instead of Compound 1-4.

Example 5-18

An experiment was carried out in the same manner as in Example 5-1 except that Compound 1-36 was used as the electron transfer layer instead of Compound 1-4.

Example 5-19

An experiment was carried out in the same manner as in Example 5-1 except that Compound 1-49 was used as the electron transfer layer instead of Compound 1-4.

Example 5-20

An experiment was carried out in the same manner as in Example 5-1 except that Compound 1-50 was used as the electron transfer layer instead of Compound 1-4.

Example 5-21

An experiment was carried out in the same manner as in Example 5-1 except that Compound 1-51 was used as the electron transfer layer instead of Compound 1-4.

Example 5-22

An experiment was carried out in the same manner as in Example 5-1 except that Compound 1-52 was used as the electron transfer layer instead of Compound 1-4.

Example 5-23

An experiment was carried out in the same manner as in Example 5-1 except that Compound 1-53 was used as the electron transfer layer instead of Compound 1-4.

Example 5-24

An experiment was carried out in the same manner as in Example 5-1 except that Compound 1-54 was used as the electron transfer layer instead of Compound 1-4.

Example 5-25

An experiment was carried out in the same manner as in Example 5-1 except that Compound 1-55 was used as the electron transfer layer instead of Compound 1-4.

Example 5-26

An experiment was carried out in the same manner as in Example 5-1 except that Compound 1-56 was used as the electron transfer layer instead of Compound 1-4.

Example 5-27

An experiment was carried out in the same manner as in Example 5-1 except that Compound 1-57 was used as the electron transfer layer instead of Compound 1-4.

Example 5-28

An experiment was carried out in the same manner as in Example 5-1 except that Compound 1-58 was used as the electron transfer layer instead of Compound 1-4.

Comparative Example 5

An experiment was carried out in the same manner as in Example 5-1 except that the following Compound ET1 was used as the electron transfer layer instead of Compound 1-4.

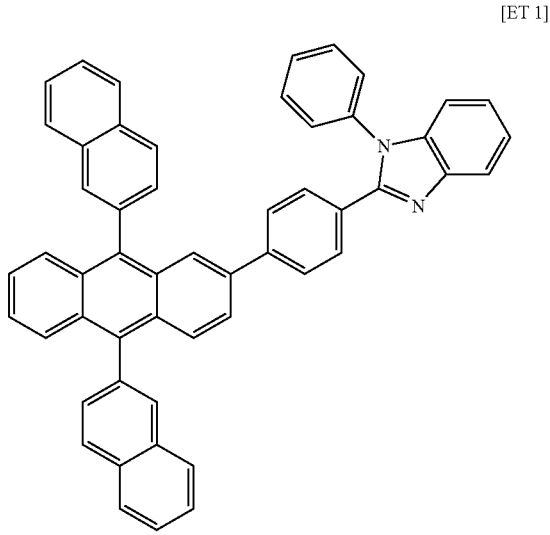 [SMILES: c1ccc(-n2c(-c3ccc(-c4ccc5c(-c6ccc7ccccc7c6)c6ccccc6c(-c6ccc7ccccc7c6)c5c4)cc3)nc3ccccc32)cc1]

[ET 1]

When a current was applied to the organic light emitting devices manufactured in Examples 5-1 to 5-28 and Comparative Example 5, results of Table 5 were obtained.

TABLE 5

| | Compound (Host) | Voltage (V@10 mA/cm$^2$) | Efficiency (cd/A@10 mA/cm$^2$) | EL Peak (nm) |
|---|---|---|---|---|
| Example 5-1 | Compound 1-4 | 6.88 | 41.93 | 517 |
| Example 5-2 | Compound 1-5 | 6.85 | 41.79 | 518 |
| Example 5-3 | Compound 1-6 | 6.19 | 46.15 | 517 |
| Example 5-4 | Compound 1-7 | 6.28 | 44.31 | 515 |
| Example 5-5 | Compound 1-20 | 6.23 | 45.63 | 516 |
| Example 5-6 | Compound 1-21 | 6.29 | 45.62 | 516 |
| Example 5-7 | Compound 1-22 | 6.17 | 46.64 | 517 |
| Example 5-8 | Compound 1-23 | 6.14 | 46.68 | 518 |
| Example 5-9 | Compound 1-24 | 6.48 | 44.83 | 517 |
| Example 5-10 | Compound 1-25 | 6.46 | 45.24 | 516 |
| Example 5-11 | Compound 1-26 | 6.84 | 41.94 | 518 |
| Example 5-12 | Compound 1-27 | 6.95 | 42.22 | 517 |
| Example 5-13 | Compound 1-28 | 6.83 | 41.75 | 515 |
| Example 5-14 | Compound 1-29 | 6.15 | 46.16 | 516 |
| Example 5-15 | Compound 1-33 | 6.24 | 44.34 | 516 |
| Example 5-16 | Compound 1-34 | 6.25 | 45.62 | 517 |
| Example 5-17 | Compound 1-35 | 6.27 | 45.64 | 518 |
| Example 5-18 | Compound 1-36 | 6.15 | 46.66 | 517 |
| Example 5-19 | Compound 1-49 | 6.13 | 46.67 | 516 |
| Example 5-20 | Compound 1-50 | 6.42 | 44.41 | 518 |
| Example 5-21 | Compound 1-51 | 6.47 | 45.55 | 517 |
| Example 5-22 | Compound 1-52 | 6.82 | 41.74 | 515 |
| Example 5-23 | Compound 1-53 | 6.94 | 42.62 | 516 |
| Example 5-24 | Compound 1-54 | 6.81 | 41.55 | 516 |
| Example 5-25 | Compound 1-55 | 6.18 | 46.16 | 517 |
| Example 5-26 | Compound 1-56 | 6.27 | 44.94 | 518 |
| Example 5-27 | Compound 1-57 | 6.23 | 45.32 | 517 |
| Example 5-28 | Compound 1-58 | 6.24 | 45.14 | 516 |
| Comparative Example 5 | ET 1 | 7.27 | 32.52 | 517 |

As shown in Table 5, it was identified that Examples 5-1 to 5-28 had excellent electron transfer and injection abilities when compared to Comparative Example 5. It was seen that the compounds having triazine, benzimidazole, arylphosphine, quinoline, benzothiazole, imidazoquinazoline and the like as substituents were suited in an organic light emitting device.

Hereinbefore, preferred embodiments of the present disclosure (electron blocking layer, hole transfer layer, green light emitting layer, red light emitting layer, electron transfer layer) have been described, however, the present disclosure is not limited thereto, and various modifications may be made within the scope of the claims and the detailed descriptions, and the modifications are also included in the scope of the present disclosure.

The invention claimed is:
1. A compound represented by the following Chemical Formula 1:

[Chemical Formula 1]

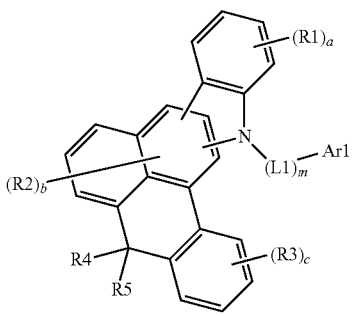

wherein, in Chemical Formula 1,
L1 is a direct bond; substituted or unsubstituted arylene; or substituted or unsubstituted heteroarylene;
m is an integer of 0 to 5;
when m is 2 or greater, L1s are the same as or different from each other;
Ar1 is hydrogen; deuterium; a halogen group; a nitrile group; a nitro group; a hydroxyl group; a carbonyl group; an ester group; an imide group; an amino group; a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylheteroarylamine group; a substituted or unsubstituted arylphosphine group; a substituted or unsubstituted phosphine oxide group; a substituted or unsubstituted aryl group; or a substituted or unsubstituted heterocyclic group;
a, b and c are each an integer of 0 to 4;
R1 to R3 are the same as or different from each other, and each independently hydrogen;
deuterium; a halogen group; a nitrile group; a nitro group; a hydroxyl group; a carbonyl group;
an ester group; an imide group; an amino group; a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylheteroarylamine group; a substituted or unsubstituted arylphosphine group; a substituted or unsubstituted phosphine oxide group; a substituted or unsubstituted aryl group; or a substituted or unsubstituted heterocyclic group, or bond to adjacent groups to form a substituted or unsubstituted ring;

when a is 2 or greater, R1s are the same as or different from each other;

when b is 2 or greater, R2s are the same as or different from each other;

when c is 2 or greater, R3s are the same as or different from each other; and

R4 and R5 are the same as or different from each other, and each independently hydrogen; deuterium; a halogen group; a nitrile group; a nitro group; a hydroxyl group; a carbonyl group; an ester group; an imide group; an amino group; a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylheteroarylamine group; a substituted or unsubstituted arylphosphine group; or a substituted or unsubstituted phosphine oxide group.

2. The compound of claim 1, wherein the compound represented by Chemical Formula 1 is represented by the following Chemical Formula 2-1 or Chemical Formula 2-2:

[Chemical Formula 2-1]

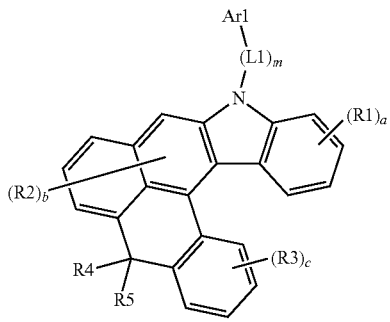

[Chemical Formula 2-2]

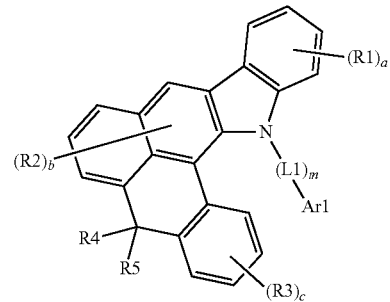

wherein, in Chemical Formula 2-1 and Chemical Formula 2-2,

L1, m, Ar1, a, b, c and R1 to R5 have the same definitions as in Chemical Formula 1.

3. The compound of claim 1, wherein the compound represented by Chemical Formula 1 is represented by any one of the following Chemical Formulae 3 to 8:

[Chemical Formula 3]

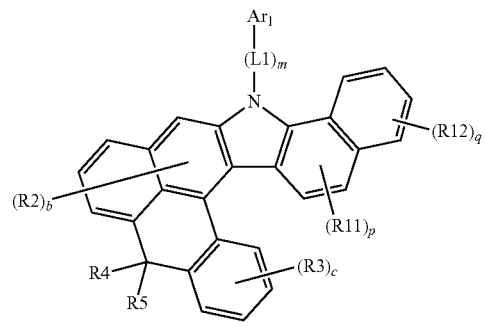

[Chemical Formula 4]

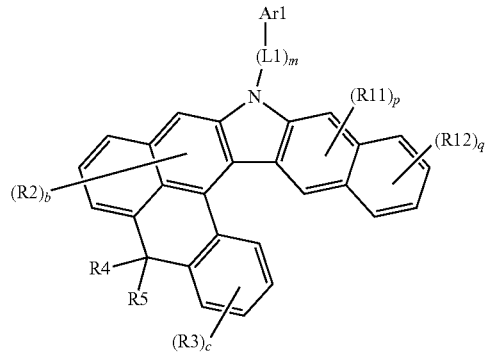

[Chemical Formula 5]

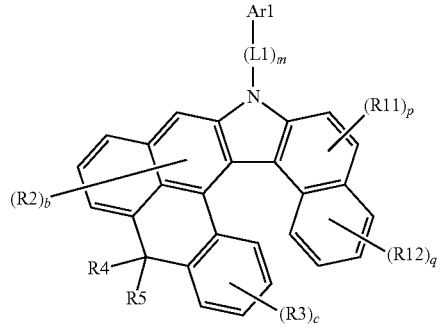

[Chemical Formula 6]

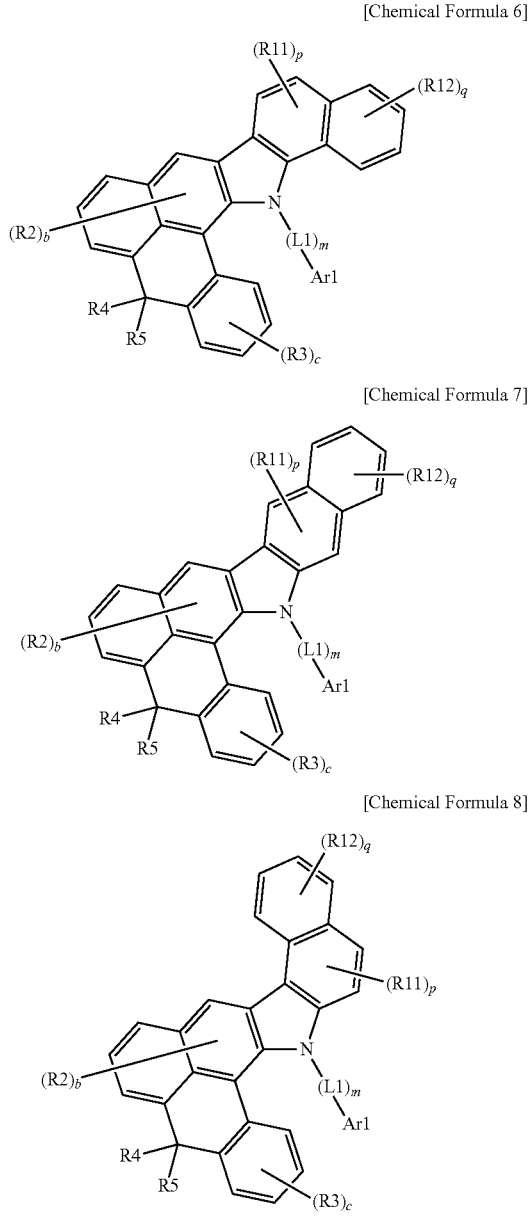

[Chemical Formula 7]

[Chemical Formula 8]

wherein, in Chemical Formulae 3 to 5,

R2 to R5, L1, Ar1, b, c and m each independently have the same definition as in Chemical Formula 1;

p is an integer of 0 to 2;

q is an integer of 0 to 4;

R11 and R12 each independently have the same definition as R1 in Chemical Formula 1;

when p is 2, R11s are the same as or different from each other; and when q is 2 or greater, R12s are the same as or different from each other.

4. The compound of claim 1, wherein R4 and R5 are an alkyl group.

5. The compound of claim 1, wherein L1 is a direct bond or selected from among the following structures:

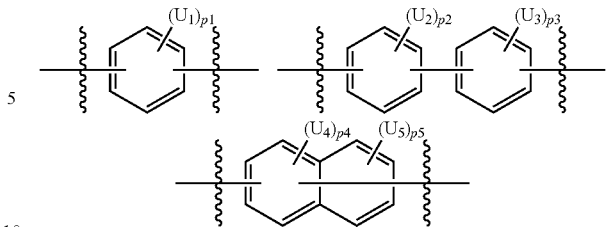

in the structural formulae, $U_1$ to $U_5$ are the same as or different from each other, and each independently hydrogen; deuterium; a halogen group; a substituted or unsubstituted alkyl group; a substituted or unsubstituted cycloalkyl group; a substituted or unsubstituted alkenyl group; a substituted or unsubstituted aryl group; a substituted or unsubstituted heterocyclic group; a substituted or unsubstituted alkylamine group; a substituted or unsubstituted heteroarylamine group; or a substituted or unsubstituted arylamine group, or adjacent two or more substituents bond to each other to form a ring;

p1, p2 and p3 are an integer of 0 to 4, and p4 and p5 are an integer of 0 to 3;

when p1 is 2 or greater, $U_1$s are the same as or different from each other;

when p2 is 2 or greater, $U_2$s are the same as or different from each other;

when p3 is 2 or greater, $U_3$s are the same as or different from each other;

when p4 is 2 or greater, $U_4$s are the same as or different from each other; and when p5 is 2 or greater, $U_5$s are the same as or different from each other.

6. The compound of claim 1, wherein Ar1 in Chemical Formula 1 is hydrogen or any one selected from among the following structures:

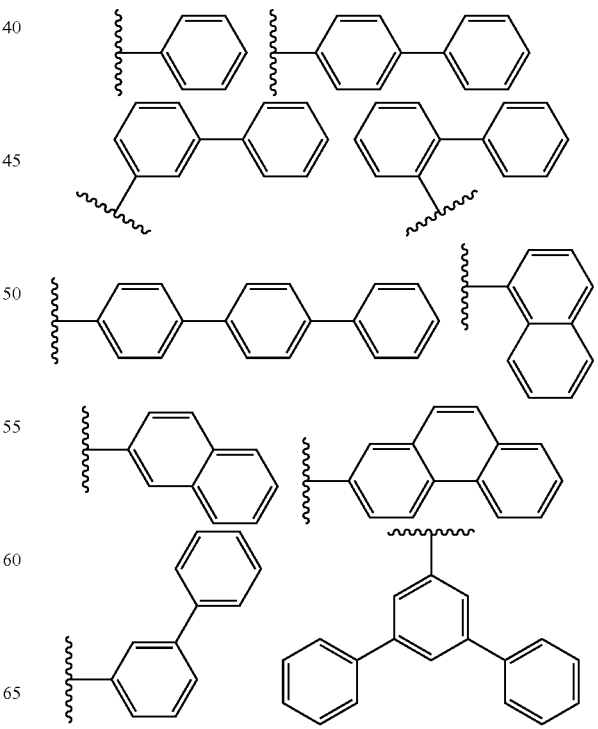

-continued
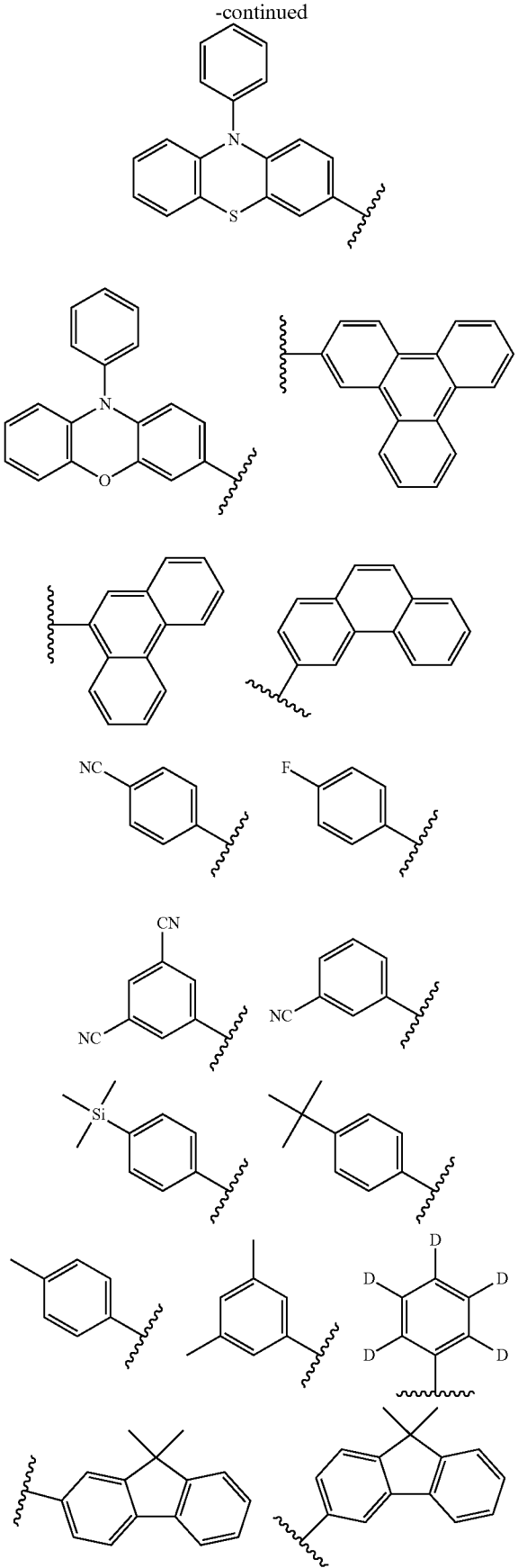
-continued
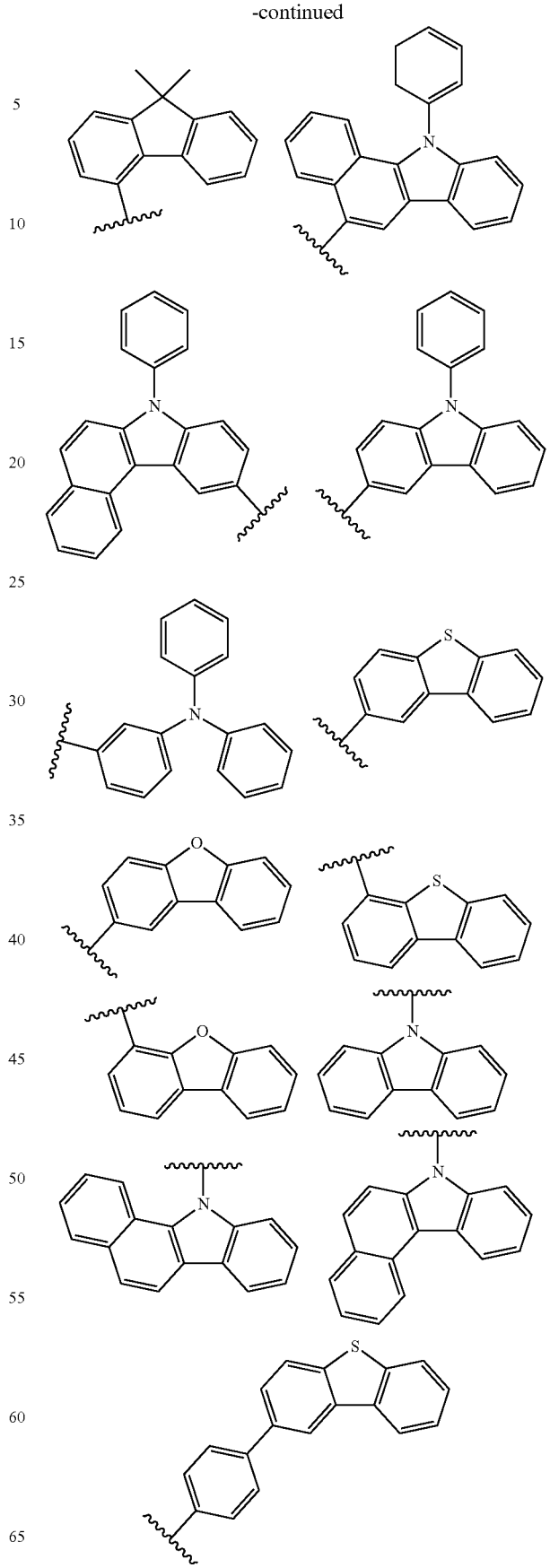

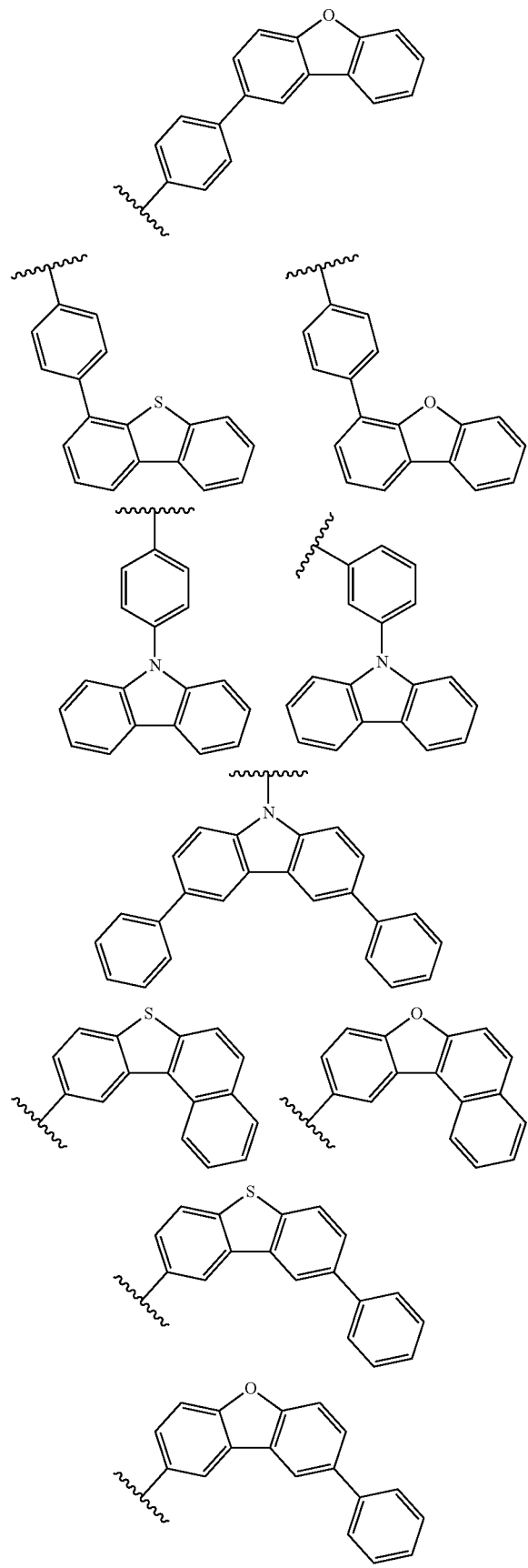
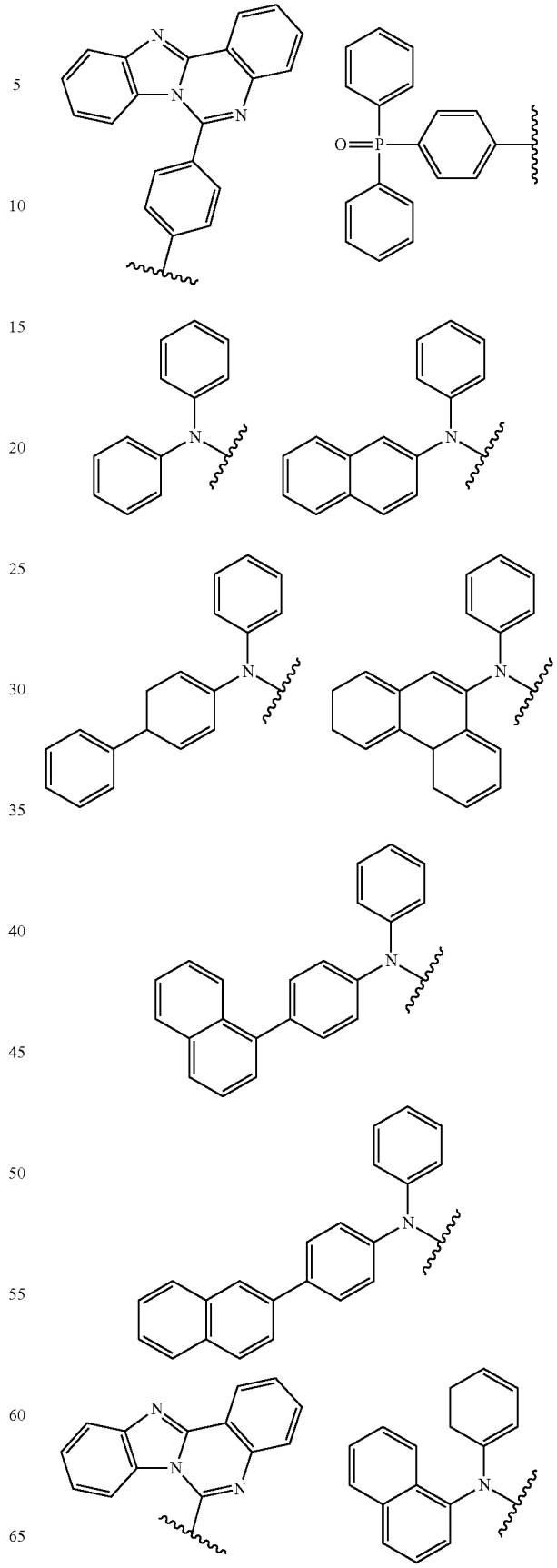

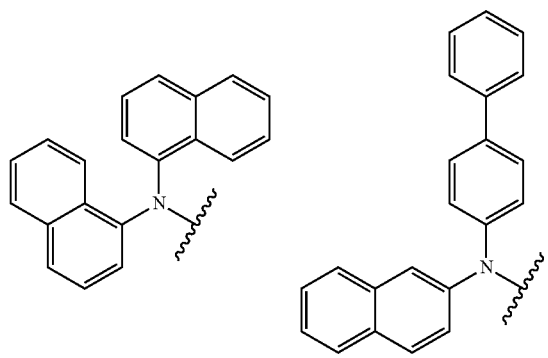
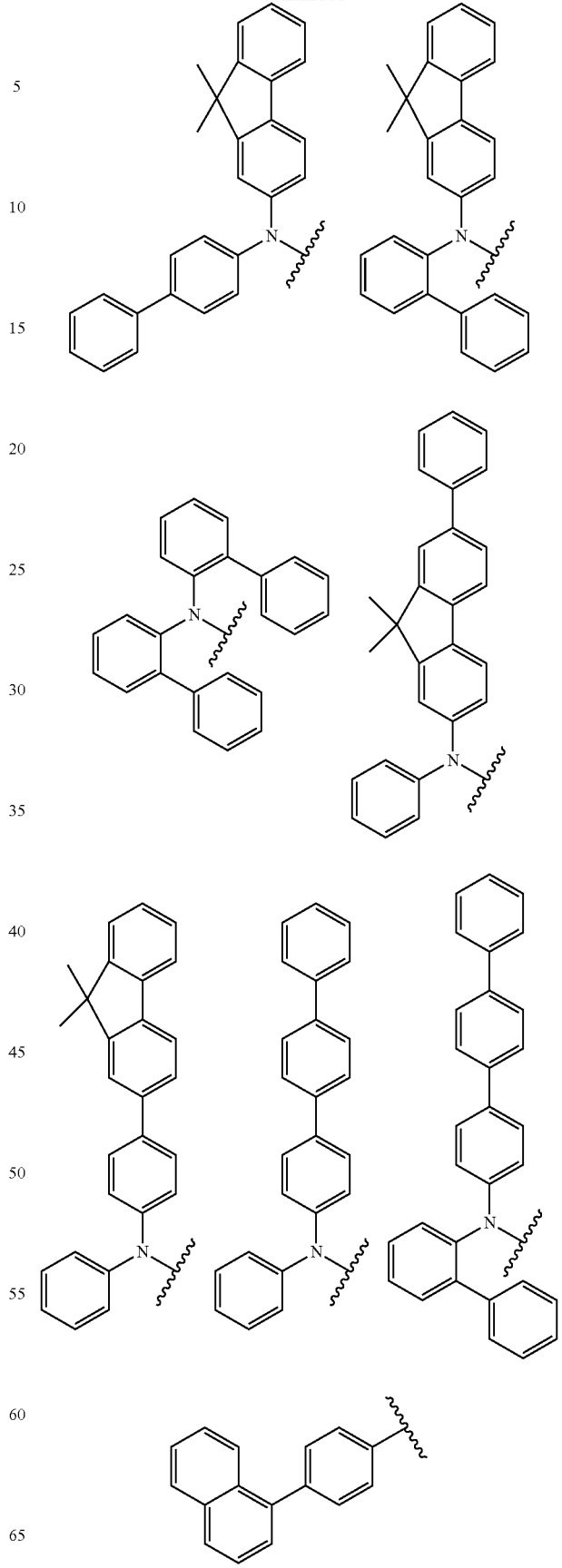

225
-continued
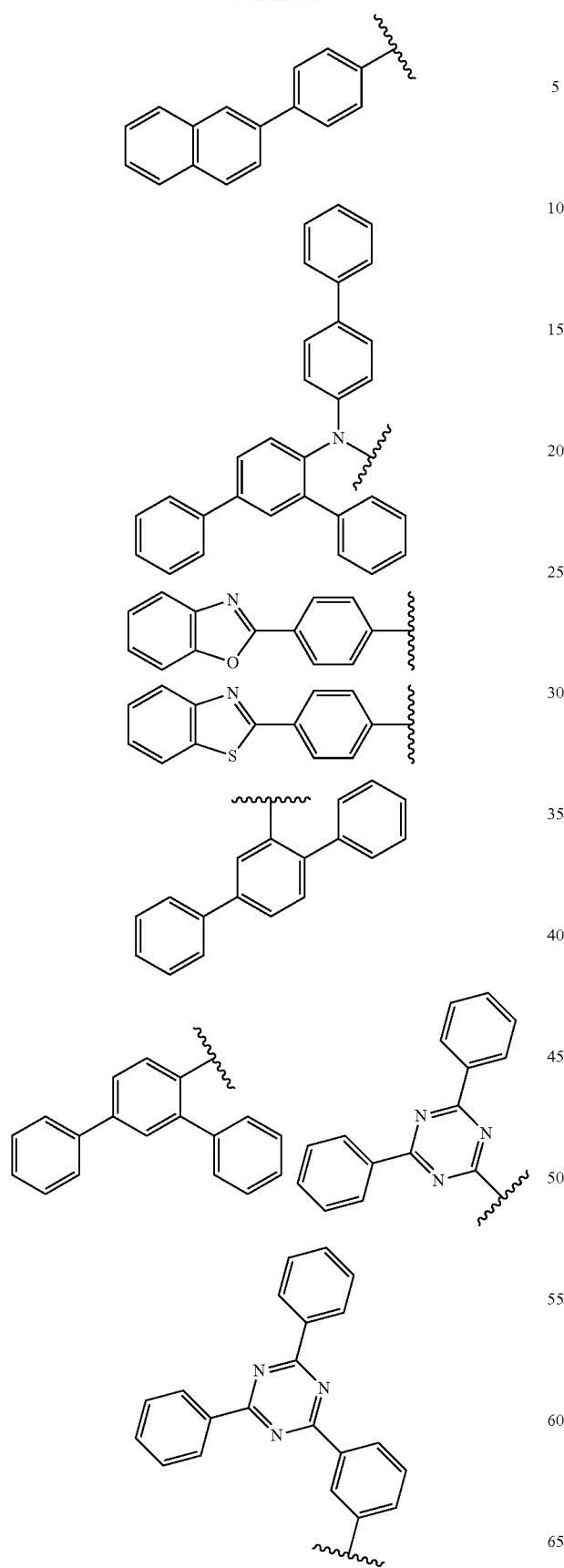
226
-continued
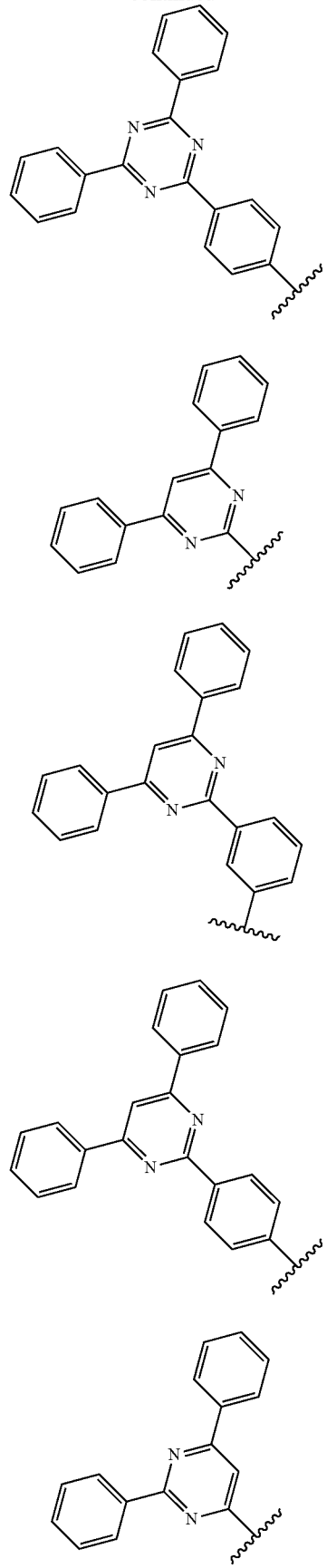

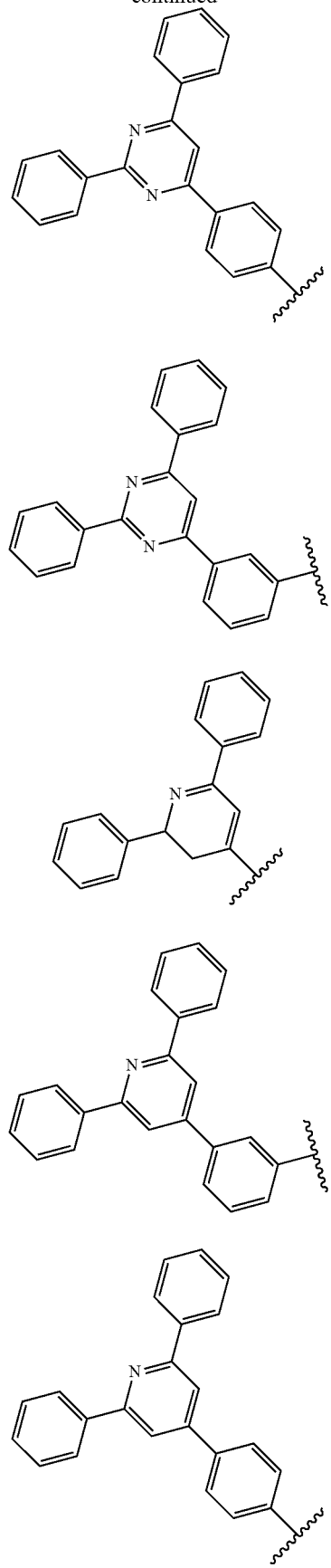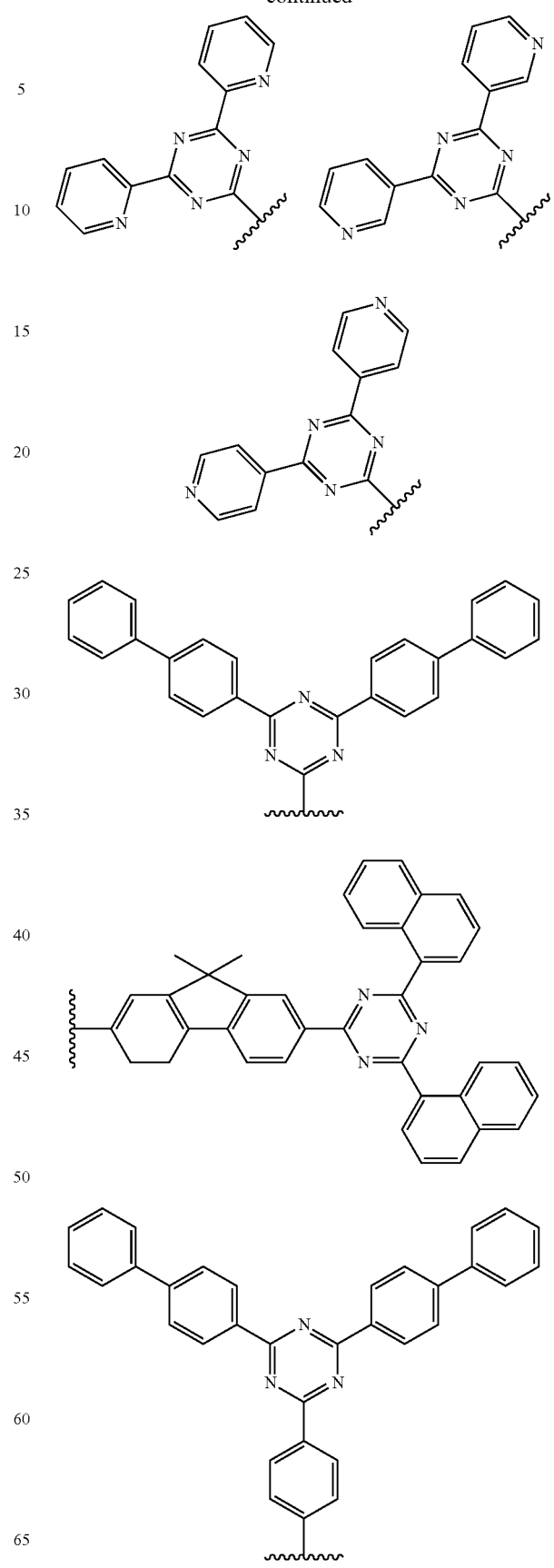

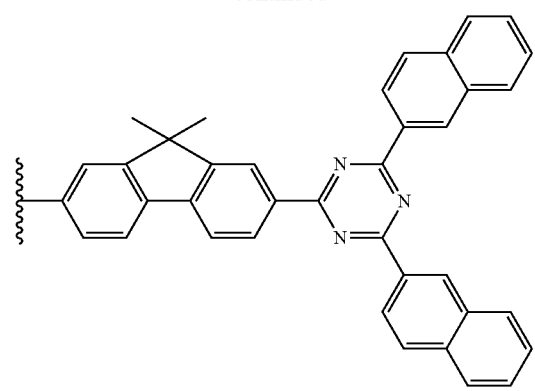
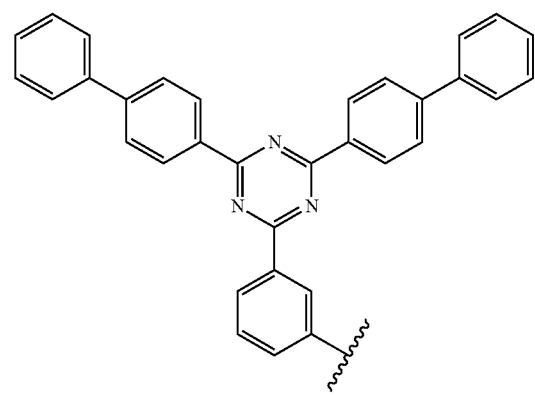
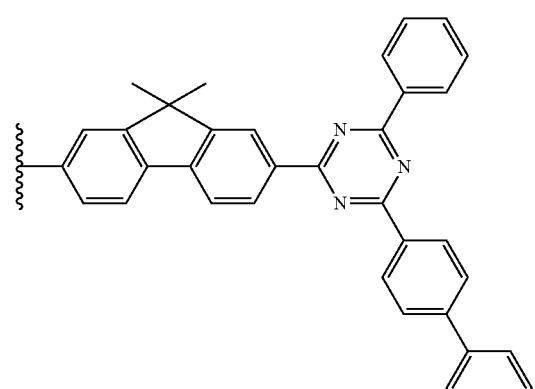
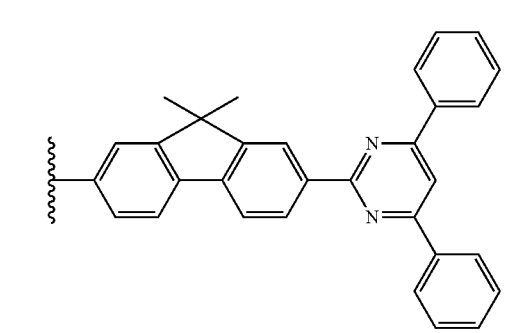
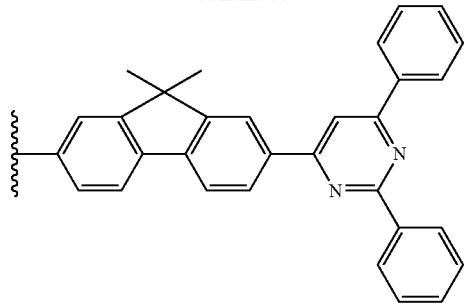
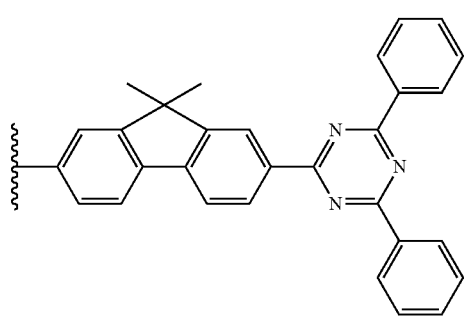
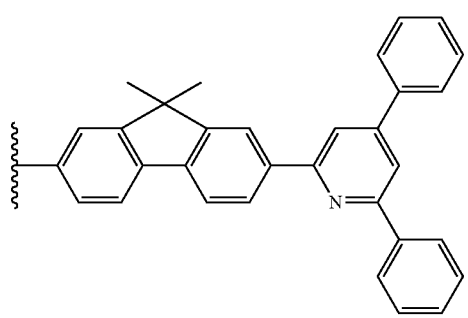
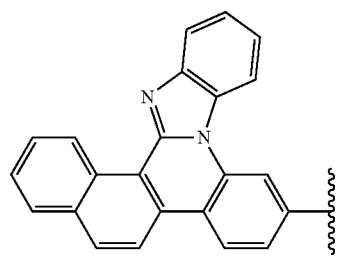
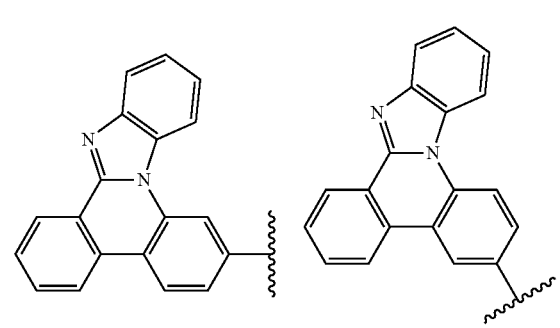

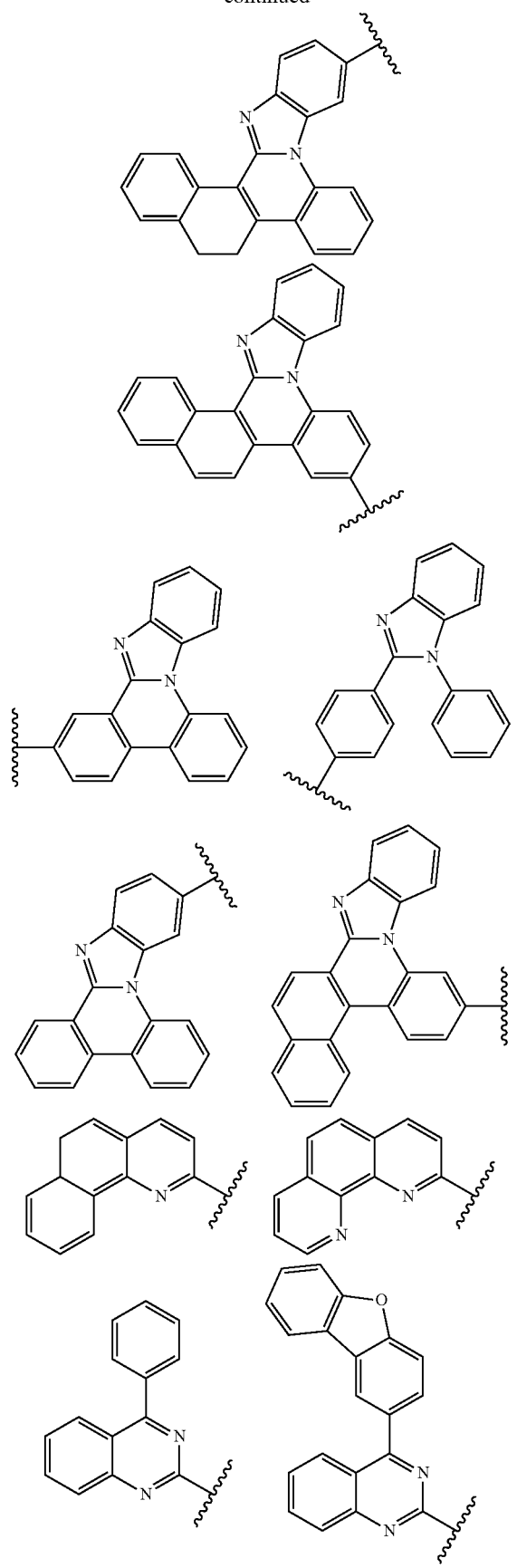
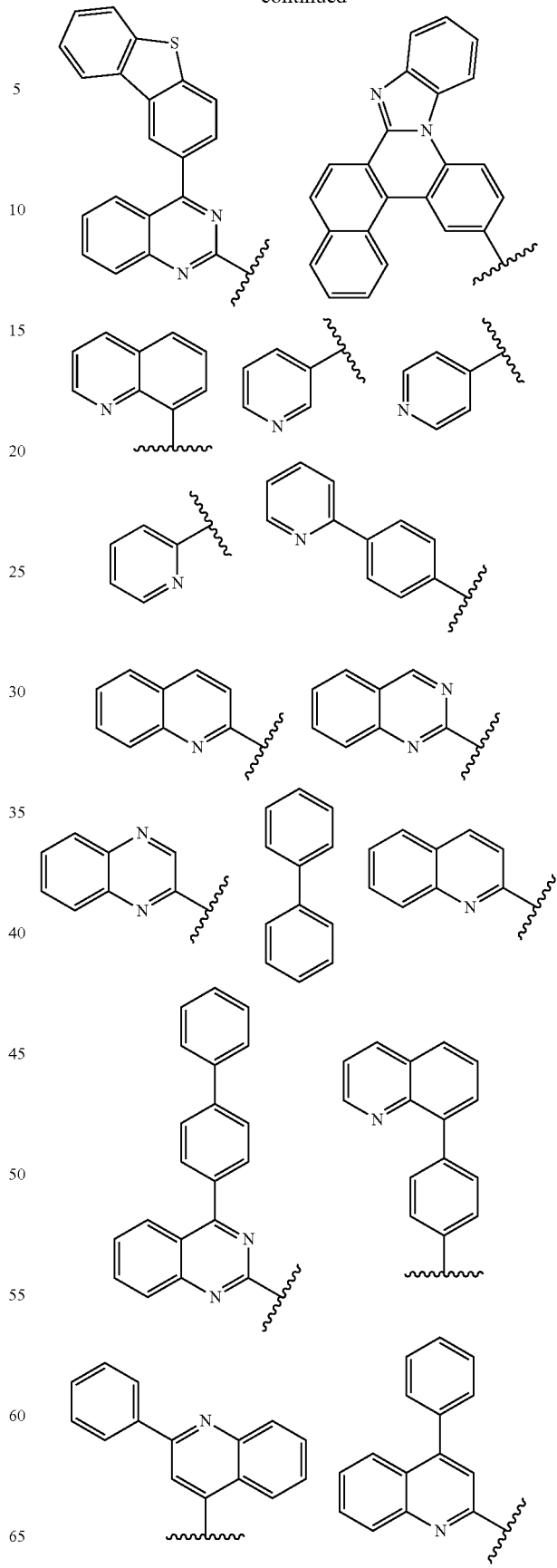

-continued
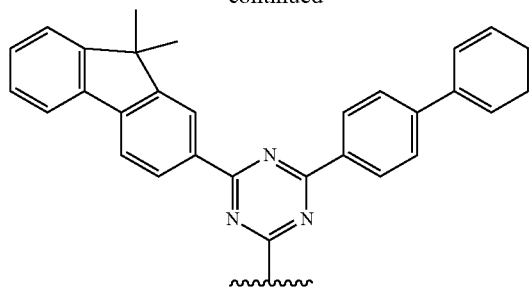
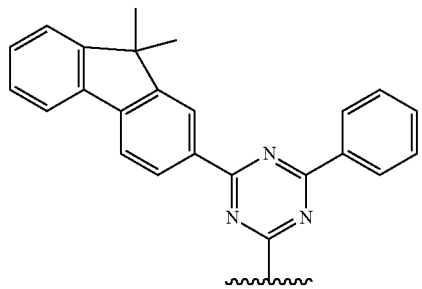
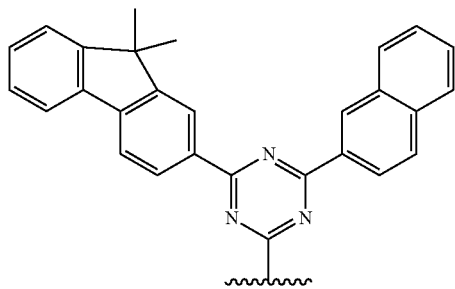
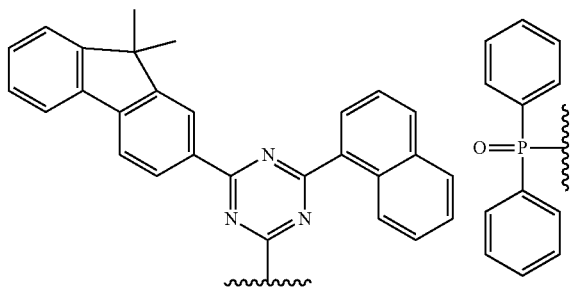
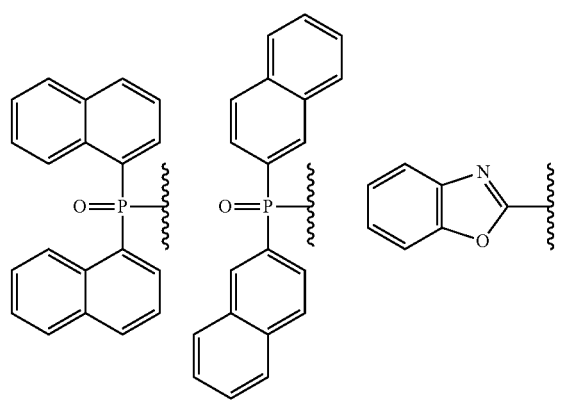
-continued
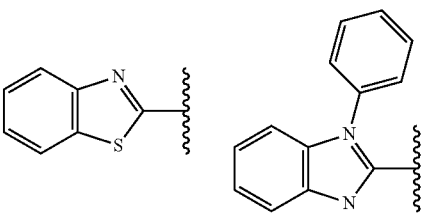
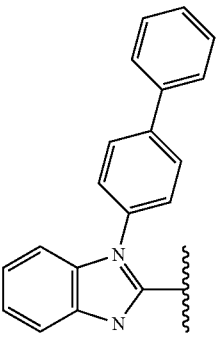
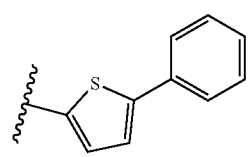
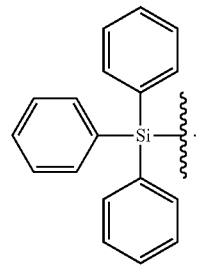
7. The compound of claim 1, wherein Ar1 in Chemical Formula 1 is any one selected from among the following structures:
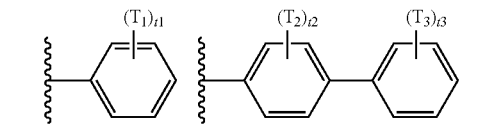
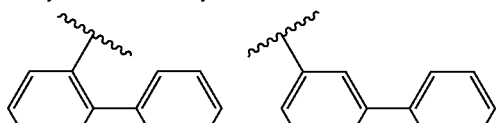
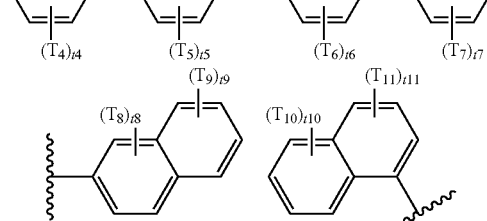
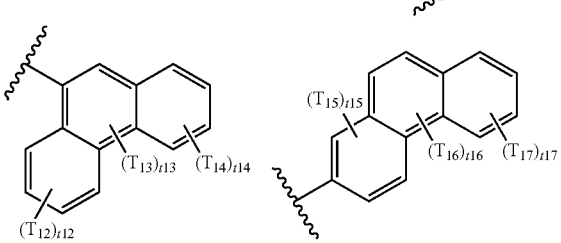

-continued

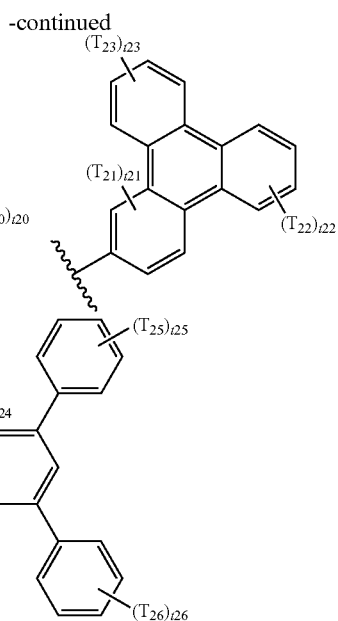

in the structural formulae, $T_1$ to $T_{26}$ are the same as or different from each other, and each independently hydrogen; deuterium; a halogen group; a substituted or unsubstituted alkyl group; a substituted or unsubstituted cycloalkyl group; a substituted or unsubstituted alkenyl group; a substituted or unsubstituted aryl group; a substituted or unsubstituted heterocyclic group; a substituted or unsubstituted alkylamine group; a substituted or unsubstituted heteroarylamine group; or a substituted or unsubstituted arylamine group, or adjacent two or more substituents bond to each other to form a ring;

t1, t3, t5 t7, t25 and t26 are the same as or different from each other, and each independently an integer of 0 to 5;

t2, t4, t6, t9, t10, t12, t14, t17, t20, t22 and t23 are the same as or different from each other, and each independently an integer of 0 to 4;

t8, t11, t15, t18, t21 and t24 are the same as or different from each other, and each independently an integer of 0 to 3;

t13 is an integer of 0 or 1;

t16 and t19 are the same as or different from each other, and each independently an integer of 0 to 2;

when t1 is 2 or greater, $T_1$s are the same as or different from each other;

when t2 is 2 or greater, $T_2$s are the same as or different from each other;

when t3 is 2 or greater, $T_3$s are the same as or different from each other;

when t4 is 2 or greater, $T_4$s are the same as or different from each other;

when t5 is 2 or greater, $T_5$s are the same as or different from each other;

when t6 is 2 or greater, $T_6$s are the same as or different from each other;

when t7 is 2 or greater, $T_7$s are the same as or different from each other;

when t8 is 2 or greater, $T_8$s are the same as or different from each other;

when t9 is 2 or greater, $T_9$s are the same as or different from each other;

when t10 is 2 or greater, $T_{10}$s are the same as or different from each other;

when t11 is 2 or greater, $T_{11}$s are the same as or different from each other;

when t12 is 2 or greater, $T_{12}$s are the same as or different from each other;

when t14 is 2 or greater, $T_{14}$s are the same as or different from each other;

when t15 is 2 or greater, $T_{15}$s are the same as or different from each other;

when t16 is 2, $T_{16}$s are the same as or different from each other;

when t17 is 2 or greater, $T_{17}$s are the same as or different from each other;

when t18 is 2 or greater, $T_{18}$s are the same as or different from each other;

when t19 is 2, $T_{19}$s are the same as or different from each other;

when t20 is 2 or greater, $T_{20}$s are the same as or different from each other;

when t21 is 2 or greater, $T_{21}$s are the same as or different from each other;

when t22 is 2 or greater, $T_{22}$s are the same as or different from each other;

when t23 is 2 or greater, $T_{23}$s are the same as or different from each other;

when t24 is 2 or greater, $T_{24}$s are the same as or different from each other;

when t25 is 2 or greater, $T_{25}$s are the same as or different from each other; and when t26 is 2 or greater, $T_{26}$s are the same as or different from each other.

8. The compound of claim 1, wherein Ar1 in Chemical Formula 1 is represented by any one of the following Chemical Formulae 9 to 11:

[Chemical Formula 9]

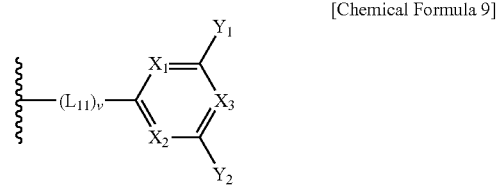

wherein, in Chemical Formula 9, $X_1$ to $X_3$ are the same as or different from each other, and each independently CR or N;

at least one or more of $X_1$ to $X_3$ are N;

Rs are the same as or different from each other, and each independently hydrogen; deuterium; a halogen group; a substituted or unsubstituted alkyl group; a substituted or unsubstituted cycloalkyl group; a substituted or unsubstituted alkenyl group; a substituted or unsubstituted aryl group; a substituted or unsubstituted heterocyclic group; a substituted or unsubstituted alkylamine group; a substituted or unsubstituted heteroarylamine group; or a substituted or unsubstituted arylamine group, or adjacent two or more substituents bond to each other to form a ring;

$Y_1$ and $Y_2$ are the same as or different from each other, and each independently substituted or unsubstituted aryl;

$L_{11}$ is a direct bond; substituted or unsubstituted arylene; or substituted or unsubstituted heteroarylene; and v is an integer of 0 to 5, and when v is 2 or greater, $L_{11}$s are the same as or different from each other,

[Chemical Formula 10]

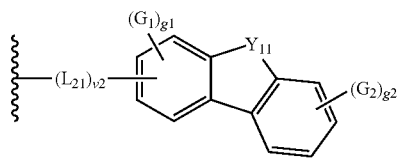

wherein, in Chemical Formula 10, $Y_{11}$ is $CR_aR_b$, $NR_c$, S or O;

$R_a$ and $R_b$ are the same as or different from each other, and each independently hydrogen; deuterium; a halogen group; a substituted or unsubstituted alkyl group; a substituted or unsubstituted cycloalkyl group; a substituted or unsubstituted alkenyl group; a substituted or unsubstituted aryl group; a substituted or unsubstituted heterocyclic group; a substituted or unsubstituted alkylamine group; a substituted or unsubstituted heteroarylamine group; or a substituted or unsubstituted arylamine group, or adjacent substituents bond to each other to form a ring;

$R_c$ is hydrogen; deuterium; a halogen group; a substituted or unsubstituted alkyl group; a substituted or unsubstituted cycloalkyl group; a substituted or unsubstituted alkenyl group; a substituted or unsubstituted aryl group; a substituted or unsubstituted heterocyclic group; a substituted or unsubstituted alkylamine group; a substituted or unsubstituted heteroarylamine group; or a substituted or unsubstituted arylamine group, or bonds to adjacent groups to form a ring;

$L_{21}$ is a direct bond; substituted or unsubstituted arylene; or substituted or unsubstituted heteroarylene;

$G_1$ and $G_2$ are the same as or different from each other, and each independently hydrogen; deuterium; a halogen group; a substituted or unsubstituted alkyl group; a substituted or unsubstituted cycloalkyl group; a substituted or unsubstituted alkenyl group; a substituted or unsubstituted aryl group; a substituted or unsubstituted heterocyclic group; a substituted or unsubstituted alkylamine group; a substituted or unsubstituted heteroarylamine group; or a substituted or unsubstituted arylamine group, or adjacent two or more substituents bond to each other to form a ring;

g1 is an integer of 0 to 3, g2 is an integer of 0 to 4, and v2 is an integer of 0 to 5;

when g1 is 2 or greater, $G_1$s are the same as or different from each other;

when g2 is 2 or greater, $G_2$s are the same as or different from each other; and when v2 is 2 or greater, $L_{21}$s are the same as or different from each other,

[Chemical Formula 11]

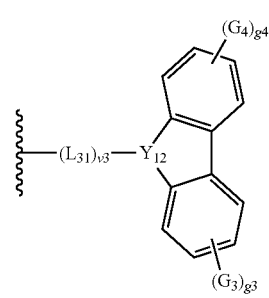

wherein, in Chemical Formula 11, $Y_{12}$ is $CR_e$ or N;

$R_e$ is hydrogen; deuterium; a halogen group; a substituted or unsubstituted alkyl group; a substituted or unsubstituted cycloalkyl group; a substituted or unsubstituted alkenyl group; a substituted or unsubstituted aryl group; a substituted or unsubstituted heterocyclic group; a substituted or unsubstituted alkylamine group; or a substituted or unsubstituted heteroarylamine group;

$L_{31}$ is a direct bond; substituted or unsubstituted arylene; or substituted or unsubstituted heteroarylene;

$G_3$ and $G_4$ are the same as or different from each other, and each independently hydrogen; deuterium; a halogen group; a substituted or unsubstituted alkyl group; a substituted or unsubstituted cycloalkyl group; a substituted or unsubstituted alkenyl group; a substituted or unsubstituted aryl group; a substituted or unsubstituted heterocyclic group; a substituted or unsubstituted alkylamine group; a substituted or unsubstituted heteroarylamine group; or a substituted or unsubstituted arylamine group, or adjacent two or more substituents bond to each other to form a ring;

g3 and g4 are the same as or different from each other, and each independently an integer of 0 to 4;

v3 is an integer of 0 to 5;

when g3 is 2 or greater, $G_3$s are the same as or different from each other;

when g4 is 2 or greater, $G_4$s are the same as or different from each other; and when v3 is 2 or greater, $L_{31}$s are the same as or different from each other.

9. The compound of claim 1, wherein Ar1 in Chemical Formula 1 is represented by the following Chemical Formula 12-a or Chemical Formula 12-b:

[Chemical Formula 12-a]

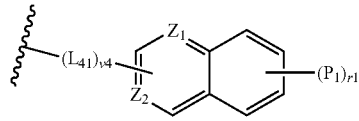

[Chemical Formula 12-b]

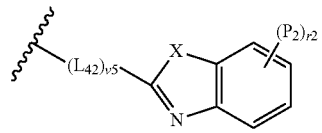

wherein, in Chemical Formula 12-a and Chemical Formula 12-b, $Z_1$ and $Z_2$ are the same as or different from each other, and each independently N or $CR_f$;

$R_f$ is hydrogen; deuterium; a halogen group; a substituted or unsubstituted alkyl group; a substituted or unsubstituted cycloalkyl group; a substituted or unsubstituted alkenyl group; a substituted or unsubstituted aryl group; a substituted or unsubstituted heterocyclic group; a substituted or unsubstituted alkylamine group; a substituted or unsubstituted heteroarylamine group; or a substituted or unsubstituted arylamine group, or adjacent substituents bond to each other to form a ring;

$L_{41}$ is a direct bond; substituted or unsubstituted arylene; or substituted or unsubstituted heteroarylene;

X is an O atom, an S atoms or $NR_g$;

$R_g$ is hydrogen; deuterium; a halogen group; a substituted or unsubstituted alkyl group; a substituted or unsubstituted cycloalkyl group; a substituted or unsubstituted alkenyl group; a substituted or unsubstituted aryl group; a substituted or unsubstituted heterocyclic group; a substituted or unsubstituted alkylamine group; a substituted or unsubstituted heteroarylamine group; or a substituted or unsubstituted arylamine group, or adjacent substituents bond to each other to form a ring;

$P_1$ and $P_2$ are hydrogen; deuterium; a halogen group; a substituted or unsubstituted alkyl group; a substituted or unsubstituted cycloalkyl group; a substituted or unsubstituted alkenyl group; a substituted or unsubstituted aryl group; a substituted or unsubstituted heterocyclic group; a substituted or unsubstituted alkylamine group; a substituted or unsubstituted heteroarylamine group; or a substituted or unsubstituted arylamine group, or adjacent two or more substituents bond to each other to form a ring;

r1 is an integer of 0 to 5;

r2 is an integer of 0 to 4;

v4 and v5 are the same as or different from each other, and each independently an integer of 0 to 5;

when r1 is 2 or greater, $P_1$s are the same as or different from each other;

when r2 is 2 or greater, $P_2$s are the same as or different from each other;

when v4 is 2 or greater, $L_{41}$s are the same as or different from each other; and when v5 is 2 or greater, $L_{42}$s are the same as or different from each other.

10. The compound of claim 1, wherein Chemical Formula 1 is any one selected from among the following structures:

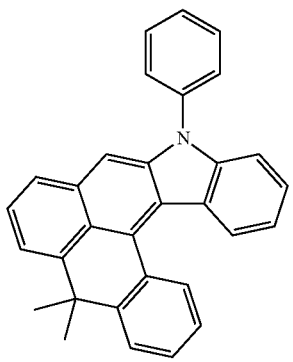

2-1-1

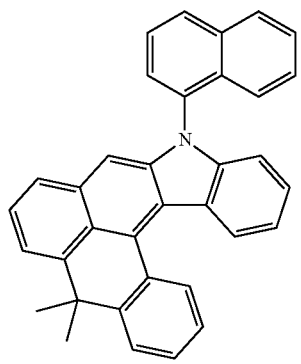

2-1-2

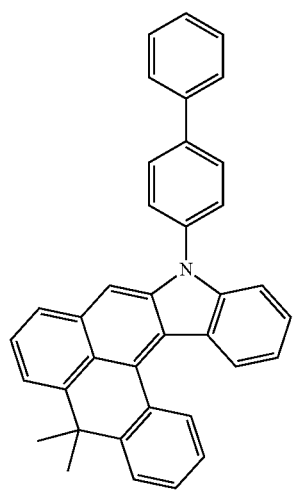

2-1-3

2-1-4

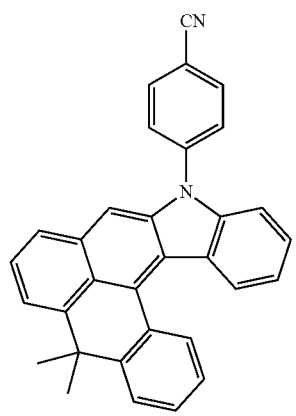

2-1-5

US 10,580,996 B2
241 -continued
2-1-6
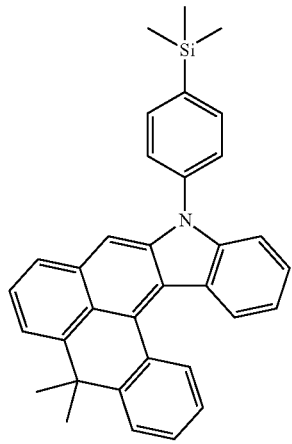
2-1-7
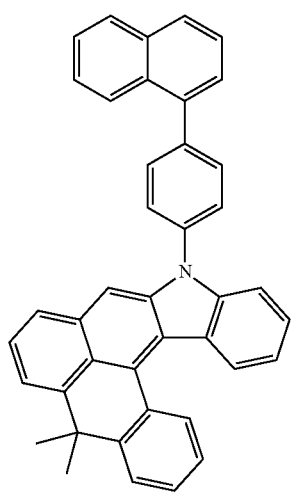
2-1-8
242 -continued
2-1-9
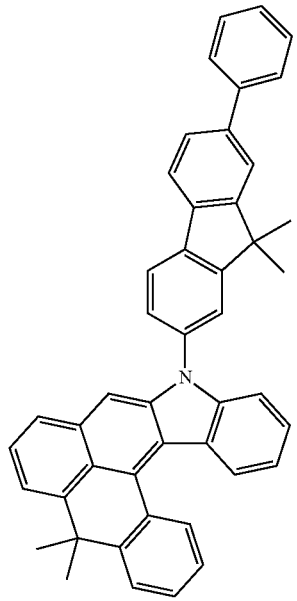
2-1-10
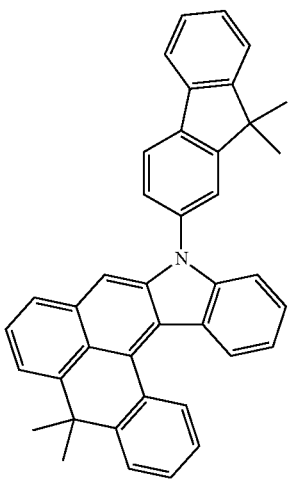
2-1-11
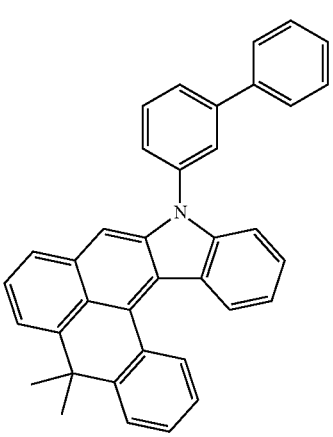

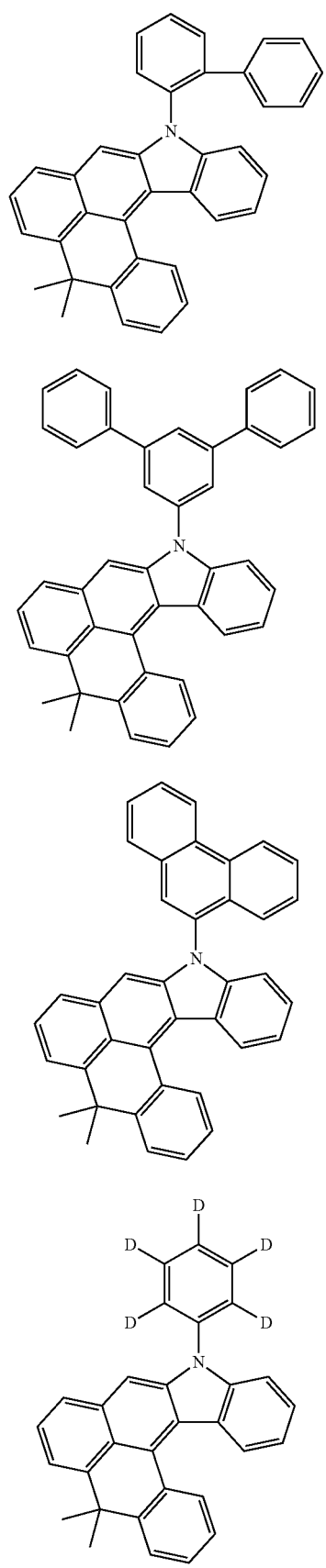
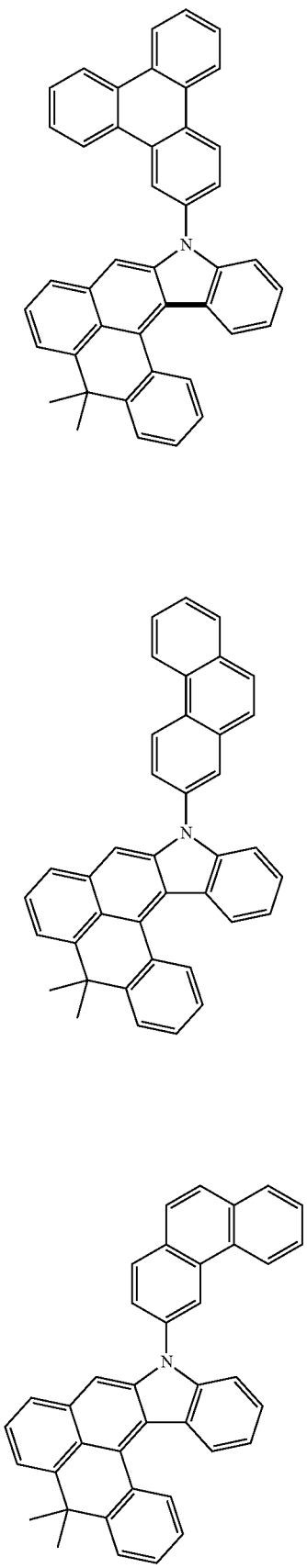

2-1-19
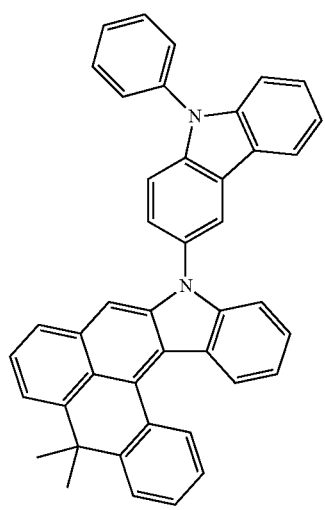
2-1-20
2-1-21
2-1-22
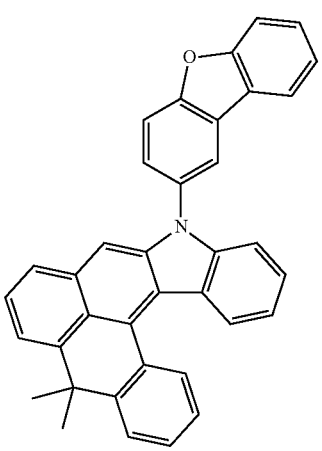
2-1-23
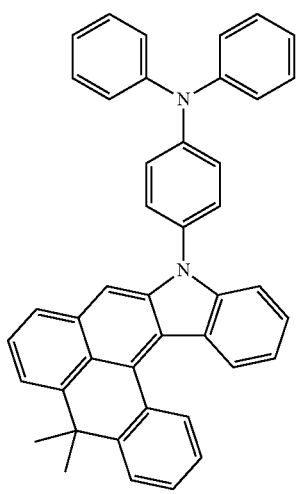
2-1-24
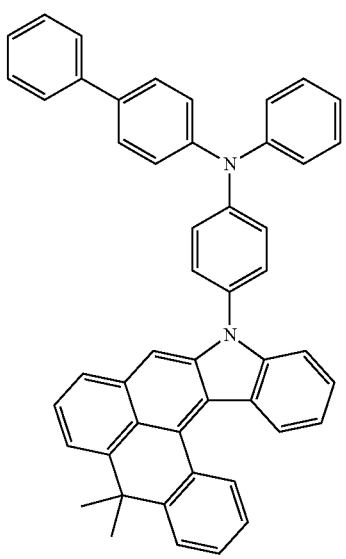

2-1-25
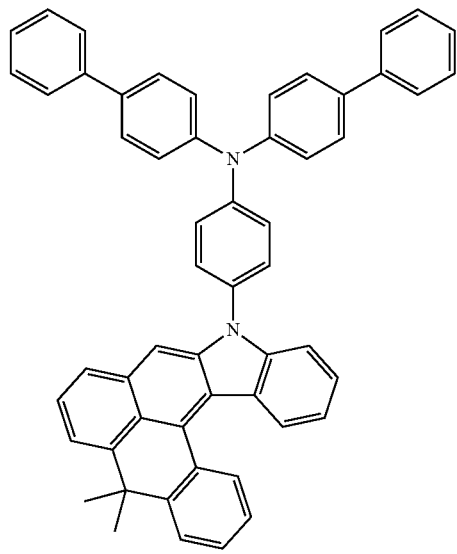
2-1-26
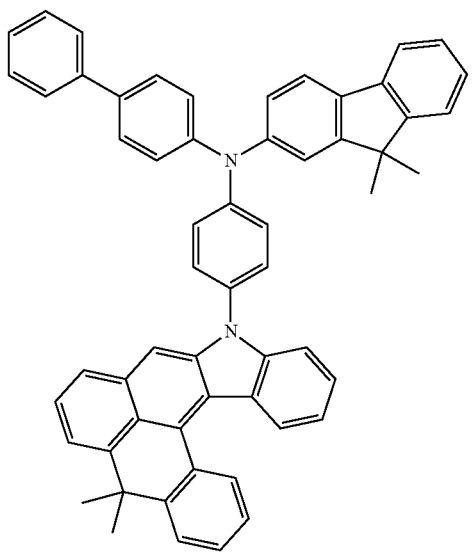
2-1-27
2-1-28
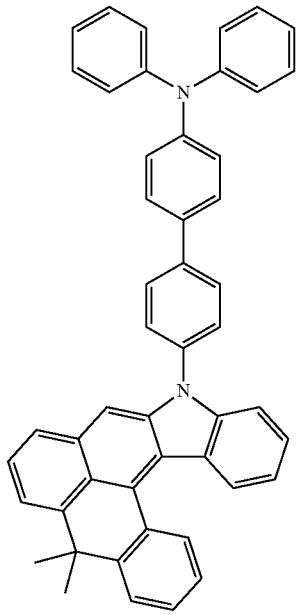
2-1-29
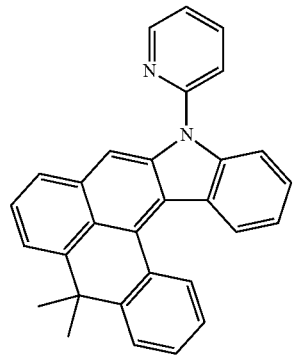
2-1-30
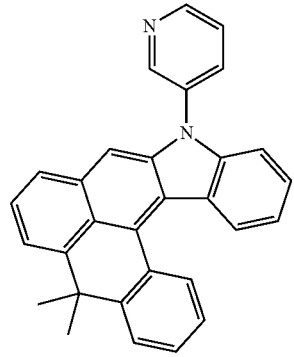

2-1-31
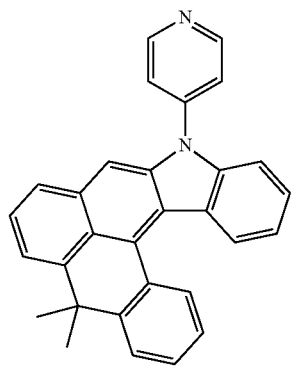
2-1-32
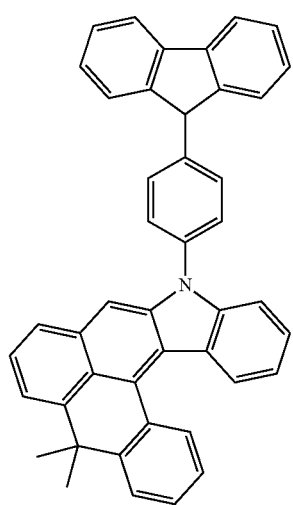
2-1-33
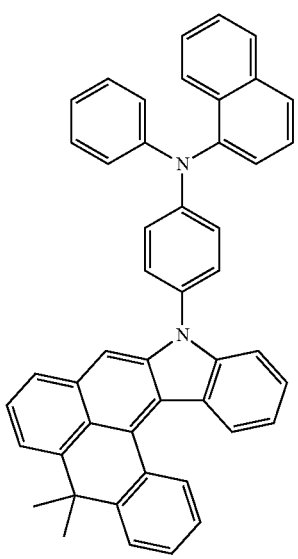
2-1-34
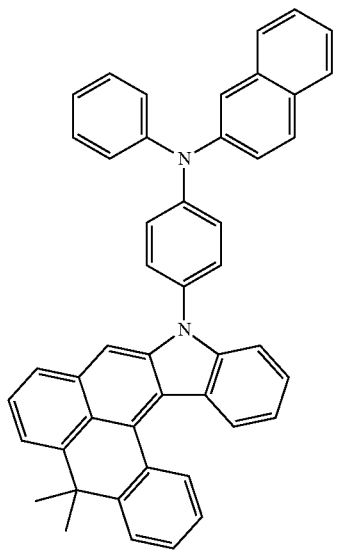
2-1-35
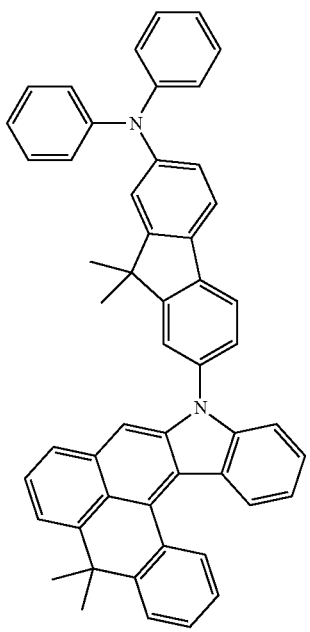

2-1-36
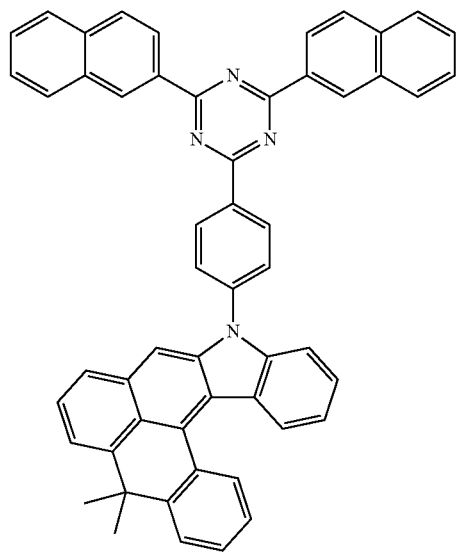
2-1-37
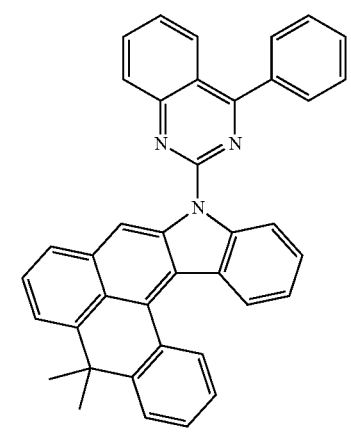
2-1-38
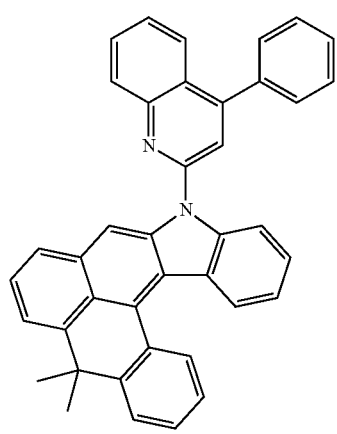
2-1-39
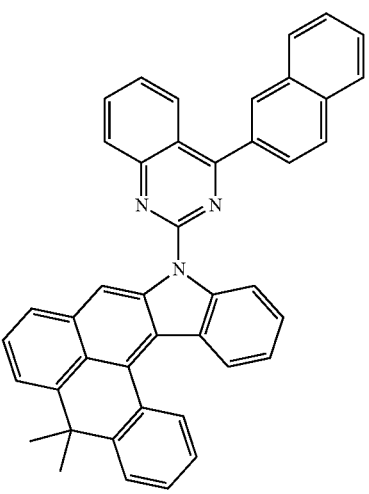
2-1-40
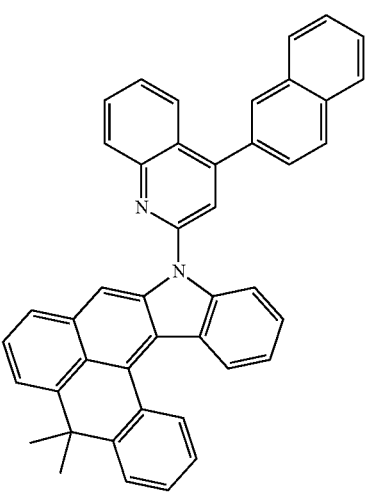
2-1-41
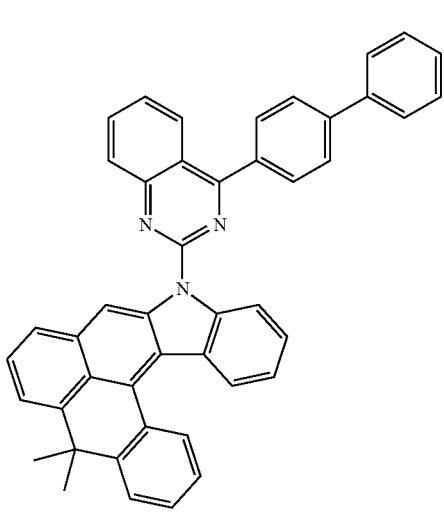

-continued
2-1-42
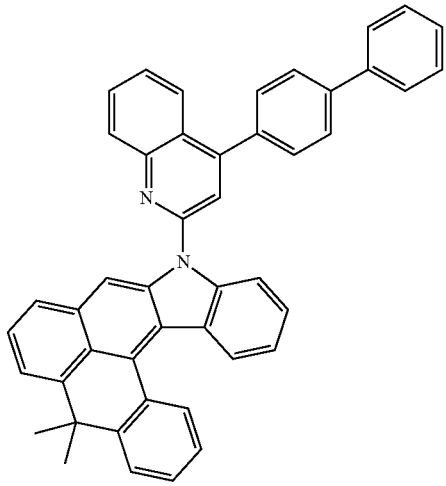
2-1-43
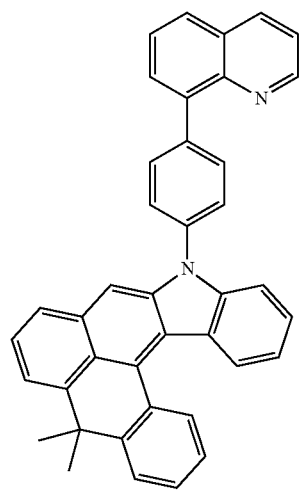
2-1-44
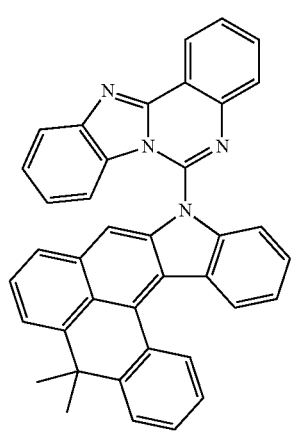
-continued
2-1-45
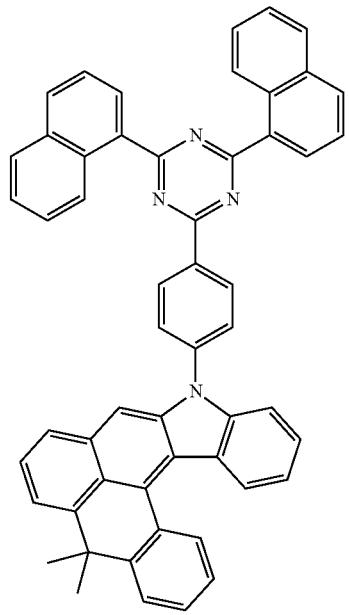
2-1-46
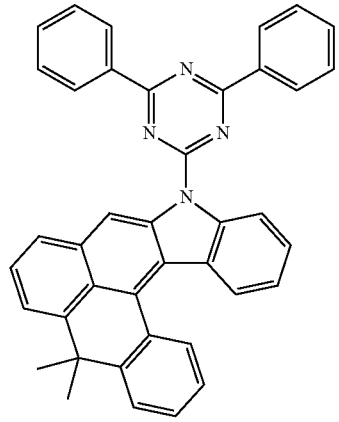
2-1-47
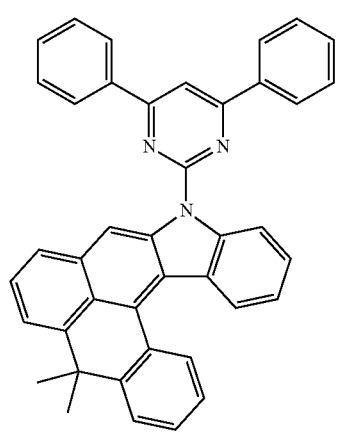

-continued
2-1-48
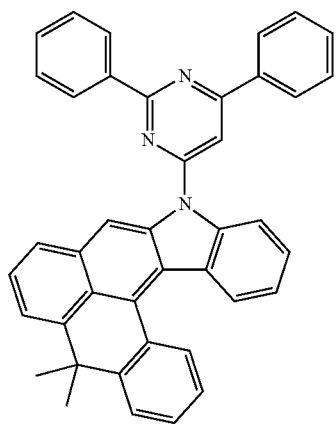
2-1-49
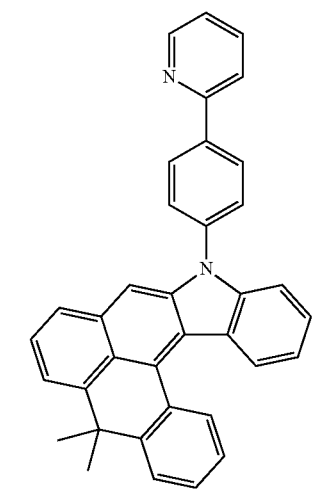
2-1-50
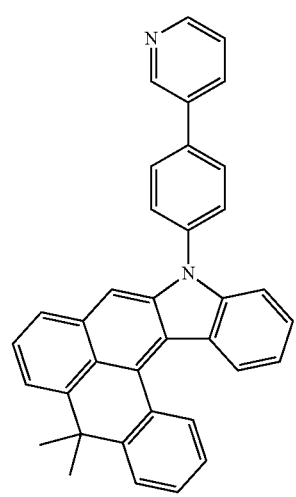
-continued
2-1-51
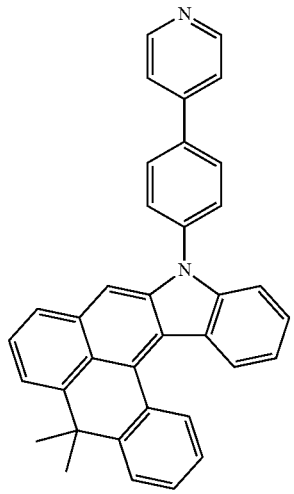
2-1-52
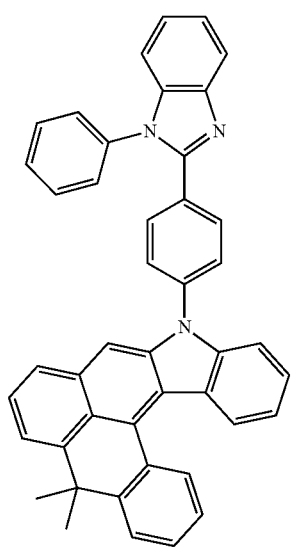
2-1-53
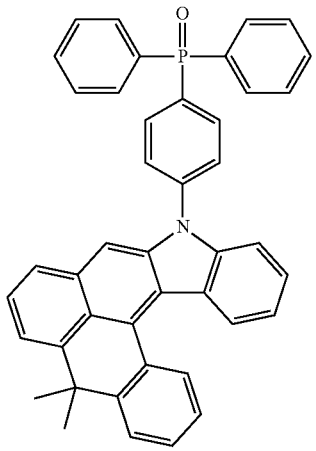

257
-continued
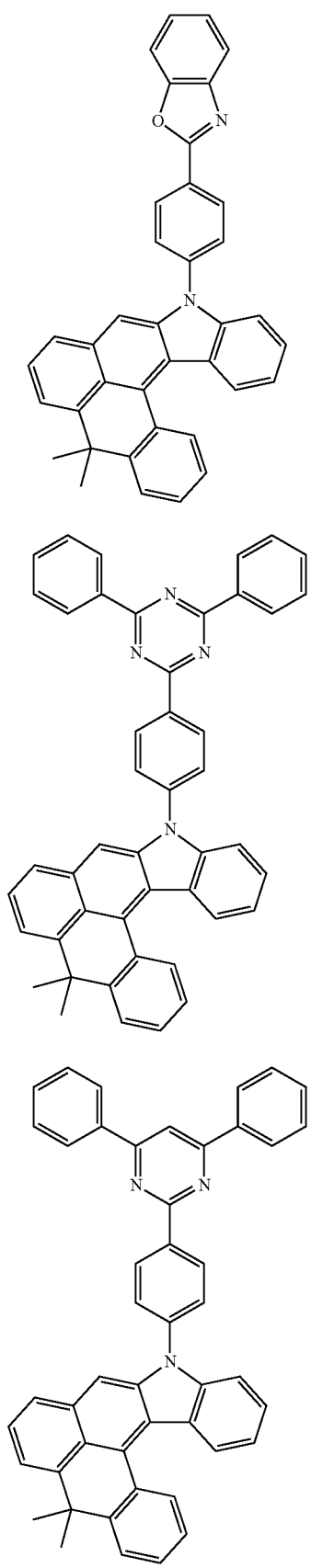
2-1-54
2-1-55
2-1-56
258
-continued
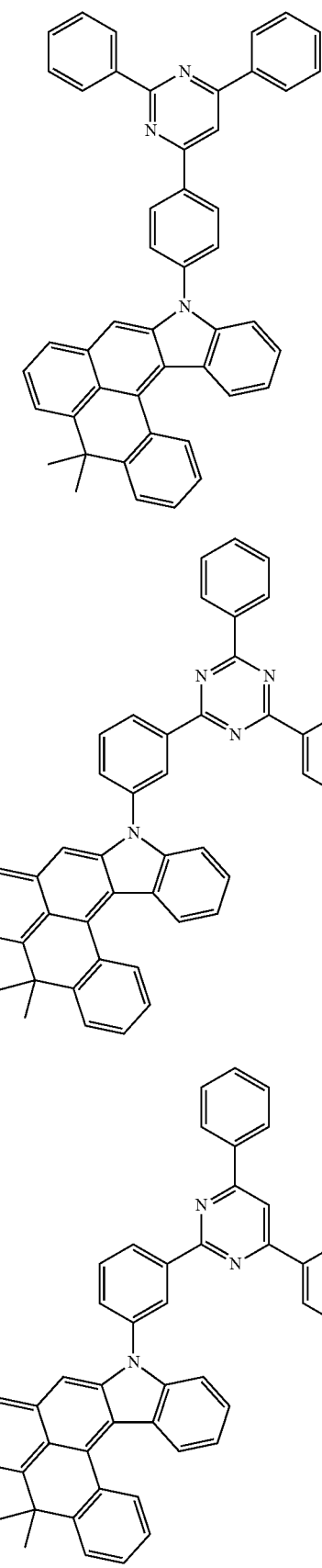
2-1-57
2-1-58
2-1-59

2-1-60
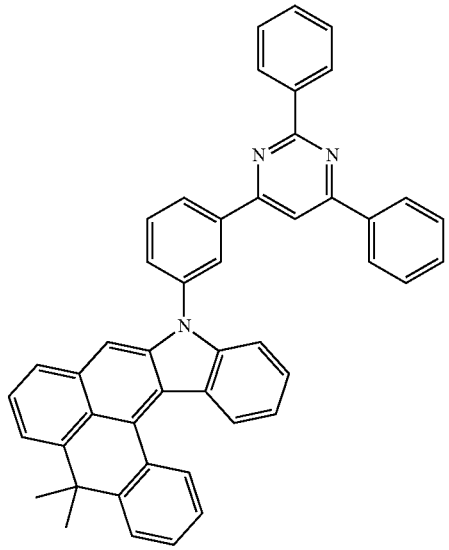
2-1-61
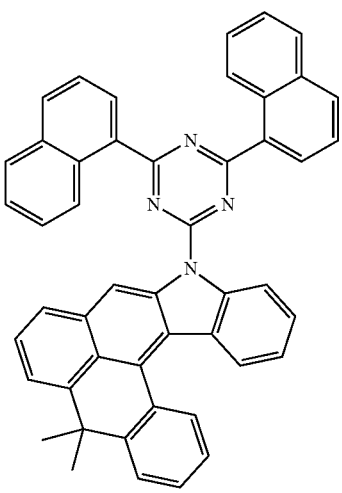
2-1-62
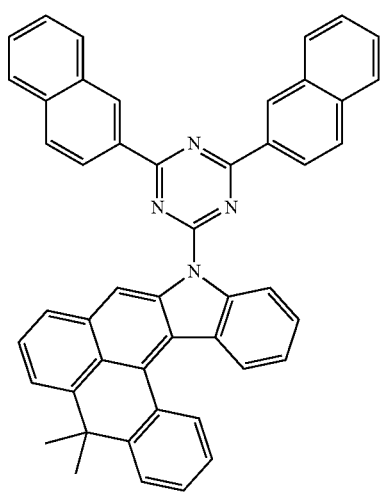
2-1-63
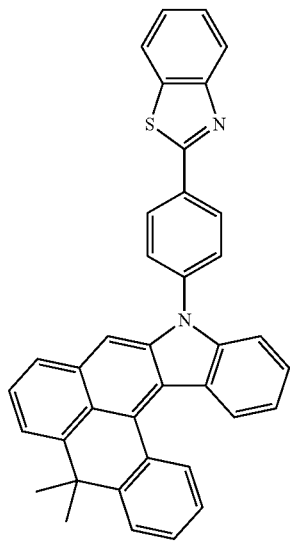
2-1-64
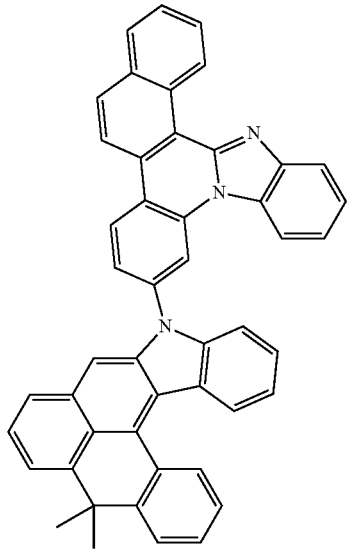
2-1-65
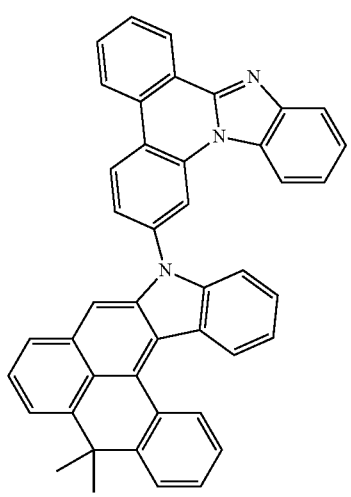

2-1-66
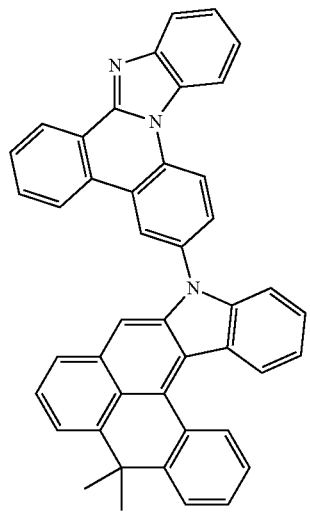
2-1-67
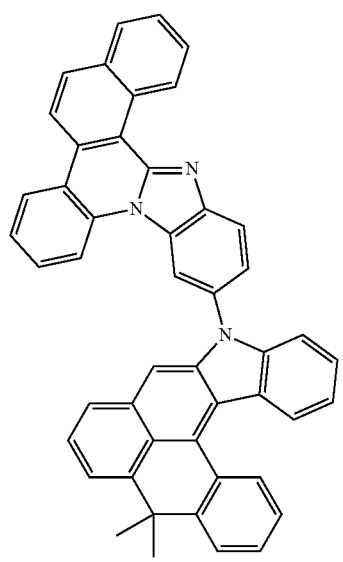
2-1-68
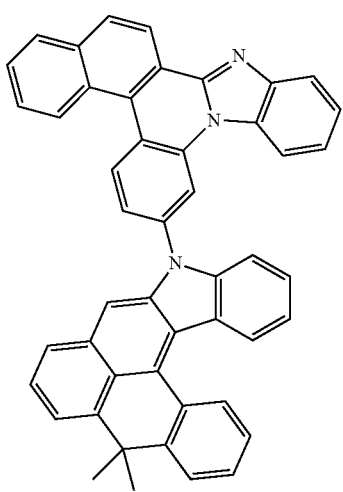
2-1-69
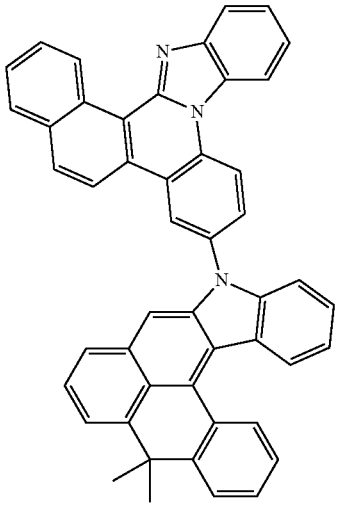
2-1-70
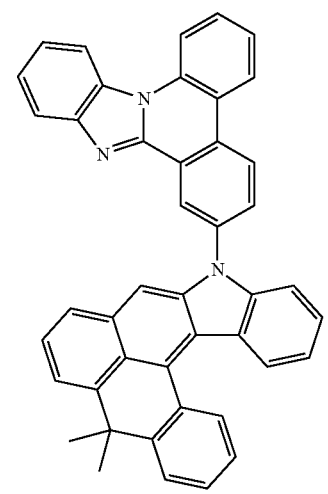
2-1-71
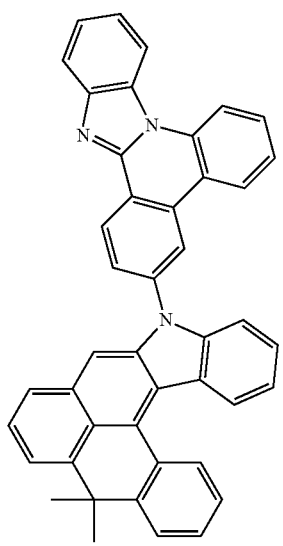

263
-continued
2-1-72
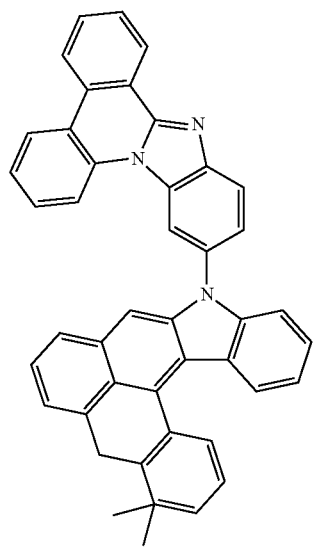
2-1-73
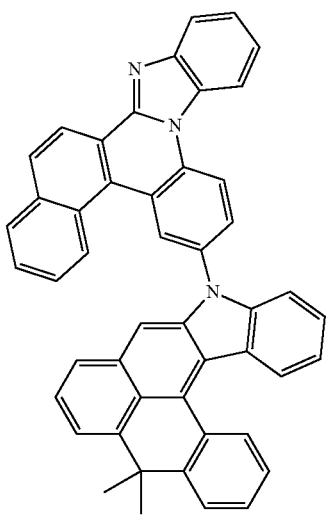
2-1-74
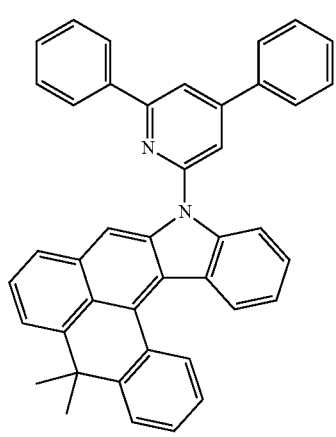
264
-continued
2-1-75
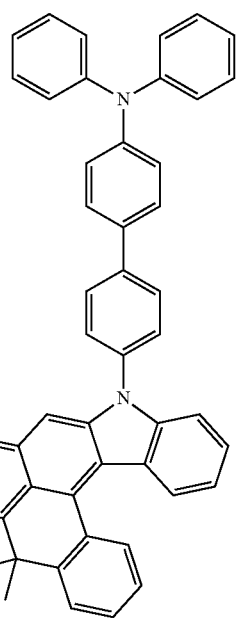
2-1-76
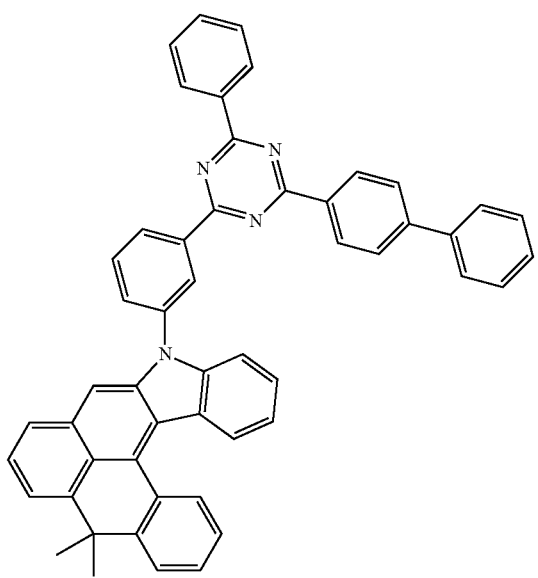

2-1-77
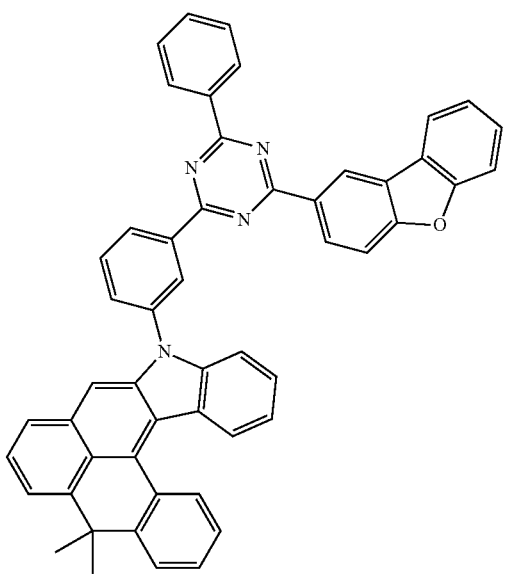
2-1-78
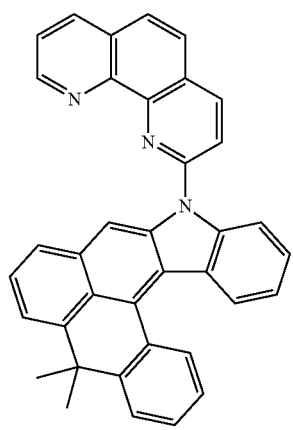
2-1-79
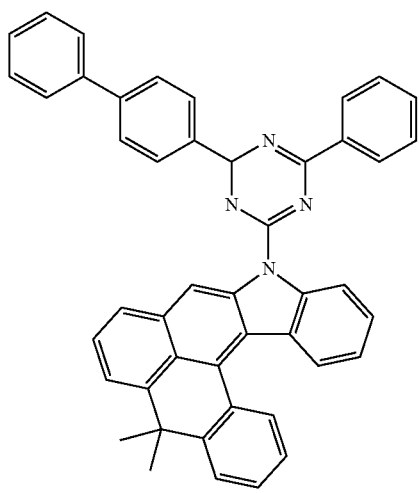
2-1-80
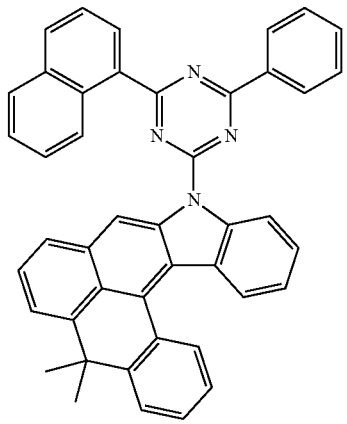
2-1-81
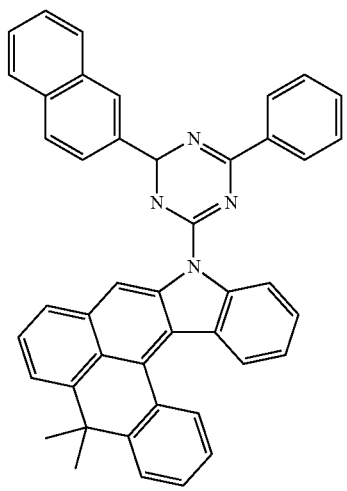
2-1-82
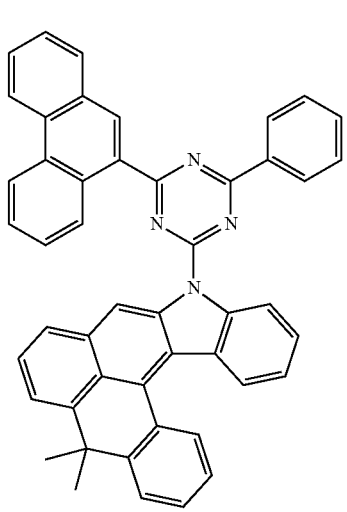

2-1-83
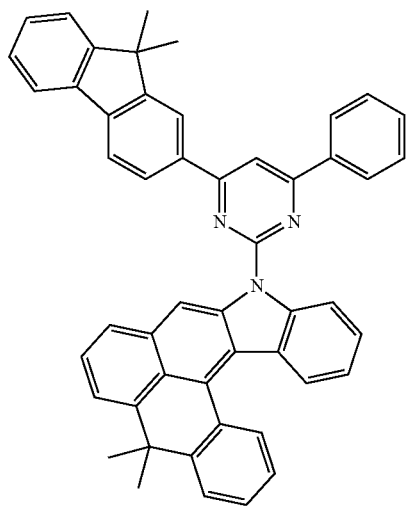
2-2-1
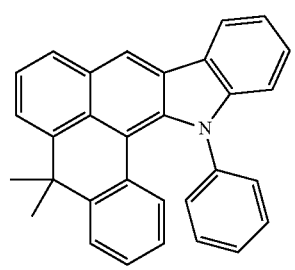
2-2-2
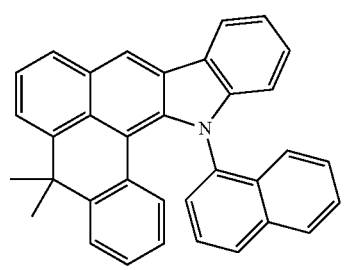
2-2-3
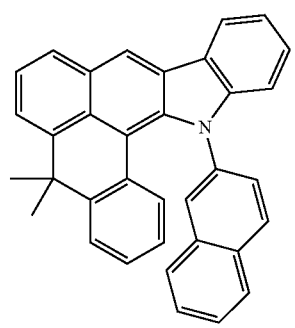
2-2-4
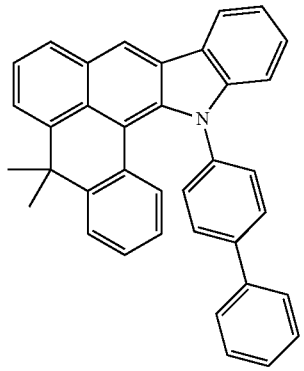
2-2-5
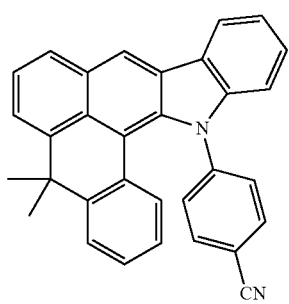
2-2-6
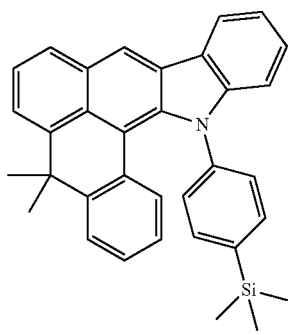
2-2-7
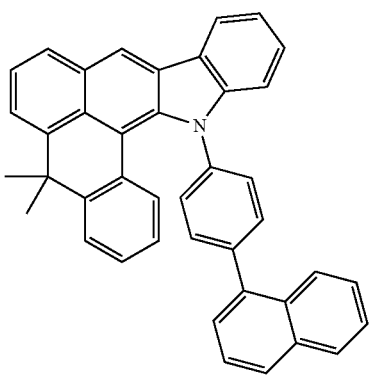

269
-continued
2-2-8
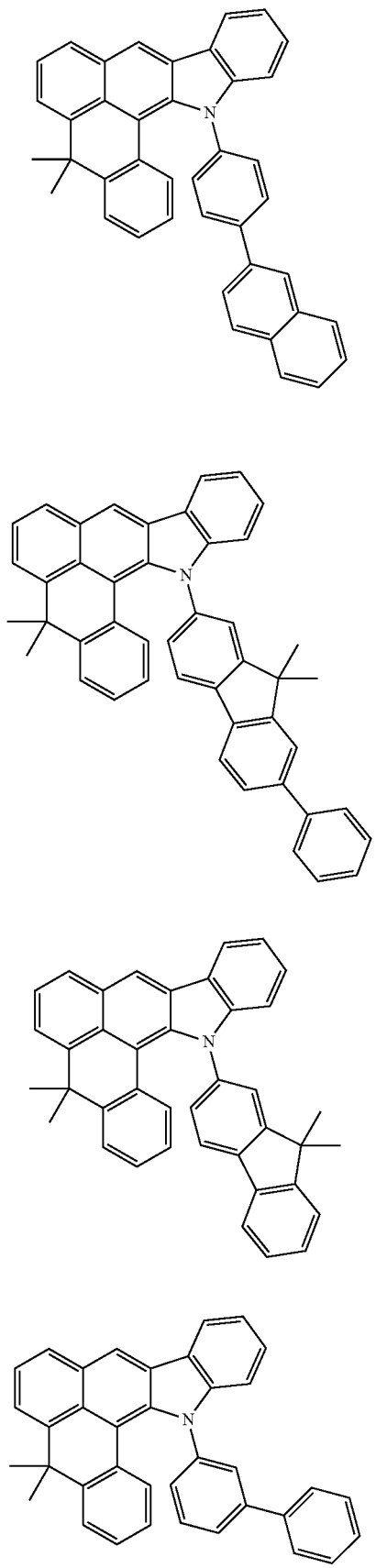
2-2-9
2-2-10
2-2-11
270
-continued
2-2-12
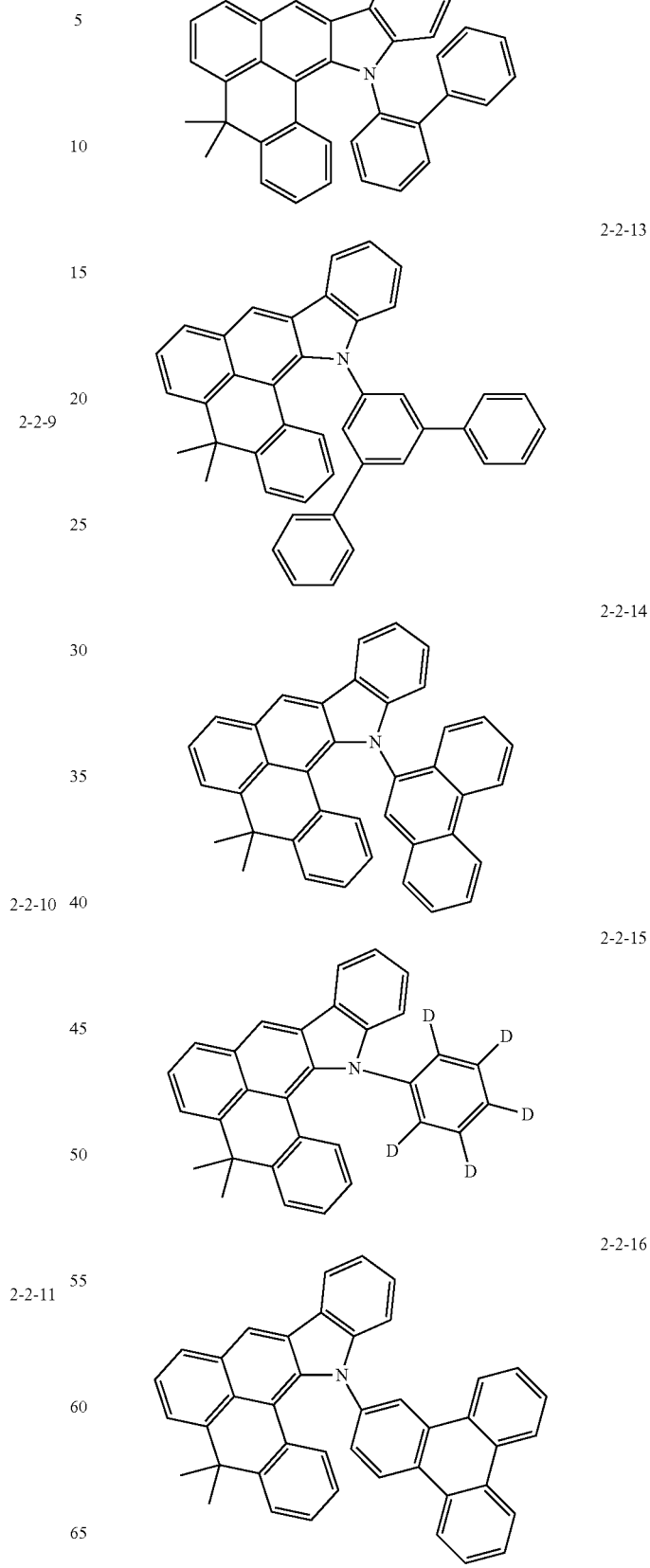
2-2-13
2-2-14
2-2-15
2-2-16

2-2-17
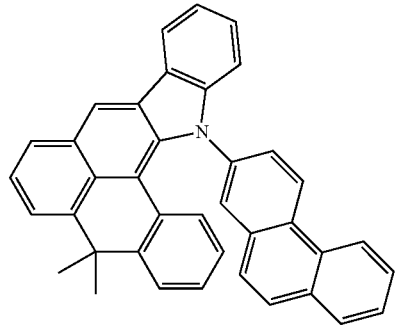
2-2-18
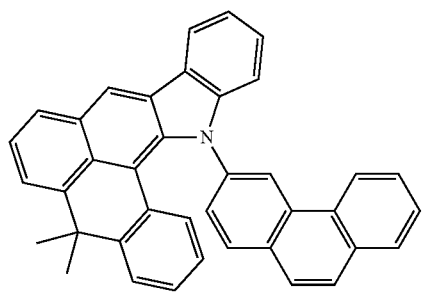
2-2-19
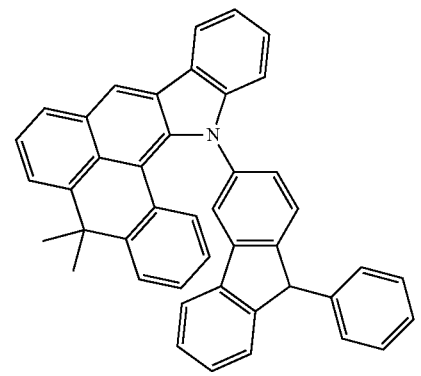
2-2-20
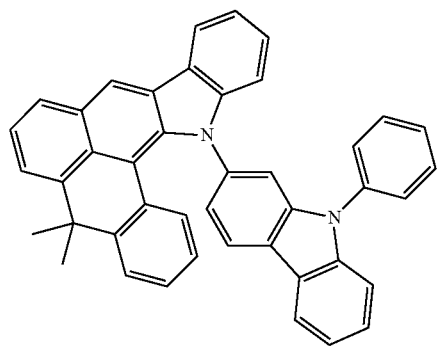
2-2-21
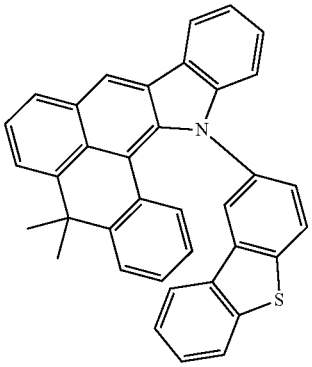
2-2-22
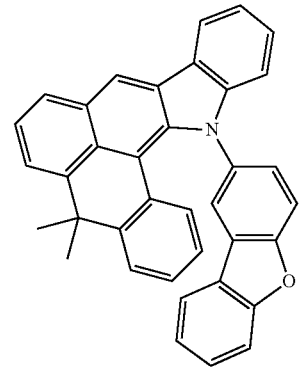
2-2-23
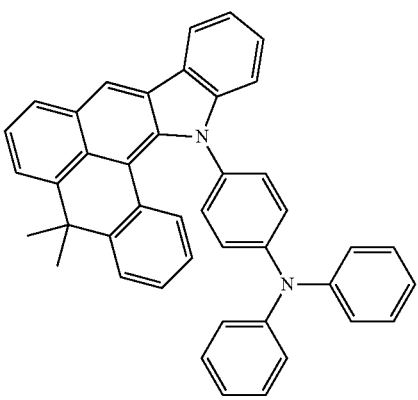
2-2-24
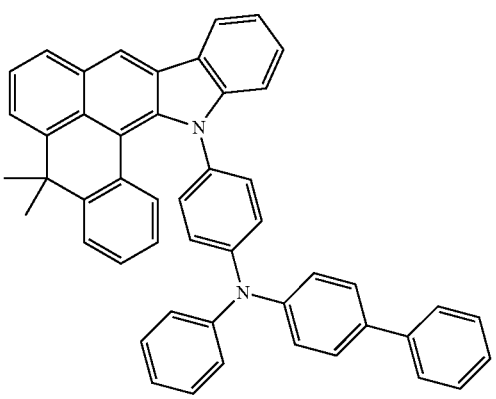

2-2-25
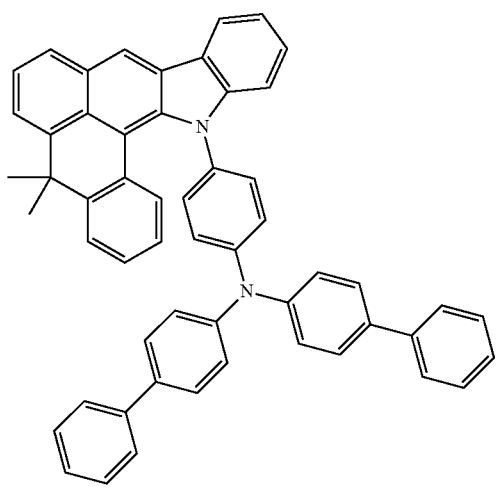
2-2-26
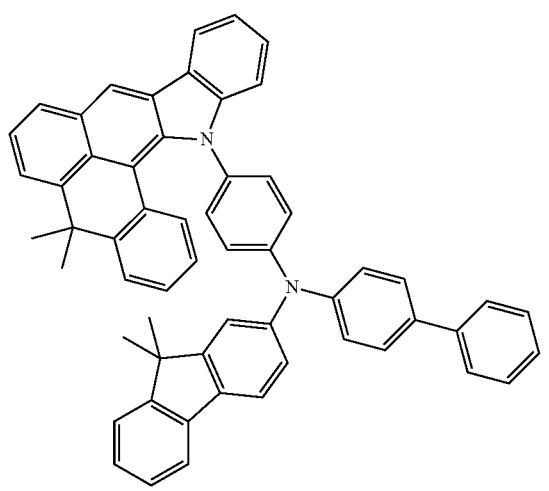
2-2-27
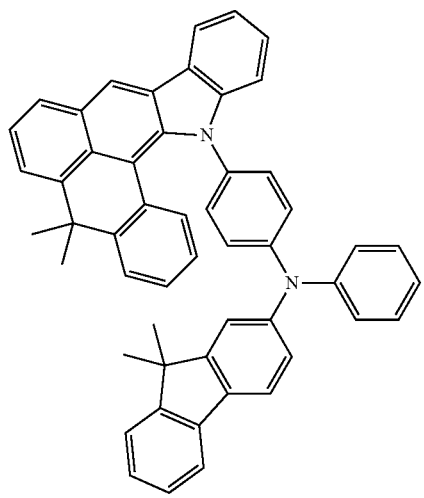
2-2-28
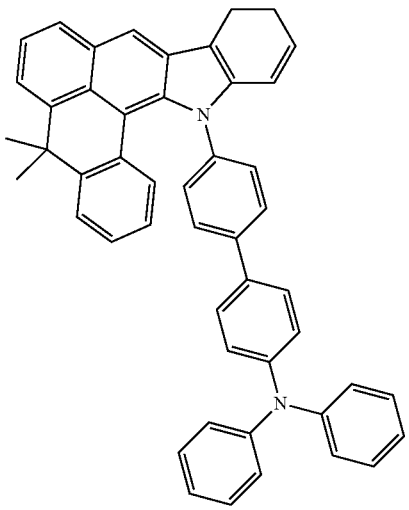
2-2-29
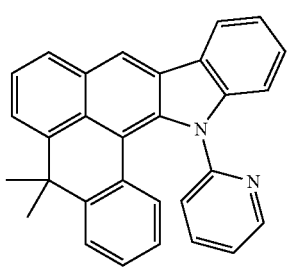
2-2-30
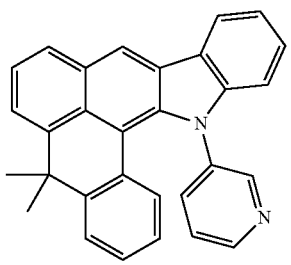
2-2-31
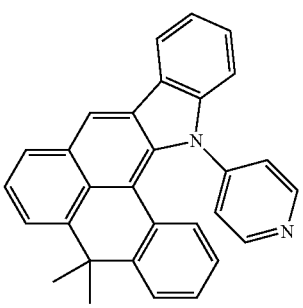

-continued
2-2-32
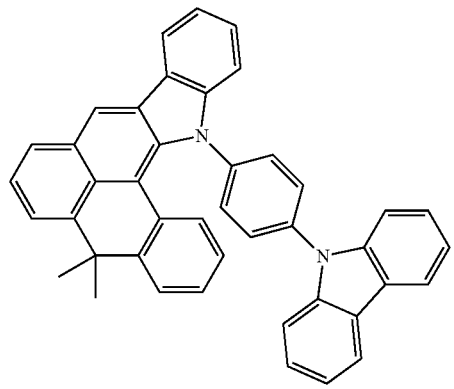
2-2-33
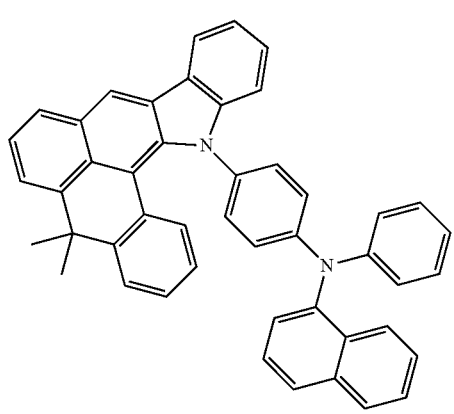
2-2-34
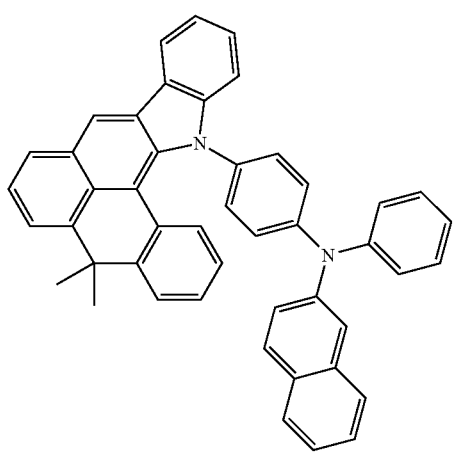
-continued
2-2-35
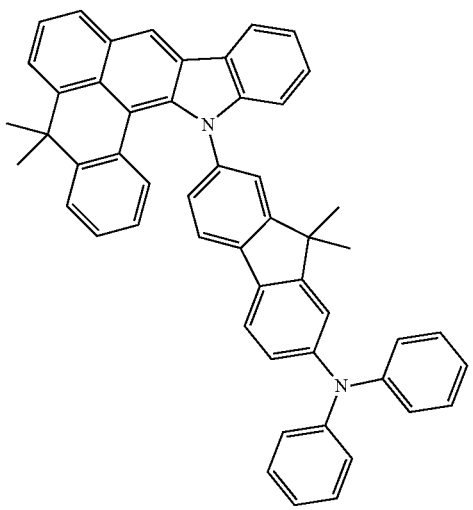
2-2-36
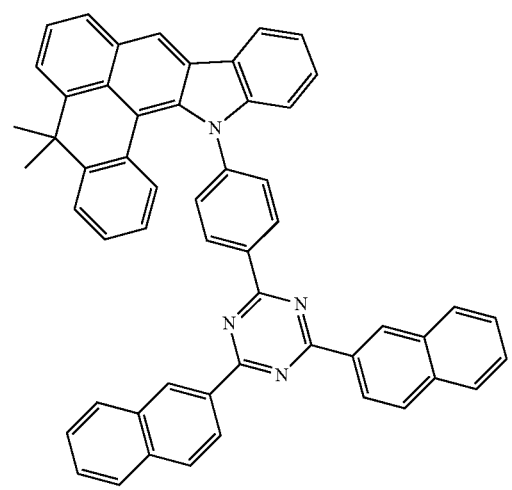
2-2-37
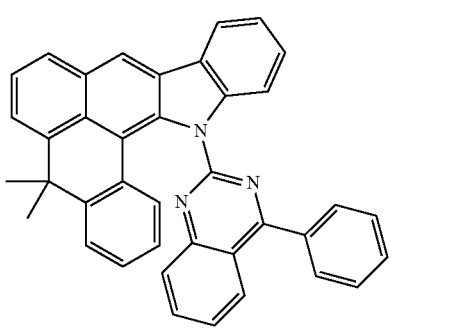
2-2-38
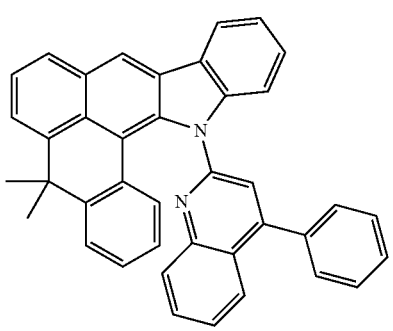

2-2-39
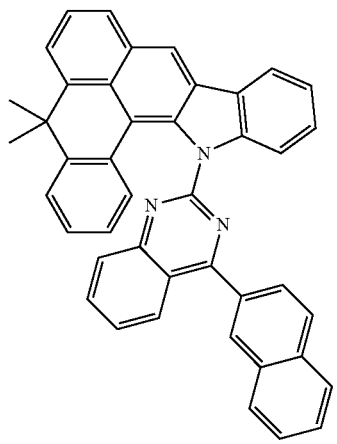
2-2-40
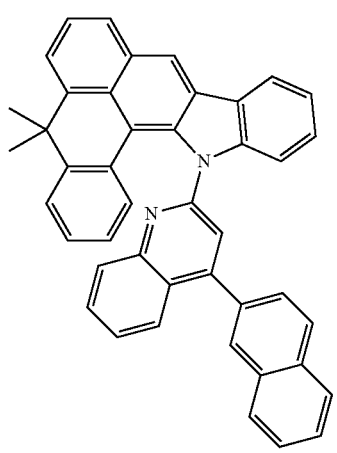
2-2-41
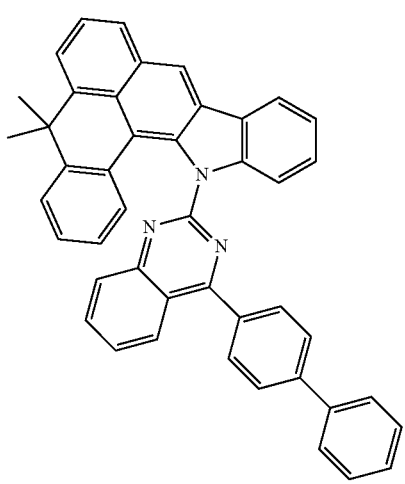
2-2-42
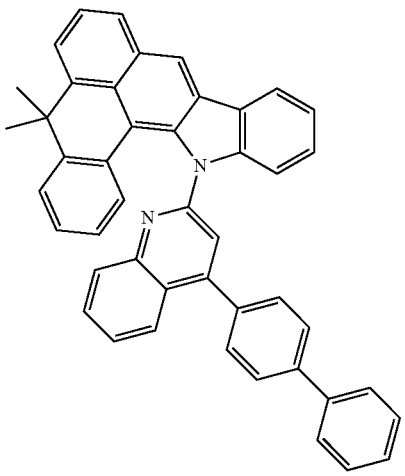
2-2-43
2-2-44
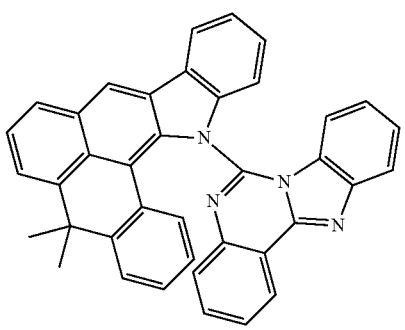

-continued
2-2-45
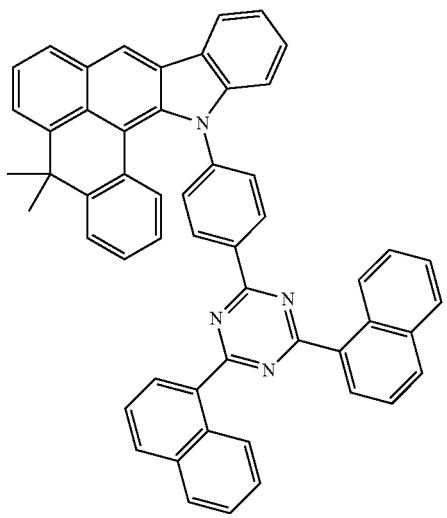
2-2-46
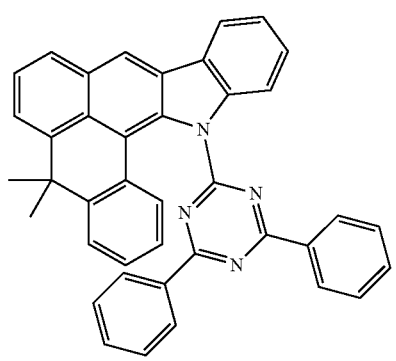
2-2-47
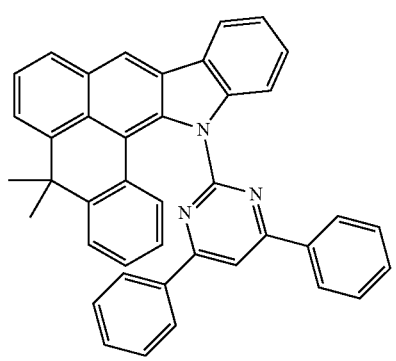
2-2-48
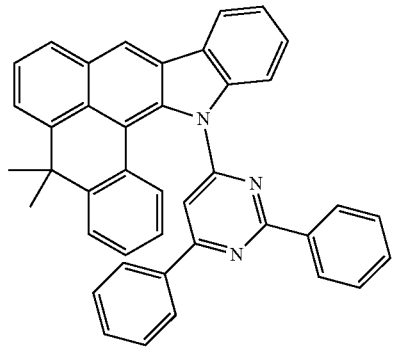
-continued
2-2-49
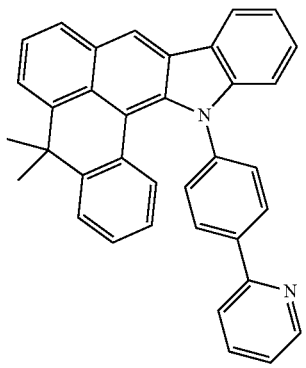
2-2-50
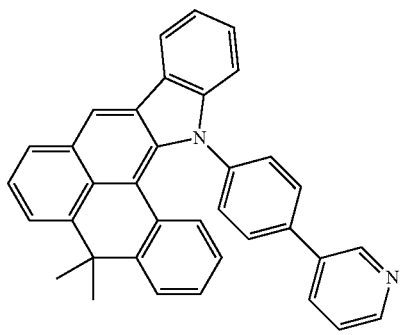
2-2-51
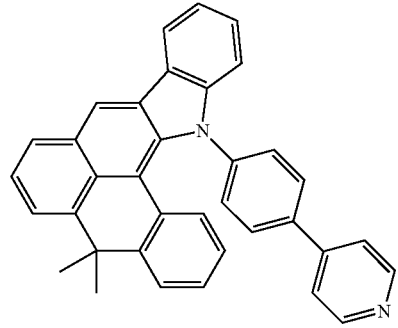
2-2-52
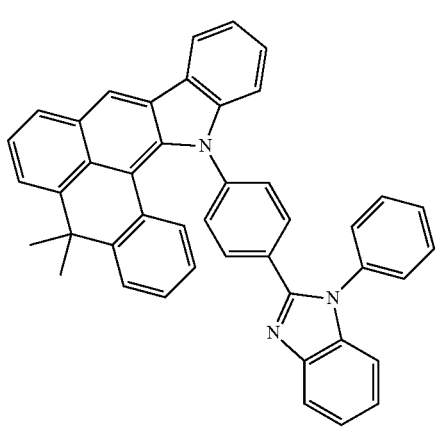

2-2-53
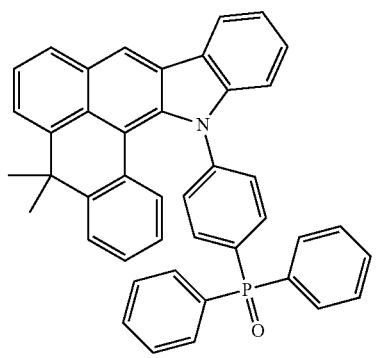
2-2-54
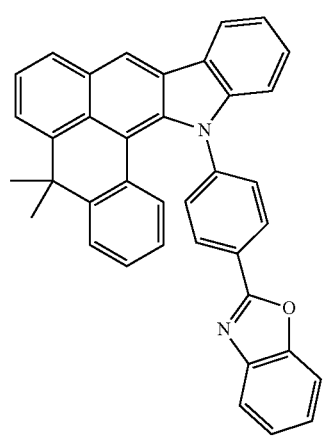
2-2-55
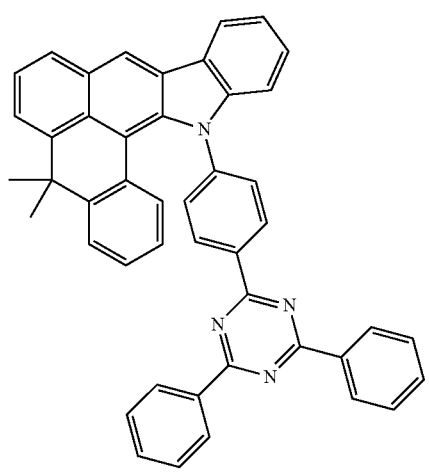
2-2-56
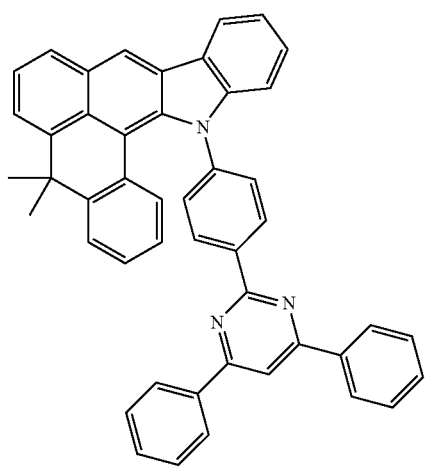
2-2-57
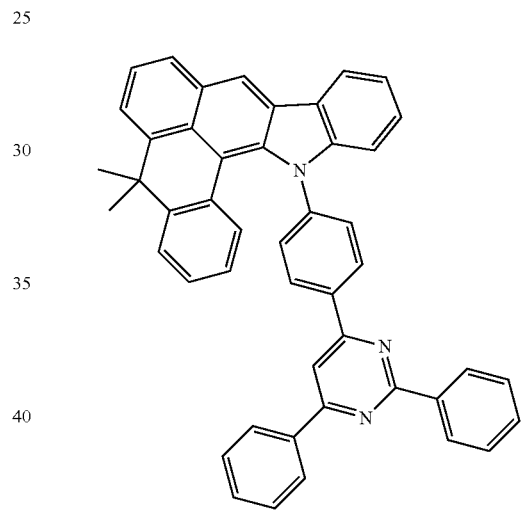
2-2-58
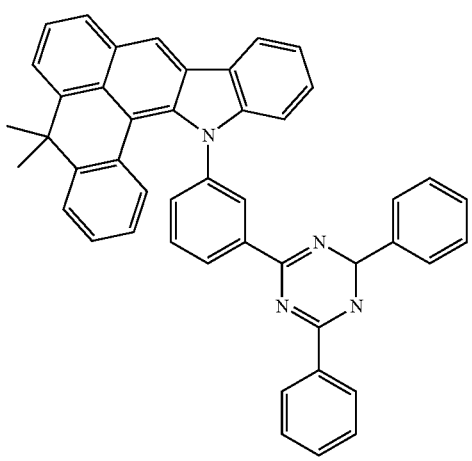

2-2-59
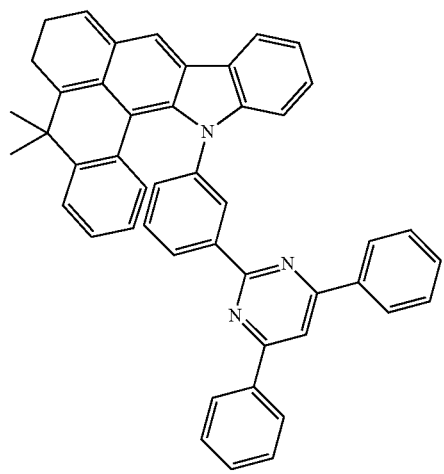
2-2-60
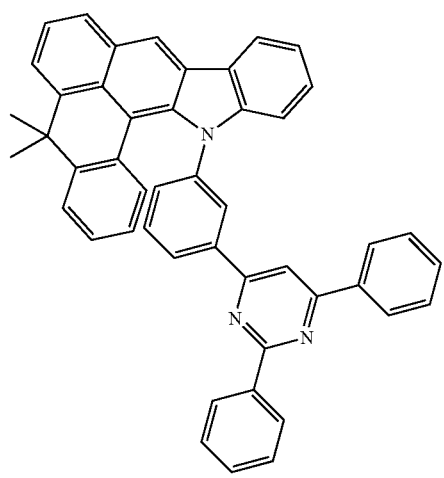
2-2-61
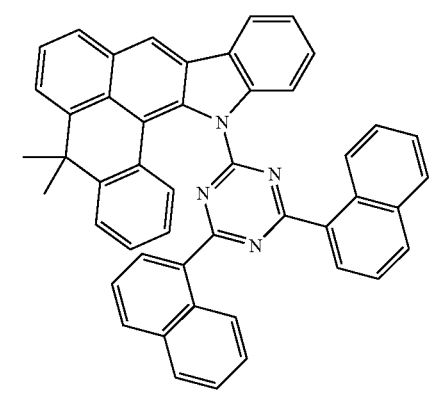
2-2-62
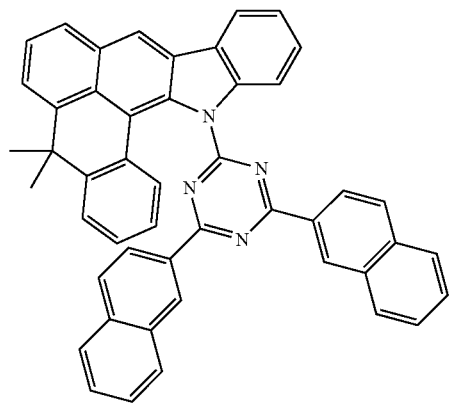
2-2-63
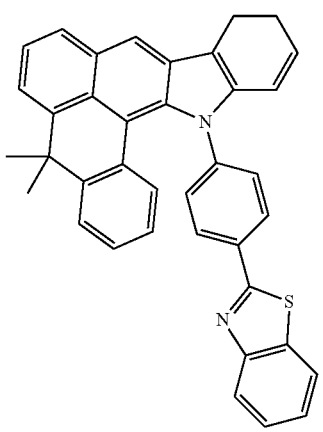
2-2-64
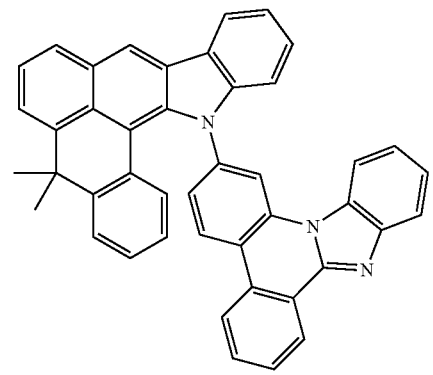
2-2-65
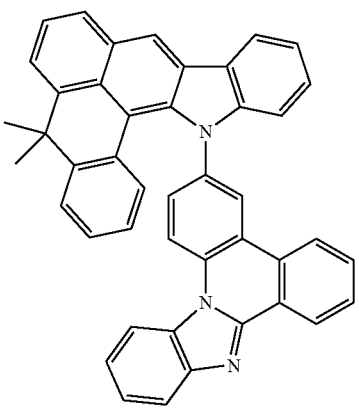

2-2-66 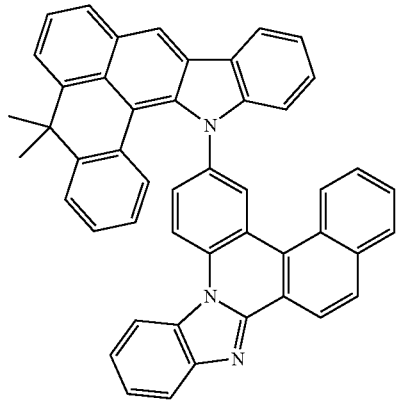
2-2-69 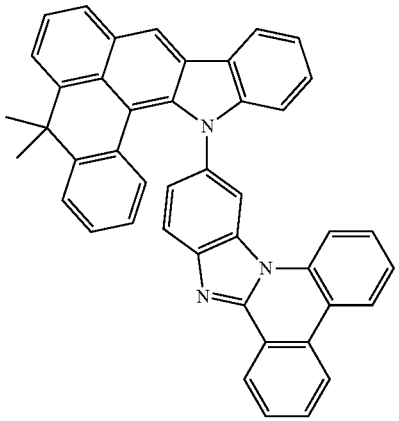
2-2-67 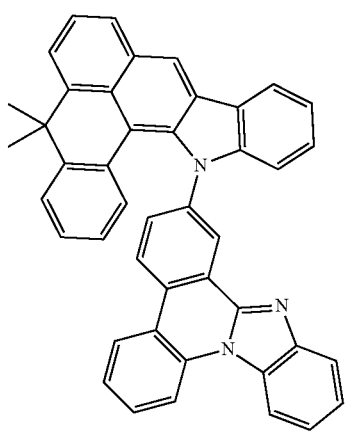
2-2-70 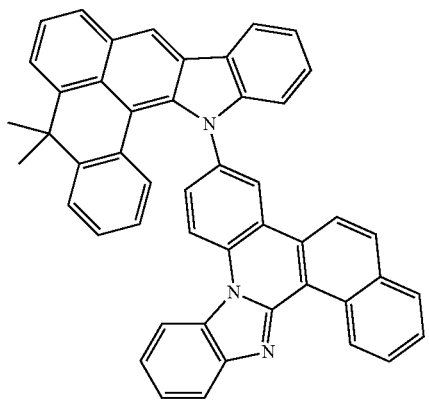
2-2-68 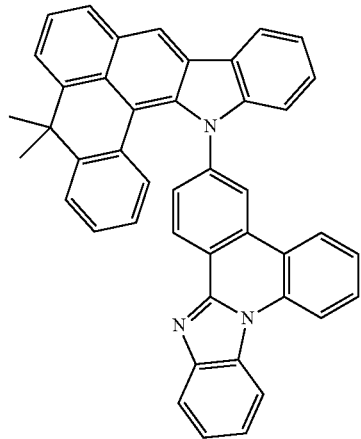
2-2-71 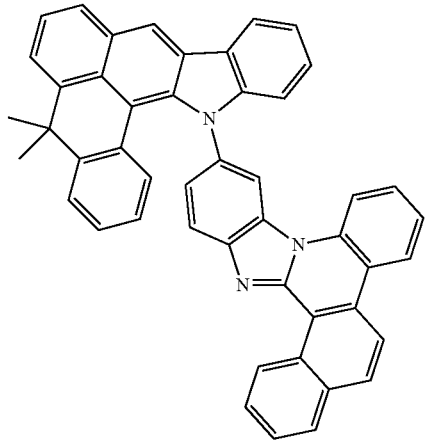

2-2-72
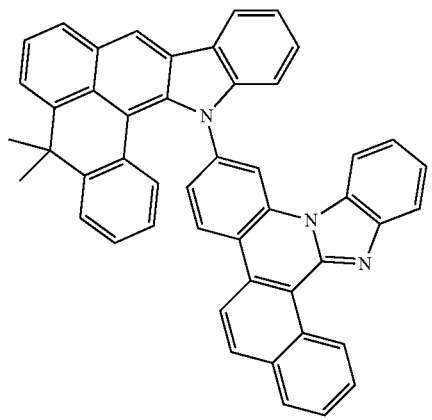
2-2-75
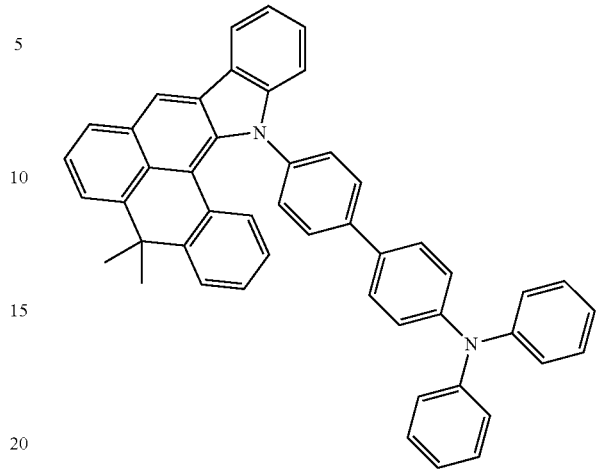
2-2-73
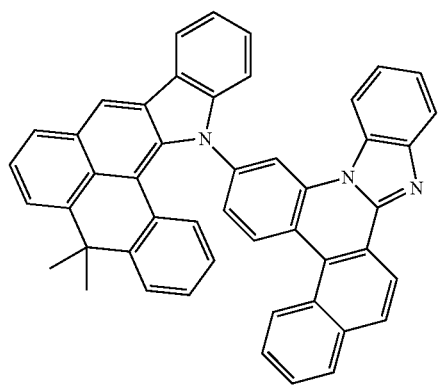
2-2-76
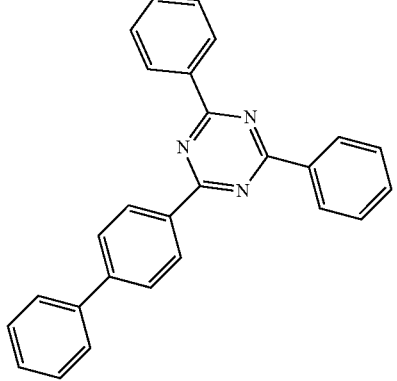
2-2-74
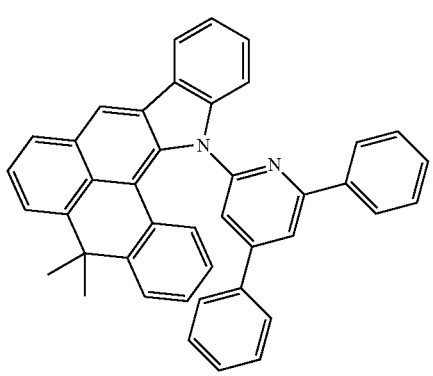

2-2-77
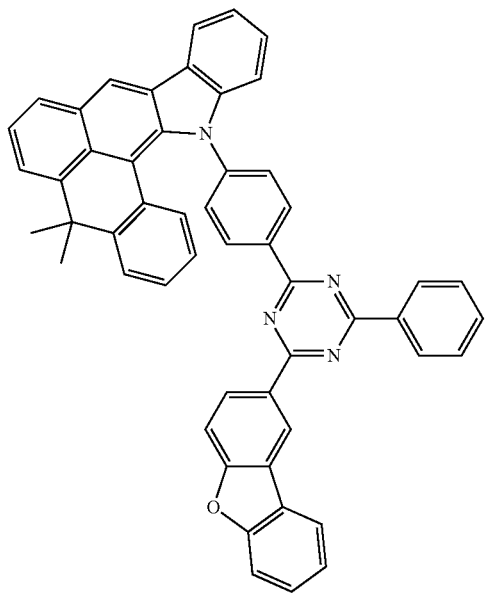
2-2-78
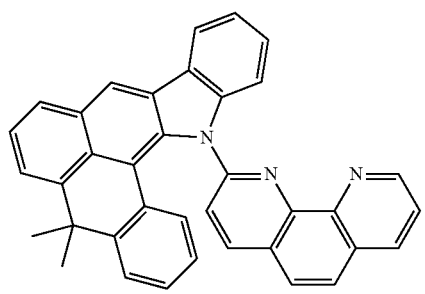
2-2-79
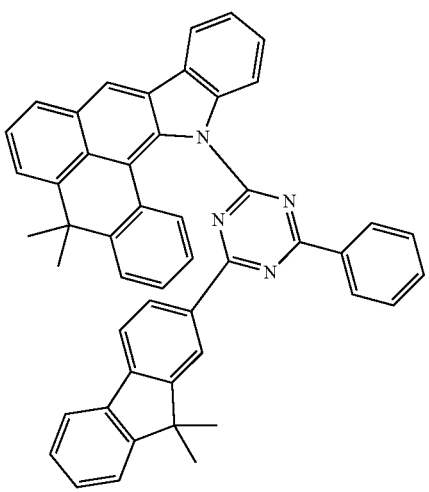
2-2-80
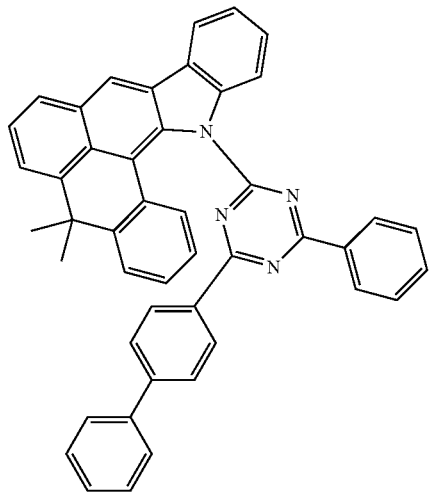
2-2-81
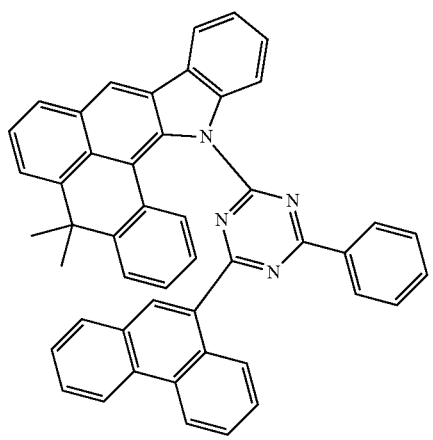
2-2-82
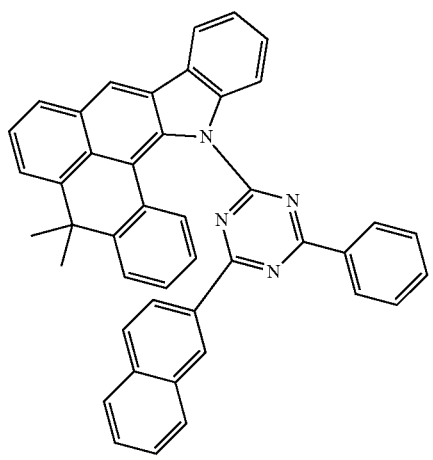

2-2-83
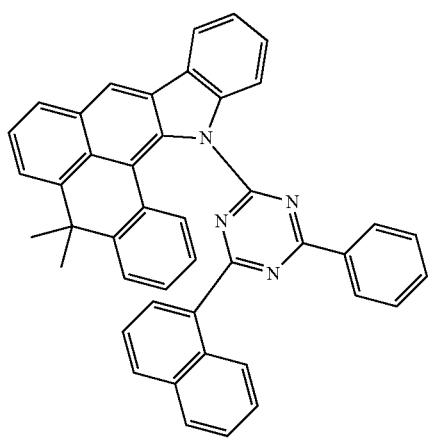
3-1
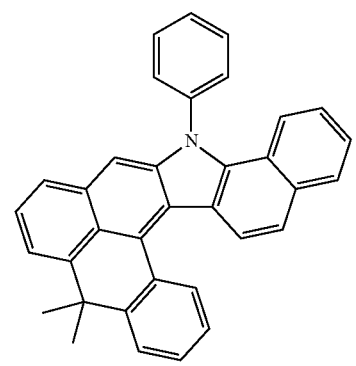
3-2
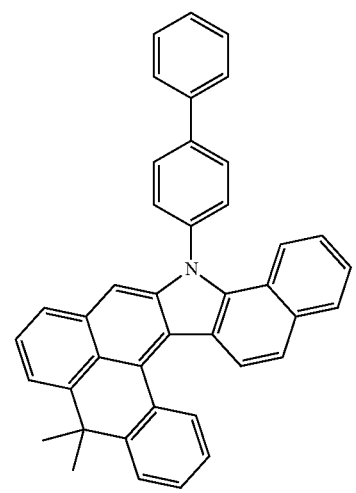
3-3
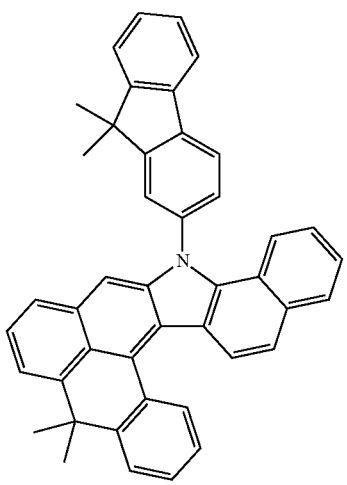
3-4
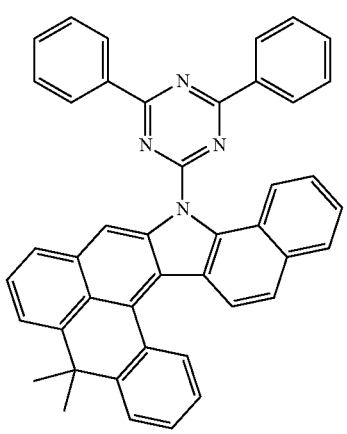
3-5
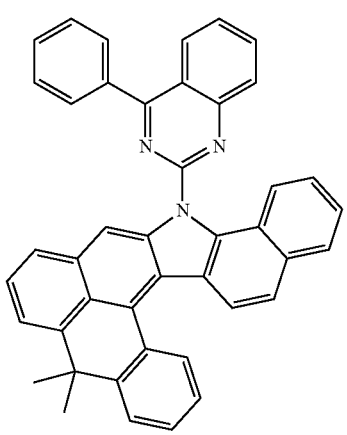

293
-continued
3-6
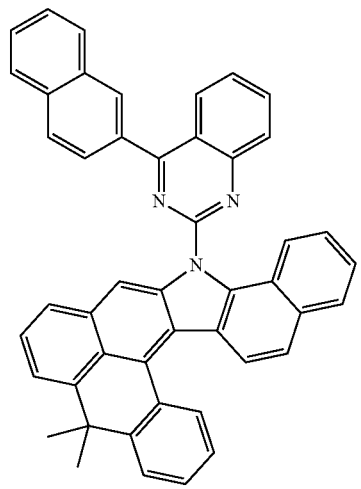
3-7
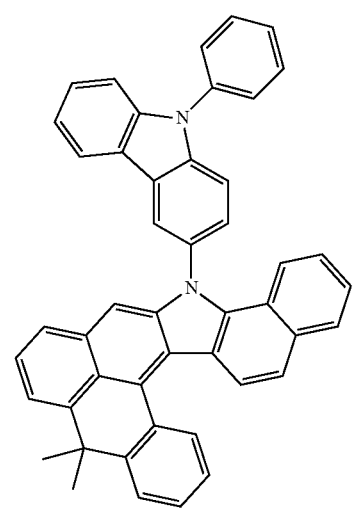
3-8
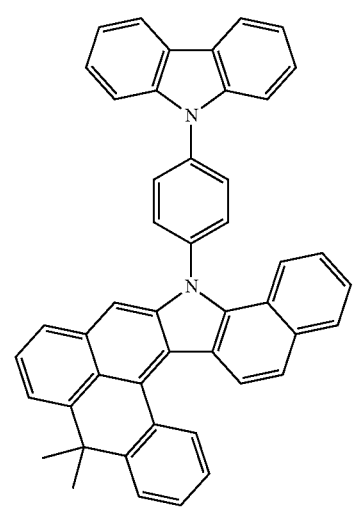
294
-continued
3-9
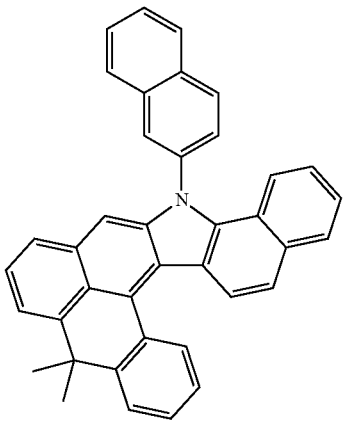
3-10
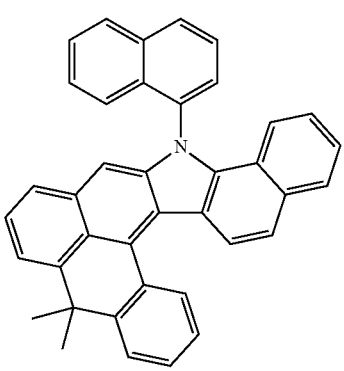
3-11
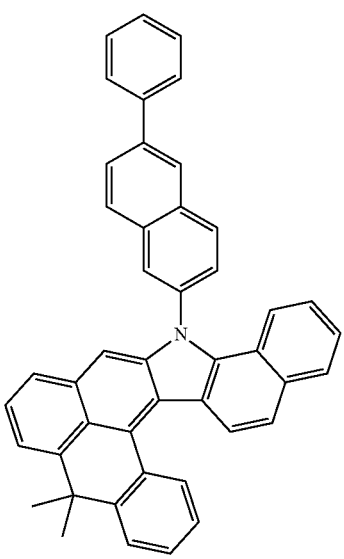

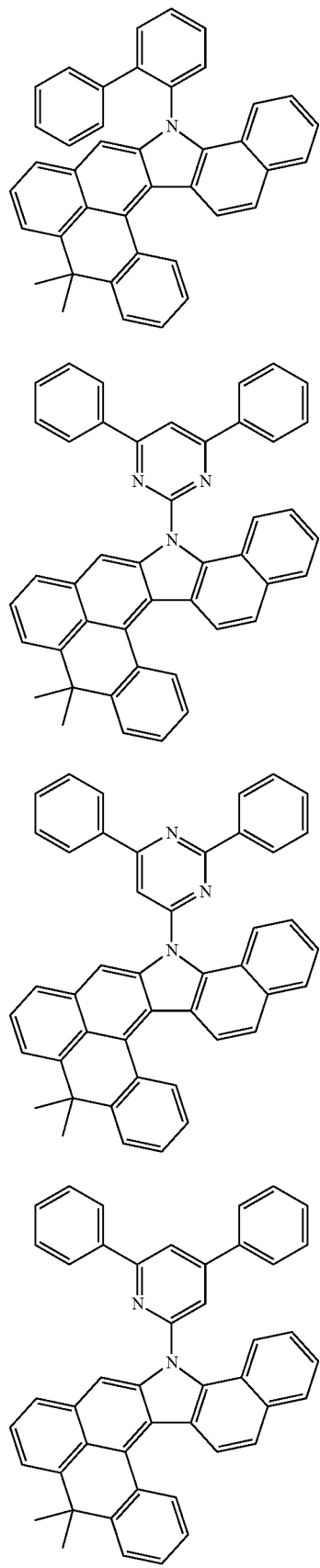
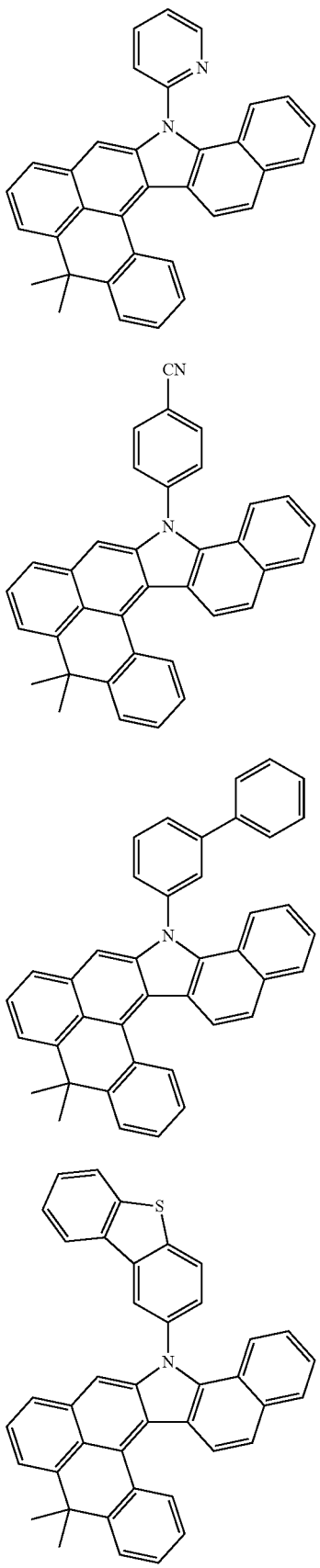

3-20
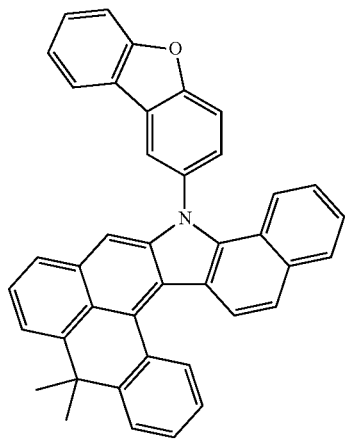
3-21
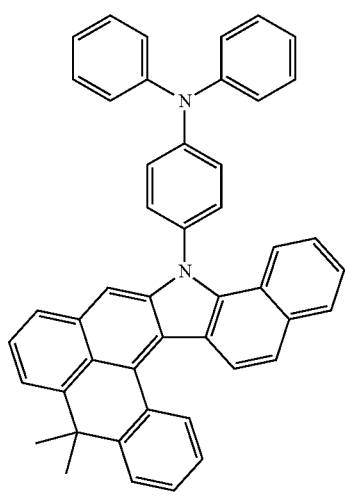
3-22
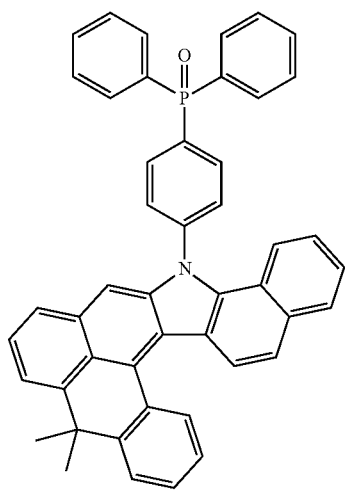
3-23
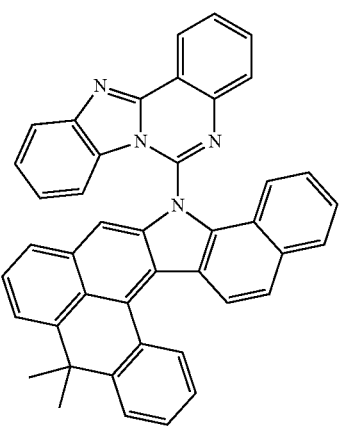
4-1
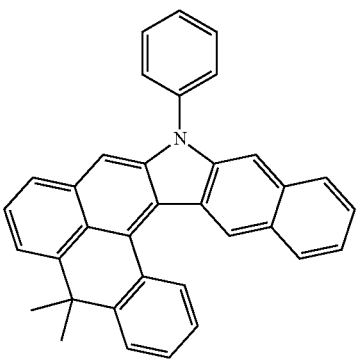
4-2
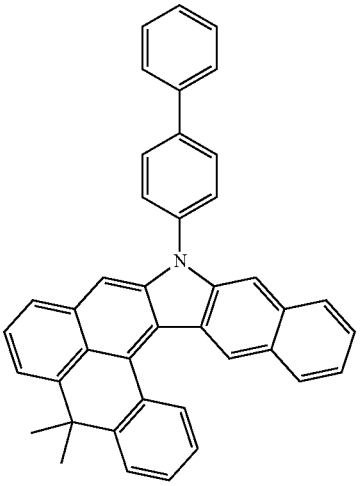

299
-continued
4-3
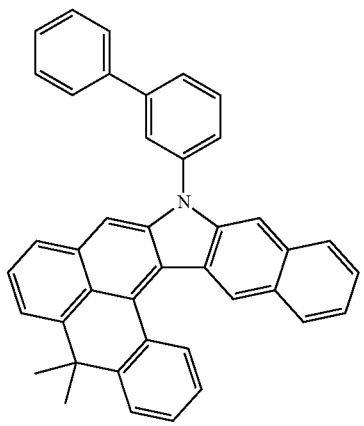
4-4
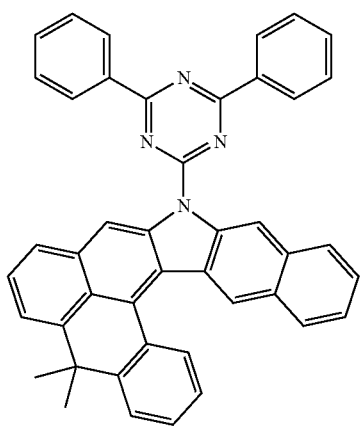
4-5
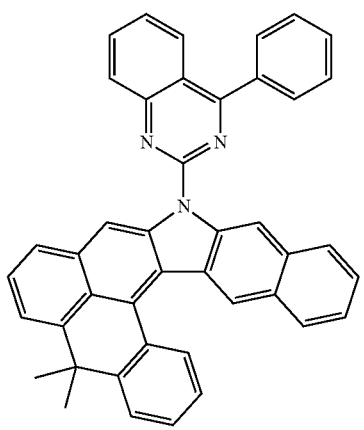
300
-continued
4-6
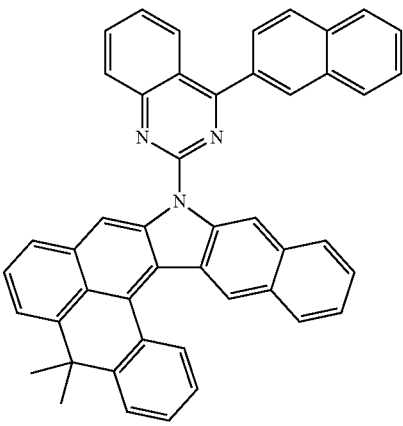
4-7
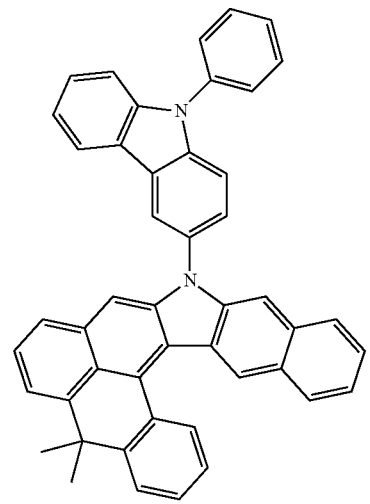
4-8
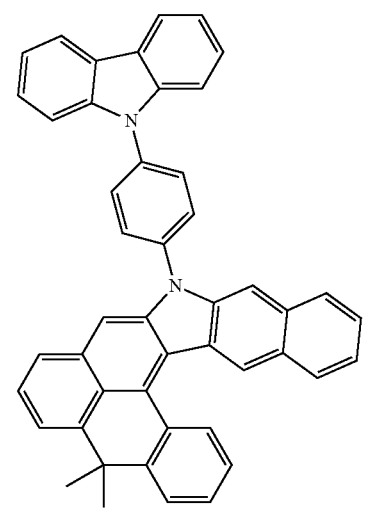

301
-continued
4-9
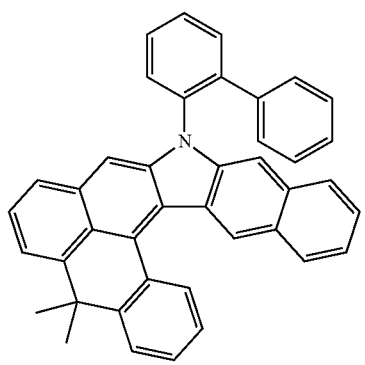
4-10
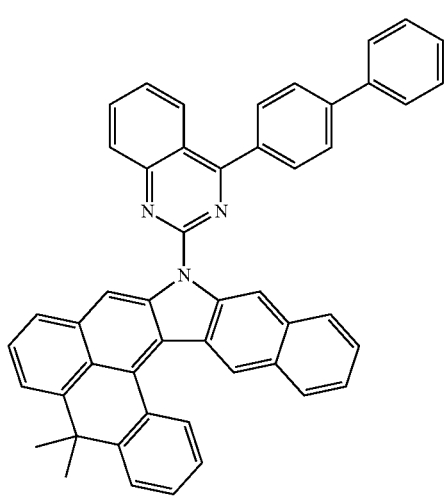
4-11
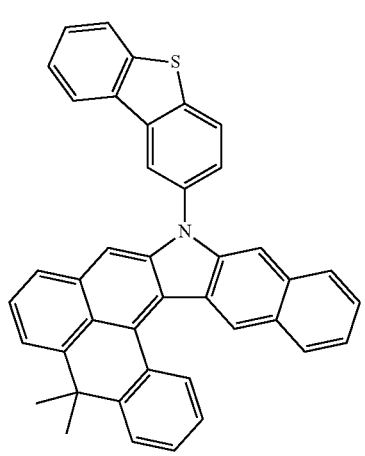
302
-continued
4-12
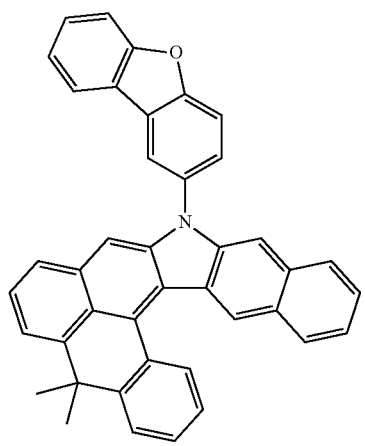
4-13
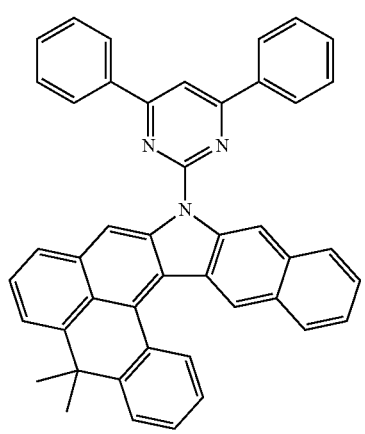
4-14
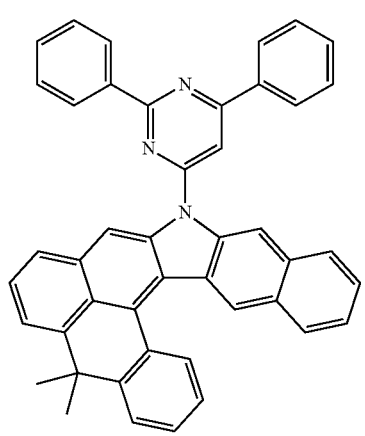

303
-continued
304
-continued
4-15
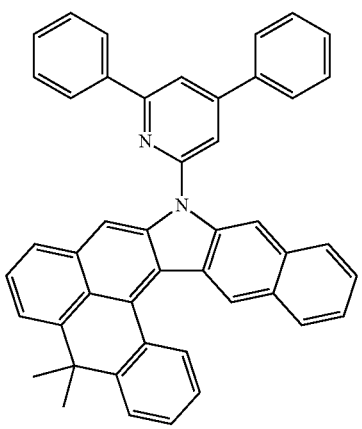
4-16
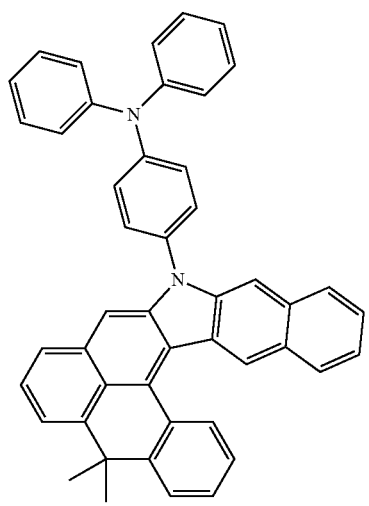
4-17
5-1
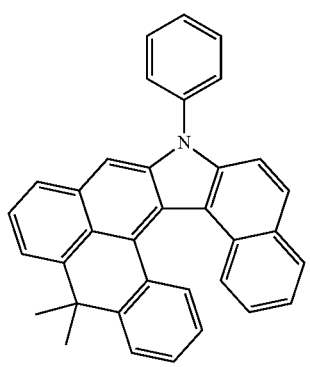
5-2
5-3
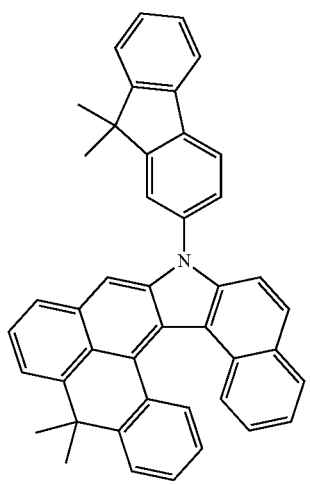

305
-continued
5-4
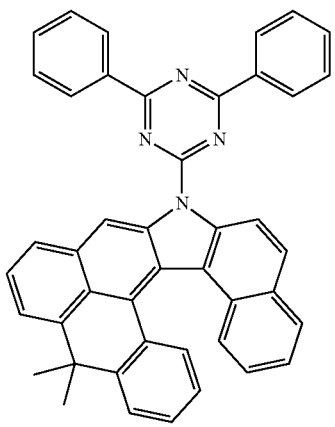
5-5
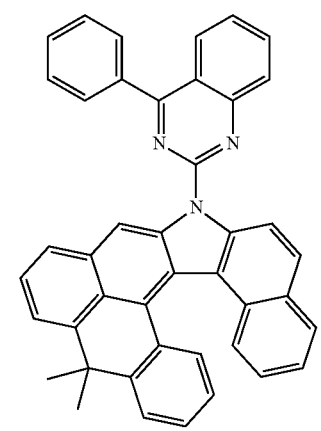
5-6
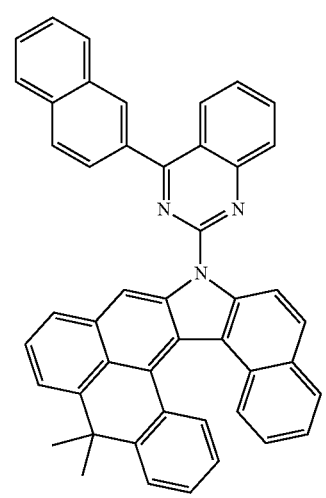
306
-continued
5-7
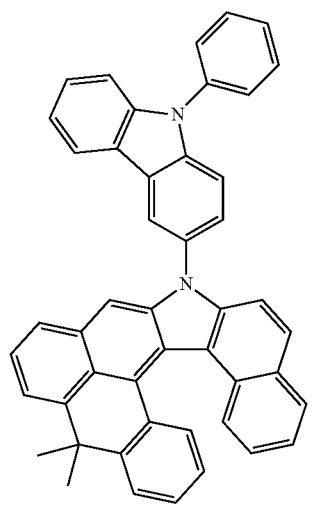
5-8
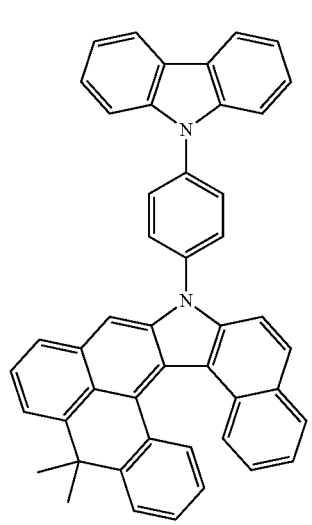
5-9
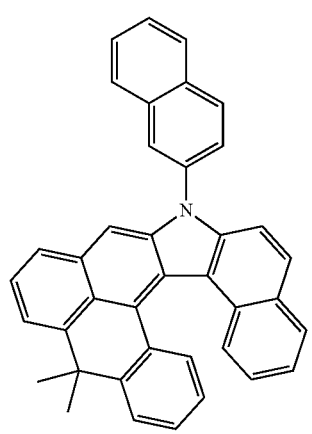

5-10
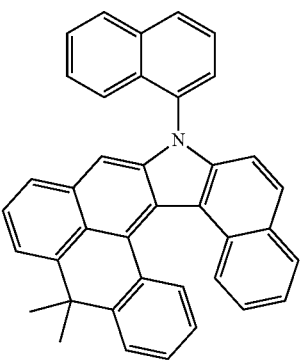
5-11
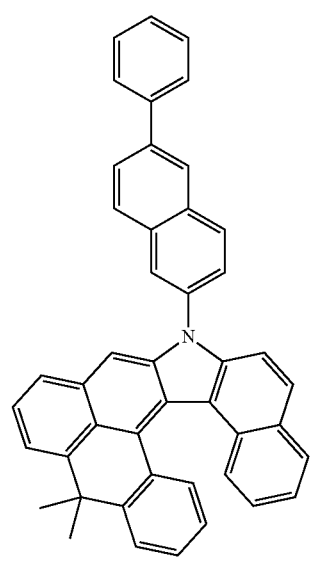
5-12
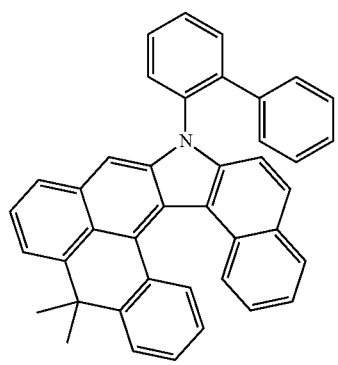
5-13
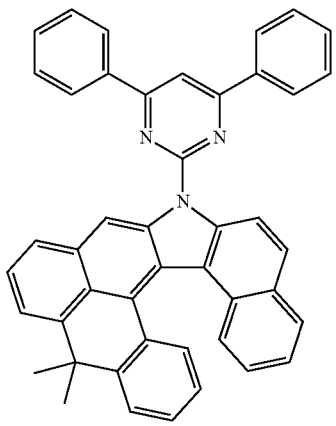
5-14
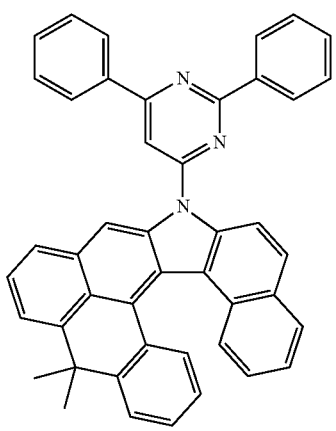
5-15
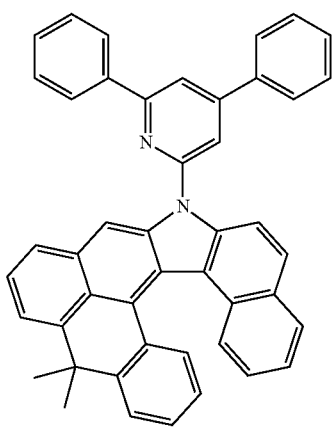
5-16
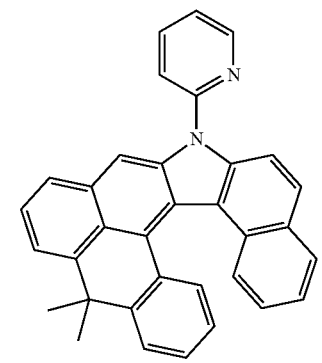

-continued
5-17
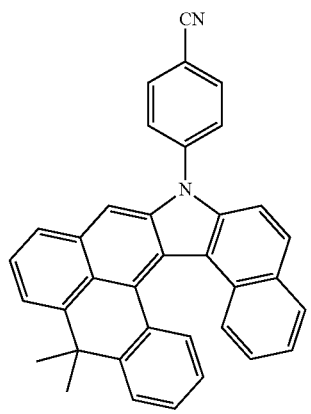
5-18
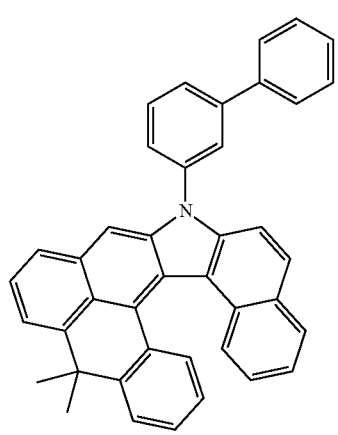
5-19
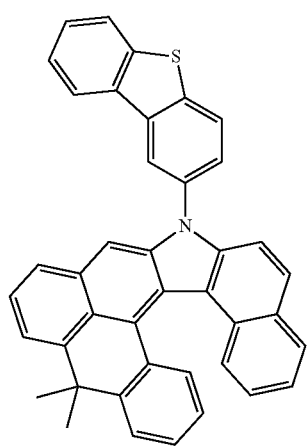
-continued
5-20
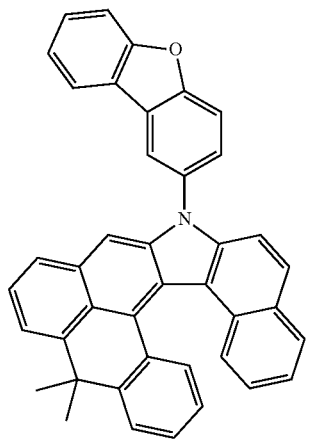
5-21
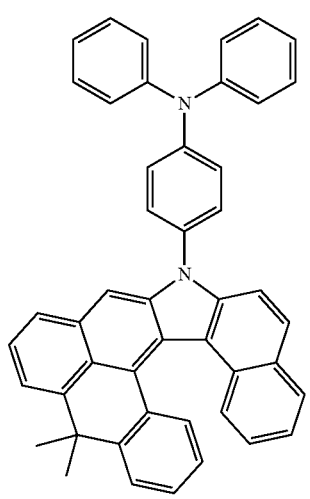
5-22
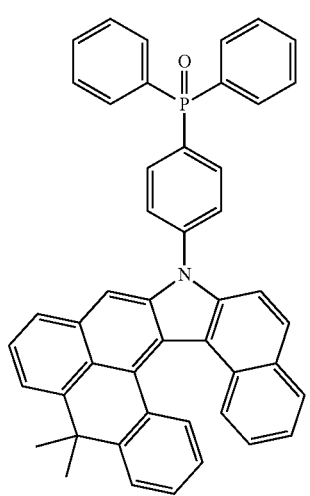

311
-continued
5-23
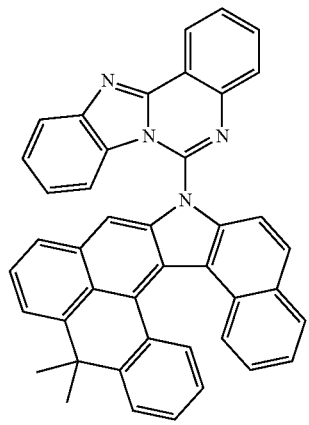
6-1
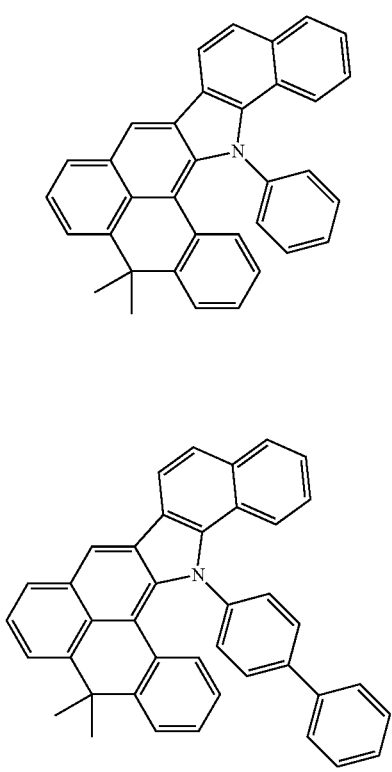
6-2
6-3
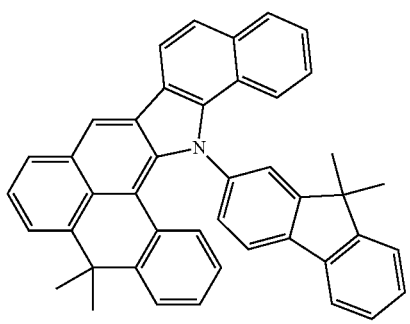
312
-continued
6-4
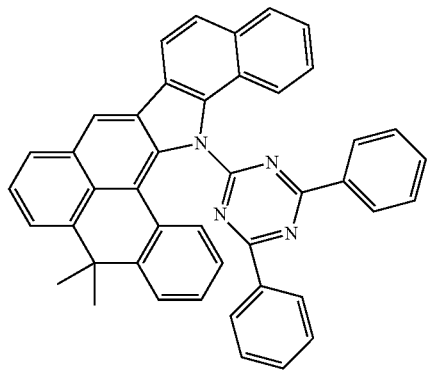
6-5
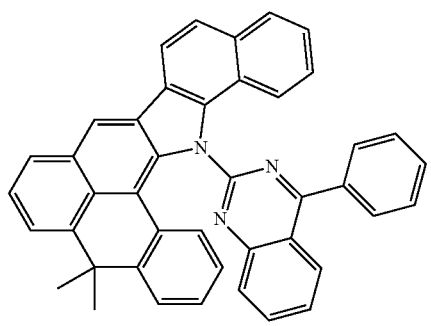
6-6
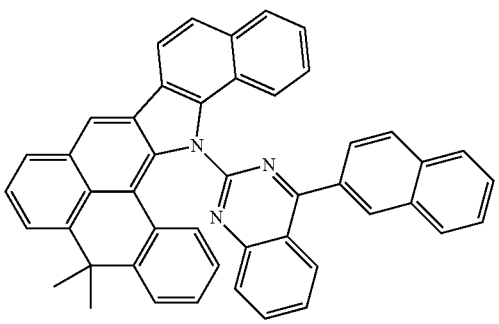
6-7
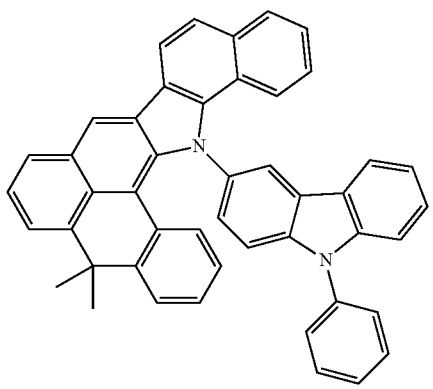

313
-continued
6-8
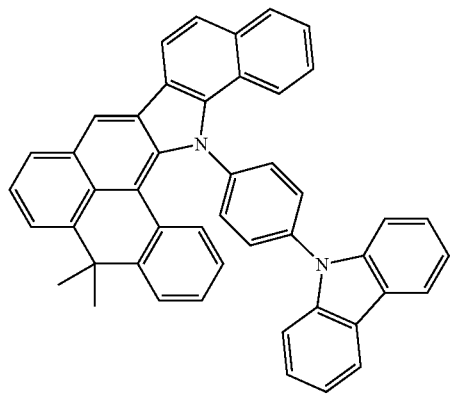
6-9
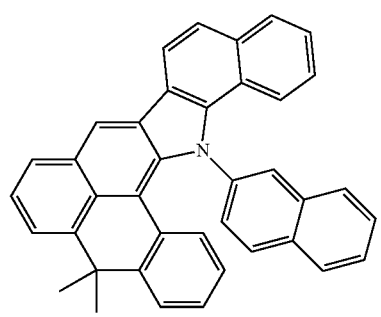
6-10
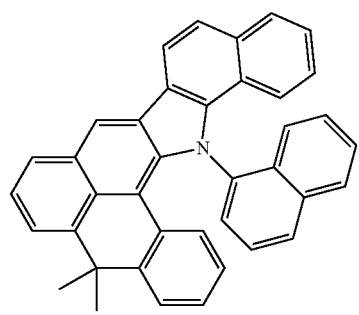
6-11
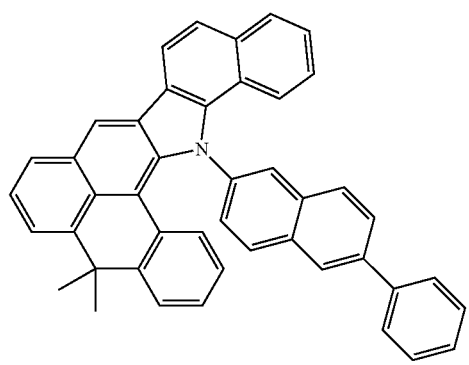
314
-continued
6-12
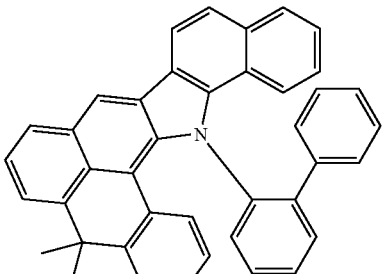
6-13
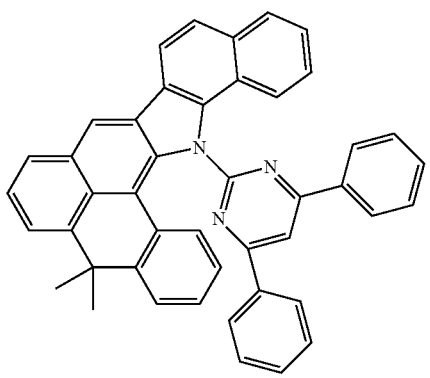
6-14
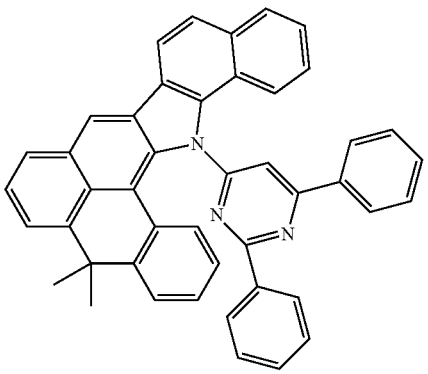
6-15
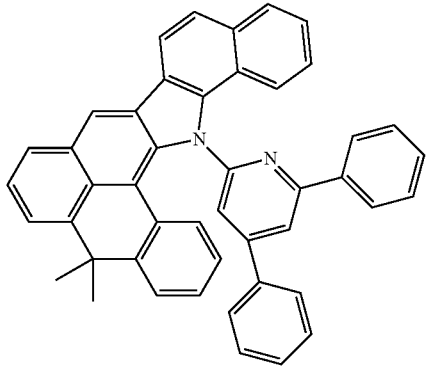

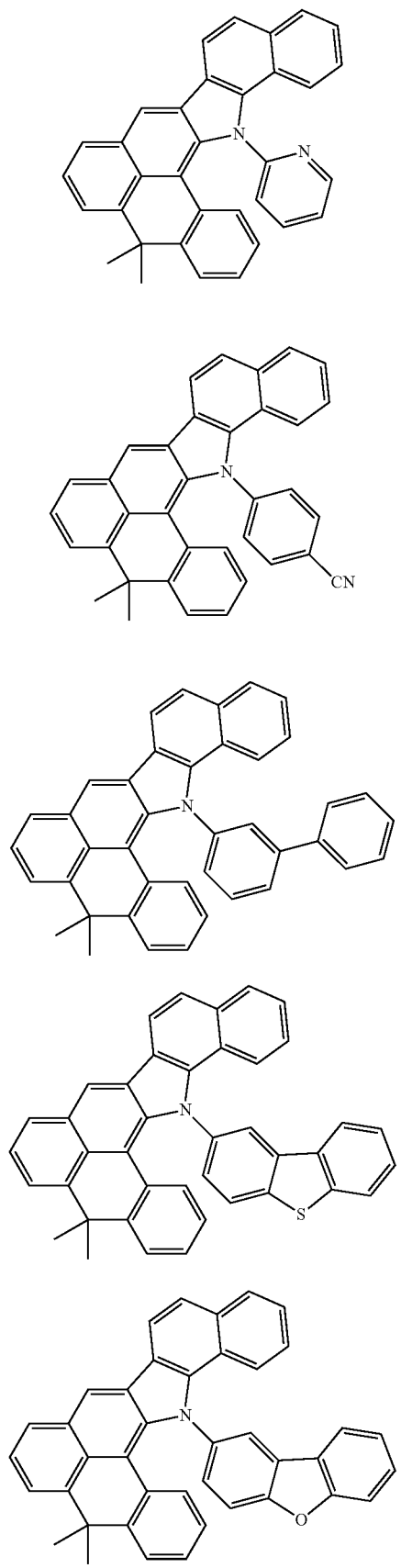
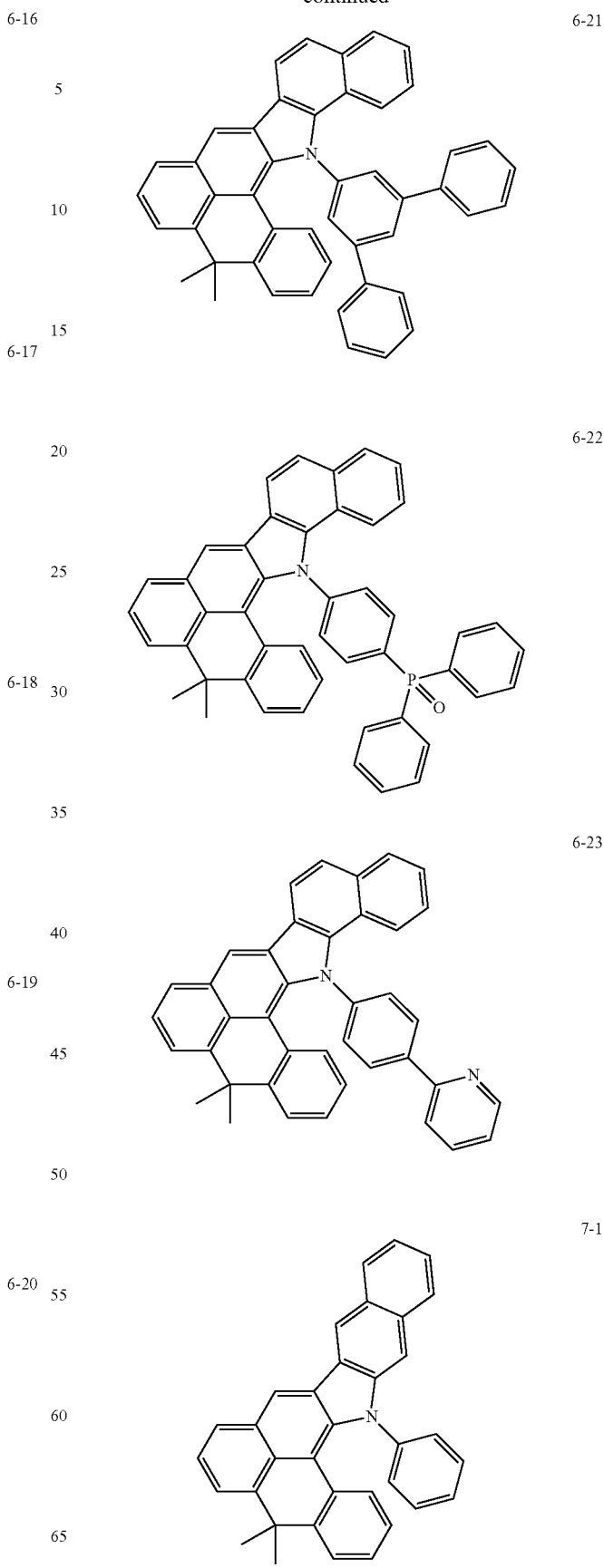

317
-continued
318
-continued
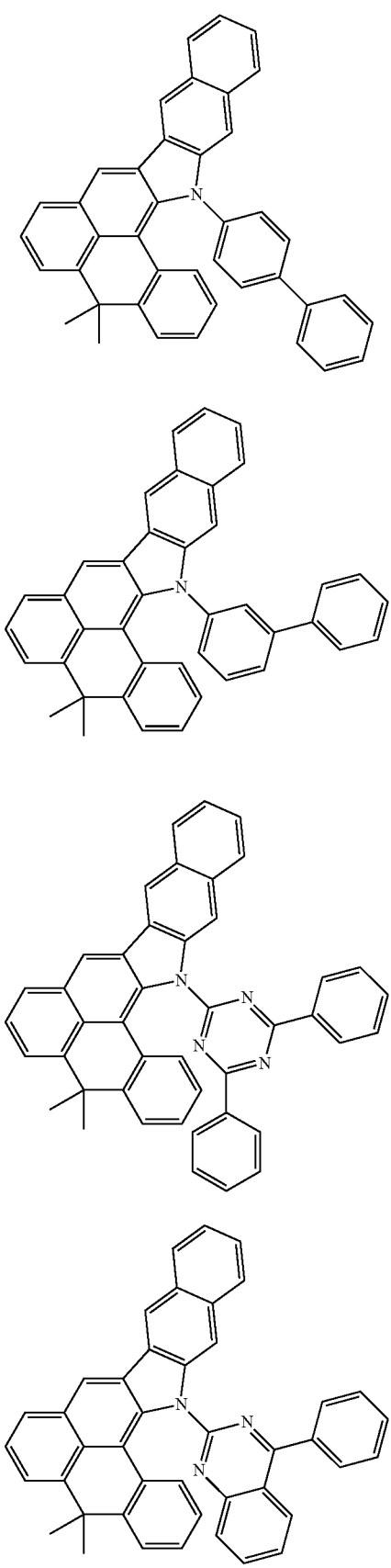
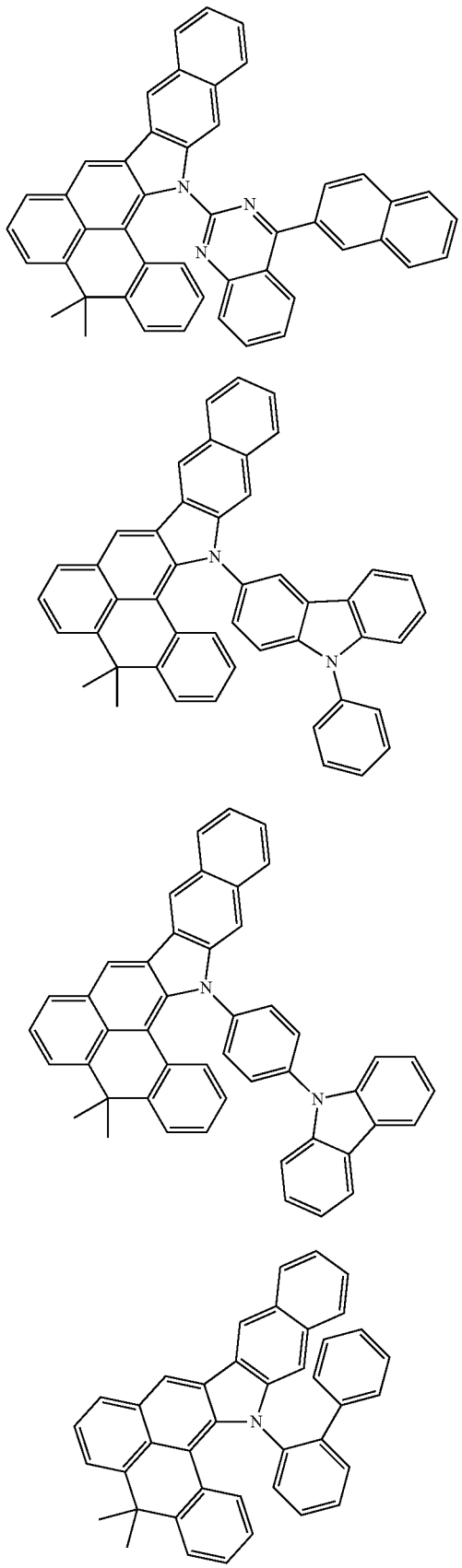

7-10
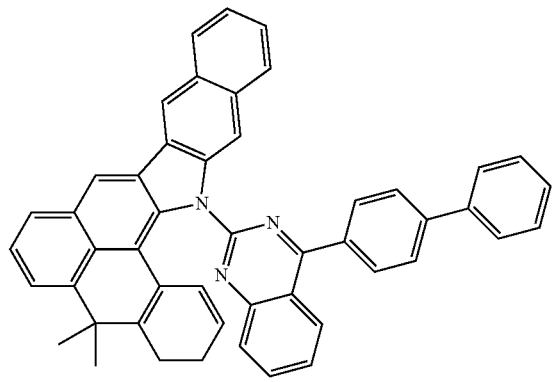
7-11
7-12
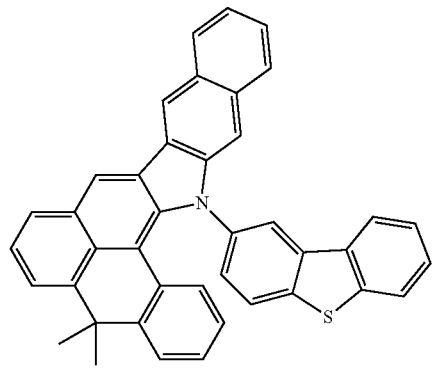
7-13
7-14
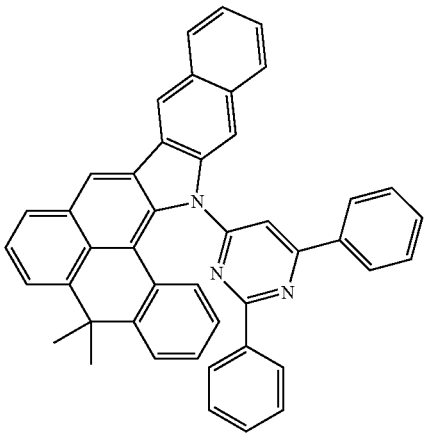
7-15
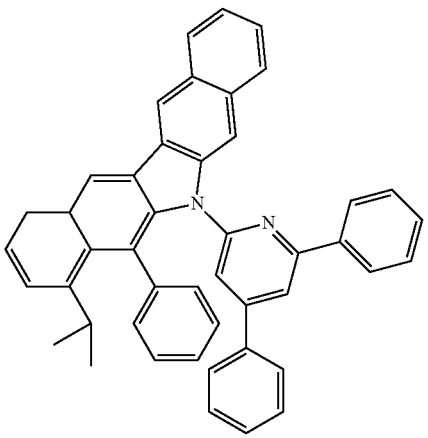
7-16
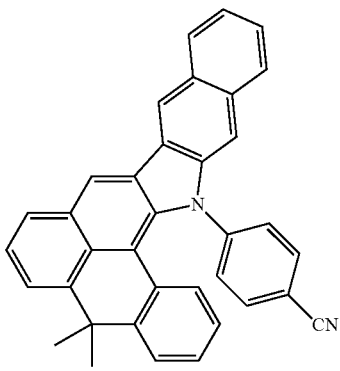

7-17
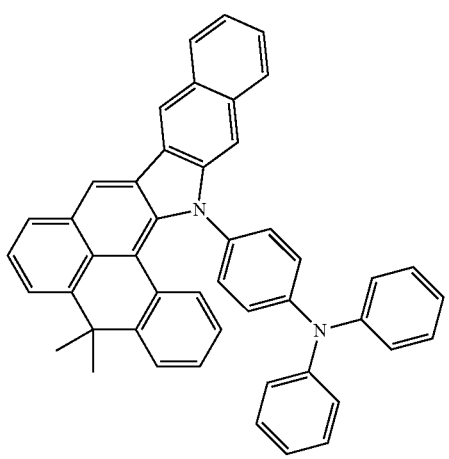
8-1
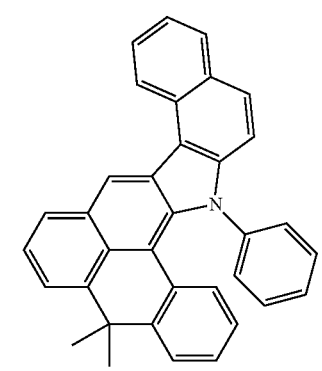
8-2
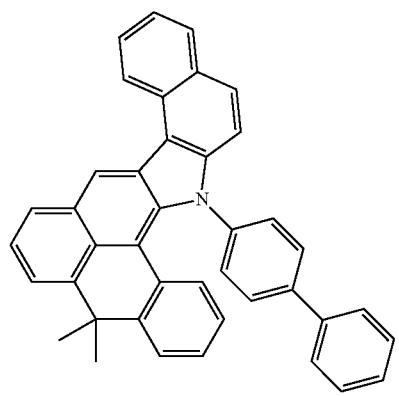
8-3
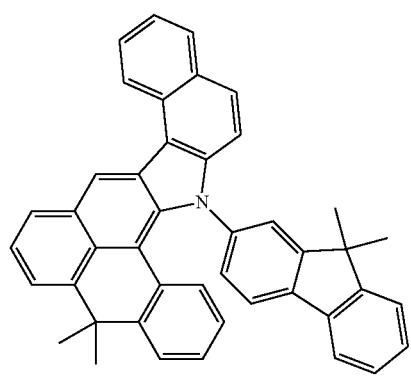
8-4
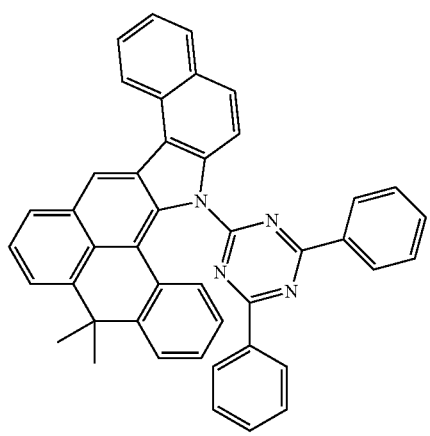
8-5
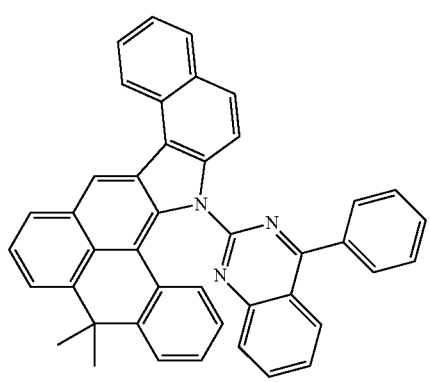
8-6
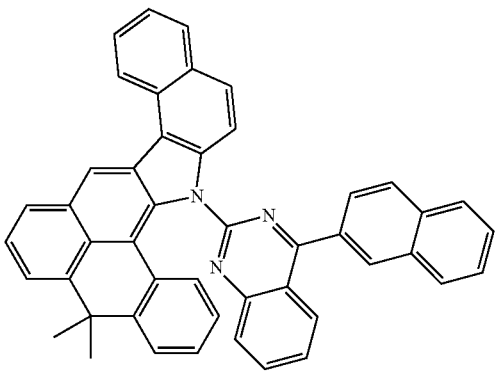
8-7
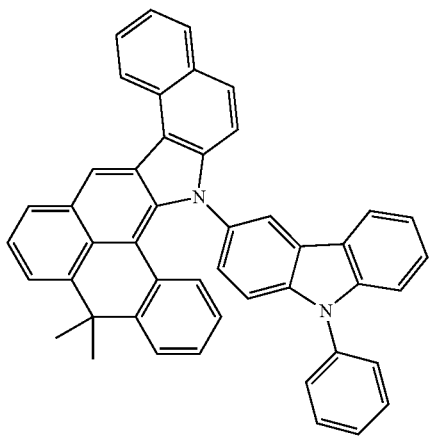

323
-continued
324
-continued
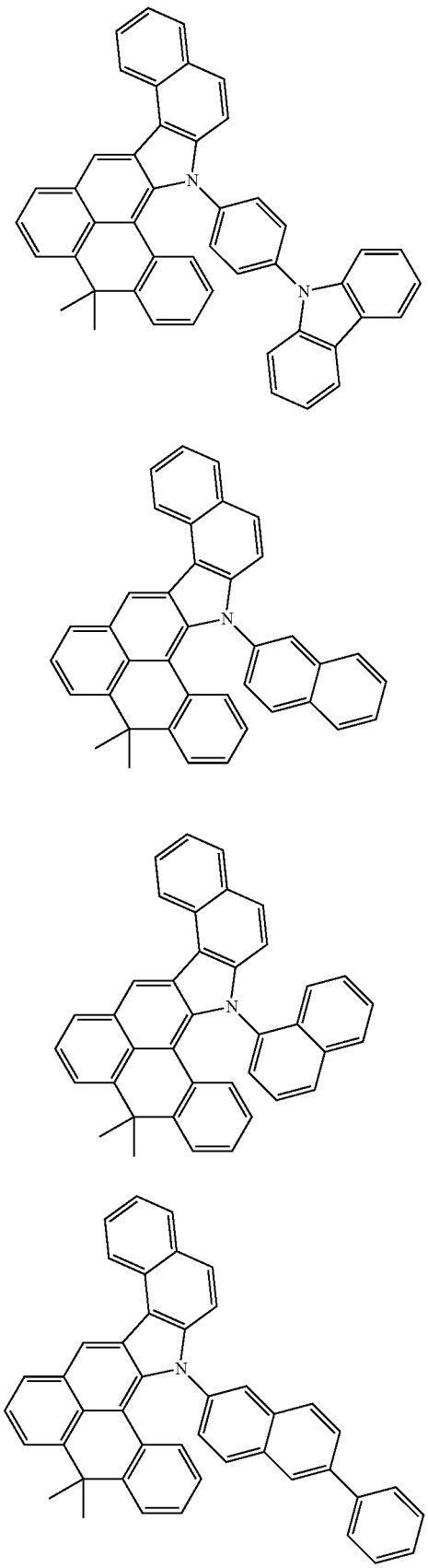
8-8
8-9
8-10
8-11
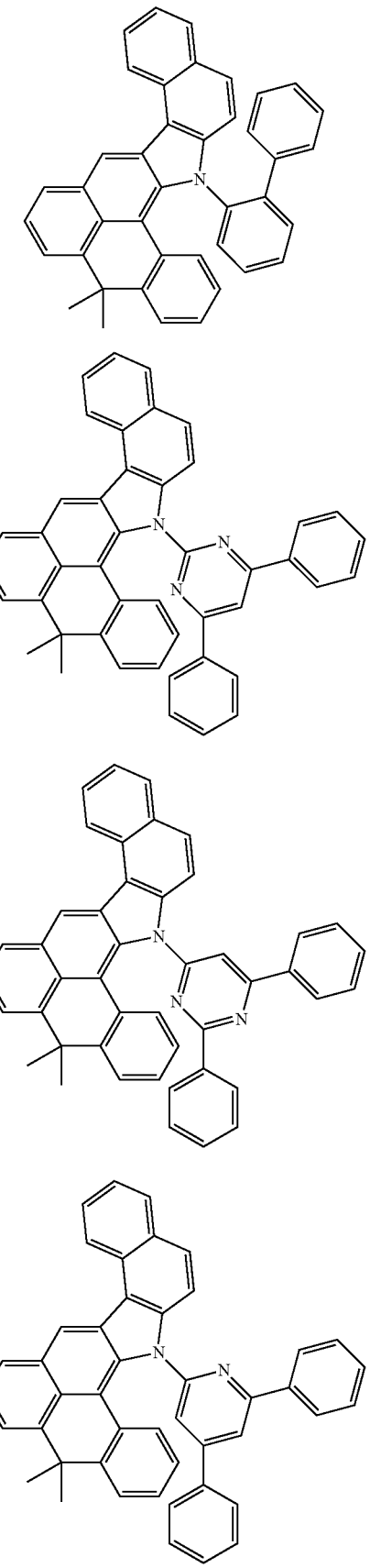
8-12
8-13
8-14
8-15

8-16
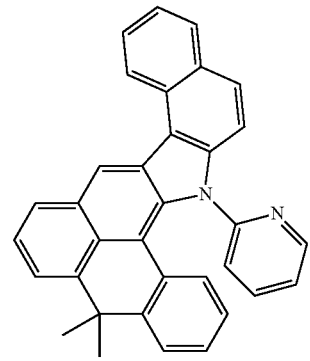
8-17
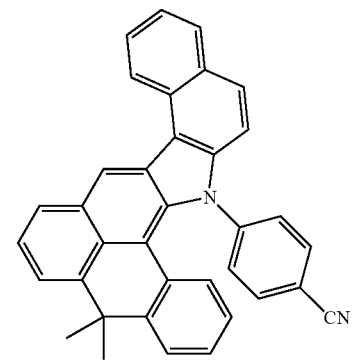
8-18
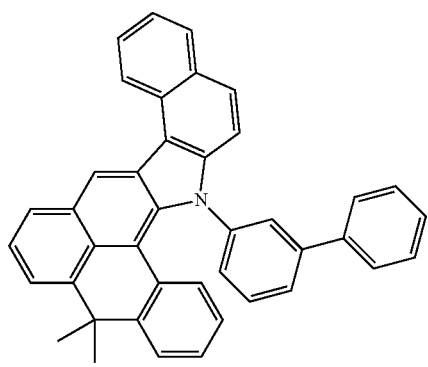
8-19
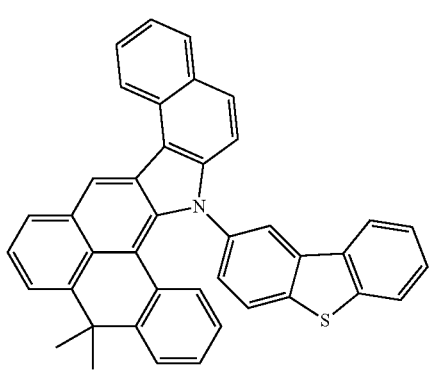
8-20
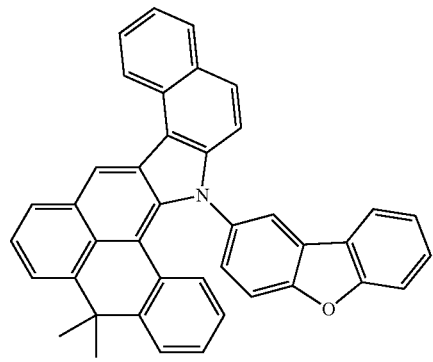
8-21
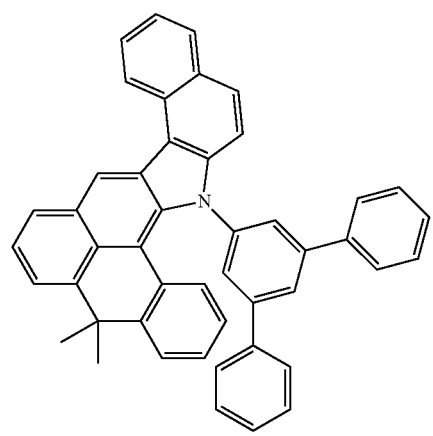
8-22
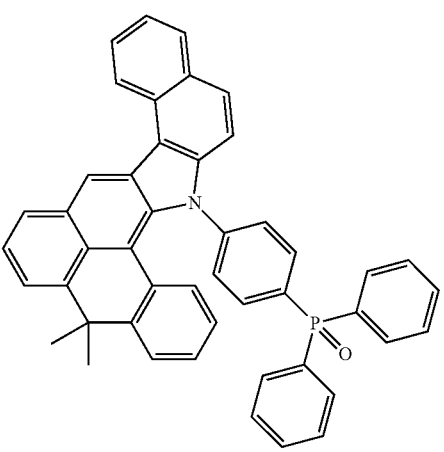
8-23
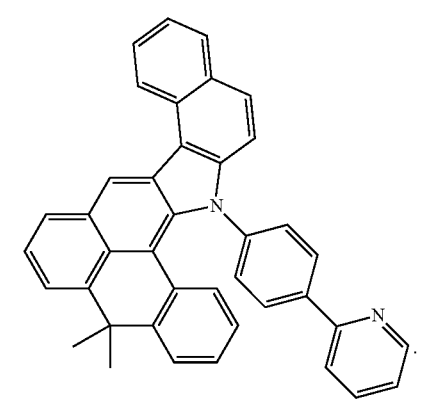

11. An organic light emitting device comprising:
a first electrode;
a second electrode; and
one or more organic material layers disposed between the first electrode and the second electrode,
wherein one or more layers of the organic material layers comprise the compound of Chemical Formula 1 of claim 1.

12. The organic light emitting device of claim 11, wherein the organic material layer comprises at least one of an electron injection layer and an electron transfer layer, and at least one of the electron injection layer and the electron transfer layer comprises the compound of Chemical Formula 1.

13. The organic light emitting device of claim 11, wherein the organic material layer comprises a light emitting layer, and the light emitting layer comprises the compound of Chemical Formula 1 as a host of a light emitting layer.

14. The organic light emitting device of claim 11, wherein the organic material layer comprises an electron blocking layer, and the electron blocking layer comprises the compound of Chemical Formula 1.

15. The organic light emitting device of claim 11, wherein the organic material layer comprises one or more layers of a hole injection layer, a hole transfer layer, and a layer carrying out hole injection and hole transfer at the same time, and one of the layers comprises the compound of Chemical Formula 1.

16. The organic light emitting device of claim 11, wherein the organic material layer comprises the compound represented by Chemical Formula 1 as a host, and comprises other organic compounds, metals or metal compounds as a dopant.

17. The organic light emitting device of claim 11, wherein the organic material layer comprises a light emitting layer comprising a compound of the following Chemical Formula 14:

[Chemical Formula 14]

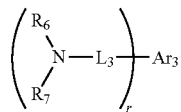

wherein, in Chemical Formula 14,
$Ar_3$ is a benzofluorene skeleton, a fluoranthene skeleton, a pyrene skeleton or a chrysene skeleton;
$L_3$ is a single bond, a $C_6$ to $C_{30}$ arylene group or a $C_5$ to $C_{30}$ divalent heterocyclic group;
$R_6$ and $R_7$ are the same as or different from each other, and each independently selected from the group consisting of a substituted or unsubstituted $C_6$ to $C_{30}$ aryl group, a substituted or unsubstituted $C_5$ to $C_{30}$ heterocyclic group, a substituted or unsubstituted $C_1$ to $C_{30}$ alkyl group, and a substituted or unsubstituted $C_7$ to $C_{30}$ aralkyl group, and $R_6$ and $R_7$ bond to each other to form a saturated or unsaturated ring;
r is an integer of 1 or greater; and
when r is 2 or greater, $R_6$s are the same as or different from each other, and $R_7$s are the same as or different from each other.

18. The organic light emitting device of claim 11, wherein the organic material layer comprises a light emitting layer comprising a compound of the following Chemical Formula 15:

[Chemical Formula 15]

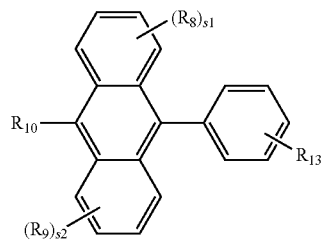

wherein, in Chemical Formula 15,
$R_{10}$ is a substituted or unsubstituted 1-naphthyl group, a substituted or unsubstituted 2-naphthyl group, a substituted or unsubstituted 1-anthryl group, a substituted or unsubstituted 2-anthryl group, a substituted or unsubstituted 1-phenanthryl group, a substituted or unsubstituted 2-phenanthryl group, a substituted or unsubstituted 3-phenanthryl group, a substituted or unsubstituted 4-phenanthryl group, a substituted or unsubstituted 9-phenanthryl group, a substituted or unsubstituted 1-naphthacenyl group, a substituted or unsubstituted 2-naphthacenyl group, a substituted or unsubstituted 9-naphthacenyl group, a substituted or unsubstituted 1-pyrenyl group, a substituted or unsubstituted 2-pyrenyl group, a substituted or unsubstituted 4-pyrenyl group, a substituted or unsubstituted 3-methyl-2-naphthyl group, a substituted or unsubstituted 4-methyl-1-naphthyl group or the following structural formula

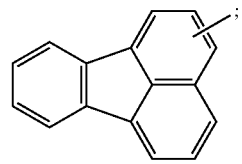

$R_{13}$ is a group selected from the group consisting of a phenyl group, a 1-naphthyl group, a 2-naphthyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 3-biphenylyl group, a 4-biphenylyl group, a p-terphenyl-4-yl group, a p-terphenyl-3-yl group, a p-terphenyl-2-yl group, an m-terphenyl-4-yl group, an m-terphenyl-3-yl group, an m-terphenyl-2-yl group, an o-tolyl group, an m-tolyl group, a p-tolyl group, a p-t-butylphenyl group, a p-(2-phenylpropyl) phenyl group, a 3-methyl-2-naphthyl group, a 4-methyl-1-naphthyl group, a 4-methyl-1-anthryl group, a 4'-methylbiphenylyl group, a 4"-t-butyl-p-terphenyl-4-yl group and a 3-fluoranthenyl group;
$R_8$ and $R_9$ are the same as or different from each other, and each independently a substituted or unsubstituted aryl group having 6 to 50 carbon atoms, a substituted or unsubstituted heteroaryl group having 5 to 50 nuclear atoms, a substituted or unsubstituted alkyl group having 1 to 50 carbon atoms, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 nuclear atoms, a substituted or unsubstituted arylthio group having 5 to 50 nuclear atoms, a substituted or unsubstituted alkoxycarbonyl group having 1 to 50 carbon atoms, a carboxyl group, a halogen atom, a cyano group, a nitro group or a hydroxyl group; and $s1$ and $s2$ are each an integer of 0 to 4.

* * * * *